(12) United States Patent
Hidaka et al.

(10) Patent No.: US 8,883,792 B2
(45) Date of Patent: Nov. 11, 2014

(54) SUBSTITUTED ISOQUINOLINE DERIVATIVE

(75) Inventors: Hiroyoshi Hidaka, Nagoya (JP); Kengo Sumi, Nagoya (JP); Kouichi Takahashi, Nagoya (JP); Yoshihiro Inoue, Nagoya (JP)

(73) Assignee: D. Western Therapeutics Institute, Inc., Nagoya-shi (JP)

( * ) Notice: Subject to any disclaimer, the term of this patent is extended or adjusted under 35 U.S.C. 154(b) by 0 days.

(21) Appl. No.: 13/995,300

(22) PCT Filed: Dec. 21, 2011

(86) PCT No.: PCT/JP2011/079725
§ 371 (c)(1),
(2), (4) Date: Jun. 18, 2013

(87) PCT Pub. No.: WO2012/086727
PCT Pub. Date: Jun. 28, 2012

(65) Prior Publication Data
US 2013/0274269 A1  Oct. 17, 2013

(30) Foreign Application Priority Data
Dec. 22, 2010  (JP) .................................. 2010-286445

(51) Int. Cl.
C07D 401/12 (2006.01)
C07D 217/04 (2006.01)
A61K 31/4725 (2006.01)
C07D 217/02 (2006.01)
C07D 417/12 (2006.01)
C07D 405/12 (2006.01)
C07D 409/12 (2006.01)
C07D 217/22 (2006.01)

(52) U.S. Cl.
CPC ............ *C07D 217/04* (2013.01); *C07D 401/12* (2013.01); *C07D 217/02* (2013.01); *C07D 417/12* (2013.01); *C07D 405/12* (2013.01); *C07D 409/12* (2013.01); *C07D 217/22* (2013.01)
USPC ...... 514/253.05; 546/139; 546/148; 544/363; 514/307

(58) Field of Classification Search
None
See application file for complete search history.

(56) References Cited

U.S. PATENT DOCUMENTS

| 5,705,500 | A | 1/1998 | Getman et al. |
|---|---|---|---|
| 5,985,870 | A | 11/1999 | Getman et al. |
| 6,169,085 | B1 | 1/2001 | Getman et al. |
| 6,271,224 | B1 | 8/2001 | Kapin et al. |
| 6,380,188 | B1 | 4/2002 | Getman et al. |
| 6,403,590 | B1 | 6/2002 | Hellberg et al. |
| 6,667,307 | B2 | 12/2003 | Getman et al. |
| 7,045,518 | B2 | 5/2006 | Getman et al. |
| 2003/0191166 | A1 | 10/2003 | Getman et al. |
| 2004/0147758 | A1 | 7/2004 | Getman et al. |
| 2005/0272723 | A1 | 12/2005 | Glick |
| 2006/0079556 | A1 | 4/2006 | Sher et al. |
| 2006/0264483 | A1 | 11/2006 | Getman et al. |
| 2009/0186917 | A1 | 7/2009 | Delong et al. |
| 2009/0275099 | A1 | 11/2009 | Glick |
| 2010/0144713 | A1 | 6/2010 | Delong et al. |
| 2010/0280011 | A1 | 11/2010 | Delong et al. |
| 2011/0028461 | A1 | 2/2011 | Berger et al. |
| 2012/0035159 | A1 | 2/2012 | Hidaka et al. |

FOREIGN PATENT DOCUMENTS

| JP | 2005 232175 | 9/2005 |
|---|---|---|
| WO | 96 28418 | 9/1996 |
| WO | 97 23222 | 7/1997 |
| WO | WO 2006036664 A1 * | 4/2006 |
| WO | 2006 073448 | 7/2006 |
| WO | 2009 091898 | 7/2009 |
| WO | 2009 123870 | 10/2009 |
| WO | 2010 127330 | 11/2010 |
| WO | 2010 146881 | 12/2010 |

OTHER PUBLICATIONS

WebMD, 2013, Glaucoma—Questions and Answers, http://www.webmd.com/eye-health/glaucoma-facts-you-need.*
Lizarzaburu, M. E. et al., "Convenient preparation of aryl ether derivatives using a sequence of functionalized polymers", Tetrahedron Letters, vol. 44, pp. 4873-4876, (2003).
International Search Report Issued Jan. 24, 2012 in PCT/JP11/079725 Filed Dec. 21, 2011. English translation of Written Opinion Issued Jan. 24, 2012 in PCT/JP11/079725 Filed Dec. 21, 2011.
Office Action issued Apr. 11, 2014 in European Patent Application No. 11 851 146.8.
Mark J. Bamford, et al., "(1*H*-Imidazo[4,5-*c*]pyridin-2-yl)-1,2,5-oxadiazol-3-ylamine derivatives: A novel class of potent MSK-1-inhibitors", Bioorganic & Medicinal Chemistry Letters, vol. 15, No. 14, XP027801589, Jul. 15, 2005, pp. 3402-3406.

* cited by examiner

*Primary Examiner* — Zinna Northington Davis
(74) *Attorney, Agent, or Firm* — Oblon, Spivak, McClelland, Maier & Neustadt, L.L.P.

(57) ABSTRACT

The present invention provides a novel isoquinoline-6-sulfonamide derivative that is useful as a medicine. The present invention provides an isoquinoline-6-sulfonamide derivative represented by Formula (1), a salt thereof, or a solvate of the derivative or the salt, wherein $R^1$ and $R^2$ each independently represent a hydrogen atom, or the like; $R^3$ and $R^4$ each independently represent a hydrogen atom, an alkyl group, or the like; $R^5$ represents a hydrogen atom, an optionally substituted alkyl group, an optionally substituted alkenyl group, an optionally substituted alkynyl group, an optionally substituted cycloalkyl group, an optionally substituted alkanoyl group, or the like; and A represents a linear or branched alkylene group having 2 to 6 carbon atoms.

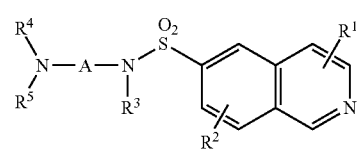

(1)

11 Claims, No Drawings

SUBSTITUTED ISOQUINOLINE DERIVATIVE

CONTINUING DATA

This application is a 371 of PCT/JP11/79725 filed Dec. 21, 2011.

FIELD OF THE INVENTION

The present invention relates to isoquinoline-6-sulfonamide derivatives that are useful for the treatment and/or prevention of glaucoma, ocular hypertension, and cardiovascular disease.

BACKGROUND OF THE INVENTION

Among compounds having an isoquinoline ring, there exist a number of compounds useful as pharmaceuticals, while a limited number of disclosures have been made on compounds having an isoquinoline ring substituted at the 6th position by an aminosulfonyl group. Examples of the limited number of disclosures include cannabinoid receptor antagonists disclosed in Patent Document 1, F1F0 ATPase inhibitors disclosed in Patent Document 2, β3 adrenergic receptor antagonists disclosed in Patent Document 3, cyclic aminosulfonylisoquinoline derivatives disclosed in Patent Document 4, and compounds having a phenoxy group disclosed in Non Patent Document 1.

PRIOR ART DOCUMENT

Patent Document

[Patent Document 1] U.S. Patent Publication No. US-20060079556
[Patent Document 2] WO2006/073448
[Patent Document 3] WO2009/123870
[Patent Document 4] WO2010/146881

Non Patent Document

[Non Patent Document 1] Tetrahedron Letters 44, 4873-4876 (2003)

SUMMARY OF THE INVENTION

Problem to be Solved by the Invention

An object of the present invention is to provide novel isoquinoline-6-sulfonamide derivatives that are useful as medicines.

Solution to Problem

The present inventors conducted a study to introduce various substituents to the 6th position of an isoquinoline ring and used isoquinoline-6-sulfonyl chloride as a key intermediate to synthesize novel isoquinoline-6-sulfonamide derivatives represented by Formula (1) described below. As a result of studying the pharmacological effects of these compounds, it was found that they have excellent ocular hypotensive effect and blood pressure lowering effect and are useful as active ingredients for medicines for treatment and/or prevention of glaucoma, ocular hypertension, and cardiovascular disease.

Specifically, the present invention provides isoquinoline-6-sulfonamide derivatives represented by Formula (1), salts thereof, or solvates of the derivative or the salt:

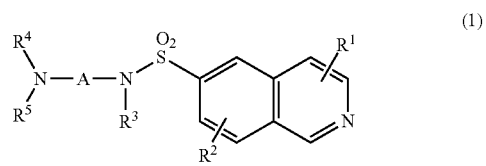

wherein
$R^1$ and $R^2$ each independently represent a hydrogen atom, a halogen atom, a cyano group, an alkyl group, a halogenoalkyl group, an alkenyl group, an alkynyl group, an alkoxy group, an alkylthio group, a hydroxyl group, a mercapto group, a nitro group, an amino group, an aminoalkylthio group, or a heteroaryl group;

$R^3$ and $R^4$ each independently represent a hydrogen atom, an alkyl group, a hydroxyalkyl group, a dialkylaminoalkyl group, or an aminoalkanoyl group;

$R^5$ represents a hydrogen atom, an optionally substituted alkyl group, an optionally substituted alkenyl group, an optionally substituted alkynyl group, an optionally substituted cycloalkyl group, or an optionally substituted alkanoyl group, or $R^4$ and $R^5$ may form a saturated heterocyclic ring together with the adjacent nitrogen atom, wherein the substituent on the alkyl group, the alkenyl group, the alkynyl group, the cycloalkyl group, or the alkanoyl group in $R^5$ is one or two or more substituents selected from (a) a cycloalkyl group, an aryl group, a heteroaryl group, an aryloxy group, a heteroaryloxy group, an arylene group, or a heteroarylene group optionally having, on the ring, one or two or more substituents selected from a halogen atom, a cyano group, an alkyl group, a halogenoalkyl group, an alkenyl group, an alkynyl group, an alkoxy group, an alkylthio group, a hydroxyl group, an oxo group, a formyl group, an alkanoyl group, a carboxyl group, an alkyloxycarbonyl group, a mercapto group, a nitro group, an amino group, an urea group, a thiourea group, and an aminoalkyl group, (b) a hydroxyl group, (c) an oxo group, (d) an alkanoyloxy group, (e) an amino group, (f) a carboxyl group, (g) an alkoxy group, and (h) an alkyloxycarbonyl group; and A represents a linear or branched alkylene group having 2 to 6 carbon atoms and optionally having one or two or more substituents selected from a carboxyl group, a halogen atom, a cyano group, an oxo group, an alkenyl group, an alkynyl group, an alkoxy group, a hydroxyl group, an alkyloxycarbonyl group, an aminoalkyl group, an aryl group, a heteroaryl group, an optionally substituted aralkyl group, and an optionally substituted heteroarylalkyl group, wherein the aralkyl group or the heteroarylalkyl group in A optionally has one or two or more substituents selected from a halogen atom, a cyano group, an alkyl group, a halogenoalkyl group, an alkenyl group, an alkynyl group, an alkoxy group, an alkylthio group, a hydroxyl group, an oxo group, a formyl group, an alkanoyl group, a carboxyl group, an alkyloxycarbonyl group, a mercapto group, a nitro group, an amino group, an urea group, a thiourea group, and an aminoalkyl group.

Moreover, the present invention provides pharmaceutical compositions containing a compound of Formula (1), a salt thereof, or a solvate of the compound or the salt.

Moreover, the present invention provides a method for treating or preventing glaucoma, ocular hypertension, or cardiovascular disease including administering an effective amount of a compound of Formula (1), a salt thereof, or a solvate of the compound or the salt. Moreover, the present invention provides compounds of Formula (1), salts thereof, or solvates of the compound or the salt for use in treatment and/or prevention of glaucoma, ocular hypertension, or cardiovascular disease.

Furthermore, the present invention provides use of a compound of Formula (1), a salt thereof, or a solvate of the compound or the salt for production of a therapeutic and/or preventive drug for glaucoma, ocular hypertension, or cardiovascular disease.

Effects of the Invention

Isoquinoline-6-sulfonamide derivatives of the present invention have excellent ocular hypotensive effect and blood pressure lowering effect and are useful as active ingredients for pharmaceutical agents for treatment and/or prevention of glaucoma, ocular hypertension, and cardiovascular disease.

MODE FOR CARRYING OUT THE INVENTION

In Formula (1), $R^1$ and $R^2$ each independently represent a hydrogen atom, a halogen atom, a cyano group, an alkyl group, a halogenoalkyl group, an alkenyl group, an alkynyl group, an alkoxy group, an alkylthio group, a hydroxyl group, a mercapto group, a nitro group, an amino group, an aminoalkylthio group, or a heteroaryl group.

Examples of the halogen atom include fluorine, chlorine, bromine, and iodine atoms. Of them, a fluorine, chlorine, or bromine atom is preferable.

Examples of the alkyl group include linear, branched, or cyclic alkyl groups having 1 to 8 carbon atoms ($C_{1-8}$ alkyl groups). Alkyl groups having 1 to 6 carbon atoms are preferable, with alkyl groups having 1 to 3 carbon atoms further preferred.

Specific examples thereof can include methyl, ethyl, n-propyl, isopropyl, n-butyl, isobutyl, sec-butyl, tert-butyl, n-pentyl, isopentyl, n-hexyl, isohexyl, and cyclopropyl groups. Among them, those having 1 to 3 carbon atoms are preferable, with a methyl or ethyl group particularly preferred.

The halogenoalkyl group is preferably a halogeno $C_{1-8}$ alkyl group, more preferably a halogeno $C_{1-6}$ alkyl group. Specific examples thereof include chloromethyl, fluoromethyl, chloroethyl, fluoroethyl, and trifluoromethyl groups.

Examples of the alkenyl group include linear or branched alkenyl groups having 2 to 8 carbon atoms ($C_{2-8}$ alkenyl groups). Alkenyl groups having 2 to 6 carbon atoms are preferable. Specific examples thereof can include vinyl, allyl, isopropenyl, 2-methallyl, 2-butenyl, and 3-butenyl groups. Among them, those having 2 to 4 carbon atoms are preferable.

Examples of the alkynyl group include linear or branched alkynyl groups having 2 to 8 carbon atoms ($C_{2-8}$ alkynyl groups). Alkynyl groups having 2 to 6 carbon atoms are preferable. Specific examples thereof include ethynyl, propynyl, and butynyl groups. Among them, those having 2 to 4 carbon atoms are preferable.

Examples of the alkoxy group include linear or branched alkoxy groups having 1 to 8 carbon atoms ($C_{1-8}$ alkoxy groups). Alkoxy groups having 1 to 6 carbon atoms are preferable. Specific examples thereof can include methoxy, ethoxy, n-propoxy, isopropoxy, n-butoxy, isobutoxy, sec-butoxy, and tert-butoxy groups.

Examples of the alkylthio group include linear or branched alkylthio groups having 1 to 8 carbon atoms ($C_{1-8}$ alkylthio groups). Alkylthio groups having 1 to 6 carbon atoms are preferable. Specific examples thereof include methylthio, ethylthio, isopropylthio, and n-propylthio groups.

The aminoalkylthio group is preferably an amino $C_{1-8}$ alkylthio group, more preferably an amino $C_{1-6}$ alkylthio group. Specific examples thereof include aminomethylthio, aminoethylthio, and aminopropylthio groups.

Examples of the heteroaryl group include 5- to 6-membered heteroaryl groups having 1 to 3 atoms selected from nitrogen, oxygen, and sulfur atoms. Specific examples thereof include pyrrolyl, furyl, thienyl, imidazolyl, pyrazolyl, oxazolyl, isoxazolyl, thiazolyl, isothiazolyl, pyridyl, pyrimidinyl, and pyrazyl groups. Of them, a furyl, thienyl, or pyridyl group is particularly preferable.

Preferably, $R^1$ and $R^2$ are each independently a hydrogen atom, a halogen atom, a $C_{1-8}$ alkyl group, a nitro group, a cyano group, a halogeno $C_{1-8}$ alkyl group, a phenyl group, a $C_{2-8}$ alkenyl group, a $C_{2-8}$ alkynyl group, a hydroxyl group, an amino group, an amino $C_{1-8}$ alkylthio group, or a thienyl group. Moreover, more preferably, they are each independently a hydrogen atom, a halogen atom, a hydroxyl group, a $C_{1-6}$ alkyl group, or a halogeno $C_{1-6}$ alkyl group. Further preferably, they are each independently a hydrogen atom, a halogen atom, a hydroxyl group, or a $C_{1-3}$ alkyl group. Furthermore, $R^2$ is preferably a hydrogen atom.

$R^1$ may be substituted at any of the 1st, 3rd, and 4th positions of the isoquinoline ring. Moreover, $R^2$ may be substituted at any of the 5th, 7th, and 8th positions of the isoquinoline ring.

$R^3$ and $R^4$ each independently represent a hydrogen atom, an alkyl group, a hydroxyalkyl group, a dialkylaminoalkyl group, or an aminoalkanoyl group.

Examples of the alkyl group include those illustrated above as examples of $R^1$ and $R^2$. Alkyl groups having 1 to 6 carbon atoms are preferable, with alkyl groups having 1 to 3 carbon atoms further preferred.

Examples of the hydroxyalkyl group include hydroxy $C_{1-8}$ alkyl groups. Hydroxy $C_{1-6}$ alkyl groups are preferable.

The dialkylaminoalkyl group is preferably a dialkylaminoalkyl group whose dialkyl moiety has 1 to 3 carbon atoms in each alkyl and whose aminoalkyl moiety has 1 to 6 carbon atoms.

Examples of the aminoalkanoyl group include amino $C_{1-6}$ alkanoyl groups and specifically include glycyl, alanyl, leucyl, isoleucyl, and valyl groups.

$R^3$ is preferably a hydrogen atom or a $C_{1-6}$ alkyl group. $R^4$ is preferably a hydrogen atom or an amino $C_{1-6}$ alkanoyl group.

$R^5$ represents a hydrogen atom, an optionally substituted alkyl group, an optionally substituted alkenyl group, an optionally substituted alkynyl group, an optionally substituted cycloalkyl group, or an optionally substituted alkanoyl group, or $R^4$ and $R^5$ may form a saturated heterocyclic ring together with the adjacent nitrogen atom, wherein the substituent on the alkyl group, the alkenyl group, the alkynyl group, the cycloalkyl group, or the alkanoyl group is one or two or more substituents selected from (a) a cycloalkyl group, an aryl group, a heteroaryl group, an aryloxy group, a heteroaryloxy group, an arylene group, or a heteroarylene group optionally having, on the ring, one or two or more substituents selected from a halogen atom, a cyano group, an alkyl group, a halogenoalkyl group, an alkenyl group, an alkynyl group, an alkoxy group, an alkylthio group, a hydroxyl group, an oxo group, a formyl group, an alkanoyl group, a carboxyl group, an alkyloxycarbonyl group, a mercapto group, a nitro group, an amino group, an urea group, a thiourea group, and an aminoalkyl group, (b) a hydroxyl group, (c) an oxo group, (d) an alkanoyloxy group, (e) an amino group, (f) a carboxyl group, (g) an alkoxy group, and (h) an alkyloxycarbonyl group.

Examples of the alkyl group and the alkenyl group represented by $R^5$ include those illustrated above as examples of $R^1$ and $R^2$. Of them, the alkyl group is preferably a $C_{1-8}$ linear or branched alkyl group. Specific examples thereof can include methyl, ethyl, n-propyl, isopropyl, n-butyl, isobutyl, sec-butyl, tert-butyl, n-pentyl, isopentyl, n-hexyl, and isohexyl groups.

The alkenyl group is preferably a $C_{2-8}$ alkenyl group. Specific examples thereof can include vinyl, allyl, isopropenyl, 2-propenyl, 2-methallyl, 2-butenyl, and 3-butenyl groups. Among them, those having 2 to 6 carbon atoms are preferable.

Examples of the alkynyl group include linear or branched alkynyl groups having 2 to 8 carbon atoms ($C_{2-8}$ alkynyl groups). Alkynyl groups having 2 to 6 carbon atoms are preferable. Specific examples thereof include ethynyl, propynyl, and butynyl groups. Among them, those having 2 to 4 carbon atoms are preferable.

Examples of the cycloalkyl group include cycloalkyl groups having 3 to 8 carbon atoms ($C_{3-8}$ cycloalkyl groups). Cycloalkyl groups having 3 to 6 carbon atoms are preferable. Specific examples thereof include cyclopropyl, cyclobutyl, cyclopentyl, and cyclohexyl groups.

Examples of the alkanoyl group include linear or branched alkanoyl groups having 1 to 8 carbon atoms ($C_{1-8}$ alkanoyl groups). $C_{2-6}$ alkanoyl groups are preferable. Specific examples thereof include acetyl, propionyl, butyryl, and pentanoyl groups.

The saturated heterocyclic ring formed by $R^4$ and $R^5$ together is preferably a 5- to 6-membered saturated heterocyclic ring containing 1 or 2 nitrogen atoms. Specific examples thereof include pyrrolidine, piperidine, and piperazine rings.

Examples of the substituent on the alkyl group, the alkenyl group, the alkynyl group, the cycloalkyl group, or the alkanoyl group include (a) a cycloalkyl group, an aryl group, a heteroaryl group, an aryloxy group, a heteroaryloxy group, an arylene group, or a heteroarylene group optionally having the substituent described above, (b) a hydroxyl group, (c) an oxo group, (d) an alkanoyloxy group, (e) an amino group, (f) a carboxyl group, (g) an alkoxy group, and (h) an alkyloxycarbonyl group. Examples of the cycloalkyl group include cycloalkyl groups having 3 to 8 carbon atoms ($C_{3-8}$ cycloalkyl groups). Cycloalkyl groups having 3 to 6 carbon atoms are preferable. Specific examples thereof include cyclopropyl, cyclobutyl, cyclopentyl, and cyclohexyl groups.

Examples of the aryl group include aryl groups having 6 to 14 carbon atoms, for example, phenyl, naphthyl, phenanthryl, and biphenyl groups. Of them, a phenyl group is particularly preferable.

Examples of the aryloxy group include aryloxy groups having 6 to 14 carbon atoms and specifically include phenoxy, naphthyloxy, and biphenyloxy groups. Of them, a phenoxy group is particularly preferable.

Examples of the heteroaryl group include 5- to 10-membered heteroaryl groups having 1 to 3 atoms selected from nitrogen, oxygen, and sulfur atoms. Specific examples thereof include pyrrolyl, furyl, thienyl, imidazolyl, pyrazolyl, oxazolyl, isoxazolyl, thiazolyl, isothiazolyl, pyridyl, pyrimidinyl, pyrazyl, indolyl, isoindolyl, indazolyl, quinolyl, isoquinolyl, pyridylphenyl, benzofuryl, benzothienyl, benzoxazolyl, benzisoxazolyl, benzothiazolyl, benzisothiazolyl, and benzimidazolyl groups. Of them, a furyl, thienyl, pyridyl, or indolyl group is particularly preferable.

Examples of the heteroaryloxy group include these heteroaryl groups bonded to an oxygen atom.

Examples of the arylene group include arylene groups having 6 to 14 carbon atoms and specifically include o-phenylene and α,β-naphthalene groups. Of them, a o-phenylene group is particularly preferable. Examples of the heteroarylene group include divalent groups of the heteroaryl groups illustrated above.

Of these cycloalkyl groups, aryl groups, heteroaryl groups, aryloxy groups, heteroaryloxy groups, arylene groups, and heteroarylene groups, an aryl, heteroaryl, or o-phenylene group is particularly preferable.

Of these substituents on the ring in the group (a), examples of the halogen atom include fluorine, chlorine, bromine, and iodine atoms. Of them, a fluorine, chlorine, or bromine atom is preferable.

Examples of the alkyl group include linear or branched alkyl groups having 1 to 8 carbon atoms ($C_{1-8}$ alkyl groups). Alkyl groups having 1 to 6 carbon atoms are preferable, with alkyl groups having 1 to 3 carbon atoms further preferred.

Specific examples thereof can include methyl, ethyl, n-propyl, isopropyl, n-butyl, isobutyl, sec-butyl, tert-butyl, n-pentyl, isopentyl, n-hexyl, and isohexyl groups. Among them, those having 1 to 3 carbon atoms are preferable, with a methyl or ethyl group particularly preferred.

The halogenoalkyl group is preferably a halogeno $C_{1-8}$ alkyl group, more preferably a halogeno $C_{1-6}$ alkyl group. Specific examples thereof include chloromethyl, fluoromethyl, chloroethyl, fluoroethyl, and trifluoromethyl groups.

Examples of the alkenyl group include linear or branched alkenyl groups having 2 to 8 carbon atoms ($C_{2-8}$ alkenyl groups). Alkenyl groups having 2 to 6 carbon atoms are preferable. Specific examples thereof can include vinyl, allyl, isopropenyl, 2-methallyl, 2-butenyl, and 3-butenyl groups. Among them, those having 2 to 4 carbon atoms are preferable.

Examples of the alkynyl group include linear or branched alkynyl groups having 2 to 8 carbon atoms ($C_{2-8}$ alkynyl groups). Alkynyl groups having 2 to 6 carbon atoms are preferable. Specific examples thereof include ethynyl, propynyl, and butynyl groups. Among them, those having 2 to 4 carbon atoms are preferable.

Examples of the alkoxy group include linear or branched alkoxy groups having 1 to 8 carbon atoms ($C_{1-8}$ alkoxy groups). Alkoxy groups having 1 to 6 carbon atoms are preferable. Specific examples thereof can include methoxy, ethoxy, n-propoxy, isopropoxy, n-butoxy, isobutoxy, sec-butoxy, and tert-butoxy groups.

Examples of the alkylthio group include linear or branched alkylthio groups having 1 to 8 carbon atoms ($C_{1-8}$ alkylthio groups). Alkylthio groups having 1 to 6 carbon atoms are preferable. Specific examples thereof include methylthio, ethylthio, isopropylthio, and n-propylthio groups.

Examples of the alkanoyl group include linear or branched alkanoyl having 1 to 8 carbon atoms ($C_{1-8}$ alkanoyl groups). $C_{2-6}$ alkanoyl groups are preferable. Specific examples thereof include acetyl, propionyl, butyryl, and pentanoyl groups.

Examples of the alkyloxycarbonyl group include $C_{1-8}$ alkoxycarbonyl groups and specifically include methoxycarbonyl, ethoxycarbonyl, isopropyloxycarbonyl, and tert-butoxycarbonyl groups.

Examples of the aminoalkyl group include amino $C_{1-8}$ alkyl groups and specifically include aminomethyl, aminoethyl, and aminopropyl groups. The ring in the group (a) can be substituted by one or two or more of these substituents and may be substituted by, for example, 1 to 3 of these substituents.

Examples of the alkanoyloxy group in the group (d) include linear or branched alkanoyloxy groups having 1 to 8 carbon atoms ($C_{1-8}$ alkanoyl groups). $C_{2-6}$ alkanoyloxy groups are preferable. Specific examples thereof include formyloxy, acetoxy, and propionyloxy groups.

Examples of the alkoxy group in the group (g) include linear or branched alkoxy groups having 1 to 8 carbon atoms, for example, methoxy, ethoxy, and t-butoxy.

Examples of the alkyloxycarbonyl group in the group (h) include $C_{1-8}$ alkyloxycarbonyl groups such as methoxycarbonyl and ethoxycarbonyl groups.

The substituent on the alkyl group, the alkenyl group, the alkynyl group, the cycloalkyl group, or the alkanoyl group in $R^5$ is preferably one or two substituents selected from (a) an aryl group, a heteroaryl group, or an arylene group optionally having, on the ring, one or two substituents selected from a halogen atom, a cyano group, a $C_{1-8}$ alkyl group, a halogeno $C_{1-8}$ alkyl group, a $C_{2-8}$ alkenyl group, a $C_{2-8}$ alkynyl group, a $C_{1-8}$ alkoxy group, a $C_{1-8}$ alkylthio group, a hydroxyl group, an oxo group, a formyl group, a $C_{2-8}$ alkanoyl group, a carboxyl group, a $C_{1-8}$ alkyloxycarbonyl group, a mercapto group, a nitro group, an amino group, an urea group, a thiourea group, and an amino $C_{1-8}$ alkyl group, (b) a hydroxyl group, (c) an oxo group, (d) a $C_{2-8}$ alkanoyloxy group, (e) an amino group, (f) a carboxyl group, (g) a $C_{1-8}$ alkoxy group, and (h) a $C_{1-8}$ alkyloxycarbonyl group.

The substituent on the alkyl group, the alkenyl group, or the alkanoyl group is more preferably one or two substituents selected from (a) an aryl group, a heteroaryl group, or an arylene group optionally having, on the ring, one or two substituents selected from a halogen atom, a cyano group, a $C_{1-8}$ alkyl group, a halogeno $C_{1-8}$ alkyl group, a $C_{2-8}$ alkenyl group, a $C_{2-8}$ alkynyl group, a $C_{1-8}$ alkoxy group, a $C_{1-8}$ alkylthio group, a hydroxyl group, an oxo group, a formyl group, a $C_{2-8}$ alkanoyl group, a carboxyl group, a $C_{1-8}$ alkyloxycarbonyl group, a nitro group, an amino group, and an amino $C_{1-8}$ alkyl group, (d) a hydroxyl group, and (f) an oxo group.

A represents a linear or branched alkylene group having 2 to 6 carbon atoms and optionally having one or two or more substituents selected from a carboxyl group, a halogen atom, a cyano group, an oxo group, an alkenyl group, an alkynyl group, an alkoxy group, a hydroxyl group, an alkyloxycarbonyl group, an aminoalkyl group, an aryl group, a heteroaryl group, an optionally substituted aralkyl group, and an optionally substituted heteroarylalkyl group, wherein the aralkyl group or the heteroarylalkyl group in A optionally has one or two or more substituents selected from a halogen atom, a cyano group, an alkyl group, a halogenoalkyl group, an alkenyl group, an alkynyl group, an alkoxy group, an alkylthio group, a hydroxyl group, an oxo group, a formyl group, an alkanoyl group, a carboxyl group, an alkyloxycarbonyl group, a mercapto group, a nitro group, an amino group, an urea group, a thiourea group, and an aminoalkyl group.

Examples of the linear or branched alkylene group having 2 to 6 carbon atoms include methylene, ethylene, trimethylene, tetramethylene, pentamethylene, hexamethylene, and isopropylene (—$CH_2CH(CH_3)$—) groups. Of them, an ethylene, trimethylene, or isopropylene group is particularly preferable.

Of these groups by which the alkylene group may be substituted, examples of the alkenyl group include linear or branched alkenyl groups having 2 to 8 carbon atoms ($C_{2-8}$ alkenyl groups). Alkenyl groups having 2 to 6 carbon atoms are preferable. Specific examples thereof can include vinyl, allyl, isopropenyl, 2-methallyl, 2-butenyl, and 3-butenyl groups. Among them, those having 2 to 4 carbon atoms are preferable.

Examples of the alkynyl group include linear or branched alkynyl groups having 2 to 8 carbon atoms ($C_{2-8}$ alkynyl groups). Alkynyl groups having 2 to 6 carbon atoms are preferable. Specific examples thereof include ethynyl, propynyl, and butynyl groups. Among them, those having 2 to 4 carbon atoms are preferable.

Examples of the alkoxy group include linear or branched alkoxy groups having 1 to 8 carbon atoms ($C_{1-8}$ alkoxy groups). Alkoxy groups having 1 to 6 carbon atoms are preferable. Specific examples thereof can include methoxy, ethoxy, n-propoxy, isopropoxy, n-butoxy, isobutoxy, sec-butoxy, and tert-butoxy groups.

Examples of the alkyloxycarbonyl group include $C_{1-8}$ alkoxycarbonyl groups and specifically include methoxycarbonyl, ethoxycarbonyl, isopropyloxycarbonyl, and tert-butoxycarbonyl groups.

Examples of the aminoalkyl group include amino $C_{1-8}$ alkyl groups and specifically include aminomethyl, aminoethyl, and aminopropyl groups.

Examples of the aryl group include aryl groups having 6 to 14 carbon atoms, for example, phenyl, naphthyl, phenanthryl, and biphenyl groups. Of them, a phenyl group is particularly preferable.

Examples of the heteroaryl group include 5- to 6-membered heteroaryl groups having 1 to 3 atoms selected from nitrogen, oxygen, and sulfur atoms. Specific examples thereof include pyrrolyl, furyl, thienyl, imidazolyl, pyrazolyl, oxazolyl, isoxazolyl, thiazolyl, isothiazolyl, pyridyl, pyrimidinyl, and pyrazyl groups. Of them, a thienyl group is particularly preferable.

Examples of the aralkyl group include aralkyl groups whose alkyl moiety is linear or branched alkyl having 1 to 8 carbon atoms and whose aryl moiety is aryl having 6 to 12 carbon atoms. Phenyl $C_{1-8}$ alkyl groups are preferable.

The heteroarylalkyl group is preferably a heteroaryl $C_{1-8}$ alkyl group whose alkyl moiety is linear or branched alkyl having 1 to 8 carbon atoms and whose heteroaryl moiety is 5- to 10-membered heteroaryl having 1 to 3 atoms selected from nitrogen, oxygen, and sulfur atoms.

Examples of the substituent on the aralkyl group or the heteroarylalkyl group in A include the same as in the substituent group (a) on the alkyl group or the like in $R^5$. Specifically, the substituent is preferably one or two substituents selected from a halogen atom, a cyano group, a $C_{1-8}$ alkyl group, a halogeno $C_{1-8}$ alkyl group, a $C_{2-8}$ alkenyl group, a $C_{2-8}$ alkynyl group, a $C_{1-8}$ alkoxy group, a $C_{1-8}$ alkylthio group, a hydroxyl group, an oxo group, a formyl group, a $C_{2-8}$ alkanoyl group, a carboxyl group, a $C_{1-8}$ alkyloxycarbonyl group, a nitro group, an amino group, and an amino $C_{1-8}$ alkyl group.

When A is a linear or branched alkylene group having 2 to 6 carbon atoms substituted by a group selected from an optionally substituted aralkyl group and an optionally substituted heteroarylalkyl group, $R^4$ and $R^5$ preferably are a hydrogen atom or a $C_{1-3}$ alkyl group. In this case, more preferably, A is a linear or branched alkylene group having 2 to 6 carbon atoms substituted by a group selected from an optionally substituted phenyl $C_{1-8}$ alkyl group and an optionally substituted heteroaryl $C_{1-8}$ alkyl group, and $R^4$ and $R^5$ are a hydrogen atom or a $C_{1-3}$ alkyl group.

When A is an unsubstituted linear or branched alkylene group having 2 to 6 carbon atoms, $R^5$ represents a group other than a hydrogen atom, i.e., an optionally substituted alkyl group, an optionally substituted alkenyl group, an optionally substituted alkynyl group, an optionally substituted cycloalkyl group, or an optionally substituted alkanoyl group, or $R^4$ and $R^5$ may form a saturated heterocyclic ring together with the adjacent nitrogen atom, wherein the substituent on the alkyl group, the alkenyl group, the alkynyl group, the cycloalkyl group, or the alkanoyl group in $R^5$ is preferably one or two or more substituents selected from (a) a cycloalkyl group, an aryl group, a heteroaryl group, an aryloxy group, a heteroaryloxy group, an arylene group, or a heteroarylene group optionally having, on the ring, one or two or more substituents selected from a halogen atom, a cyano group, an alkyl group, a halogenoalkyl group, an alkenyl group, an alkynyl group, an alkoxy group, an alkylthio group, a hydroxyl group, an oxo group, a formyl group, an alkanoyl group, a carboxyl group, an alkyloxycarbonyl group, a mercapto group, a nitro group, an amino group, an urea group, a thiourea group and an aminoalkyl group, (b) a hydroxyl group, (c) an oxo group, (d) an alkanoyloxy group, (e) an amino group, (f) a carboxyl group, (g) an alkoxy group, and (h) an alkyloxycarbonyl group.

Furthermore, when A is an unsubstituted linear or branched alkylene group having 2 to 6 carbon atoms, $R^5$ represents an optionally substituted $C_{1-8}$ alkyl group, an optionally substituted $C_{2-8}$ alkenyl group, a $C_{2-8}$ alkynyl group, a $C_{3-8}$ cycloalkyl group, or an optionally substituted $C_{2-8}$ alkanoyl group, or $R^4$ and $R^5$ may form a saturated heterocyclic ring together with the adjacent nitrogen atom, wherein the substituent on the alkyl group, the alkenyl group, or the alkanoyl group is preferably one or two substituents selected from (a) an aryl group, a heteroaryl group, or an arylene group optionally having, on the ring, one or two substituents selected from a halogen atom, a cyano group, a $C_{1-8}$ alkyl group, a halogeno $C_{1-8}$ alkyl group, a $C_{2-8}$ alkenyl group, a $C_{2-8}$ alkynyl group, a $C_{1-8}$ alkoxy group, a $C_{1-8}$ alkylthio group, a hydroxyl group, an oxo group, a formyl group, a $C_{2-8}$ alkanoyl group, a carboxyl group, a $C_{1-8}$ alkyloxycarbonyl group, a nitro group, an amino group, and an amino $C_{1-8}$ alkyl group, (b) a hydroxyl group, (c) an oxo group, and (d) a $C_{2-8}$ alkanoyloxy group.

Preferable examples of the compound of Formula (1) include the following compounds:
(R)—N-{1-(ethylamino)propan-2-yl}isoquinoline-6-sulfonamide,
(R)—N-{1-(propylamino)propan-2-yl}isoquinoline-6-sulfonamide,
(R)—N-{1-(butylamino)propan-2-yl}isoquinoline-6-sulfonamide,
(S)—N-{1-(butylamino)propan-2-yl}isoquinoline-6-sulfonamide,
(R)—N-{1-(but-2-enylamino)propan-2-yl}isoquinoline-6-sulfonamide,
(S)—N-{1-(but-2-enylamino)propan-2-yl}isoquinoline-6-sulfonamide,
(R)—N-{1-(allylamino)propan-2-yl}isoquinoline-6-sulfonamide,
N-{2-(allylamino)ethyl}isoquinoline-6-sulfonamide,
(R)—N-{4-(propylamino)butan-2-yl}isoquinoline-6-sulfonamide,
(R)—N-{1-(piperazine-1-yl)propan-2-yl}isoquinoline-6-sulfonamide,
(R)—N-{1-(isobutylamino)propan-2-yl}isoquinoline-6-sulfonamide,
(R)—N-{1-(cyclopropylamino)propan-2-yl}isoquinoline-6-sulfonamide,
(R)—N-{1-(cyclobutylamino)propan-2-yl}isoquinoline-6-sulfonamide,
(R)—N-{1-(neopentylamino)propan-2-yl}isoquinoline-6-sulfonamide,
(R)—N-{1-(cyclopropylmethylamino)propan-2-yl}isoquinoline-6-sulfonamide,
(R)—N-{1-(pentylamino)propan-2-yl}isoquinoline-6-sulfonamide,
(R)—N-{1-(methylbutylamino)propan-2-yl}isoquinoline-6-sulfonamide,
(R)—N-{1-(isopentylamino)propan-2-yl}isoquinoline-6-sulfonamide,
(R)—N-{1-(hexylamino)propan-2-yl}isoquinoline-6-sulfonamide,
(R)—N-{1-(phenethylamino)propan-2-yl}isoquinoline-6-sulfonamide,
(S)—N-{1-(phenethylamino)propan-2-yl}isoquinoline-6-sulfonamide,
N—[(R)-1-{(R)-2-phenylpropylamino}propan-2-yl]isoquinoline-6-sulfonamide,
N—[(R)-1-{(S)-2-phenylpropylamino}propan-2-yl]isoquinoline-6-sulfonamide,
(R)—N-{1-(2-methoxyphenethylamino)propan-2-yl}isoquinoline-6-sulfonamide,
(R)—N-{1-(3-methoxyphenethylamino)propan-2-yl}isoquinoline-6-sulfonamide,
(R)—N-{1-(4-methoxyphenethylamino)propan-2-yl}isoquinoline-6-sulfonamide,
(R)—N-{1-(2-fluorophenethylamino)propan-2-yl}isoquinoline-6-sulfonamide,
(R)—N-{1-(2-cyclohexylethylamino)propan-2-yl}isoquinoline-6-sulfonamide,
(R)—N-{1-(3-phenylpropylamino)propan-2-yl}isoquinoline-6-sulfonamide,
(R)—N-{1-(4-phenylbutylamino)propan-2-yl}isoquinoline-6-sulfonamide,
(R)—N-[1-{2-(1H-indol-3-yl)ethylamino}propan-2-yl]isoquinoline-6-sulfonamide,
(S)—N-[1-{2-(1H-indol-3-yl)ethylamino}propan-2-yl]isoquinoline-6-sulfonamide,
(R)—N-{1-(2-chlorophenethylamino)propan-2-yl}isoquinoline-6-sulfonamide,
(R)—N-{1-(4-chlorophenethylamino)propan-2-yl}isoquinoline-6-sulfonamide,
(R)—N-[1-{2-(thiophen-2-yl)ethylamino}propan-2-yl]isoquinoline-6-sulfonamide,
(R)—N-[1-{2-(thiophen-3-yl)ethylamino}propan-2-yl]isoquinoline-6-sulfonamide,
(R)—N-{1-(2-phenoxyethylamino)propan-2-yl}isoquinoline-6-sulfonamide,
(R)—N-[1-{2-(naphthalen-1-yl)ethylamino}propan-2-yl]isoquinoline-6-sulfonamide,
(R)—N-{1-(prop-2-yn-1-ylamino)propan-2-yl}isoquinoline-6-sulfonamide,
N—[(R)-1-{(S)-2-methoxy-2-phenylethylamino}propan-2-yl]isoquinoline-6-sulfonamide,
(R)—N-[1-{2-(pyridin-3-yl)ethylamino}propan-2-yl]isoquinoline-6-sulfonamide,
N—[(R)-1-{(R)-3-hydroxy-3-phenylpropylamino}propan-2-yl]isoquinoline-6-sulfonamide,
(R)—N-{1-(3-fluorophenethylamino)propan-2-yl}isoquinoline-6-sulfonamide,
(R)—N-{1-(4-fluorophenethylamino)propan-2-yl}isoquinoline-6-sulfonamide,
(R)—N-{1-(3-chlorophenethylamino)propan-2-yl}isoquinoline-6-sulfonamide,
(R)—N-{1-(4-bromophenethylamino)propan-2-yl}isoquinoline-6-sulfonamide,
(R)—N-{1-(2-methylphenethylamino)propan-2-yl}isoquinoline-6-sulfonamide,
(R)—N-{1-(3-methylphenethylamino)propan-2-yl}isoquinoline-6-sulfonamide,
(R)—N-[1-(4-methylphenethylamino)propan-2-yl]isoquinoline-6-sulfonamide, (R)—N-{1-(4-nitrophenethylamino)propan-2-yl}isoquinoline-6-sulfonamide,
(R)—N-{1-(4-trifluoromethylphenethylamino)propan-2-yl}isoquinoline-6-sulfonamide,
(R)—N-{1-(cyclohexylamino)propan-2-yl}isoquinoline-6-sulfonamide,
(R)—N-{1-(2,3-dihydro-1H-inden-2-ylamino)propan-2-yl}isoquinoline-6-sulfonamide,
(R)—N-[1-{2-(5-chloro-1H-indol-3-yl)ethylamino}propan-2-yl]isoquinoline-6-sulfonamide,
(R)—N-[1-{2-(1-methyl-1H-indol-3-yl)ethylamino}propan-2-yl]isoquinoline-6-sulfonamide,
(R)—N-[1-{2-(quinolin-4-yl)ethylamino}propan-2-yl]isoquinoline-6-sulfonamide,
(R)—N-[1-{2-(furan-2-yl)ethylamino}propan-2-yl]isoquinoline-6-sulfonamide,
(R)—N-[1-{2-(furan-3-yl)ethylamino}propan-2-yl]isoquinoline-6-sulfonamide,
(R)—N-{1-(4-aminophenethylamino)propan-2-yl}isoquinoline-6-sulfonamide,
(R)—N-{1-(4-dimethylaminophenethylamino)propan-2-yl}isoquinoline-6-sulfonamide,
(R)—N-{1-(2-cyanoethylamino)propan-2-yl}isoquinoline-6-sulfonamide,
(R)—N-[1-{2-(1H-indol-2-yl)ethylamino}propan-2-yl]isoquinoline-6-sulfonamide,
(R)—N-[1-{2-(benzofuran-2-yl)ethylamino}propan-2-yl]isoquinoline-6-sulfonamide,
(R)-7-bromo-N-{1-(4-fluorophenethylamino)propan-2-yl}-isoquinoline-6-sulfonamide,
(R)-5-bromo-N-{1-(4-fluorophenethylamino)propan-2-yl}-isoquinoline-6-sulfonamide,
(R)—N-{1-(2-methylallylamino)propan-2-yl}isoquinoline-6-sulfonamide,
(R)—N-[1-{2-(4-methylthiazol-5-yl)ethylamino}propan-2-yl]isoquinoline-6-sulfonamide,
(R)—N-[1-{3-(1H-indol-3-yl)propylamino}propan-2-yl]isoquinoline-6-sulfonamide,
(R)—N-[1-{2-(pyridin-2-yl)ethylamino}propan-2-yl]isoquinoline-6-sulfonamide,
N—[(R)-1-{(S)-2-hydroxy-2-phenylethylamino}propan-2-yl]isoquinoline-6-sulfonamide,
N—[(R)-1-{(S)-2-(4-fluorophenyl)-2-hydroxyethylamino}propan-2-yl]isoquinoline-6-sulfonamide,
N-{(2R)-1-(2-hydroxy-2-phenylpropylamino)propan-2-yl}isoquinoline-6-sulfonamide,
N—[(R)-1-{(S)-2-hydroxy-2-phenylpropylamino}propan-2-yl]isoquinoline-6-sulfonamide,
N—[(R)-1-{(R)-2-hydroxy-2-phenylethylamino}propan-2-yl]isoquinoline-6-sulfonamide,
N-[(2R)-1-{2-hydroxy-2-(pyridin-3-yl)ethylamino}propan-2-yl]isoquinoline-6-sulfonamide,
N—[(R)-1-{(S)-2-hydroxy-2-(thiophen-3-yl)ethylamino}propan-2-yl]isoquinoline-6-sulfonamide,
N-[(2R)-1-{2-(3-chlorophenyl)-2-hydroxyethylamino}propan-2-yl]isoquinoline-6-sulfonamide,
(R)—N-[1-{2-(biphenyl-4-yl)ethylamino}propan-2-yl]isoquinoline-6-sulfonamide,
(R)—N-[1-{4-(pyridin-4-yl)phenethylamino}propan-2-yl]isoquinoline-6-sulfonamide,
(R)—N-[1-{2-(1H-1,2,3-triazol-4-yl)ethylamino}propan-2-yl]isoquinoline-6-sulfonamide,
(R)—N-[1-{2-(1H-tetrazol-5-yl)ethylamino}propan-2-yl]isoquinoline-6-sulfonamide,
(R)—N-{1-(butylamino)propan-2-yl}-N-ethylisoquinoline-6-sulfonamide,
(R)—N-(2-hydroxyethyl)-N-{1-(phenethylamino)propan-2-yl}isoquinoline-6-sulfonamide,
(R)—N-[1-{methyl(phenethyl)amino}propan-2-yl]isoquinoline-6-sulfonamide,
(R)-2-amino-N-{2-(isoquinoline-6-sulfonamide)propyl}-N-phenylethylacetamide,
(R)—N-{1-(2-oxo-2-phenylethylamino)propan-2-yl}isoquinoline-6-sulfonamide,
N-{(2R)-1-(2-hydroxy-3-phenoxypropylamino)propan-2-yl}isoquinoline-6-sulfonamide,
(R)—N-{1-(phenethylamino)propan-2-yl}-1-hydroxyisoquinoline-6-sulfonamide,
(R)—N-{1-(phenethylamino)propan-2-yl}-4-methyl-isoquinoline-6-sulfonamide,
(R)—N-{1-(4-fluorophenethylamino)propan-2-yl}-4-methyl-isoquinoline-6-sulfonamide,
(R)—N-{1-(phenethylamino)propan-2-yl}-4-hydroxy-isoquinoline-6-sulfonamide,
(R)—N-{1-(phenethylamino)propan-2-yl}-4-(thiophen-3-yl) isoquinoline-6-sulfonamide,
N-{(2R, 3S)-3-amino-6-phenylhexan-2-yl)isoquinoline-6-sulfonamide,
N-{(2R)-4-amino-6-phenylhexan-2-yl}isoquinoline-6-sulfonamide, and
N-{(2R)-4-(methylamino)-6-phenylhexan-2-yl}isoquinoline-6-sulfonamide.

A salt of the compound (1) of the present invention needs only to be a pharmaceutically acceptable salt, and examples thereof include acid-addition salts. Examples of inorganic acids for forming such salts can include hydrochloric acid, hydrobromic acid, hydroiodic acid, hydrofluoric acid, sulfuric acid, phosphoric acid, hypophosphoric acid, metaphosphoric acid, and pyrophosphoric acid. Moreover, examples of organic acids therefor can include acetic acid, phenylacetic acid, trifluoroacetic acid, acrylic acid, ascorbic acid, benzoic acid, chlorobenzoic acid, dinitrobenzoic acid, hydroxybenzoic acid, methoxybenzoic acid, methylbenzoic acid, o-acetoxybenzoic acid, naphthalene-2-carboxylic acid, isobutyric acid, phenylbutyric acid, α-hydroxybutyric acid, butane-1,4-dicarboxylic acid, hexane-1, 6-dicarboxylic acid, capric acid, caproic acid, cinnamic acid, citric acid, formic acid, fumaric acid, glycolic acid, heptanoic acid, hippuric acid, lactic acid, malic acid, maleic acid, hydroxymaleic acid, malonic acid, mandelic acid, nicotinic acid, isonicotinic acid, oxalic acid, phthalic acid, terephthalic acid, propiolic acid, propionic acid, phenylpropionic acid, salicylic acid, sebacic acid, succinic acid, suberic acid, benzenesulfonic acid, bromobenzenesulfonic acid, chlorobenzenesulfonic acid, 2-hydroxyethanesulfonic acid, methanesulfonic acid, ethanesulfonic acid, naphthalene-1-sulfonic acid, naphthalene-2-sulfonic acid, naphthalene-1, 5-disulfonic acid, p-toluenesulfonic acid, xylenesulfonic acid, tartaric acid, and camphorsulfonic acid. Preferable examples of the salt of the compound of Formula (1) include hydrochloride, hydrobromide, oxalate, sulfate, phosphate, acetate, benzoate, citrate, and maleate.

The compound (1) of the present invention can be produced by various methods. Some of them will be described in schemes and Examples shown below. However, the present invention is not intended to be limited to them.

Scheme 1

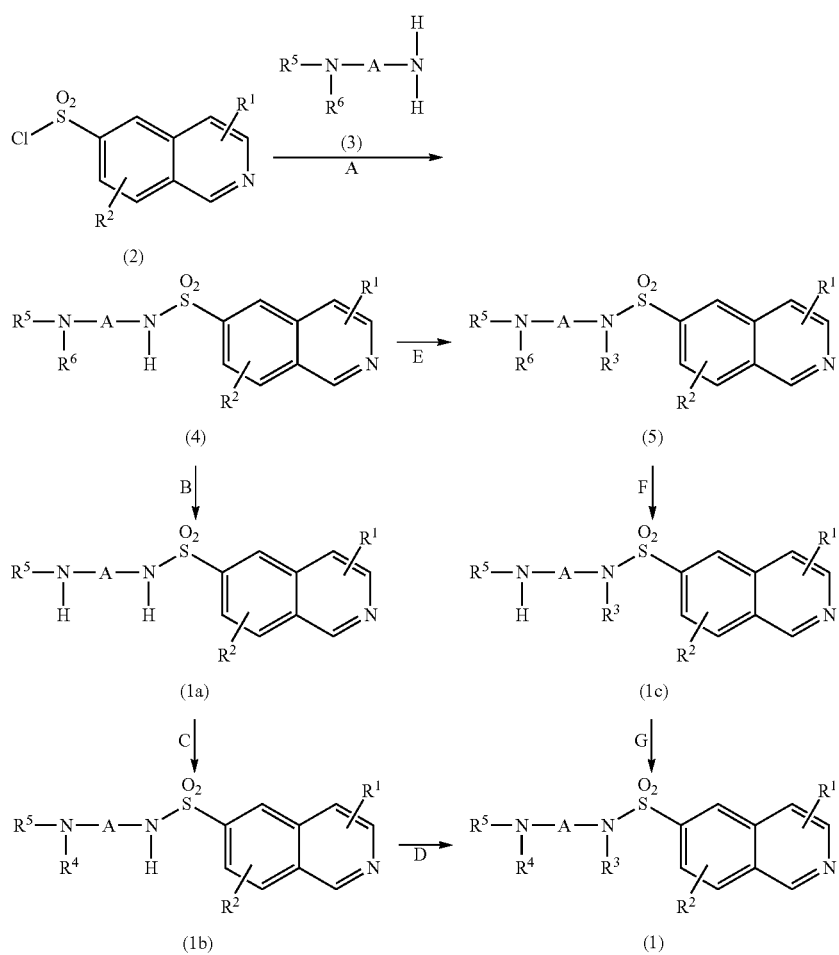

wherein $R^6$ represents a protective group for the amino group, and $R^1$, $R^2$, $R^3$, $R^4$, $R^5$, and A are the same as above.

As shown in Scheme 1, all of a compound (1a) wherein both $R^3$ and $R^4$ in Formula (1) are hydrogen, a compound (1b) wherein $R^3$ in Formula (1) is hydrogen, and a compound (1c) wherein $R^4$ in Formula (1) is hydrogen can be produced using compounds (2) and (3). The compound (1) of the present invention can be synthesized through either the compounds (1b) or (1c).

(Step A)

A sulfonyl chloride compound (2) is reacted with a primary amine compound (3) under temperature conditions of 0° C. to 60° C. for approximately 1 to 24 hours in the presence of an organic tertiary amine base such as triethylamine in a solvent such as dichloromethane to obtain a compound (4). The sulfonyl chloride compound (2) can be obtained by diazotization reaction using a corresponding amino compound and subsequent chlorosulfonylation reaction.

(Step B)

The protective group $R^6$ for the secondary amino group in the compound (4) is removed by a method known in the art, for example, hydrogenolysis or hydrolysis to obtain the compound (1a). Examples of $R^6$ include benzyl, benzyloxycarbonyl, tert-butoxycarbonyl, trifluoroacetyl, and 2-nitrobenzenesulfonyl.

(Step C)

The secondary amino group in the compound (1a) is modified with $R^4$ to obtain the compound (1b). The modification is performed by a method known in the art involving reacting a compound such as alkyl halide, alkanoyl halide, or alkylaldehyde with a base, a condensing agent, and the like.

(Step D)

The nitrogen atom of sulfonamide in the compound (1b) is modified with $R^3$ to obtain the compound (1) of the present invention. The modification is performed by a method known in the art involving reacting a compound such as alkyl halide or alkyl alcohol with a base, a condensing agent, and the like.

(Step E)

The nitrogen atom of sulfonamide in the compound (4) is modified with $R^3$ to obtain a compound (5). The modification can be performed in the same way as in Step D.

(Step F)

The protective group $R^6$ for the secondary amino group in the compound (5) is removed in the same way as in Step B to obtain the compound (1c).

(Step G)

The secondary amino group in the compound (1c) can be modified with $R^4$ to obtain the compound (1). The modification can be performed in the same way as in Step C.

The compound (3) used in Scheme 1 can be produced according to, for example, the following Scheme 2:

Scheme 2

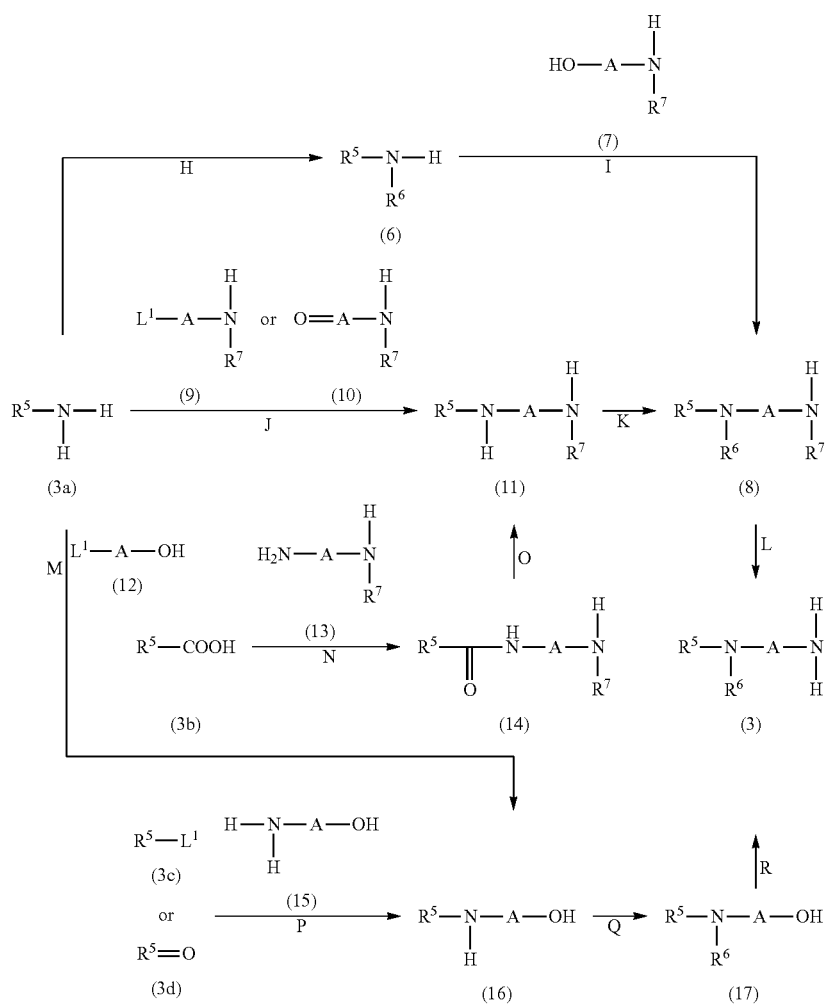

wherein $R^6$ and $R^7$ represent different protective groups for the amino group; $R^5$ and A are the same as above; $L^1$ represents a leaving group such as a methanesulfonyloxy group, a p-toluenesulfonyloxy group, a chlorine atom, a bromine atom, or an iodine atom.

As shown in Scheme 2, the compound (3) may be produced through a plurality of synthesis pathways with a compound (3a) as a starting material. These pathways are preferably selected according to the chemical properties of $R^5$ on a case-by-case basis. Also, the compound (3a) may be difficult to obtain depending on the type of $R^5$. In this case, a compound having corresponding $R^5$, such as a compound (3b), (3c), or (3d), can be used to prepare the compound (3).

(Step H)

The amino group in the compound (3a) is protected with $R^6$ to obtain a compound (6). In this case, examples of the protective group for the amino group used include benzenesulfonyl protective groups, for example, 2-nitrobenzenesulfonyl. The compound (3a) can be reacted with corresponding sulfonyl chloride in the presence of a base.

(Step I)

The compound (6) is bonded to a compound (7) under conditions of Mitsunobu reaction to obtain a compound (8).

(Step J)

The compound (3a) is reacted with a compound (9) or (10) to obtain a compound (11). When the compound (9) is used, the reaction is performed under temperature conditions of room temperature to 100° C. for approximately 1 to 24 hours in a solvent such as tetrahydrofuran or acetonitrile. The compound (3a) is used in an amount of preferably 2- to 5-fold moles with respect to the compound (9). Alternatively, when the compound (10) is used, conditions of so-called reductive amination reaction are used.

(Step K)

The secondary amino group in the compound (11) is protected with $R^6$ to obtain a compound (8). Examples of $R^6$ include benzyl, benzyloxycarbonyl, tert-butoxycarbonyl, trifluoroacetyl, and 2-nitrobenzenesulfonyl, each of which can be used in the protection by a method known in the art.

(Step L)

The protective group $R^7$ for the amino group in the compound (8) is deprotected to obtain the compound (3). In this case, examples of $R^7$ include benzyl, benzyloxycarbonyl, tert-butoxycarbonyl, trifluoroacetyl, and 2-nitrobenzenesulfonyl, each of which can be deprotected by a method known in the art such as hydrogenolysis or hydrolysis.

(Step M)

The compound (3a) is reacted with a compound (12) under temperature conditions of room temperature to 100° C. for approximately 1 to 24 hours in a solvent such as tetrahydrofuran or acetonitrile to obtain a compound (16). The compound (3a) is used in an amount of preferably 2- to 5-fold moles with respect to the compound (12).

(Step N)

The compound (3b) and a compound (13) are subjected to dehydration condensation under temperature conditions of room temperature in a solvent such as N,N-dimethylformamide to obtain a compound (14).

(Step O)

The carbonyl group in the compound (14) can be reduced with hydride of boron, aluminum, or the like under temperature conditions of room temperature to 80° C. in a solvent such as tetrahydrofuran to obtain a compound (11).

(Step P)

The compound (3c) or (3d) is reacted with a compound (15) to obtain a compound (16). When the compound (3c) is used, the reaction is performed under temperature conditions of room temperature to 100° C. for approximately 1 to 24 hours in a solvent such as tetrahydrofuran or acetonitrile. The compound (15) is used in an amount of preferably 2- to 5-fold moles with respect to the compound (3c). Alternatively, when the compound (3d) is used, conditions of so-called reductive amination reaction are used.

(Step Q)

The secondary amino group in the compound (16) is protected with $R^6$ in the same way as in Step K to obtain a compound (17).

(Step R)

The hydroxyl group in the compound (17) is converted to an amino group to obtain the compound (3). The conversion to an amino group can be performed by, for example, a method involving converting the hydroxyl group to a phthalimidyl group, which is then converted to an amino group by the removal of the phthaloyl group with hydrazine or the like, or a method involving converting the hydroxyl group to an azide group, which is then converted to an amino group under reductive conditions.

Moreover, the compound of the present invention can also be produced according to Scheme 3.

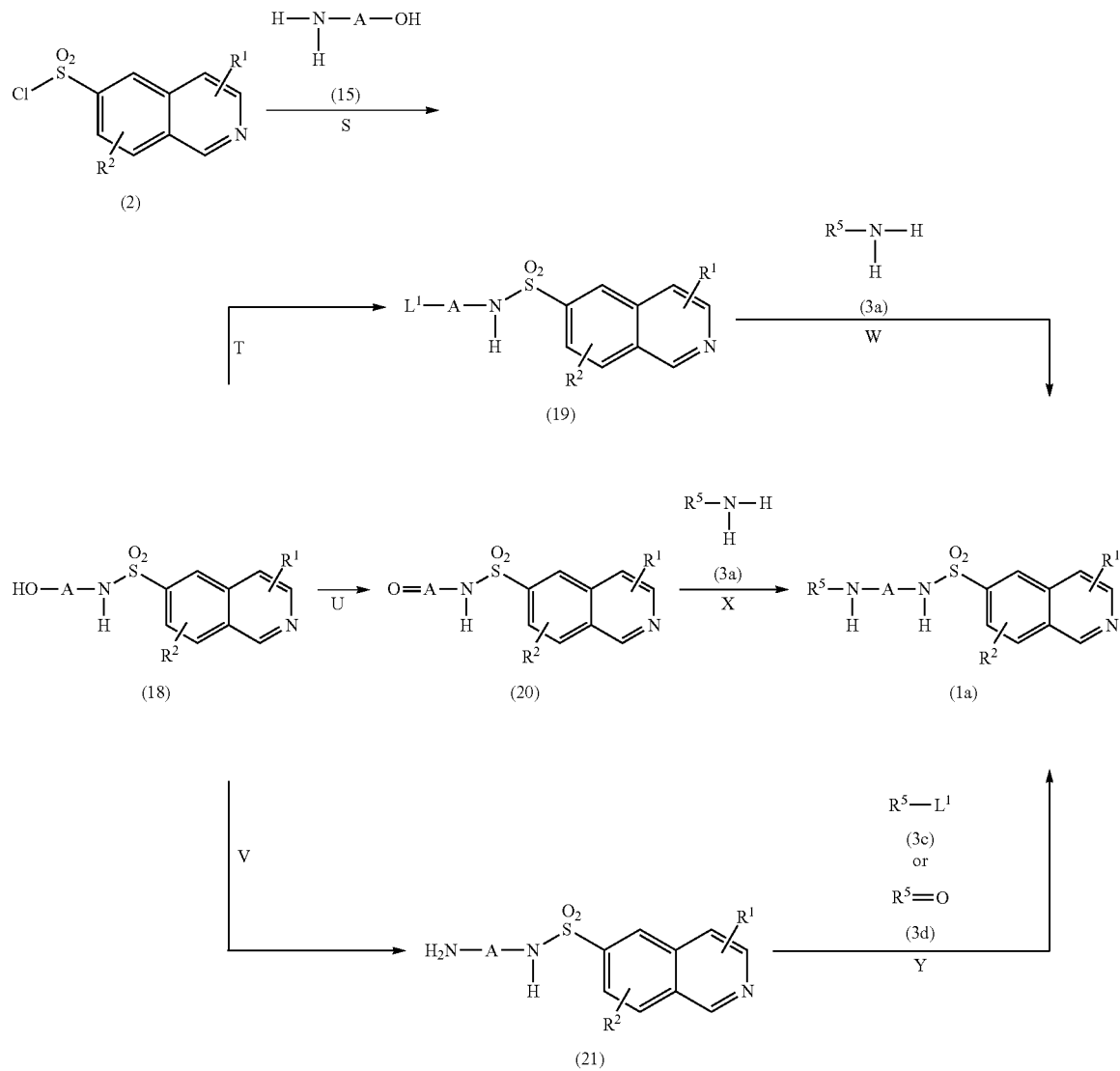

Scheme 3 wherein $L^1$, $R^1$, $R^2$, $R^3$, $R^4$, $R^5$, and A are the same as above.

Specifically, the compound (1a) in Scheme 1 can also be obtained according to steps shown in Scheme 3.

(Step S)

A sulfonyl chloride compound (2) is reacted with a compound (15) under temperature conditions of 0° C. to 60° C. for approximately 1 to 24 hours in the presence of an organic tertiary amine base such as triethylamine in a solvent such as dichloromethane to obtain a compound (18).

(Step T)

The hydroxyl group in the compound (18) is converted to the leaving group $L^1$ to obtain a compound (19). Examples of the leaving group include methanesulfonyloxy and p-toluenesulfonyloxy groups, for which methanesulfonyl chloride and p-toluenesulfonyl chloride, respectively, can be reacted with the compound (18). Alternatively, halogen such as chlorine, bromine, or iodine may be used as the leaving group, and the hydroxyl group in the compound (18) can be converted to each halogen by a method known in the art.

(Step U)

The hydroxyl group in the compound (18) can be oxidized to obtain a compound (20). The oxidation can be performed using a general method well known in the art, for example, chromium oxidation, Swern oxidation, or Dess-Martine oxidation.

(Step V)

The hydroxyl group in the compound (18) is converted to an amino group to obtain a compound (21). The conversion can be performed using the method as used in Step R.

(Step W) and (Step X)

In Steps W and X, compounds (19) and (20), respectively, are reacted with the compound (3a) to obtain the compound (1a). The same reaction conditions as in Step J can be used.

(Step Y)

A compound (21) can be reacted with the compound (3c) or (3d) to obtain the compound (1a). The same reaction conditions as in Step P can be used.

Some compounds of the present invention have one or two asymmetric carbon atoms and include optical isomers and diastereomers. Each of these isomers and any of their mixtures are also encompassed by the present invention. Each of these isomeric mixtures has pharmacological activity in itself. Each isomer can be obtained, if desired, by synthesis using commercially available optically active starting compounds (S or R configuration). When racemic bodies are used as starting materials, each optically active starting compound can be obtained by an optical resolution method known in the art, for example, a method involving generating a salt with an optically active acidic or basic compound, followed by fractional crystallization, a method using an optically active column, or a method using enzymatic reaction.

The compound of the present invention can form the salt by a method known in the art. For example, hydrochloride of the compound of the present invention can be obtained by dissolving the compound of the present invention in an alcohol solution or ethyl ether solution of hydrogen chloride.

The compound of the present invention or the salt thereof may be recrystallized from an appropriate solvent (also including water) to obtain a solvate (also including a hydrate). These solvates are also included in the present invention. For example, hydrate of the compound of the present invention may be obtained by recrystallizing the compound of the present invention from hydrous alcohol.

The compound of the present invention may take a crystal polymorph form. This crystal polymorph is also included in the present invention.

The compound of the present invention thus produced can be isolated and purified in a free base form or acid-addition salt form by means known per se in the art, for example, concentration, liquid conversion, solvent conversion, solvent extraction, crystallization, fractionation, and chromatography.

The compound of the present invention has, as shown later in Examples, excellent ocular hypotensive effect and blood pressure lowering effect. Thus, the compounds of the present invention are useful as therapeutic and/or preventive drugs for glaucoma, ocular hypertension, and cardiovascular disease.

In this context, the glaucoma according to the present invention includes primary open-angle glaucoma, normal tension glaucoma, hypersecretion glaucoma, acute closed-angle glaucoma, chronic closed-angle glaucoma, mixed glaucoma, steroid-induced glaucoma, pigmentary glaucoma, exfoliation glaucoma, amyloidotic glaucoma, neovascular glaucoma, malignant glaucoma, capsular glaucoma, plateau iris syndrome, and the like. Moreover, the ocular hypertension refers to a symptom which exhibits a high intraocular pressure in spite of the absence of an observable distinct lesion in the optic nerve and includes various hypertensive states such as postoperative manifestation of high intraocular pressures.

Moreover, the cardiovascular disease according to the present invention includes, but not limited to, hypertension, arteriosclerosis, cerebrovascular diseases, heart diseases, peripheral vascular diseases, and ocular vascular diseases.

More specifically, examples of the hypertension include essential hypertension, renal hypertension, renovascular hypertension, pregnancy-induced hypertension, endocrine hypertension, cardiovascular hypertension, neurogenic hypertension, iatrogenic hypertension, and pulmonary hypertension. Examples of the arteriosclerosis include those having a lesion in the main artery in the whole body, such as coronary artery/abdominal aorta/renal artery/carotid artery/ocular fundus artery/cerebral artery. Examples of the cerebrovascular diseases include cerebral thrombosis, cerebral infarction, cerebral hemorrhage, cerebrovascular spasm, transient ischemic attack, hypertensive encephalopathy, cerebral arteriosclerosis, subdural hematoma, epidural hematoma, subarachnoid hemorrhage, brain hypoxia, brain edema, encephalitis, brain abscess, head injury, psychosis, metabolic poisoning, medicinal poisoning, transient cessation of breathing, and deep anesthesia during operation. The heart disease includes congestive heart failure, acute myocardial infarction, old myocardial infarction, subendocardial infarction, right ventricular infarction, atypical myocardial infarction, ischemic cardiomyopathy, variant angina, stable angina, effort angina, coronary spastic angina, post-infarction angina, unstable angina, arrhythmia, acute cardiac death, and the like.

The peripheral vascular disease includes: arterial disease such as Buerger disease, arteriosclerosis obliterans, and Raynaud's syndrome; venous disease such as phlebothrombosis and thrombophlebitis; and blood hyperviscosity syndrome, frostbite, cold feeling and sleep initiation disorder due to poor blood circulation, decubitus ulcer, chapped skin, and alopecia.

Furthermore, the ocular vascular disease includes: glaucoma, diabetic retinopathy, retinitis pigmentosa, macular degeneration, ischemic optic neuropathy, iridocyclitis, hypertensive retinopathy, retinal artery obstruction, retinal venous obstruction, ischemic optic neuropathy, choroidal disease secondary to retinal lesions, and choroidal and retinal disease accompanied by systemic disease.

The compound of the present invention can be administered alone or in the form of a pharmaceutical composition.

The composition contains the compound of the present invention combined with a pharmaceutically acceptable carrier. The ratio therebetween or their properties are determined depending on the chemical properties or solubility of the selected compound, administration routes, and standard pharmaceutical practice. Thus, the present invention provides a pharmaceutical composition containing a compound of Formula (1) and a pharmaceutically acceptable carrier. The compound of Formula (1) may be administered through various routes. For effective treatment of patients with any of the diseases described herein, the compound of Formula (1) can be administered through an arbitrary form or method which allows the organisms to utilize an effective amount thereof. It includes oral administration and parenteral administration. The compound of Formula (1) may be administered, for example, orally, by inhalation, subcutaneously, intramuscularly, intravenously, percutaneously, nasally, intrarectally, ophthalmically, locally, sublingually, into the oral cavity, or by other administration routes. Examples of more specific dosage forms include tablets, capsules, granules, powders, aerosols, inhalants, suppositories, solutions, suspensions, and liniments.

The oral agents such as tablets, capsules, granules, and powders can be prepared by combining the compound of the present invention, as appropriate, with, for example, a diluent (e.g., lactose, mannitol, starch, crystalline cellulose, light anhydrous silicic acid, calcium carbonate, and calcium hydrogen phosphate), a lubricant (e.g., stearic acid, magnesium stearate, and talc), a binder (e.g., starch, hydroxypropylcellulose, hydroxypropylmethylcellulose, and polyvinylpyrrolidone), a disintegrant (e.g., carboxymethylcellulose, low substituted hydroxypropylmethylcellulose, and calcium citrate), a coating agent (e.g., hydroxypropylmethylcellulose, macrogol, and silicone resin), a stabilizer (e.g., ethyl p-oxybenzoate and benzyl alcohol), a corrigent (e.g., sweetening agents, acidulants, and flavors), and the like.

Moreover, the liquid preparations such as injections and ophthalmic solutions can be prepared by combining the compound of the present invention, as appropriate, with, for example, a tonicity agent (e.g., glycerin, propylene glycol, sodium chloride, potassium chloride, sorbitol, and mannitol), a buffering agent (e.g., phosphoric acid, phosphate, citric acid, glacial acetic acid, ε-aminocaproic acid, and Trometamol), a pH adjuster (e.g., hydrochloric acid, citric acid, phosphoric acid, glacial acetic acid, sodium hydroxide, potassium hydroxide, sodium carbonate, and sodium bicarbonate), a solubilizing or dispersing agent (e.g., polysorbate 80, polyoxyethylene hydrogenated castor oil 60, macrogol 4000, purified soybean lecithin, polyoxyethylene (160), and polyoxypropylene (30) glycol), a cellulose polymer (e.g., hydroxypropylmethylcellulose and hydroxypropylcellulose), a thickening agent (e.g., polyvinyl alcohol and polyvinylpyrrolidone), a stabilizer (e.g., edetic acid and sodium edetate), a preservative or antiseptic routinely used (e.g., sorbic acid, potassium sorbate, benzalkonium chloride, benzethonium chloride, methyl p-oxybenzoate, propyl p-oxybenzoate, and chlorobutanol), and a soothing agent (e.g., chlorobutanol, benzyl alcohol, and lidocaine).

In this context, the pH of the injection or ophthalmic solution is preferably set to 4.0 to 8.0, and the osmotic pressure ratio is preferably set to around 1.0.

The dose of the compound of the present invention can be selected appropriately for use according to conditions, age, dosage forms, etc.

For example, the ophthalmic solution can usually be administered at single or divided doses at a concentration of 0.0001% to 10% (w/v), preferably 0.01% to 5% (w/v). Intravenous administration is performed at a dose ranging from 0.1 to 100 mg/human, preferably 1 to 30 mg/human, per day. Oral administration is performed at a dose ranging from 1 to 1,000 mg/human, preferably 10 to 30 mg/human, per day. According to circumstances, a dose below this range suffices, or on the contrary, a dose above the range may be required. Moreover, the daily dose can also be divided into two or three portions for administration.

EXAMPLES

The present invention will be described more specifically with reference to Examples shown below. These examples are given for well understanding the present invention and are not intended to limit the scope of the present invention. Moreover, in chemical structural formulas and schemes, Boc represents a tert-butoxycarbonyl group; Cbz represents a benzyloxycarbonyl group; n-Bu represents a normal butyl group; Bn represents a benzyl group; Ts represents a p-toluenesulfonyl group; Ms represents a methanesulfonyl group; Ns represents a 2-nitrobenzenesulfonyl group; TBS represents a tert-butyldimethylsilyl group; Tf represents a trifluoromethanesulfonyl group; PMB represents a p-methoxybenzyl group; TFA represents trifluoroacetic acid; mCPBA represents m-chloroperbenzoic acid; EDC represents 1-ethyl-3-(3-dimethylaminopropyl)carbodiimide; HOBt represents 1-hydroxybenzotriazole; Red-Al represents sodium bis(2-methoxyethoxy)aluminum hydride; DIAD represents diisopropyl azodicarboxylate; TBAF represents tetra-n-butyl ammonium fluoride; LAH represents lithium aluminum hydride; DMP represents Dess-Martin-periodinane; Boc-Gly-OH represents N-(tert-butoxycarbonyl)glycine; Cbz-Ala-OH represents N-(benzyloxycarbonyl)-D-alanine; and Boc-Ala-OH represents N-(tert-butoxycarbonyl)-D-alanine, unless otherwise specified.

$^1$H nuclear magnetic resonance spectra ($^1$H-NMR spectra) were measured using JNM-A500 (manufactured by JEOL Ltd.). δ values for chemical shifts were indicated by ppm, while J values for coupling constants were indicated by Hz. Tetramethylsilane (TMS) (δ0) or a residual nondeuterated solvent (δ4.65) in heavy water (D$_2$O) was used as standards. The abbreviations s, d, t, q, quin., m, br, and dd for signal splitting patterns mean singlet, doublet, triplet, quartet, quintet, multiplet, broad, and double doublet, respectively.

Thin-layer chromatography (TLC) for analysis was conducted using TLC Glass Plates, Silica Gel 60 F254 (manufactured by Merck) and involved spot confirmation by UV (254 nm) irradiation or by color development with iodine, anisaldehyde, ninhydrin, or sodium phosphomolybdate. Column chromatography was conducted using 40 to 50 μm Silica Gel 60N (spherical, neutral) (manufactured by Kanto Kagaku).

Substantially all chemicals used in each operation of reaction, extraction, drying, column chromatography, and $^1$H-NMR spectrum measurement were commercially available products used directly, unless otherwise specified.

Reference Example 1

Isoquinoline-6-sulfonyl chloride

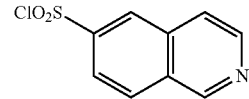 [SMILES: O=S(=O)(Cl)c1ccc2cnccc2c1]

4.0 g of commercially available 6-aminoisoquinoline was suspended in 40 mL of concentrated hydrochloric acid (35%) with cooling at 0° C. To the suspension, 4.0 g of sodium nitrite was added in small portions, and the mixture was stirred for 30 minutes. This reaction solution was added dropwise at 0° C. to a mixed solution of 20 mL of acetic acid saturated with sulfite gas generated from sodium bisulfite and sulfuric acid, and 298 mg of copper chloride, and the mixture was stirred for 1 hour. The mixture was neutralized by the addition of a saturated aqueous solution of sodium bicarbonate, followed by extraction with dichloromethane (100 mL×2). The obtained organic layer was washed with saturated saline and then dried over anhydrous sodium sulfate. A dichloromethane solution obtained by filtration was used in the next reaction without being further purified because the compound of interest was unstable.

Reference Example 2

(R)-tert-butyl 2-aminopropyl(butyl)carbamate

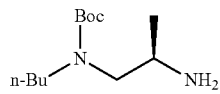

The title compound was synthesized according to the following Scheme 4:

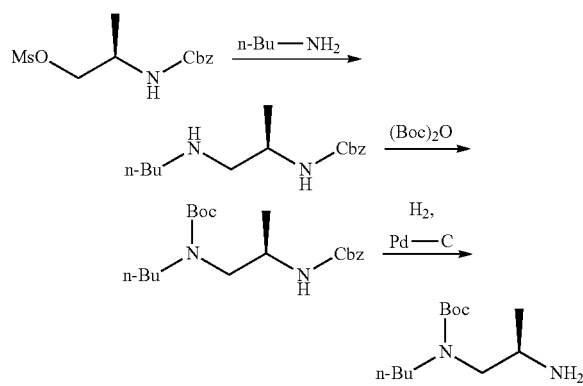

Steps 1 and 2

Synthesis of (R)-benzyl 1-{tert-butoxycarbonyl(butyl)amino}propan-2-ylcarbamate 1 g of (R)-2-(benzyloxycarbonylamino)propyl methanesulfonate synthesized with reference to the method described in J. Org. Chem., 62, 3586 (1997) was dissolved in 20 mL of tetrahydrofuran. To the solution, 1 mL of n-butylamine was added, and the mixture was heated to reflux for 16 hours. After cooling to room temperature, 50 mL of water was added to the reaction solution, followed by extraction with ethyl acetate (50 mL×3). The organic layer was washed with saturated saline and dried over anhydrous sodium sulfate. After filtration, the filtrate was concentrated under reduced pressure. The obtained crude product was dissolved in 50 mL of dichloromethane and cooled to 0° C. 0.5 mL of triethylamine and 0.9 g of di-tert-butyl dicarbonate were added thereto, and the mixture was stirred at room temperature for 4 hours. Water was added thereto, followed by extraction with dichloromethane (50 mL×2). The organic layer was dried over anhydrous sodium sulfate. After filtration, the filtrate was concentrated under reduced pressure. The obtained crude product was purified by silica gel column chromatography (hexane:ethyl acetate=2:1) to obtain 660 mg of the title compound as a white solid (52%).

$^1$H-NMR spectrum (CDCl$_3$, δ ppm): 0.91 (t, J=7.3 Hz, 3H), 1.14 (d, J=6.1 Hz, 3H), 1.24-1.29 (m, 2H), 1.42 (s, 9H), 1.44-1.49 (m, 2H), 2.92 (d, J=13.4 Hz, 1H), 3.04-3.10 (m, 1H), 3.22-3.28 (m, 1H), 3.54 (t, J=11.9 Hz, 1H), 3.89 (s, 1H), 5.06-5.08 (m, 2H), 5.57 (br s, 1H), 7.29-7.38 (m, 5H).

Step 3

Synthesis of (R)-tert-butyl 2-aminopropyl(butyl)carbamate

A suspension of 300 mg of (R)-benzyl 1-{tert-butoxycarbonyl(butyl)amino}propan-2-ylcarbamate and 30 mg of 10% palladium-carbon in 10 mL of methanol was vigorously stirred at room temperature for 16 hours in a hydrogen gas atmosphere. The reaction solution was filtered through celite, and the filtrate was concentrated under reduced pressure. The obtained crude product was purified by silica gel column chromatography (dichloromethane:methanol=10:1) to obtain 180 mg of the title compound as a colorless oil (95%).

$^1$H-NMR spectrum (CDCl$_3$, δ ppm): 0.92 (t, J=7.3 Hz, 3H), 1.10 (d, J=4.3 Hz, 3H), 1.25-1.33 (m, 2H), 1.46 (s, 9H), 1.48-1.53 (m, 2H), 2.51 (s, 2H), 3.08-3.15 (m, 2H), 3.20 (s, 3H).

Reference Example 3

(R)-tert-butyl 2-aminopropyl(benzyl)carbamate

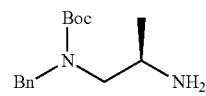

The title compound was synthesized according to the following Scheme 5:

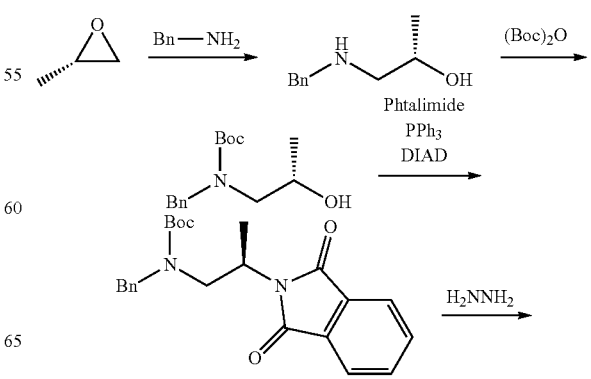

-continued

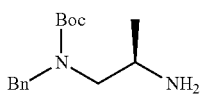

Steps 1 and 2

Synthesis of (S)-tert-butyl benzyl(2-hydroxypropyl)carbamate

With reference to the method described in Tetrahedron, 59, 2435 (2003), 290 mg of (S)-(−)-propylene oxide was dissolved in 15 mL of acetonitrile. To the solution, 850 mg of calcium triflate and 535 mg of benzylamine were added at room temperature, and the mixture was stirred for 3 hours. The reaction solution was concentrated under reduced pressure, and water was added thereto, followed by extraction with dichloromethane (30 mL×3). The organic layer was washed with saturated saline and dried over anhydrous sodium sulfate. After filtration, the filtrate was concentrated under reduced pressure. The obtained crude product was dissolved in 20 mL of dichloromethane and cooled to 0° C. 0.836 mL of triethylamine and 1.31 g of di-tert-butyl dicarbonate were added thereto, and the mixture was stirred at room temperature for 1 hour. Water was added thereto, followed by extraction with dichloromethane (30 mL×3). The organic layer was washed with saturated saline and dried over anhydrous sodium sulfate. After filtration, the filtrate was concentrated under reduced pressure, and the obtained crude product was purified by silica gel column chromatography (hexane: ethyl acetate=3:1) to obtain 827 mg of the title compound as a colorless oil (62%).

$^1$H-NMR spectrum (CDCl$_3$, δ ppm): 1.02 (d, J=7.0 Hz, 3H), 1.46 (s, 9H), 3.12-3.15 (m, 1H), 3.30 (br s, 1H), 3.95-4.00 (m, 1H), 4.49 (br s, 2H), 7.21-7.26 (m, 4H), 7.31-7.34 (m, 1H).

Step 3

Synthesis of (R)-tert-butyl benzyl{2-(1,3-dioxoisoindolin-2-yl)propyl}carbamate 209 mg of (S)-tert-butyl benzyl(2-hydroxypropyl)carbamate was dissolved in 10 mL of tetrahydrofuran in a nitrogen atmosphere and cooled to 0° C. 173 mg of phthalimide, 413 mg of triphenylphosphine, and 0.31 mL of diisopropyl azodicarboxylate were added thereto, and the mixture was stirred at room temperature for 10 hours. The reaction solution was concentrated under reduced pressure, and the obtained crude product was purified by silica gel column chromatography (hexane:ethyl acetate=6:1) to obtain 278 mg of the title compound as a pale yellow oil (89%).

$^1$H-NMR spectrum (CDCl$_3$, δ ppm): 1.26 (d, J=6.0 Hz, 3H), 1.40 (s, 9H), 3.28-3.35 (m, 1H), 3.85-4.00 (m, 1H), 4.18-4.21 (m, 1H), 4.52-4.69 (m, 2H), 7.09-7.21 (m, 5H), 7.69 (br s, 2H), 7.76-7.78 (m, 2H).

Step 4

Synthesis of (R)-tert-butyl 2-aminopropyl(benzyl)carbamate 278 mg of (R)-tert-butyl benzyl{2-(1,3-dioxoisoindolin-2-yl)propyl}carbamate was dissolved in 5 mL of methanol. To the solution, 1 mL of hydrazine hydrate was added, and the mixture was stirred at 80° C. for 12 hours. The reaction solution was cooled to room temperature and concentrated under reduced pressure. A 10% aqueous potassium hydroxide solution was added thereto, followed by extraction with dichloromethane (40 mL×3). The organic layer was washed with saturated saline and dried over anhydrous sodium sulfate. After filtration, the filtrate was concentrated under reduced pressure, and the obtained crude product was purified by silica gel column chromatography (dichloromethane:methanol=2:1) to obtain 147 mg of the title compound as a colorless oil (79%).

$^1$H-NMR spectrum (CDCl$_3$, δ ppm): 1.02 (d, J=5.0 Hz, 3H), 1.45 (s, 9H), 3.08-3.12 (m, 3H), 4.48-4.54 (m, 2H), 7.20-7.26 (m, 3H), 7.30-7.33 (m, 2H).

Reference Example 4

(R)-tert-butyl 2-aminopropyl(2-methylallyl)carbamate

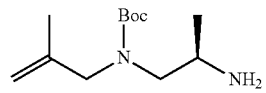

The title compound was synthesized according to the following Scheme 6:

Scheme 6

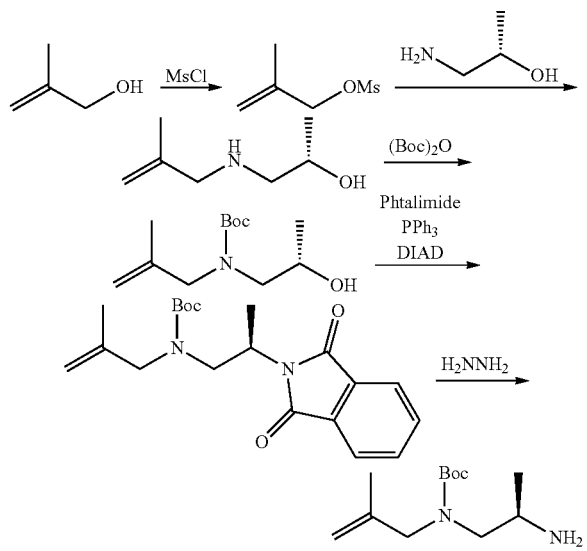

Steps 1, 2, and 3

Synthesis of (S)-tert-butyl 2-hydroxypropyl(2-methylallyl)carbamate 1.59 g of 2-methylallylmethanesulfonate synthesized with reference to the method described in J. Chem. Soc., Chem. Commun., 3, 277 (1994) was dissolved in 30 mL of tetrahydrofuran. To the solution, 2.36 g of (S)-1-aminopropan-2-ol was added, and the mixture was stirred at 80° C. for 16 hours. The reaction solution was cooled to room temperature and concentrated under reduced pressure. 20 mL of a 10% aqueous sodium hydroxide solution was added thereto, followed by extraction with dichloromethane (50 mL×3). The organic layer was washed with saturated saline and dried over anhydrous sodium sulfate. After filtration, the filtrate was concentrated under reduced pressure. The obtained crude product was dissolved in 10 mL of dichloromethane and cooled to 0° C. 1.67 mL of triethylamine and 2.62 g of di-tert-butyl dicarbonate were added thereto, and the mixture was stirred at room temperature for 2 hours. Water was added thereto, followed by extraction with dichloromethane (50 mL×3). The organic layer was washed with saturated saline and dried over anhydrous sodium sulfate. After filtration, the filtrate was concentrated under reduced pressure, and the obtained crude product was purified by silica gel column chromatography (hexane:ethyl acetate=3:1) to obtain 1.63 g of the title compound as a pale yellow oil (67%).

$^1$H-NMR spectrum (CDCl$_3$, δ ppm): 1.14 (d, J=7.0 Hz, 3H), 1.46 (s, 9H), 1.68 (s, 3H), 3.13-3.28 (m, 2H), 3.82 (m, 2H), 3.96-4.00 (m, 1H), 4.76 (s, 1H), 4.85 (s, 1H).

Steps 4 and 5

Synthesis of (R)-tert-butyl 2-aminopropyl(2-methylallyl)carbamate (R)-tert-butyl 2-(1,3-dioxoisoindolin-2-yl)propyl(2-methylallyl)carbamate was obtained (810 mg, 95%) in the same way as in Step 3 of Reference Example 3 using 545 mg of (S)-tert-butyl 2-hydroxypropyl(2-methylallyl)carbamate. Subsequently, 410 mg of the title compound was obtained as a colorless oil (79%) in the same way as in Step 4 of Reference Example 3.

$^1$H-NMR spectrum (CDCl$_3$, δ ppm): 1.04 (d, J=6.0 Hz, 3H), 1.45 (s, 9H), 1.67 (s, 3H), 3.07-3.14 (m, 3H), 3.82 (br s, 2H), 4.73 (s, 1H), 4.84 (s, 1H).

Reference Example 5

(R)-tert-butyl 2-aminopropyl{2-(pyridin-2-yl)ethyl}carbamate

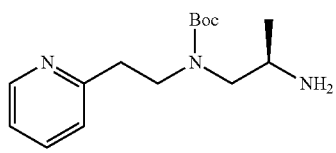 [SMILES: C[C@@H](N)CN(CCc1ccccn1)C(=O)OC(C)(C)C]

The title compound was synthesized according to the following Scheme 7:

Scheme 7

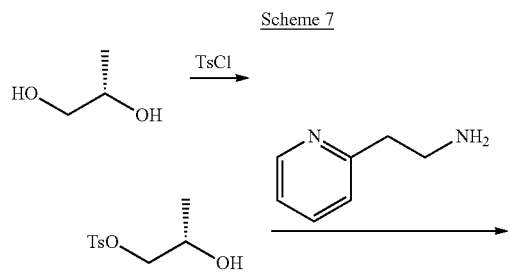

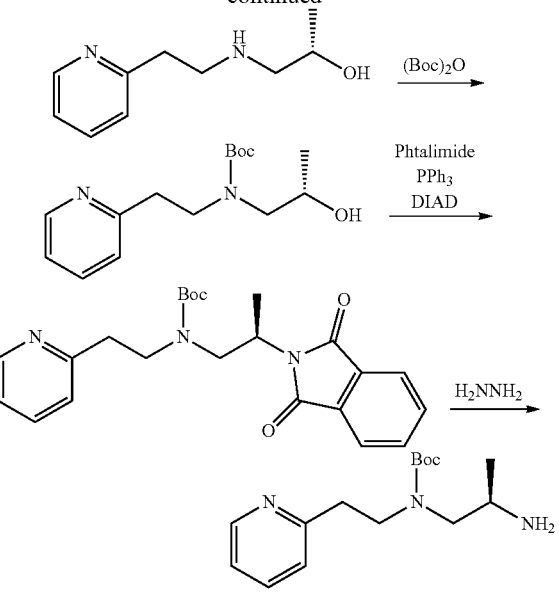

Steps 1, 2, and 3

Synthesis of (S)-tert-butyl 2-hydroxypropyl{2-(pyridin-2-yl)ethyl}carbamate 989 mg of (S)-2-hydroxypropyl-4-methylbenzenesulfonate synthesized with reference to the method described in J. Org. Chem. 57, 5383 (1992) was dissolved in 20 mL of acetonitrile. To the solution, 524 mg of 2-(pyridin-2-yl)ethylamine, 643 mg of sodium iodide, and 0.6 mL of triethylamine were added, and the mixture was stirred at 80° C. for 4 hours. The reaction solution was cooled to room temperature, and 20 mL of a 10% aqueous sodium hydroxide solution was added thereto, followed by extraction with dichloromethane (30 mL×3). The organic layer was washed with saturated saline and dried over anhydrous sodium sulfate. After filtration, the filtrate was concentrated under reduced pressure. The obtained crude product was dissolved in 10 mL of dichloromethane and cooled to 0° C. 0.7 mL of triethylamine and 1.10 g of di-tert-butyl dicarbonate were added thereto, and the mixture was stirred at room temperature for 12 hours. Water was added thereto, followed by extraction with dichloromethane (30 mL×3). The organic layer was washed with saturated saline and dried over anhydrous sodium sulfate. The filtrate was concentrated under reduced pressure, and the obtained crude product was purified by silica gel column chromatography (hexane:ethyl acetate=1:3→dichloromethane:methanol=8:1) to obtain 509 mg of the title compound as a pale yellow oil (42%).

$^1$H-NMR spectrum (CDCl$_3$, δ ppm): 1.15 (d, J=7.0 Hz, 3H), 1.48 (s, 9H), 2.90-2.98 (m, 2H), 3.16 (br s, 1H), 3.36-3.39 (m, 2H), 3.80-3.90 (m, 1H), 4.11-4.17 (m, 1H), 7.15-7.22 (m, 2H), 7.62-7.66 (m, 2H), 8.47 (br s, 1H).

Steps 4 and 5

Synthesis of (R)-tert-butyl 2-aminopropyl{2-(pyridin-2-yl)ethyl}carbamate (R)-tert-butyl 2-(1,3-dioxoisoindolin-2-yl)propyl{2-(pyridin-2-yl)ethyl}carbamate was obtained (643 mg, 88%) in the same way as in Step 3 of Reference Example 3 using 509 mg of (S)-tert-butyl 2-hydroxypropyl{2-(pyridin-2-yl)ethyl}carbamate. Subsequently, 415 mg of the title compound was obtained as a pale yellow oil (94%) in the same way as in Step 4 of Reference Example 3.

$^1$H-NMR spectrum (CDCl$_3$, δ ppm): 1.03 (d, J=6.0 Hz, 3H), 1.43 (s, 9H), 3.02-3.10 (m, 5H), 3.59-3.62 (m, 2H), 7.10-7.14 (m, 2H), 7.57-7.60 (m, 1H), 8.52 (d, J=4.0 Hz, 1H).

Reference Example 6

(R)—N-(2-aminopropyl)-N-(2-chlorophenethyl)-2-nitrobenzenesulfonamide

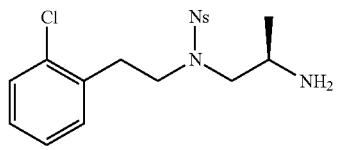

The title compound was synthesized according to the following Scheme 8:

Scheme 8

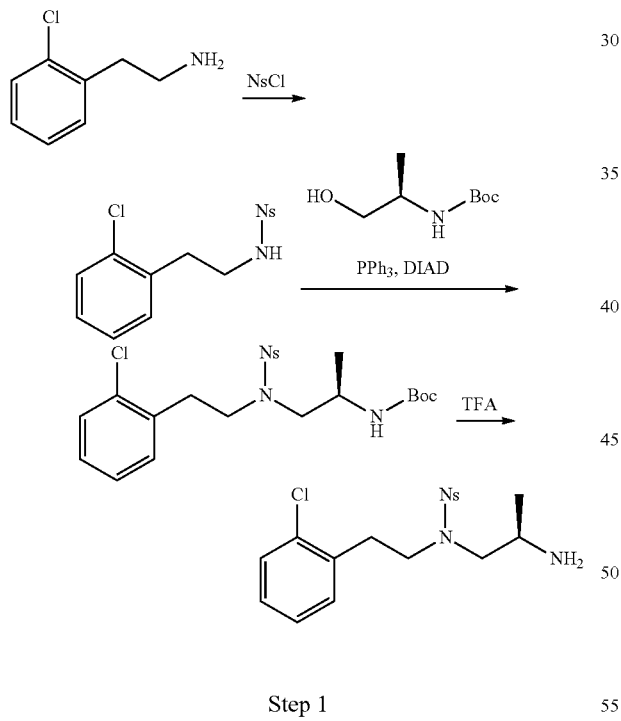

Step 1

Synthesis of N-(2-chlorophenethyl)-2-nitrobenzenesulfonamide 1 mL of 2-(2-chlorophenyl)ethylamine and 1.2 mL of triethylamine were dissolved in 50 mL of dichloromethane. To the solution, 1.6 g of 2-nitrobenzenesulfonyl chloride was added at 0° C., and the mixture was stirred at room temperature for 2 hours. The reaction solution was washed with saturated saline, and the organic layer was separated and dried over anhydrous sodium sulfate. After filtration, the filtrate was concentrated under reduced pressure, and the obtained crude product was purified by silica gel column chromatography (hexane:ethyl acetate=2:1) to obtain 2.3 g of the title compound as a pale yellow crystalline solid (92%).

$^1$H-NMR spectrum (CDCl$_3$, δ ppm): 2.98 (t, J=7.3 Hz, 2H), 3.43 (q, J=6.9 Hz, 2H), 5.34 (t, J=5.8 Hz, 1H), 7.13-7.19 (m, 3H), 7.28-7.29 (m, 1H), 7.71-7.72 (m, 2H), 7.84 (t, J=4.6 Hz, 1H), 8.11 (t, J=6.4 Hz, 1H).

Steps 2 and 3

Synthesis of (R)—N-(2-aminopropyl)-N-(2-chlorophenethyl)-2-nitrobenzenesulfonamide 740 mg of (R)-tert-butyl 1-hydroxypropan-2-ylcarbamate was dissolved in 30 mL of tetrahydrofuran in a nitrogen atmosphere, and 1.44 g of N-(2-chlorophenethyl)-2-nitrobenzenesulfonamide and 3.3 g of triphenylphosphine were added thereto. 2.5 mL of diisopropyl azodicarboxylate was added thereto at 0° C., and the mixture was stirred at room temperature for 4 hours. The reaction solution was concentrated under reduced pressure, and the obtained residue (intermediate) was dissolved in 20 mL of dichloromethane. To the solution, 2 mL of trifluoroacetic acid was added, and the mixture was stirred at room temperature for 6 hours. The reaction solution was neutralized with a saturated aqueous solution of sodium bicarbonate, followed by extraction with dichloromethane (30 mL×3). The organic layer was dried over anhydrous sodium sulfate. After filtration, the filtrate was concentrated under reduced pressure. The obtained crude product was purified by silica gel column chromatography (dichloromethane:methanol=10:1) to obtain 380 mg of the title compound as a pale yellow oil (23%).

$^1$H-NMR spectrum (CDCl$_3$, δ ppm): 1.10 (d, J=6.7 Hz, 3H), 1.32 (br s, 2H), 2.92-2.98 (m, 1H), 3.01-3.07 (m, 1H), 3.15-3.20 (m, 1H), 3.25 (s, 1H), 3.27 (d, J=3.7 Hz, 1H), 3.47-3.59 (m, 1H), 5.30 (s, 1H), 7.13-7.19 (m, 2H), 7.23 (dd, J=2.4, 7.3 Hz, 1H), 7.28-7.30 (m, 1H), 7.61-7.63 (m, 1H), 7.66-7.71 (m, 2H), 8.07 (dd, J=2.7, 6.4 Hz, 1H).

Reference Example 7

Synthesis of tert-butyl (R)-2-aminopropyl{(S)-2-hydroxy-2-phenylethyl}carbamate

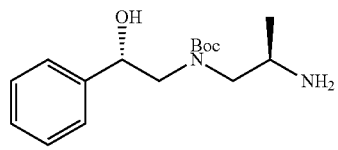 [SMILES: C[C@@H](N)CN(C[C@@H](O)c1ccccc1)C(=O)OC(C)(C)C]

The title compound was synthesized according to the following Scheme 9:

Scheme 9

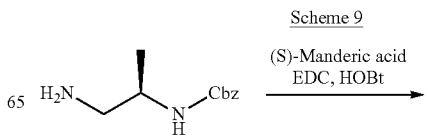

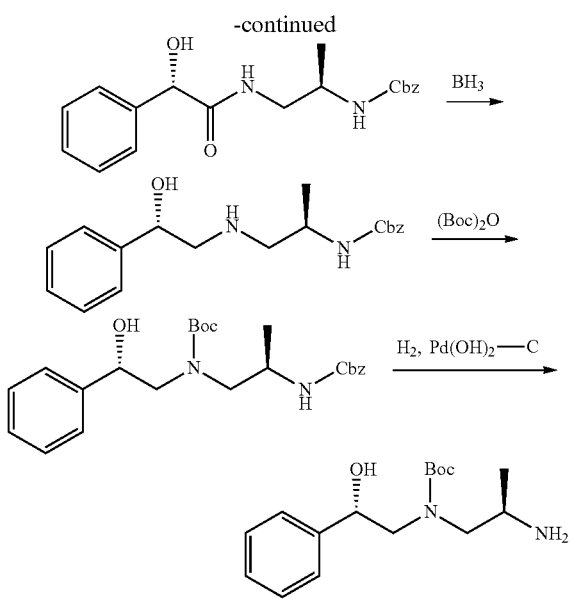

Steps 1, 2, and 3

Synthesis of (R)-benzyl 1-[tert-butoxycarbonyl{(S)-2-hydroxy-2-phenylethyl}amino]propan-2-ylcarbamate 2.10 g of (R)-benzyl 1-aminopropan-2-ylcarbamate synthesized with reference to the method described in Tetrahedron Lett., 46, 7069 (2005) was dissolved in 15 mL of N,N-dimethylformamide. To the solution, 1.52 g of (S)-mandelic acid, 1.35 g of 1-hydroxybenzotriazole, and 1.91 of 1-ethyl-3-(3-dimethylaminopropyl)carbodiimide hydrochloride were added, and the mixture was stirred at room temperature for 12 hours. 100 mL of water was added thereto, followed by extraction with ethyl acetate (30 mL×3). The organic layer was washed with 1 M hydrochloric acid and a 15% aqueous potassium carbonate solution and dried over anhydrous sodium sulfate. After filtration, the filtrate was concentrated under reduced pressure to obtain 3.30 g of a crude product as a white solid. Subsequently, 2.10 g of this crude product was dissolved in 30 mL of anhydrous tetrahydrofuran. To the solution, 12 mL of a 2 M borane-dimethyl sulfide complex-tetrahydrofuran solution was added at 0° C. in a nitrogen atmosphere, and the mixture was stirred at 75° C. for 1 hour. After the completion of reaction, 20 mL of methanol and 4 mL of concentrated hydrochloric acid were added thereto at 0° C., and the mixture was stirred at room temperature for 0.5 hours. After concentration under reduced pressure, a 30% aqueous potassium carbonate solution was added thereto, followed by extraction with ethyl acetate (30 mL×3). The organic layer was dried over anhydrous sodium sulfate. After filtration, the filtrate was concentrated under reduced pressure. The obtained crude product was purified by silica gel column chromatography (dichloromethane:methanol=20:1) to obtain 1.5 g of the compound of interest as a pale yellow oil (45%). Subsequently, this compound was dissolved in 20 mL of dichloromethane. To the solution, 0.850 mL of triethylamine and 1.33 g of di-tert-butyl dicarbonate were added thereto at 0° C., and the mixture was stirred at room temperature for 12 hours. 100 mL of water was added thereto, followed by extraction with dichloromethane (30 mL×3). The organic layer was washed with saturated saline and dried over anhydrous sodium sulfate. After filtration, the filtrate was concentrated under reduced pressure, and the obtained crude product was purified by silica gel column chromatography (hexane:ethyl acetate=2:1) to obtain 1.61 g of the title compound as a pale yellow oil (82%).

$^1$H-NMR spectrum (CDCl$_3$, δ ppm): 1.10 (d, J=7.0 Hz, 3H), 1.47 (s, 9H), 3.02-3.51 (m, 4H), 3.96 (br s, 1H), 4.95 (br s, 1H), 5.06 (br s, 2H), 7.31-7.34 (m, 10H).

Step 4

Synthesis of tert-butyl (R)-2-aminopropyl{(S)-2-hydroxy-2-phenylethyl}carbamate 2.85 g of (R)-benzyl 1-[tert-butoxycarbonyl{(S)-2-hydroxy-2-phenylethyl}amino]propan-2-ylcarbamate was dissolved in 40 mL of methanol. To the solution, 1.42 g of 20% palladium hydroxide-carbon was added, and the mixture was vigorously stirred at room temperature for 14 hours in a hydrogen gas atmosphere. The reaction solution was filtered through celite, and the filtrate was concentrated under reduced pressure. The obtained crude product was purified by silica gel column chromatography (dichloromethane:methanol=4:1) to obtain 1.86 g of the title compound as a colorless oil (96%).

$^1$H-NMR spectrum (CDCl$_3$, δ ppm): 1.13 (br s, 3H), 1.53 (s, 9H), 2.60-3.01 (m, 3H), 3.47 (br s, 1H), 3.83-3.86 (m, 1H), 5.03 (br s, 1H), 7.33-7.43 (m, 5H).

Reference Example 8

Synthesis of N—{(R)-2-aminopropyl}-N—{(S)-2-hydroxy-2-(thiophen-3-yl)ethyl}-2-nitrobenzenesulfonamide

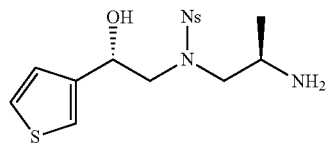

The title compound was synthesized according to the following Scheme 10:

Scheme 10

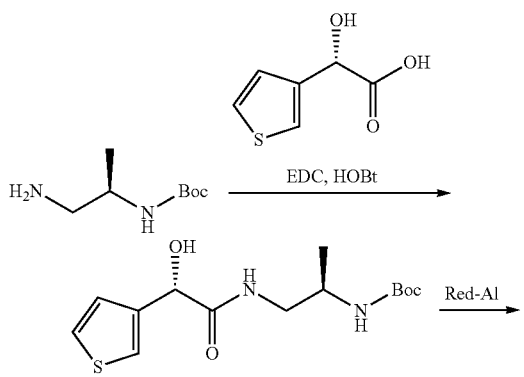

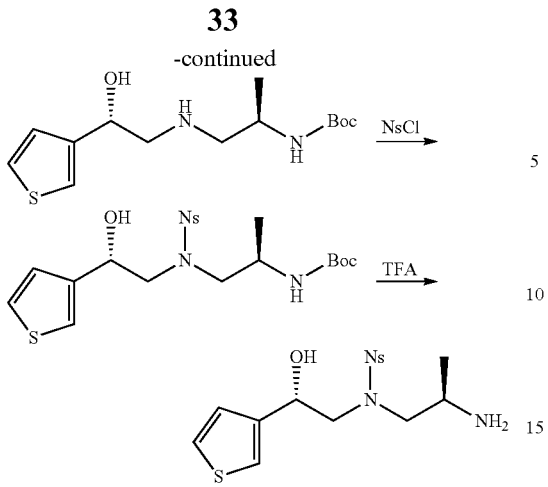

Steps 1, 2, and 3

Synthesis of tert-butyl (R)-1-[N—{(S)-2-hydroxy-2-(thiophen-3-yl)ethyl]-2-nitrophenylsulfonamido}propan-2-ylcarbamate 2.93 g of (R)-tert-butyl (1-aminopropan-2-yl)carbamate synthesized with reference to the method described in Tetrahedron Lett., 46, 7069 (2005) was dissolved in a mixed solvent of 20 mL of N,N-dimethylformamide and 40 mL of dichloromethane. 2.66 g of (S)-2-hydroxy-2-(thiophen-3-yl) acetic acid obtained by the optical resolution of 2-hydroxy-2-(thiophen-3-yl)acetic acid with lipase, 454 mg of 1-hydroxybenzotriazole, and 3.87 g of 1-ethyl-3-(3-dimethylaminopropyl)carbodiimide hydrochloride were added thereto, and the mixture was stirred at room temperature for 12 hours. 100 mL of dichloromethane was added thereto, and the organic layer was washed with water (30 mL×5) and saturated saline and dried over anhydrous sodium sulfate. After filtration, the filtrate was concentrated under reduced pressure, and the residue was purified by silica gel column chromatography (hexane:ethyl acetate=1:2) to obtain 4.0 g of the compound of interest (75%). Subsequently, 3.6 g of this product was dissolved in a mixed solvent of 25 mL of anhydrous tetrahydrofuran and 50 mL of toluene. 25.4 mL of a 3.6 M sodium bis(2-methoxyethoxy)aluminum hydride-toluene solution was added dropwise thereto at 0° C. in a nitrogen atmosphere, and the mixture was stirred at 50° C. for 1 hour. After consumption of the starting materials, 50 mL of a 2 M aqueous sodium hydroxide solution was added dropwise thereto at 0° C. to stop the reaction. After stirring for 10 minutes, the organic layer was separated, and the aqueous layer was subjected to extraction with dichloromethane (50 mL×3). The combined organic layer was dried over anhydrous sodium sulfate. After filtration, the filtrate was concentrated under reduced pressure. The obtained crude product was dissolved in 40 mL of dichloromethane. To the solution, 4.76 mL of triethylamine and 3.05 g of 2-nitrobenzenesulfonyl chloride were added at 0° C. in a nitrogen atmosphere, and the mixture was stirred at room temperature for 24 hours. 150 mL of ethyl acetate was added thereto, and the organic layer was washed with 0.5 M hydrochloric acid, a saturated aqueous solution of sodium bicarbonate, and saturated saline and dried over anhydrous sodium sulfate. After filtration, the filtrate was concentrated under reduced pressure, and the residue was purified by silica gel column chromatography (hexane:ethyl acetate=3:2) to obtain 4.4 g of the compound of interest as a pale yellow oil (60%).

$^1$H-NMR spectrum (CDCl$_3$, δ ppm): 1.17 (d, J=7.0 Hz, 3H), 1.44 (t, J=7.6 Hz, 9H), 3.20-3.38 (m, 2H), 3.50-3.62 (m, 2H), 3.86 (br s, 1H), 4.00-4.10 (m, 1H), 4.66 (br s, 1H), 5.09 (d, J=9.8 Hz, 1H), 7.06 (d, J=4.5 Hz, 1H), 7.24-7.29 (m, 2H), 7.62 (dd, J=1.5, 7.0 Hz, 1H), 7.65-7.72 (m, 2H), 8.05 (d, J=6.0 Hz, 1H).

Step 4

Synthesis of N—{(R)-2-aminopropyl}-N—{(S)-2-hydroxy-2-(thiophen-3-yl)ethyl}-2-nitrobenzenesulfonamide 602 mg of tert-butyl (R)-1-[N—{(S)-2-hydroxy-2-(thiophen-3-yl)ethyl}-2-nitrophenylsulfonamido]propan-2-ylcarbamate was dissolved in 4 mL of dichloromethane. To the solution, 1 mL of trifluoroacetic acid was added, and the mixture was stirred at room temperature for 1 hour. The reaction solution was concentrated under reduced pressure, and the residue was dissolved in 4 mL of methanol. 1 g of sodium bicarbonate was added thereto, and the mixture was stirred for 1 hour. After filtration, the filtrate was concentrated under reduced pressure, and the residue was purified by silica gel column chromatography (dichloromethane:methanol=8:1) to obtain 338 mg of the title compound as a colorless oil (71%).

$^1$H-NMR spectrum (CDCl$_3$, δ ppm): 1.21 (d, J=6.1 Hz, 3H), 3.05-3.17 (m, 2H), 3.62-3.67 (m, 2H), 3.84 (d, J=13.4 Hz, 1H), 5.15 (d, J=8.5 Hz, 1H), 7.08 (d, J=4.9 Hz, 1H), 7.25-7.30 (m, 2H), 7.63 (d, J=7.9 Hz, 1H), 7.71-7.75 (m, 2H), 7.90 (d, J=7.3 Hz, 1H).

Example 1

(R)—N-{1-(benzylamino)propan-2-yl}isoquinoline-6-sulfonamide dihydrochloride

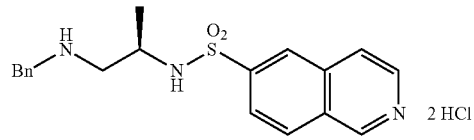 [SMILES: C[C@H](CNCc1ccccc1)NS(=O)(=O)c1ccc2cnccc2c1 ; "2 HCl"]

The title compound was synthesized according to the following Scheme 11:

Scheme 11

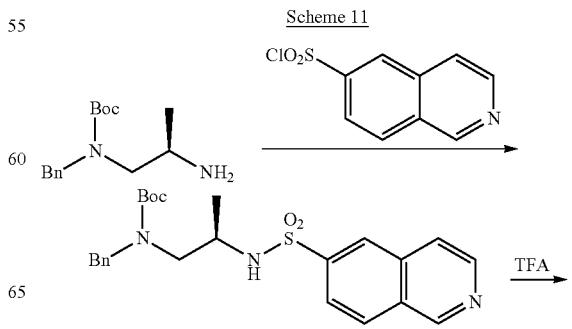

-continued

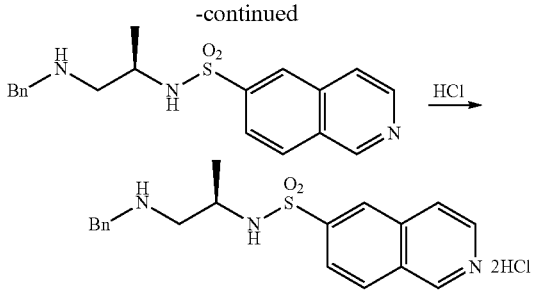

Step 1

Synthesis of (R)-tert-butyl benzyl{2-(isoquinoline-6-sulfonamide)propyl}carboxylate 332 mg of (R)-tert-butyl 2-aminopropylbenzylcarbamate synthesized by the method described in Reference Example 3 was dissolved in 10 mL of dichloromethane. To the solution, 0.35 mL of triethylamine was added, and the mixture was cooled to 0° C. A dichloromethane solution of isoquinoline-6-sulfonyl chloride prepared by the method described in Reference Example 1 was added thereto, and the mixture was stirred at room temperature for 1 hour. Water was added thereto, followed by extraction with dichloromethane (20 mL×3). The organic layer was washed with saturated saline and dried over anhydrous sodium sulfate. After filtration, the filtrate was concentrated under reduced pressure, and the obtained crude product was purified by silica gel column chromatography (hexane:acetone=3:2) to obtain 550 mg of the title compound as a pale yellow oil (96%).

$^1$H-NMR spectrum (CDCl$_3$, δ ppm): 1.07 (d, J=6.0 Hz, 3H), 1.44 (s, 9H), 2.83 (d, J=15.0 Hz, 1H), 3.47-3.55 (m, 2H), 3.94 (d, J=15.0 Hz, 1H), 4.24 (d, J=15.0 Hz, 1H), 6.17 (br s, 1H), 7.00-7.01 (m, 2H), 7.21-7.23 (m, 3H), 7.78 (d, J=6.0 Hz, 1H), 7.96 (d, J=8.0 Hz, 1H), 8.10 (d, J=8.0 Hz, 1H), 8.41 (s, 1H), 8.69 (d, J=6.0 Hz, 1H), 9.37 (s, 1H).

Step 2

Synthesis of (R)—N-{1-(benzylamino)propan-2-yl}isoquinoline-6-sulfonamide 550 mg of (R)-tert-butyl benzyl{2-(isoquinoline-6-sulfonamide)propyl)carboxylate was dissolved in 10 mL of dichloromethane, and 4 mL of trifluoroacetic acid was added thereto. The mixture was stirred at room temperature for 2 hours. The reaction solution was neutralized by the addition of an aqueous sodium bicarbonate solution, followed by extraction with dichloromethane. Then, the organic layer was washed with saturated saline and dried over anhydrous sodium sulfate. After filtration, the filtrate was concentrated under reduced pressure, and the obtained crude product was purified by silica gel column chromatography (dichloromethane:methanol:ammonia water=2:1:0.05) to obtain 368 mg of the title compound as a colorless oil (86%).

$^1$H-NMR spectrum (CDCl$_3$, δ ppm): 1.13 (d, J=6.0 Hz, 3H), 2.47-2.51 (m, 1H), 2.55-2.59 (m, 1H), 3.30-3.33 (m, 1H), 3.54 (d, J=13.0 Hz, 1H), 3.57 (d, J=13.5 Hz, 1H), 7.13-7.14 (m, 2H), 7.24-7.29 (m, 3H), 7.71 (d, J=5.5 Hz, 1H), 7.92 (d, J=8.5 Hz, 1H), 8.01 (d, J=8.5 Hz, 1H), 8.41 (s, 1H), 8.65 (d, J=5.5 Hz, 1H), 9.31 (s, 1H).

Step 3

Synthesis of (R)—N-{1-(benzylamino)propan-2-yl}isoquinoline-6-sulfonamide dihydrochloride 368 mg of (R)—N-{1-(benzylamino)propan-2-yl}isoquinoline-6-sulfonamide was dissolved in 2 mL of dichloromethane. To the solution, 3 mL of a 1 M hydrochloric acid-diethyl ether solution was added, and the mixture was stirred at room temperature for 4 hours. The deposited crystal was collected using a Kiriyama funnel and dried under reduced pressure at 60° C. to obtain 360 mg of the title compound as a white solid (84%).

$^1$H-NMR spectrum D$_2$O, δ ppm): 0.76 (d, J=6.5 Hz, 3H), 2.91-2.96 (m, 1H), 3.04-3.07 (m, 1H), 3.74 (br s, 1H) 4.20 (d, J=13.5 Hz, 1H), 4.27 (d, J=13.5 Hz, 1H), 7.38-7.39 (m, 5H), 8.20 (d, J=8.5 Hz, 1H), 8.44 (d, J=6.0 Hz, 1H), 8.55 (d, J=8.5 Hz, 1H), 8.59 (br s, 1H), 8.70 (s, 1H), 9.68 (br s, 1H).

Compounds of Examples 2 to 37 were synthesized according to the method described in Example 1 from intermediates synthesized by the method described in Reference Example 2 using the compound of Reference Example 1 and the respective appropriate starting materials.

Example 2

(R)—N-{1-(methylamino)propan-2-yl}isoquinoline-6-sulfonamide dihydrochloride

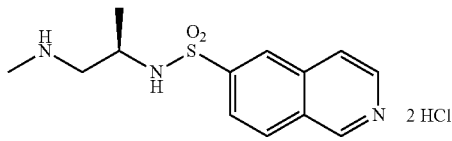 [SMILES: CNC[C@@H](C)NS(=O)(=O)c1ccc2cnccc2c1 ; "2 HCl"]

20 mg of the title compound was obtained as a yellow solid (36%) from 44 mg of a free form synthesized according to the method described in Example 1.

$^1$H-NMR spectrum (D$_2$O, δ ppm): 0.70 (d, J=7.3 Hz, 3H), 2.67 (s, 3H), 2.89-2.97 (m, 1H), 2.98-3.07 (m, 1H), 3.63-3.72 (m, 1H), 8.21 (d, J=9.3 Hz, 1H), 8.48 (d, J=6.7 Hz, 1H), 8.52-8.61 (m, 2H), 8.72 (s, 1H), 9.68 (s, 1H).

Example 3

(R)—N-{1-(ethylamino)propan-2-yl}isoquinoline-6-sulfonamide dihydrochloride

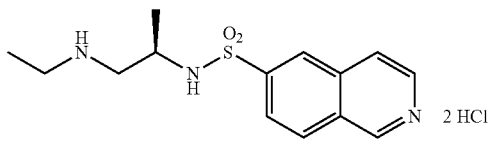 [SMILES: CCNC[C@@H](C)NS(=O)(=O)c1ccc2cnccc2c1 ; "2 HCl"]

50 mg of the title compound was obtained as a pale yellow solid (89%) from 45 mg of a free form synthesized according to the method described in Example 1.

$^1$H-NMR spectrum (D$_2$O, δ ppm): 0.70 (d, J=6.5 Hz, 3H), 1.20 (t, J=7.5 Hz, 3H), 2.91-3.07 (m, 4H), 3.60-3.68 (m, 1H), 8.19 (d, J=8.5 Hz, 1H), 8.40 (d, J=6.5 Hz, 1H), 8.54-8.56 (m, 2H), 8.70 (s, 1H), 9.68 (s, 1H).

Example 4

(R)—N-{1-(propylamino)propan-2-yl}isoquinoline-6-sulfonamide dihydrochloride

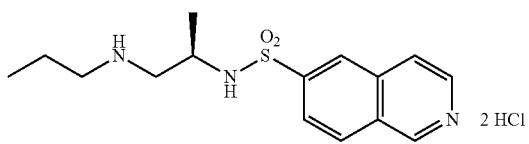 [SMILES: CCCNC[C@@H](C)NS(=O)(=O)c1ccc2cnccc2c1 ; "2 HCl"]

108 mg of the title compound was obtained as a white solid (80%) from 109 mg of a free form synthesized according to the method described in Example 1.

¹H-NMR spectrum (D$_2$O, δ ppm): 0.69 (d, J=7.0 Hz, 3H), 0.84 (t, J=7.0 Hz, 3H), 1.58-1.62 (m, 2H), 2.88-3.02 (m, 4H), 3.60-3.68 (m, 1H), 8.14 (d, J=9.0 Hz, 1H), 8.36 (d, J=6.5 Hz, 1H), 8.50 (d, J=9.0 Hz, 1H), 8.54 (d, J=6.5 Hz, 1H), 8.65 (s, 1H), 9.60 (s, 1H).

Example 5

(R)—N-{1-(butylamino)propan-2-yl}isoquinoline-6-sulfonamide dihydrochloride

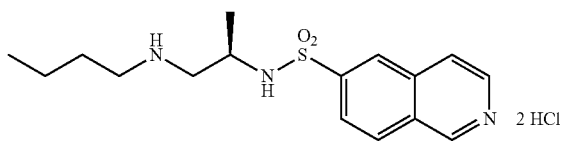 [SMILES: CCCCNC[C@@H](C)NS(=O)(=O)c1ccc2cnccc2c1 ; "2 HCl"]

220 mg of the title compound was obtained as a white solid (76%) from 236 mg of a free form synthesized according to the method described in Example 1.

¹H-NMR spectrum (D$_2$O, δ ppm): 0.71 (d, J=6.7 Hz, 3H), 0.81 (t, J=7.6 Hz, 3H), 1.23-1.31 (m, 2H), 1.54-1.60 (m, 2H), 2.89-3.05 (m, 4H), 3.66-3.70 (m, 1H), 8.17-8.22 (m, 1H), 8.45 (d, J=6.1 Hz, 1H), 8.54-8.56 (m, 2H), 8.70 (s, 1H), 9.66 (s, 1H).

Example 6

(S)—N-{1-(butylamino)propan-2-yl}isoquinoline-6-sulfonamide dihydrochloride

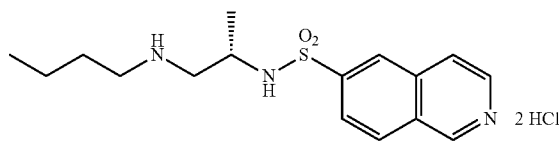 [SMILES: CCCCNC[C@H](C)NS(=O)(=O)c1ccc2cnccc2c1 ; "2 HCl"]

160 mg of the title compound was obtained as a white solid (68%) from 250 mg of a Boc form synthesized according to the method described in Example 1.

¹H-NMR spectrum (D$_2$O, δ ppm): 0.76 (d, J=6.5 Hz, 3H), 0.85 (t, J=7.5 Hz, 3H), 1.27-1.34 (m, 2H), 1.58-1.63 (m, 2H), 2.93-3.07 (m, 4H), 3.69-3.73 (m, 1H), 8.21 (d, J=9.0 Hz, 1H), 8.44 (d, J=5.5 Hz, 1H), 8.56 (d, J=9.0 Hz, 1H), 8.62 (d, J=5.5 Hz, 1H), 8.71 (s, 1H), 9.70 (s, 1H).

Example 7

(R)-N-{1-(but-2-enylamino)propan-2-yl}isoquinoline-6-sulfonamide dihydrochloride

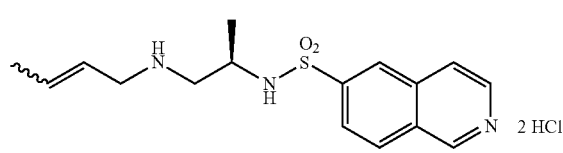

55 mg of the title compound was obtained as a white solid (74%) from 60 mg of a free form synthesized according to the method described in Example 1.

¹H-NMR spectrum (D$_2$O, δ ppm): 0.69 (d, J=1.8 Hz, 1.5H), 0.71 (d, J=1.8 Hz, 1.5H), 1.58 (d, J=6.8 Hz, 1.5H), 1.61 (d, J=6.8 Hz, 1.5H), 2.83-2.91 (m, 1H), 2.98-3.05 (m, 1H), 3.53-3.55 (m, 1H), 3.61-3.73 (m, 2H), 5.35-5.47 (m, 1H), 5.85-5.94 (m, 1H), 8.17 (d, J=8.7 Hz, 1H), 8.40 (d, J=6.6 Hz, 1H), 8.52-8.55 (m, 2H), 8.68 (s, 1H), 9.63 (s, 1H).

Example 8

(S)—N-{1-(but-2-enylamino)propan-2-yl}isoquinoline-6-sulfonamide dihydrochloride

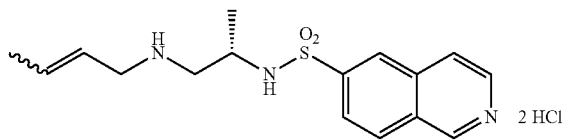

20 mg of the title compound was obtained as a pale yellow solid (42%) from 51 mg of a Boc form synthesized according to the method described in Example 1.

¹H-NMR spectrum (D$_2$O, δ ppm): 0.90 (d, J=7.0 Hz, 3H), 1.74-1.79 (m, 3H), 3.02-3.10 (m, 1H), 3.15-3.21 (m, 1H), 3.66-3.71 (m, 1H), 3.82-3.87 (m, 2H), 5.56-5.62 (m, 1H), 6.05-6.09 (m, 1H), 8.36 (d, J=8.5 Hz, 1H), 8.64 (br s, 1H), 8.71 (d, J=8.5 Hz, 1H), 8.82-8.89 (m, 2H), 9.70 (br s, 1H).

Example 9

(R)—N-{1-(allylamino)propan-2-yl}isoquinoline-6-sulfonamide dihydrochloride

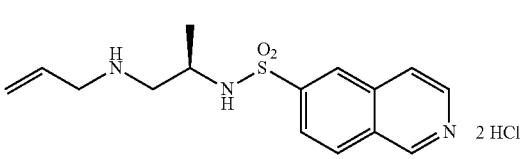 [SMILES: C=CCNC[C@@H](C)NS(=O)(=O)c1ccc2cnccc2c1 ; "2 HCl"]

55 mg of the title compound was obtained as a white solid (62%) from 71 mg of a free form synthesized according to the method described in Example 1.

$^1$H-NMR spectrum (D$_2$O, δ ppm): 0.71 (d, J=6.6 Hz, 3H), 2.89-2.94 (m, 1H), 3.04 (dd, J=3.6, 13.3 Hz, 1H), 3.59-3.69 (m, 3H), 5.39-5.43 (m, 2H), 5.77-5.85 (m, 1H), 8.15 (d, J=8.5 Hz, 1H), 8.37 (d, J=5.5 Hz, 1H), 8.50-8.55 (m, 2H), 8.65 (s, 1H), 9.60 (s, 1H).

Example 10

N-{2-(allylamino)ethyl}isoquinoline-6-sulfonamide dihydrochloride

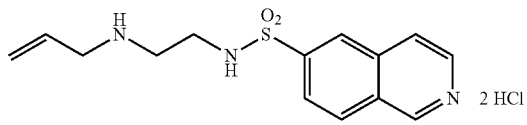 [SMILES: C=CCNCCNS(=O)(=O)c1ccc2cnccc2c1 ; "2 HCl"]

57 mg of the title compound was obtained as a brown solid (68%) from 67 mg of a free form synthesized according to the method described in Example 1.

$^1$H-NMR spectrum (D$_2$O, δ ppm): 3.08-3.14 (m, 2H), 3.16-3.23 (m, 2H), 3.61 (d, J=6.7 Hz, 2H), 5.34-5.47 (m, 2H), 5.74-5.86 (m, 1H), 8.16 (d, J=9.2 Hz, 1H), 8.43 (d, J=6.7 Hz, 1H), 8.50-8.58 (m, 2H), 8.67 (s, 1H), 9.64 (s, 1H).

Example 11

(R)—N-{2-(butylamino)propyl}isoquinoline-6-sulfonamide dihydrochloride

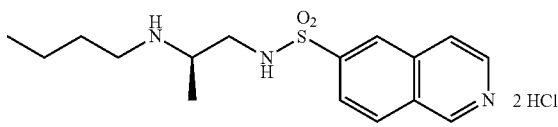 [SMILES: CCCCN[C@H](C)CNS(=O)(=O)c1ccc2cnccc2c1 ; "2 HCl"]

215 mg of the title compound was obtained as a white solid (80%) from 217 mg of a free form synthesized according to the method described in Example 1.

$^1$H-NMR spectrum (D$_2$O, δ ppm): 0.81 (t, J=7.5 Hz, 3H), 1.17 (d, J=6.5 Hz, 3H), 1.24-1.32 (m, 2H), 1.53-1.57 (m, 2H), 2.98 (t, J=8.0 Hz, 2H), 3.07 (dd, J=5.0, 15 Hz, 1H), 3.21 (dd, J=5.0, 15 Hz, 1H), 3.33-3.35 (m, 1H), 8.16 (d, J=8.5 Hz, 1H), 8.45 (d, J=6.5 Hz, 1H), 8.54-8.56 (m, 2H), 8.67 (s, 1H), 9.67 (s, 1H).

Example 12

(R)—N-{4-(propylamino)butan-2-yl}isoquinoline-6-sulfonamide dihydrochloride

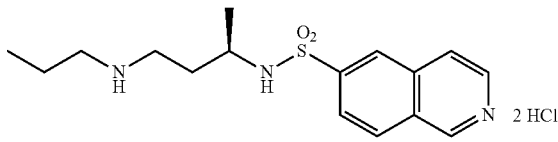 [SMILES: CCCNCC[C@@H](C)NS(=O)(=O)c1ccc2cnccc2c1 ; "2 HCl"]

64 mg of the title compound was obtained as a pale yellow solid (74%) from 70 mg of a free form synthesized according to the method described in Example 1.

$^1$H-NMR spectrum (D$_2$O, δ ppm): 0.76 (d, J=7.0 Hz, 3H), 0.81 (t, J=8.0 Hz, 3H), 1.48-1.56 (m, 2H), 1.64-1.69 (m, 1H), 1.72-1.78 (m, 1H), 2.84 (t, J=7.5 Hz, 2H), 2.92-3.05 (m, 2H), 3.40-3.45 (m, 1H), 8.17 (d, J=8.5 Hz, 1H), 8.43 (d, J=6.0 Hz, 1H), 8.52-8.54 (m, 2H), 8.66 (s, 1H), 9.67 (s, 1H).

Example 13

(R)—N-{1-(piperazin-1-yl)propan-2-yl}isoquinoline-6-sulfonamide trihydrochloride

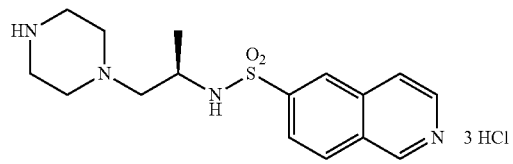 [SMILES: C[C@H](CN1CCNCC1)NS(=O)(=O)c1ccc2cnccc2c1 ; "3 HCl"]

300 mg of the title compound was obtained as a white solid (92%) from 318 mg of a Boc form synthesized according to the method described in Example 1.

$^1$H-NMR spectrum (D$_2$O, δ ppm): 0.66 (d, J=6.7 Hz, 3H), 3.21 (d, J=7.3 Hz, 2H), 3.47-3.80 (m, 8H), 3.91-4.00 (m, 1H), 8.23 (d, J=9.2 Hz, 1H), 8.50 (d, J=6.7 Hz, 1H), 8.55-8.63 (m, 2H), 8.74 (s, 1H), 9.70 (s, 1H).

Example 14

(R)—N-{1-(isobutylamino)propan-2-yl}isoquinoline-6-sulfonamide dihydrochloride

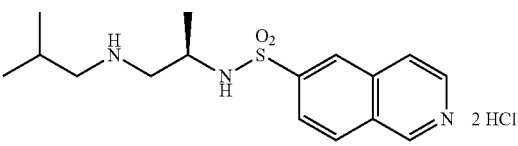 [SMILES: CC(C)CNC[C@@H](C)NS(=O)(=O)c1ccc2cnccc2c1 ; "2 HCl"]

123 mg of the title compound was obtained as a pale yellow solid (89%) from 112 mg of a free form synthesized according to the method described in Example 1.

$^1$H-NMR spectrum (D$_2$O, δ ppm): 0.70 (d, J=6.5 Hz, 3H), 0.86 (s, 6H), 1.89-1.95 (m, 1H), 2.80 (dd, J=8.0, 13.0 Hz, 1H), 2.87 (d, J=8.0, 13.0 Hz, 1H), 2.92 (d, J=10.5 Hz, 1H), 2.99 (dd, J=4.0, 13.0 Hz, 1H), 3.60-3.70 (m, 1H), 8.05 (d, J=8.5 Hz, 1H), 8.20 (d, J=6.5 Hz, 1H), 8.38 (d, J=8.5 Hz, 1H), 8.55-8.60 (m, 2H), 9.61 (s, 1H).

Example 15

(R)—N-{1-(cyclopropylamino)propan-2-yl}isoquinoline-6-sulfonamide dihydrochloride

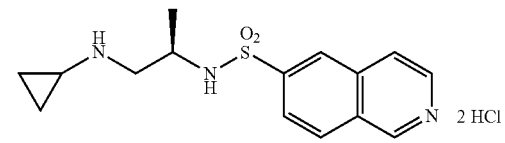 [SMILES: C[C@H](CNC1CC1)NS(=O)(=O)c1ccc2cnccc2c1 ; "2 HCl"]

103 mg of the title compound was obtained as a pale yellow solid (83%) from 100 mg of a free form synthesized according to the method described in Example 1.

$^1$H-NMR spectrum (1D$_2$O, δ ppm): 0.68 (d, J=6.5 Hz, 3H), 0.79-0.81 (m, 4H), 2.65-2.68 (m, 1H), 2.98-3.03 (m, 1H), 3.13-3.17 (m, 1H), 3.65-3.68 (m, 1H), 8.11 (d, J=9.0 Hz, 1H), 8.29 (d, J=5.5 Hz, 1H), 8.46 (d, J=8.5 Hz, 1H), 8.53 (br s, 1H), 8.62 (s, 1H), 9.56 (s, 1H).

Example 16

(R)—N-{1-(cyclobutylmethylamino)propan-2-yl}isoquinoline-6-sulfonamide hydrochloride

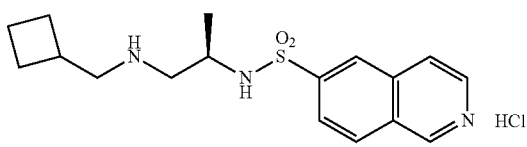 [SMILES: C[C@H](CNCC1CCC1)NS(=O)(=O)c1ccc2cnccc2c1 ; Cl]

90 mg of the title compound was obtained as a white solid (72%) from 102 mg of a free form synthesized according to the method described in Example 1.

$^1$H-NMR spectrum (D$_2$O, δ ppm): 0.70 (d, J=7.0 Hz, 3H), 1.65-1.73 (m, 3H), 1.81-1.84 (m, 1H), 1.97-2.02 (m. 2H), 2.53-2.56 (m, 1H), 2.85-2.90 (m, 1H), 2.97-3.10 (m, 3H), 3.63-3.65 (m, 1H), 8.02 (d, J=8.5 Hz, 1H), 8.08 (d, J=6.5 Hz, 1H), 8.34 (d, J=8.5 Hz, 1H), 8.50-8.52 (m, 1H), 9.39 (s, 1H).

Example 17

(R)—N-{1-(neopentylamino)propan-2-yl}isoquinoline-6-sulfonamide dihydrochloride

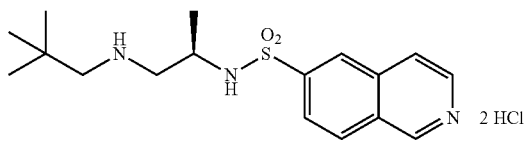 [SMILES: C[C@H](CNCC(C)(C)C)NS(=O)(=O)c1ccc2cnccc2c1 ; "2 HCl"]

33 mg of the title compound was obtained as a pale yellow solid (33%) from 82 mg of a free form synthesized according to the method described in Example 1.

$^1$H-NMR spectrum (D$_2$O, δ ppm): 0.71 (d, J=6.5 Hz, 3H), 0.96 (s, 9H), 2.77 (d, J=12.0 Hz, 1H), 2.96-2.98 (m, 2H), 3.02 (dd, J=4.0, 12.0 Hz, 1H), 3.73-3.77 (m, 1H), 8.02 (d, J=8.5 Hz, 1H), 8.07 (d, J=5.0 Hz, 1H), 8.34 (d, J=8.5 Hz, 1H), 8.50-8.55 (m, 2H), 9.42 (br s, 1H).

Example 18

(R)—N-{1-(cyclopropylmethylamino)propan-2-yl}isoquinoline-6-sulfonamide dihydrochloride

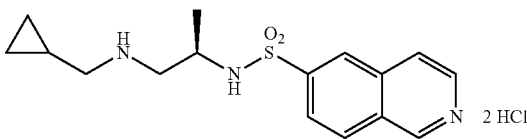 [SMILES: C[C@H](CNCC1CC1)NS(=O)(=O)c1ccc2cnccc2c1 ; "2 HCl"]

52 mg of the title compound was obtained as a pale yellow solid (32%) from 130 mg of a free-form synthesized according to the method described in Example 1.

$^1$H-NMR spectrum (D$_2$O, δ ppm): 0.27-0.35 (m, 2H), 0.36-0.40 (m, 2H), 0.75 (br s, 1H), 1.12 (d, J=6.5 Hz, 3H) 2.20 (dd, J=6.5 Hz, 2H), 2.46 (dd, J=8.5, 13 Hz, 1H), 2.58 (dd, J=4.5, 12 Hz, 1H), 3.20-3.28 (m, 1H), 7.78 (d, J=5.5 Hz, 1H), 8.01 (d, J=8.5 Hz, 1H), 8.12 (d, J=8.5 Hz, 1H), 8.44 (s, 1H), 8.68 (d, J=5.5 Hz, 1H), 9.36 (s, 1H).

Example 19

(R)—N-{1-(pentylamino)propan-2-yl}isoquinoline-6-sulfonamide dihydrochloride

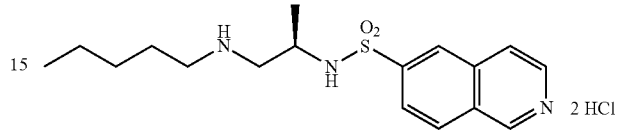

254 mg of the title compound was obtained as a pale yellow solid (98%) from 212 mg of a free form synthesized according to the method described in Example 1.

$^1$H-NMR spectrum (D$_2$O, δ ppm): 0.70 (d, J=6.5 Hz, 3H), 0.75 (t, J=6.5 Hz, 3H), 1.19-1.20 (m, 4H), 1.50-1.58 (m, 2H), 2.87-3.02 (m, 4H), 3.62-3.66 (m, 1H), 8.09 (d, J=9.0 Hz, 1H), 8.24 (d, J=5.0 Hz, 1H), 8.42 (d, J=9.0 Hz, 1H), 8.55 (d, J=5.0 Hz, 1H), 8.58 (s, 1H), 9.54 (br s, 1H).

Example 20

N-(2R)-{1-(methylbutylamino)propan-2-yl}isoquinoline-6-sulfonamide hydrochloride

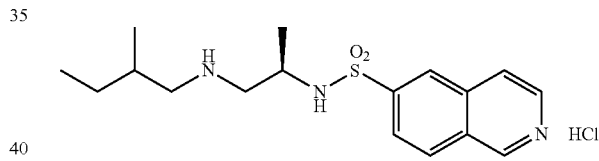

820 mg of the title compound was obtained as a light brown solid (81%) from 912 mg of a free form synthesized according to the method described in Example 1.

$^1$H-NMR spectrum (D$_2$O, δ ppm): 0.70-0.83 (m, 9H), 1.04-1.09 (m, 1H), 1.20-1.28 (m, 1H), 1.63-1.68 (m. 1H), 2.71-2.79 (m, 1H), 2.85-2.95 (m, 3H), 3.61 (br s, 1H), 7.12 (d, J=5.5 Hz, 1H), 7.80 (d, J=8.5 Hz, 1H), 8.04 (d, J=8.5 Hz, 1H), 8.25 (s, 1H), 8.35 (d, J=5.5 Hz, 1H), 9.06 (s, 1H).

Example 21

(R)—N-{1-(isopentylamino)propan-2-yl}isoquinoline-6-sulfonamide hydrochloride

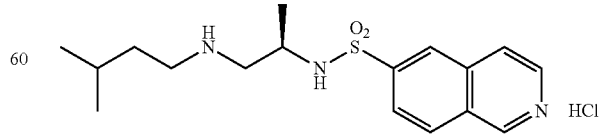

350 mg of the title compound was obtained as a white solid (77%) from 407 mg of a free form synthesized according to the method described in Example 1.

¹H-NMR spectrum (D₂O, δ ppm): 0.71 (d, J=7.0 Hz, 3H), 0.79 (d, J=7.0 Hz, 6H), 1.45-1.53 (m, 3H), 2.87-3.10 (m, 4H), 3.60-3.65 (m, 1H), 7.95-7.98 (m, 2H), 8.26 (d, J=8.5 Hz, 1H), 8.46-8.48 (m, 2H), 9.30 (br s, 1H).

Example 22

(R)—N-{1-(hexylamino)propan-2-yl}isoquinoline-6-sulfonamide dihydrochloride

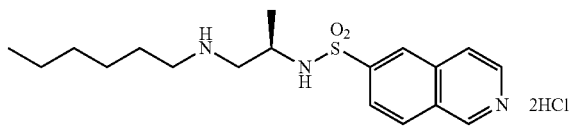 [SMILES: CCCCCCNC[C@@H](C)NS(=O)(=O)c1ccc2cnccc2c1 ; "2HCl"]

27 mg of the title compound was obtained as a pale yellow solid (74%) from 30 mg of a free form synthesized according to the method described in Example 1.

¹H-NMR spectrum (D₂O, δ ppm): 0.68-0.79 (m, 6H), 1.14-1.27 (m, 6H), 1.52-1.61 (m, 2H), 2.86-3.05 (m, 4H), 3.62-3.71 (m, 1H), 8.13 (d, J=9.2 Hz, 1H), 8.31 (d, J=6.1 Hz, 1H), 8.48 (d, J=8.5 Hz, 1H), 8.54 (d, J=6.1 Hz, 1H), 8.64 (s, 1H), 9.56 (s, 1H).

Example 23

(R)—N-{1-(phenethylamino)propan-2-yl}isoquinoline-6-sulfonamide dihydrochloride

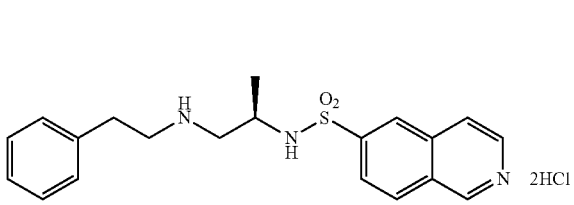 [SMILES: C[C@H](CNCCc1ccccc1)NS(=O)(=O)c1ccc2cnccc2c1 ; "2HCl"]

286 mg of the title compound was obtained as a pale yellow solid (78%) from 306 mg of a free form synthesized according to the method described in Example 1.

¹H-NMR spectrum (D₂O, δ ppm): 0.71 (d, J=7.3 Hz, 3H), 2.90-2.99 (m, 3H), 3.02-3.07 (m, 1H), 3.18-3.32 (m, 2H), 3.62-3.70 (m, 1H), 7.19-7.25 (m, 3H), 7.29 (t, J=7.3 Hz, 2H), 8.19 (dd, J=1.5, 8.9 Hz, 1H), 8.47 (d, J=6.7 Hz, 1H), 8.53-8.58 (m, 2H), 8.69 (s, 1H), 9.67 (s, 1H).

Example 24

(S)—N-{1-(phenethylamino)propan-2-yl}isoquinoline-6-sulfonamide dihydrochloride

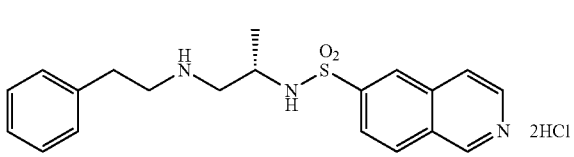 [SMILES: C[C@@H](CNCCc1ccccc1)NS(=O)(=O)c1ccc2cnccc2c1 ; "2HCl"]

675 mg of the title compound was obtained as a yellow solid (81%) from 689 mg of a free form synthesized according to the method described in Example 1.

¹H-NMR spectrum (D₂O, δ ppm): 0.72 (d, J=6.7 Hz, 3H), 2.90-3.00 (m, 3H), 3.02-3.09 (m, 1H), 3.19-3.33 (m, 2H), 3.62-3.72 (m, 1H), 7.20-7.26 (m, 3H), 7.27-7.33 (m, 2H), 8.18 (d, J=9.2 Hz, 1H), 8.45 (d, J=6.7 Hz, 1H), 8.53-8.57 (m, 2H), 8.68 (s, 1H), 9.65 (s, 1H).

Example 25

N—[(R)-1-{(R)-2-phenylpropylamino}propan-2-yl]isoquinoline-6-sulfonamide dihydrochloride

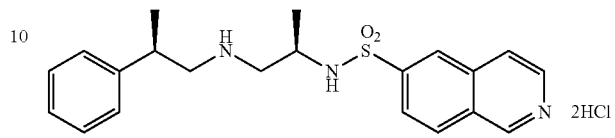

160 mg of the title compound was obtained as a yellow solid (79%) from 170 mg of a free form synthesized according to the method described in Example 1.

¹H-NMR spectrum (D₂O, δ ppm): 1.07 (d, J=7.0 Hz, 3H), 1.17 (d, J=6.5 Hz, 3H), 3.28 (dd, J=10.0, 13.0 Hz, 1H), 3.33 (dd, J=4.5, 13.0 Hz, 1H), 3.40-3.48 (m, 1H), 3.54 (dd, J=5.0, 12.0 Hz, 1H), 3.60 (dd, J=10.0, 12.0 Hz, 1H), 3.85-3.92 (m, 1H), 7.56-7.65 (m, 3H), 7.67-7.70 (m, 2H), 8.28 (d, J=8.5 Hz, 1H), 8.35 (br s, 1H), 8.64 (d, J=9.0 Hz, 1H), 8.79 (s, 1H), 8.88 (br s, 1H), 9.73 (br s, 1H).

Example 26

N—[(R)-1-{(S)-2-phenylpropylamino}propan-2-yl]isoquinoline-6-sulfonamide dihydrochloride

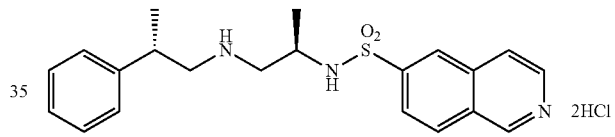

174 mg of the title compound was obtained as a white solid (74%) from 197 mg of a free form synthesized according to the method described in Example 1.

¹H-NMR spectrum (D₂O, δ ppm): 0.69 (d, J=7.0 Hz, 3H), 1.24 (d, J=6.5 Hz, 3H), 2.91 (dd, J=10.0, 13.0 Hz, 1H), 2.96 (dd, J=4.5, 13.0 Hz, 1H), 3.11-3.17 (m, 1H), 3.21 (dd, J=5.0, 12.0 Hz, 1H), 3.29 (dd, J=10.0, 12.0 Hz, 1H), 3.57-3.62 (m, 1H), 7.27-7.29 (m, 3H), 7.32-7.37 (m, 2H), 7.99 (d, J=8.5 Hz, 1H), 8.42 (br s, 1H), 8.34 (d, J=9.0 Hz, 1H), 8.52 (br s, 1H), 8.66 (s, 1H), 9.45 (br s, 1H).

Example 27

(R)—N-{3-methyl-1-(phenethylamino)butan-2-yl}isoquinoline-6-sulfonamide dihydrochloride

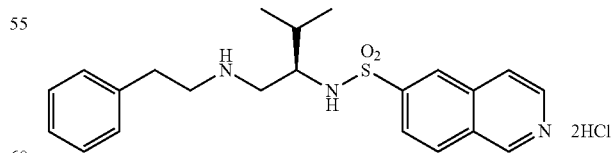

95 mg of the title compound was obtained as a yellow solid (16%) from 475 mg of a free form synthesized according to the method described in Example 1.

¹H-NMR spectrum (D₂O, δ ppm): 0.38-0.47 (m, 6H), 1.43-1.53 (m, 1H), 2.96-3.09 (m, 3H), 3.12-3.20 (m, 1H), 3.26-3.38 (m, 2H), 3.40-3.45 (m, 1H), 7.24-7.30 (m, 3H), 7.32-

7.37 (m, 2H), 8.22 (d, J=8.5 Hz, 1H), 8.44 (d, J=6.1 Hz, 1H), 8.53-8.59 (m, 2H), 8.69 (s, 1H), 9.65 (s, 1H).

Example 28

(R)—N-{1-(2-methoxyphenethylamino)propan-2-yl}isoquinoline-6-sulfonamide dihydrochloride

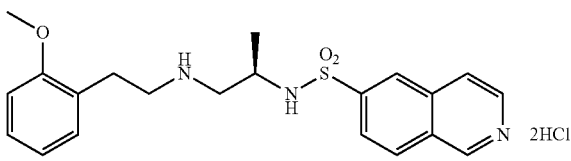 [SMILES: COc1ccccc1CCNC[C@@H](C)NS(=O)(=O)c1ccc2cnccc2c1 ; "2HCl"]

402 mg of the title compound was obtained as a yellow solid (83%) from 410 mg of a free form synthesized according to the method described in Example 1.

$^1$H-NMR spectrum (D$_2$O, δ ppm): 0.73 (d, J=6.7 Hz, 3H), 2.90-2.98 (m, 3H), 3.01-3.07 (m, 1H), 3.16-3.29 (m, 2H), 3.63-3.71 (m, 1H), 3.80 (s, 3H), 6.91 (t, J=7.3 Hz, 1H), 6.98 (d, J=7.9 Hz, 1H), 7.16 (d, J=7.3 Hz, 1H), 7.27 (t, J=7.9 Hz, 1H), 8.19 (dd, J=1.5, 8.9 Hz, 1H), 8.44 (d, J=6.7 Hz, 1H), 8.54-8.57 (m, 2H), 8.68 (s, 1H), 9.65 (s, 1H).

Example 29

(R)—N-{1-(3-methoxyphenethylamino)propan-2-yl}isoquinoline-6-sulfonamide dihydrochloride

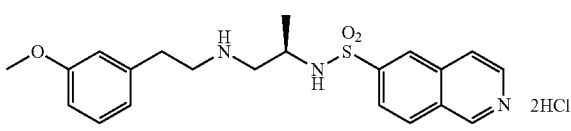 [SMILES: COc1cccc(CCNC[C@@H](C)NS(=O)(=O)c2ccc3cnccc3c2)c1 ; "2HCl"]

76 mg of the title compound was obtained as a light brown solid (59%) from 108 mg of a free form synthesized according to the method described in Example 1.

$^1$H-NMR spectrum (D$_2$O, δ ppm): 0.76 (d, J=7.0 Hz, 3H), 2.91-2.96 (m, 3H), 3.04 (dd, J=4.0, 13.0 Hz, 1H), 3.20-3.30 (m, 2H), 3.59-3.65 (m, 1H), 3.71 (s, 3H), 6.81-6.85 (m, 3H), 7.25 (t, J=8.0 Hz, 1H), 8.04 (d, J=7.5 Hz, 1H), 8.26 (br s, 1H), 8.36 (d, J=8.5 Hz, 1H), 8.48-8.52 (m, 2H), 9.27 (br s, 1H).

Example 30

(R)—N-{1-(4-methoxyphenethylamino)propan-2-yl}isoquinoline-6-sulfonamide dihydrochloride

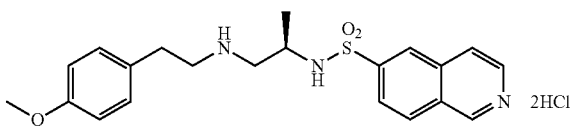 [SMILES: COc1ccc(CCNC[C@@H](C)NS(=O)(=O)c2ccc3cnccc3c2)cc1 ; "2HCl"]

476 mg of the title compound was obtained as a yellow solid (85%) from 473 mg of a free form synthesized according to the method described in Example 1.

$^1$H-NMR spectrum (D$_2$O, δ ppm): 0.74 (d, J=7.3 Hz, 3H), 2.89-2.99 (m, 3H), 3.06 (dd, J=3.6, 13.5 Hz, 1H), 3.18-3.30 (m, 2H), 3.65-3.69 (m, 1H), 3.72 (s, 3H), 6.88 (d, J=8.4 Hz, 2H), 7.16 (d, J=8.6 Hz, 2H), 8.19 (dd, J=1.2, 9.2 Hz, 1H), 8.46 (d, J=6.6 Hz, 1H), 8.55-8.57 (m, 2H), 8.69 (s, 1H), 9.66 (s, 1H).

Example 31

(R)—N-{1-(2-fluorophenethylamino)propan-2-yl}isoquinoline-6-sulfonamide dihydrochloride

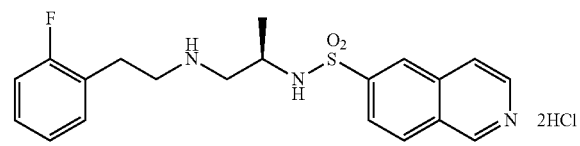 [SMILES: C[C@H](CNCCc1ccccc1F)NS(=O)(=O)c1ccc2cnccc2c1 ; "2HCl"]

88 mg of the title compound was obtained as a brown solid (93%) from 100 mg of a Boc form synthesized according to the method described in Example 1.

$^1$H-NMR spectrum (D$_2$O, δ ppm): 0.55 (d, J=6.1 Hz, 3H), 2.74-2.88 (m, 4H), 3.01-3.09 (m, 2H), 3.41-3.44 (m, 1H), 6.85-6.93 (m, 2H), 7.01-7.08 (m, 2H), 7.67 (d, J=5.5 Hz, 1H), 7.71 (d, J=8.5 Hz, 1H), 8.01 (d, J=8.5 Hz, 1H), 8.21 (s, 1H), 8.27 (d, J=5.5 Hz, 1H), 9.02 (s, 1H).

Example 32

N-{2-(phenethylamino)ethyl}isoquinoline-6-sulfonamide hydrochloride

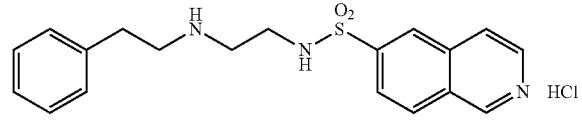 [SMILES: O=S(=O)(NCCNCCc1ccccc1)c1ccc2cnccc2c1 ; Cl]

171 mg of the title compound was obtained as a white solid (56%) from 277 mg of a free form synthesized according to the method described in Example 1.

$^1$H-NMR spectrum (D$_2$O, δ ppm): 2.87-2.91 (m, 2H), 3.06-3.14 (m, 4H), 3.17-3.22 (m, 2H), 7.14-7.30 (m, 5H), 7.77 (d, J=6.1 Hz, 1H), 7.81 (d, J=9.2 Hz, 1H), 8.10 (d, J=8.5 Hz, 1H), 8.29 (s, 1H), 8.39 (d, J=5.5 Hz, 1H), 9.12 (s, 1H).

Example 33

(R)—N-{1-(2-cyclohexylethylamino)propan-2-yl}isoquinoline-6-sulfonamide dihydrochloride

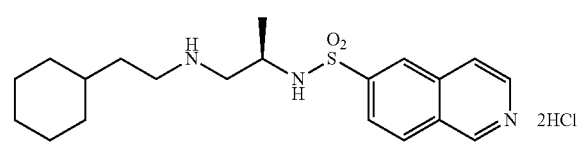 [SMILES: C[C@H](CNCCC1CCCCC1)NS(=O)(=O)c1ccc2cnccc2c1 ; "2HCl"]

296 mg of the title compound was obtained as a yellow solid (94%) from 263 mg of a free form synthesized according to the method described in Example 1.

$^1$H-NMR spectrum (D$_2$O, δ ppm): 0.74 (d, J=6.7 Hz, 3H), 0.78-0.89 (m, 2H), 0.98-1.16 (m, 3H), 1.18-1.27 (m, 1H), 1.43-1.61 (m, 7H), 2.87-3.11 (m, 4H), 3.65-3.76 (m, 1H), 8.19 (d, J=8.5 Hz, 1H), 8.43 (d, J=6.1 Hz, 1H), 8.53-8.59 (m, 2H), 8.69 (s, 1H), 9.65 (s, 1H).

Example 34

(R)—N-{1-(3-phenylpropylamino)propan-2-yl}isoquinoline-6-sulfonamide dihydrochloride

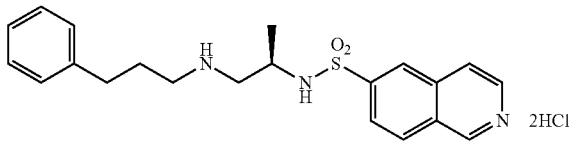 [SMILES: C[C@H](CNCCCc1ccccc1)NS(=O)(=O)c1ccc2cnccc2c1]

283 mg of the title compound was obtained as a white solid (72%) from 330 mg of a free form synthesized according to the method described in Example 1.

$^1$H-NMR spectrum (D$_2$O, δ ppm): 0.71 (d, J=6.7 Hz, 3H), 1.86-1.98 (m, 2H), 2.61 (t, J=7.3 Hz, 2H), 2.87-3.06 (m, 4H), 3.58-3.70 (m, 1H), 7.16-7.23 (m, 3H), 7.28 (t, J=7.3 Hz, 2H), 8.17 (dd, J=1.5, 8.9 Hz, 1H), 8.43 (d, J=6.7 Hz, 1H), 8.51-8.57 (m, 2H), 8.67 (s, 1H), 9.64 (s, 1H).

Example 35

(R)—N-{1-(4-phenylbutylamino)propan-2-yl}isoquinoline-6-sulfonamide dihydrochloride

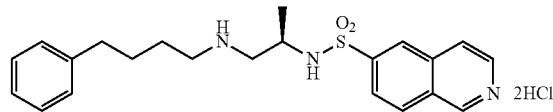 [SMILES: C[C@H](CNCCCCc1ccccc1)NS(=O)(=O)c1ccc2cnccc2c1]

290 mg of the title compound was obtained as a brown solid (85%) from 286 mg of a free form synthesized according to the method described in Example 1.

$^1$H-NMR spectrum (D$_2$O, δ ppm): 0.74 (d, J=6.7 Hz, 3H), 1.54-1.66 (m, 4H), 2.54-2.60 (m, 2H), 2.89-3.02 (m, 4H), 3.67 (s, 1H), 7.14-7.21 (m, 3H), 7.27 (t, J=7.3 Hz, 2H), 8.16 (d, J=9.2 Hz, 1H), 8.37 (d, J=6.1 Hz, 1H), 8.51 (d, J=8.5 Hz, 1H), 8.55 (d, J=6.1 Hz, 1H), 8.66 (s, 1H), 9.59 (s, 1H).

Example 36

(R)—N-[1-{2-(1H-indol-3-yl)ethylamino}propan-2-yl]isoquinoline-6-sulfonamide hydrochloride

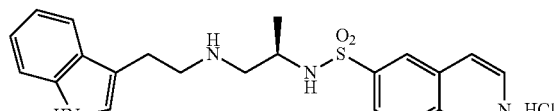

101 mg of the title compound was obtained as a white solid (61%) from 150 mg of a free form synthesized according to the method described in Example 1.

$^1$H-NMR spectrum (D$_2$O, δ ppm): 0.78 (d, J=6.7 Hz, 3H), 2.95-3.00 (m, 1H), 3.07-3.10 (m, 3H), 3.25-3.33 (m, 2H), 3.63 (br s, 1H), 7.12 (t, J=7.3 Hz, 1H), 7.18-7.23 (m, 2H), 7.45 (d, J=7.9 Hz, 1H), 7.57 (d, J=7.9 Hz, 1H), 8.01 (d, J=9.2 Hz, 1H), 8.10 (d, J=6.1 Hz, 1H), 8.33 (d, J=9.2 Hz, 1H), 8.48-8.50 (m, 2H), 9.34 (s, 1H).

Example 37

(S)—N-[1-{2-(1H-indol-3-yl)ethylamino}propan-2-yl]isoquinoline-6-sulfonamide hydrochloride

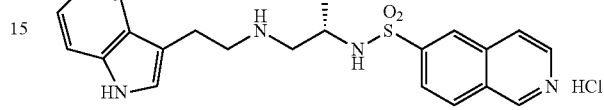

110 mg of the title compound was obtained as a yellow solid (65%) from 155 mg of a free form synthesized according to the method described in Example 1.

$^1$H-NMR spectrum (D$_2$O, δ ppm): 0.78 (d, J=6.7 Hz, 3H), 2.92-3.07 (m, 4H), 3.22 (t, J=7.0 Hz, 2H), 3.62-3.66 (m, 1H), 7.03-7.17 (m, 3H), 7.37 (dd, J=4.6, 7.0 Hz, 1H), 7.47 (t, J=6.4 Hz, 1H), 8.13 (d, J=8.5 Hz, 1H), 8.35 (d, J=6.1 Hz, 1H), 8.44-8.47 (m, 2H), 8.61 (s, 1H), 9.48 (s, 1H).

Example 38

(R)—N-{1-(2-chlorophenethylamino)propan-2-yl}isoquinoline-6-sulfonamide dihydrochloride

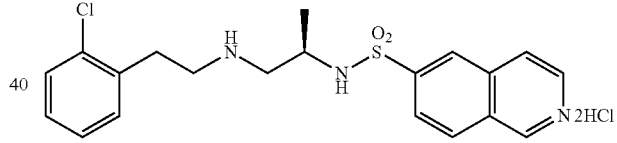

The title compound was synthesized according to the following Scheme 12:

Scheme 12

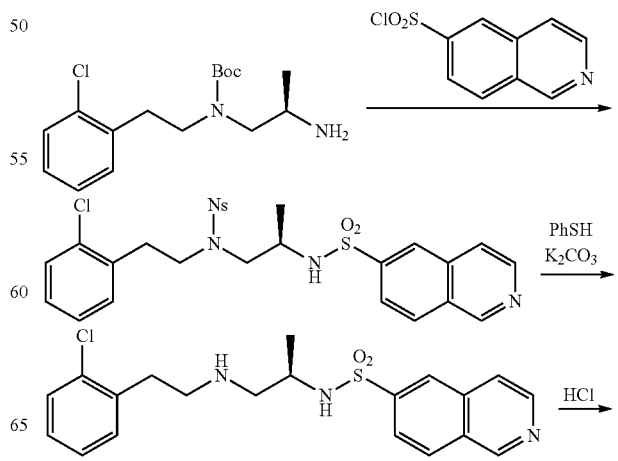

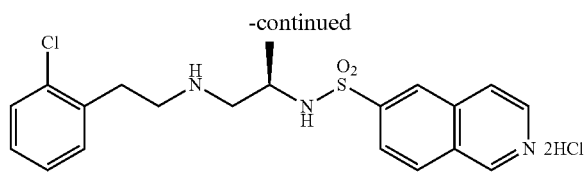

Step 1

Synthesis of (R)—N-[1-{N-(2-chlorophenethyl)-2-nitrophenylsulfonamido}propan-2-yl]isoquinoline-6-sulfonamide 0.3 mL of triethylamine and 280 mg of (R)—N-(2-aminopropyl)-N-(2-chlorophenethyl)-2-nitrobenzenesulfonamide prepared in Reference Example 6 were added with stirring at room temperature to a dichloromethane solution of isoquinoline-6-sulfonyl chloride prepared in Reference Example 1, and the mixture was then stirred for 6 hours. The reaction solution was washed with saturated saline and dried over anhydrous sodium sulfate. After filtration, the filtrate was concentrated under reduced pressure, and the obtained crude product was purified by silica gel column chromatography (hexane:ethyl acetate=1:3) to obtain 300 mg of the title compound (73%).

$^1$H-NMR spectrum (CDCl$_3$, δ ppm): 1.20 (d, J=6.7 Hz, 3H), 2.56-2.69 (m, 2H), 2.90-3.01 (m, 1H), 3.20-3.30 (m, 2H), 3.53-3.65 (m, 2H), 5.17 (d, J=6.7 Hz, 1H), 6.95 (dd, J=1.8, 7.3 Hz, 1H), 7.06-7.13 (m, 2H), 7.20 (t, J=4.6 Hz, 1H), 7.63-7.76 (m, 4H), 7.99-8.02 (m, 2H), 8.10 (d, J=8.5 Hz, 1H), 8.46 (s, 1H), 8.63 (d, J=5.5 Hz, 1H), 9.29 (s, 1H).

Step 2

Synthesis of (R)—N-{1-(2-chlorophenethylamino)propan-2-yl}isoquinoline-6-sulfonamide 0.1 mL of thiophenol was added to a suspension of 300 mg of (R)—N-[1-{N-(2-chlorophenethyl)-2-nitrophenylsulfonamido}propan-2-yl]isoquinoline-6-sulfonamide and 360 mg of potassium carbonate in 20 mL of acetonitrile, and the mixture was stirred at room temperature for 16 hours. 50 mL of water was added to the reaction solution, followed by extraction with ethyl acetate (50 mL×2). The organic layer was dried over anhydrous sodium sulfate. After filtration, the filtrate was concentrated under reduced pressure. The obtained crude product was purified by silica gel column chromatography (dichloromethane:methanol=10:1) to obtain 179 mg of the title compound as a white solid (87%).

$^1$H-NMR spectrum (CDCl$_3$, δ ppm): 1.12 (d, J=6.7 Hz, 3H), 1.49 (br s, 2H), 2.44-2.51 (m, 1H), 2.56-2.81 (m, 5H), 3.23-3.29 (m, 1H), 7.04-7.09 (m, 1H), 7.13-7.18 (m, 2H), 7.30-7.35 (m, 1H), 7.77 (d, J=5.5 Hz, 1H), 7.94 (dd, J=1.5, 8.9 Hz, 1H), 8.09 (d, J=8.5 Hz, 1H), 8.42 (s, 1H), 8.7 (d, J=8.5 Hz, 1H), 9.34 (s, 1H).

Step 3

Synthesis of (R)—N-{1-(2-chlorophenethylamino)propan-2-yl}isoquinoline-6-sulfonamide dihydrochloride 158 mg of the title compound was obtained as a yellow solid (74%) with reference to the method of Step 3 of Example 1 using 179 mg of (R)—N-{1-(2-chlorophenethylamino)propan-2-yl}isoquinoline-6-sulfonamide.

$^1$H-NMR spectrum (D$_2$O, δ ppm): 0.76 (d, J=6.6 Hz, 3H), 2.98-3.11 (m, 4H), 3.21-3.33 (m, 2H), 3.67-3.74 (m, 1H), 7.20-7.28 (m, 3H), 7.35-7.38 (m, 1H), 8.21 (d, J=8.5 Hz, 1H), 8.47 (d, J=6.1 Hz, 1H), 8.56-8.58 (m, 2H), 8.71 (s, 1H), 9.67 (s, 1H).

Compounds of Examples 39 to 50 were synthesized according to the method described in Example 38 from intermediates synthesized by the method described in Reference Example 6 using the compound of Reference Example 1 and the respective appropriate starting materials.

Example 39

(R)—N-{1-(4-chlorophenethylamino)propan-2-yl}isoquinoline-6-sulfonamide dihydrochloride

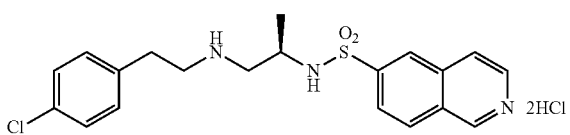 [SMILES: C[C@H](CNCCc1ccc(Cl)cc1)NS(=O)(=O)c1ccc2cnccc2c1 ; "2HCl"]

273 mg of the title compound was obtained as a yellow solid (84%) from 275 mg of a free form synthesized according to the method described in Example 38.

$^1$H-NMR spectrum (D$_2$O, δ ppm): 0.76 (d, J=6.7 Hz, 3H), 2.90-3.03 (m, 3H), 3.04-3.11 (m, 1H), 3.18-3.34 (m, 2H), 3.63-3.74 (m, 1H), 7.19 (d, J=7.9 Hz, 2H), 7.30 (d, J=7.9 Hz, 2H), 8.19 (d, J=8.5 Hz, 1H), 8.43 (d, J=6.1 Hz, 1H), 8.51-8.60 (m, 2H), 8.68 (s, 1H), 9.64 (s, 1H).

Example 40

(R)—N-[1-{2-(thiophen-2-yl)ethylamino}propan-2-yl]isoquinoline-6-sulfonamide hydrochloride

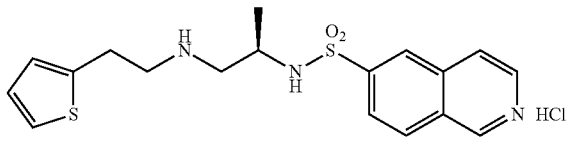 [SMILES: C[C@H](CNCCc1cccs1)NS(=O)(=O)c1ccc2cnccc2c1 ; Cl]

117 mg of the title compound was obtained as a white solid (76%) from 140 mg of a free form synthesized according to the method described in Example 38.

$^1$H-NMR spectrum (D$_2$O, δ ppm): 0.76 (d, J=6.7 Hz, 3H), 2.98 (dd, J=10.1, 13.1 Hz, 1H), 3.08 (dd, J=3.7, 12.8 Hz, 1H), 3.20-3.38 (m, 4H), 3.63-3.68 (m, 1H), 6.94 (d, J=3.1 Hz, 1H), 6.97 (t, J=4.3 Hz, 1H), 7.30 (d, J=4.9 Hz, 1H), 7.99-8.02 (m, 2H), 8.30 (d, J=8.5 Hz, 1H), 8.49-8.52 (m, 2H), 9.34 (s, 1H).

Example 41

(R)—N-[1-{2-(thiophen-3-yl)ethylamino}propan-2-yl]isoquinoline-6-sulfonamide hydrochloride

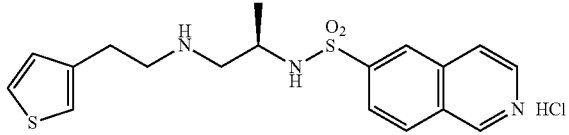 [SMILES: C[C@H](CNCCc1ccsc1)NS(=O)(=O)c1ccc2cnccc2c1 ; Cl]

20 mg of the title compound was obtained as a yellow solid (60%) from 30 mg of a free form synthesized according to the method described in Example 38.

¹H-NMR spectrum (D₂O, δ ppm): 0.69 (d, J=6.7 Hz, 3H), 2.89-3.03 (m, 4H), 3.20-3.28 (m, 2H), 3.56-3.60 (m, 1H), 6.96 (d, J=4.3 Hz, 1H), 7.14 (s, 1H), 7.36 (s, 1H), 7.86 (d, J=4.9 Hz, 1H), 7.89 (d, J=8.5 Hz, 1H), 8.19 (d, J=8.5 Hz, 1H), 8.39 (s, 1H), 8.45 (s, 1H), 9.22 (s, 1H).

Example 42

(R)—N-[1-{2-(pyridin-4-yl)ethylamino}propan-2-yl]isoquinoline-6-sulfonamide trihydrochloride

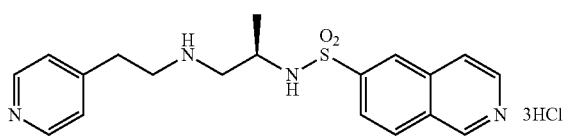 [SMILES: C[C@H](CNCCc1ccncc1)NS(=O)(=O)c1ccc2cnccc2c1 ; "3HCl"]

42 mg of the title compound was obtained as a gray solid (10%) from 320 mg of a free form synthesized according to the method described in Example 38.

¹H-NMR spectrum (D₂O, δ ppm): 0.79 (d, J=6.7 Hz, 3H), 3.08-3.21 (m, 2H), 3.38-3.44 (m, 2H), 3.46-3.59 (m, 2H), 3.77-3.81 (m, 1H), 7.99 (d, J=6.7 Hz, 2H), 8.26-8.28 (m, 1H), 8.54 (d, J=6.1 Hz, 1H), 8.61-8.64 (m, 2H), 8.70 (d, J=6.7 Hz, 2H), 8.78 (s, 1H), 9.74 (s, 1H).

Example 43

(R, E)-N-[1-{3-(4-bromophenyl)allylamino}propan-2-yl]isoquinoline-6-sulfonamide dihydrochloride

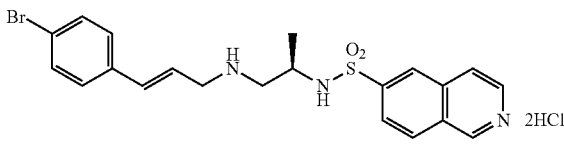 [SMILES: C[C@H](CNC/C=C/c1ccc(Br)cc1)NS(=O)(=O)c1ccc2cnccc2c1 ; "2HCl"]

120 mg of the title compound was obtained as a yellow solid from 120 mg of a free form (crude product) synthesized according to the method described in Example 38.

¹H-NMR spectrum (D₂O, δ ppm): 0.79 (d, J=6.7 Hz, 3H), 2.93 (dd, J=9.8, 13.4 Hz, 1H), 3.06 (dd, J=4.3, 13.4 Hz, 1H), 3.68-3.73 (m, 1H), 3.74-3.79 (m, 2H), 6.14 (dt, J=7.3, 15.5 Hz, 1H), 6.67 (d, J=15.9 Hz, 1H), 7.24 (d, J=7.9 Hz, 2H), 7.44 (d, J=7.3 Hz, 2H), 8.17 (d, J=8.5 Hz, 1H), 8.37 (d, J=6.1 Hz, 1H), 8.50 (d, J=9.2 Hz, 1H), 8.53 (d, J=6.7 Hz, 1H), 8.67 (s, 1H), 9.58 (s, 1H).

Example 44

(R, E)-N-{1-(cinnamylamino)propan-2-yl}isoquinoline-6-sulfonamide dihydrochloride

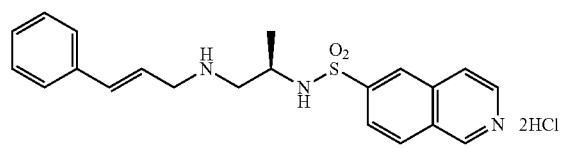 [SMILES: C[C@H](CNC/C=C/c1ccccc1)NS(=O)(=O)c1ccc2cnccc2c1 ; "2HCl"]

23 mg of the title compound was obtained as a white solid (77%) from 25 mg of a free form synthesized according to the method described in Example 38.

¹H-NMR spectrum (D₂O, δ ppm): 0.74 (d, J=3.4 Hz, 3H), 2.89 (dd, J=9.8, 12.8 Hz, 1H), 3.03 (dd, J=4.3, 12.8 Hz, 1H), 3.64-3.68 (m, 1H), 3.74 (t, J=6.1 Hz, 2H), 6.10 (dt, J=7.2, 1.61 Hz, 1H), 6.68 (d, J=15.9 Hz, 1H), 7.25-7.34 (m, 5H), 8.10 (d, J=9.2 Hz, 1H), 8.26 (s, 1H), 8.41-8.49 (m, 2H), 8.62 (d, J=8.5 Hz, 1H), 9.47 (s, 1H).

Example 45

(R)—N-{1-(2-phenoxyethylamino)propan-2-yl}isoquinoline-6-sulfonamide dihydrochloride

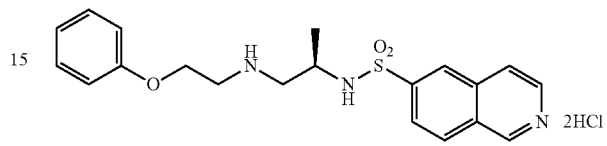

139 mg of the title compound was obtained as a yellow solid (77%) from 150 mg of a free form synthesized according to the method described in Example 38.

¹H-NMR spectrum (D₂O, δ ppm): 0.81 (d, J=6.7 Hz, 3H), 3.03 (dd, J=10.4, 12.8 Hz, 1H), 3.15 (dd, 3.7, 13.4 Hz, 1H), 3.40-3.54 (m, 2H), 3.73-3.80 (m, 1H), 4.20 (t, J=5.0 Hz, 2H), 6.86 (d, J=8.6 Hz, 2H), 6.98 (t, J=7.1 Hz, 1H), 7.27 (t, J=7.7 Hz, 2H), 8.19 (d, J=8.5 Hz, 1H), 8.41 (d, J=6.7 Hz, 1H), 8.51-8.53 (m, 2H), 8.68 (s, 1H), 9.58 (s, 1H).

Example 46

(R)—N-[1-{(2-(naphthalen-1-yl)ethylamino}propan-2-yl]isoquinoline-6-sulfonamide hydrochloride

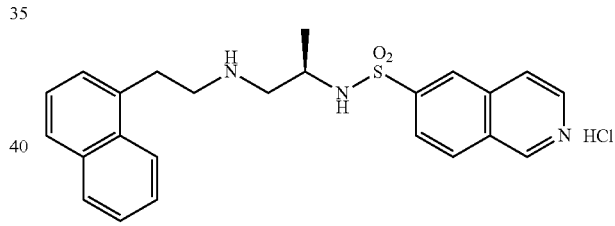

27 mg of the title compound was obtained as a white solid (62%) from 40 mg of a free form synthesized according to the method described in Example 38.

¹H-NMR spectrum (D₂O, δ ppm): 0.79 (d, J=6.7 Hz, 3H), 2.98 (dd, J=10.4, 12.8 Hz, 1H), 3.07 (dd, J=3.7, 13.4 Hz, 1H), 3.30-3.42 (m, 4H), 3.61-3.64 (m, 1H), 7.35 (d, J=7.3 Hz, 1H), 7.43 (t, J=7.6 Hz, 1H), 7.57 (dt, J=7.1, 14.5 Hz, 2H), 7.84 (t, J=8.5 Hz, 2H), 7.92 (t, J=10.1 Hz, 2H), 7.98 (d, J=8.5 Hz, 1H), 8.19 (d, J=8.5 Hz, 1H), 8.41 (s, 1H), 8.45 (d, J=6.1 Hz, 1H), 9.17 (s, 1H).

Example 47

(R)—N-{1-(prop-2-yn-1-ylamino)propan-2-yl}isoquinoline-6-sulfonamide dihydrochloride

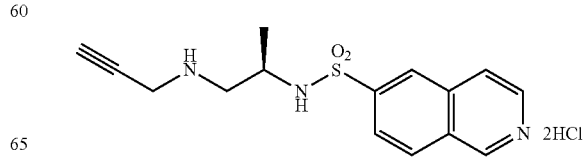

50 mg of the title compound was obtained as a pale yellow solid (50%) from 80 mg of a free form synthesized according to the method described in Example 38.

$^1$H-NMR spectrum (D$_2$O, δ ppm): 0.72 (d, J=7.0 Hz, 3H), 2.90 (s, 1H), 3.03 (dd, J=10.8, 13.7 Hz, 1H), 3.19 (dd, J=3.8, 13.2 Hz, 1H), 3.65-3.69 (m, 1H), 3.89 (d, J=2.1 Hz, 2H), 8.20 (d, J=8.4 Hz, 1H), 8.46 (t, J=7.0 Hz, 1H), 8.55-8.57 (m, 2H), 8.71 (s, 1H), 9.67 (s, 1H).

Example 48

N—[(R)-1-{(S)-2-methoxy-2-phenylethylamino}propan-2-yl]isoquinoline-6-sulfonamide hydrochloride

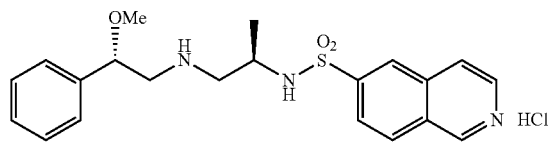 [SMILES: CO[C@H](CNC[C@@H](C)NS(=O)(=O)c1ccc2cnccc2c1)c1ccccc1 ; Cl]

225 mg of the title compound was obtained as an orange solid (90%) from 229 mg of a free form synthesized according to the method described in Example 38.

$^1$H-NMR spectrum (D$_2$O, δ ppm): 0.76 (d, J=6.7 Hz, 3H), 2.98 (t, J=11.6 Hz, 1H), 3.08 (dd, J=3.7, 13.4 Hz, 1H), 3.12-3.24 (m, 5H), 3.63-3.67 (m, 1H), 4.52 (dd, J=3.7, 9.8 Hz, 1H), 7.30 (d, J=6.7 Hz, 2H), 7.36-7.40 (m, 3H), 7.87 (d, J=6.1 Hz, 1H), 7.93 (d, J=8.5 Hz, 1H), 8.22 (d, J=8.5 Hz, 1H), 8.43 (s, 1H), 8.47 (d, J=6.1 Hz, 1H), 9.23 (s, 1H).

Example 49

(R)—N-[1-{2-(pyridin-3-yl)ethylamino}propan-2-yl]isoquinoline-6-sulfonamide hydrochloride

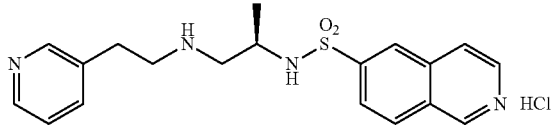 [SMILES: C[C@H](CNCCc1cccnc1)NS(=O)(=O)c1ccc2cnccc2c1 ; Cl]

480 mg of the title compound was obtained as a pale yellow solid (82%) from 532 mg of a free form synthesized according to the method described in Example 38.

$^1$H-NMR spectrum (D$_2$O, δ ppm): 0.77 (d, J=7.0 Hz, 3H), 2.95-3.02 (m, 3H), 3.08 (dd, J=4.0, 13.0 Hz, 1H), 3.21-3.32 (m, 2H), 3.64-3.68 (m, 1H), 7.38 (br s, 1H), 7.70 (d, J=8.0 Hz, 1H), 7.91 (d, J=5.5 Hz, 1H), 7.95 (dd, J=2.0, 8.5 Hz, 1H), 8.25 (d, J=9.0 Hz, 1H), 8.35-8.40 (m, 2H), 8.46 (s, 1H), 8.50 (br s, 1H), 9.26 (br s, 1H).

Example 50

N—[(R)-1-{(R)-3-hydroxy-3-phenylpropylamino}propan-2-yl]isoquinoline-6-sulfonamide hydrochloride

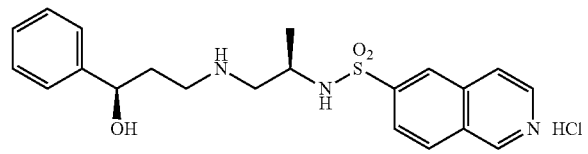 [SMILES: C[C@H](CNCC[C@@H](O)c1ccccc1)NS(=O)(=O)c1ccc2cnccc2c1 ; Cl]

46 mg of the title compound was obtained as a white solid (60%) from 90 mg of a free form synthesized according to the method described in Example 38.

$^1$H-NMR spectrum (D$_2$O, δ ppm): 0.71 (d, J=6.7 Hz, 3H), 2.05 (t, J=7.6 Hz, 2H), 2.90 (t, J=11.6 Hz, 1H), 2.95-3.03 (m, 2H), 3.16-3.21 (m, 1H), 3.57-3.63 (m, 1H), 4.79 (t, J=6.4 Hz, 1H), 7.28-7.38 (m, 5H), 7.95 (d, J=6.7 Hz, 2H), 8.27 (d, J=9.2 Hz, 1H), 8.46 (s, 1H), 8.49 (d, J=6.1 Hz, 1H), 9.29 (s, 1H).

A compound of Example 51 was synthesized according to the method described in Example 38 from 5-bromoisoquinoline-6-sulfonyl chloride obtained by the same approach as in Reference Example 1 and an intermediate synthesized for obtaining the compound of Example 49.

Example 51

(R)-5-bromo-N-[1-{2-(pyridin-3-yl)ethylamino}propan-2-yl]isoquinoline-6-sulfonamide hydrochloride

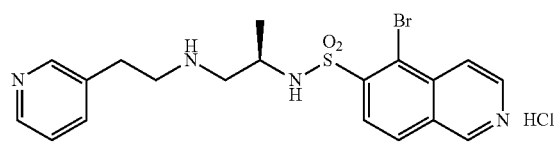 [SMILES: C[C@H](CNCCc1cccnc1)NS(=O)(=O)c1ccc2cnccc2c1Br ; Cl]

166 mg of the title compound was obtained as a pale yellow solid (80%) from 191 mg of a free form synthesized according to the method described in Example 38.

$^1$H-NMR spectrum (D$_2$O, δ ppm): 0.82 (d, J=6.5 Hz, 3H), 3.01-3.10 (m, 4H), 3.28-3.40 (m, 2H), 3.62-3.66 (m, 1H), 7.51 (dd, J=5.0, 8.0 Hz, 1H), 7.91 (d, J=8.5 Hz, 1H), 8.16-8.19 (m, 3H), 8.44-8.46 (m, 2H), 8.54 (d, J=6.5 Hz, 1H), 9.21 (s, 1H).

Compounds of Examples 52 to 75 were synthesized according to the method described in Example 1 from intermediates synthesized by the method described in Reference Example 3 using the compound of Reference Example 1 and the respective appropriate starting materials.

Example 52

(R)—N-{1-(3-fluorophenethylamino)propan-2-yl}isoquinoline-6-sulfonamide hydrochloride

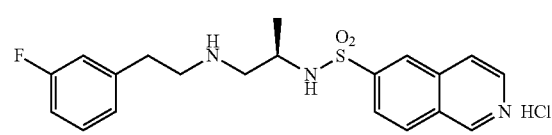 [SMILES: C[C@H](CNCCc1cccc(F)c1)NS(=O)(=O)c1ccc2cnccc2c1 ; Cl]

270 mg of the title compound was obtained as a white solid (78%) from 314 mg of a free form synthesized according to the method described in Example 1.

$^1$H-NMR spectrum (D$_2$O, δ ppm): 0.71 (d, J=6.5 Hz, 3H), 2.88-2.93 (m, 3H), 3.01 (dd, J=4.0, 13.0 Hz, 1H), 3.18-3.24 (m, 2H), 3.57-3.61 (m, 1H), 6.93-6.99 (m, 3H), 7.25-7.29 (m, 1H), 7.86 (d, J=6.0 Hz, 1H), 7.90 (d, J=9.0 Hz, 1H), 8.20 (d, J=8.5 Hz, 1H), 8.41 (s, 1H), 8.45 (d, J=6.0 Hz, 1H), 9.21 (s, 1H).

Example 53

(R)—N-{1-(4-fluorophenethylamino)propan-2-yl}isoquinoline-6-sulfonamide hydrochloride

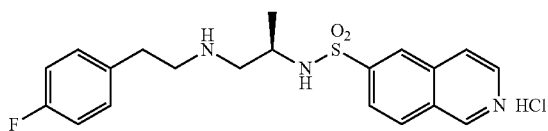 [SMILES: C[C@H](CNCCc1ccc(F)cc1)NS(=O)(=O)c1ccc2cnccc2c1 ; Cl]

106 mg of the title compound was obtained as a light brown solid (60%) from 160 mg of a free form synthesized according to the method described in Example 1.

$^1$H-NMR spectrum (D$_2$O, δ ppm): 0.71 (d, J=6.5 Hz, 3H), 2.91-2.95 (m, 3H), 3.03 (dd, J=3.5, 13.0 Hz, 1H), 3.15-3.27 (m, 2H), 3.58-3.63 (m, 1H), 6.98-7.02 (m, 2H), 7.17-7.19 (m, 2H), 7.97 (d, J=8.5 Hz, 1H), 8.03 (br s, 1H), 8.28 (d, J=9.5 Hz, 1H), 8.41-8.50 (m, 2H), 9.41 (br s, 1H).

Example 54

(R)—N-{1-(3-chlorophenethylamino)propan-2-yl}isoquinoline-6-sulfonamide hydrochloride

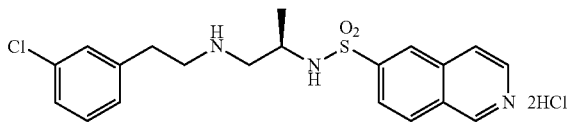 [SMILES: C[C@H](CNCCc1cccc(Cl)c1)NS(=O)(=O)c1ccc2cnccc2c1 ; "2HCl"]

177 mg of the title compound was obtained as a white solid (73%) from 220 mg of a free form synthesized according to the method described in Example 1.

$^1$H-NMR spectrum (D$_2$O, δ ppm): 0.73 (d, J=6.5 Hz, 3H), 2.91-2.96 (m, 3H), 3.04 (dd, J=4.0, 13.0 Hz, 1H), 3.19-3.23 (m, 2H), 3.59-3.65 (m, 1H), 7.11 (br s, 1H), 7.23-7.25 (m, 3H), 7.89 (d, J=5.0 Hz, 1H), 7.92 (d, J=8.5 Hz, 1H), 8.22 (d, J=8.5 Hz, 1H), 8.43 (s, 1H), 8.47 (br s, 1H), 9.27 (br s, 1H).

Example 55

(R)—N-{1-(4-bromophenethylamino)propan-2-yl}isoquinoline-6-sulfonamide hydrochloride

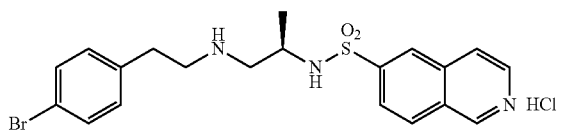 [SMILES: C[C@H](CNCCc1ccc(Br)cc1)NS(=O)(=O)c1ccc2cnccc2c1 ; Cl]

199 mg of the title compound was obtained as a white solid (86%) from 214 mg of a free form synthesized according to the method described in Example 1.

$^1$H-NMR spectrum (D$_2$O, δ ppm): 0.79 (d, J=6.7 Hz, 3H), 2.91-3.03 (m, 3H), 3.09-3.12 (m, 1H), 3.23-3.34 (m, 2H), 3.68-3.75 (m, 1H), 7.15 (d, J=8.5 Hz, 2H), 7.47 (d, J=8.5 Hz, 2H), 8.21 (dd, J=1.5, 8.9 Hz, 1H), 8.44 (d, J=6.7 Hz, 1H), 8.56 (d, J=9.2 Hz, 1H), 8.60 (d, J=6.7 Hz, 1H), 8.70 (s, 1H), 9.66 (s, 1H).

Example 56

(R)—N-{1-(2-methylphenethylamino)propan-2-yl}isoquinoline-6-sulfonamide hydrochloride

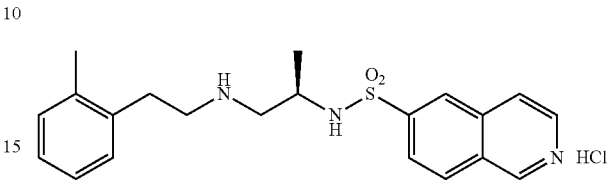

236 mg of the title compound was obtained as a white solid (81%) from 265 mg of a free form synthesized according to the method described in Example 1.

$^1$H-NMR spectrum (D$_2$O, δ ppm): 0.76 (d, J=7.5 Hz, 3H), 2.22 (s, 3H), 2.92-2.99 (m, 3H), 3.07 (dd, J=4.0, 13.0 Hz, 1H), 3.12-3.20 (m, 2H), 3.63-3.65 (m, 1H), 7.10-7.18 (m, 4H), 7.88 (d, J=6.0 Hz, 1H), 7.92 (d, J=8.5 Hz, 1H), 8.21 (d, J=9.0 Hz, 1H), 8.42-8.47 (m, 2H), 9.23 (s, 1H).

Example 57

(R)—N-{1-(3-methylphenethylamino)propan-2-yl}isoquinoline-6-sulfonamide hydrochloride

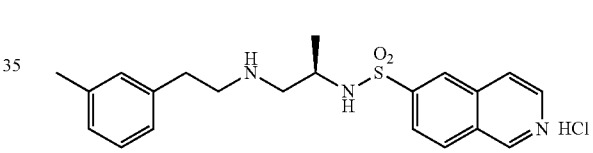

185 mg of the title compound was obtained as a white solid (63%) from 267 mg of a free form synthesized according to the method described in Example 1.

$^1$H-NMR spectrum (D$_2$O, δ ppm): 0.76 (d, J=7.5 Hz, 3H), 2.21 (s, 3H), 2.86-2.93 (m, 3H), 3.02 (dd, J=3.5, 12.0 Hz, 1H), 3.15-3.26 (m, 2H), 3.57-3.61 (m, 1H), 6.99 (d, J=7.5 Hz, 1H), 7.04 (s, 1H), 7.07 (d, J=8.0 Hz, 1H), 7.18 (t, J=7.5 Hz, 1H), 7.91-7.93 (m, 2H), 8.23 (d, J=8.5 Hz, 1H), 8.43 (s, 1H), 8.48 (br s, 1H), 9.27 (br s, 1H).

Example 58

(R)—N-{1-(4-methylphenethylamino)propan-2-yl}isoquinoline-6-sulfonamide hydrochloride

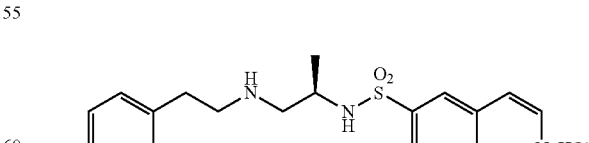

55 mg of the title compound was obtained as a white solid (64%) from 78 mg of a free form synthesized according to the method described in Example 1.

$^1$H-NMR spectrum (D$_2$O, δ ppm): 0.72 (d, J=7.0 Hz, 3H), 2.21 (s, 3H), 2.89-2.95 (m, 3H), 3.03 (dd, J=3.5, 12.0 Hz, 1H), 3.15-3.27 (m, 2H), 3.57-3.61 (m, 1H), 7.09 (d, J=7.0 Hz, 2H), 7.13 (d, J=7.0 Hz, 2H), 7.96 (d, J=8.5 Hz, 1H), 8.00 (br s, 1H), 8.27 (d, J=8.5 Hz, 1H), 8.46 (s, 1H), 8.56 (br s, 1H), 9.39 (br s, 1H).

Example 59

(R)—N-{1-(4-nitrophenethylamino)propan-2-yl}isoquinoline-6-sulfonamide hydrochloride

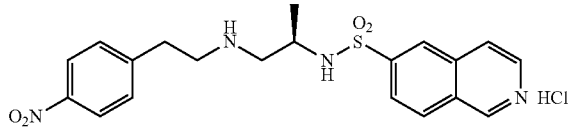 [SMILES: C[C@H](CNCCc1ccc([N+](=O)[O-])cc1)NS(=O)(=O)c1ccc2cnccc2c1 ; Cl]

55 mg of the title compound was obtained as a brown solid (76%) from 140 mg of a free form synthesized according to the method described in Example 1.
$^1$H-NMR spectrum (D$_2$O, δ ppm): 0.77 (d, J=6.7 Hz, 3H), 2.97-3.02 (m, 1H), 3.09-3.11 (m, 3H), 3.26-3.36 (m, 2H), 3.66 (br s, 1H), 7.41 (d, J=8.5 Hz, 2H), 7.94-7.97 (m, 2H), 8.11 (d, J=7.9 Hz, 2H), 8.25 (d, J=8.5 Hz, 1H), 8.45 (s, 1H), 8.48 (d, J=6.1 Hz, 1H), 9.27 (s, 1H).

Example 60

(R)—N-{1-(4-trifluoromethylphenethylamino)propan-2-yl}isoquinoline-6-sulfonamide hydrochloride

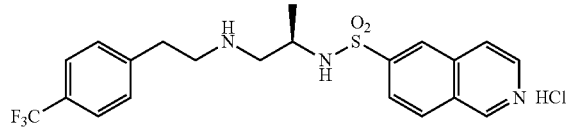 [SMILES: C[C@H](CNCCc1ccc(C(F)(F)F)cc1)NS(=O)(=O)c1ccc2cnccc2c1 ; Cl]

315 mg of the title compound was obtained as a white solid (75%) from 383 mg of a free form synthesized according to the method described in Example 1.
$^1$H-NMR spectrum (D$_2$O, δ ppm): 0.70 (d, J=6.5 Hz, 3H), 2.90-3.04 (m, 4H), 3.20-3.26 (m, 2H), 3.56-3.62 (m, 1H), 7.31 (d, J=8.0 Hz, 2H), 7.55 (d, J=8.0 Hz, 2H), 7.92-7.95 (m, 2H), 8.23 (d, J=8.5 Hz, 1H), 8.42-8.44 (m, 2H), 9.27 (s, 1H).

Example 61

(R)—N-{1-(cyclohexylamino)propan-2-yl}isoquinoline-6-sulfonamide hydrochloride

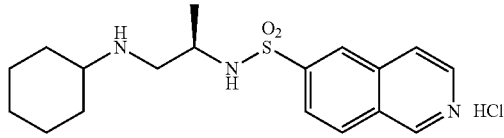 [SMILES: C[C@H](CNC1CCCCC1)NS(=O)(=O)c1ccc2cnccc2c1 ; Cl]

223 mg of the title compound was obtained as a pale yellow solid (83%) from 243 mg of a free form synthesized according to the method described in Example 1.
$^1$H-NMR spectrum (D$_2$O, δ ppm): 0.77 (d, J=6.0 Hz, 3H), 1.04-1.27 (m, 5H), 1.54-1.56 (m, 1H), 1.68-1.75 (m, 2H), 1.89-1.93 (m, 2H), 2.88 (dd, J=10.0, 13.0 Hz, 1H), 2.98-3.02 (m, 1H), 3.05 (dd, J=3.5, 12.0 Hz, 1H), 3.60-3.65 (m, 1H), 7.92-7.97 (m, 2H), 8.26 (d, J=9.0 Hz, 1H), 8.45 (m, 2H), 9.28 (s, 1H).

Example 62

(R)—N-{1-(2,3-dihydro-1H-inden-2-ylamino)propan-2-yl}isoquinoline-6-sulfonamide hydrochloride

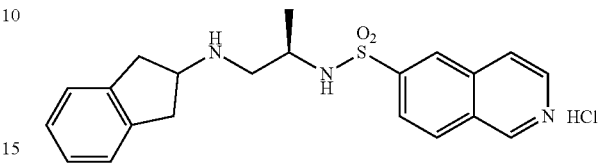

260 mg of the title compound was obtained as a white solid (63%) from 375 mg of a free form synthesized according to the method described in Example 1.
$^1$H-NMR spectrum (D$_2$O, δ ppm): 0.75 (d, J=7.0 Hz, 3H), 2.89-3.10 (m, 4H), 3.27-3.31 (m, 2H), 3.58-3.65 (m, 1H), 3.99-4.02 (m, 1H), 7.15-7.18 (m, 4H), 7.88 (d, J=5.5 Hz, 1H), 7.91 (d, J=9.0 Hz, 1H), 8.20 (d, J=9.0 Hz, 1H), 8.42 (s, 1H), 8.45 (d, J=5.5 Hz, 1H), 9.22 (s, 1H).

Example 63

(R)—N-[1-{2-(5-chloro-1H-indol-3-yl)ethylamino}propan-2-yl]isoquinoline-6-sulfonamide hydrochloride

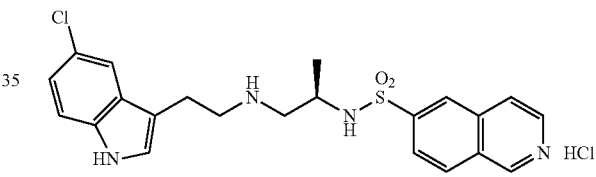

108 mg of the title compound was obtained as a yellow solid (89%) from 112 mg of a free form synthesized according to the method described in Example 1.
$^1$H-NMR spectrum (D$_2$O, δ ppm): 0.73 (d, J=7.0 Hz, 3H), 2.90-3.05 (m, 4H), 3.19-3.22 (m, 2H), 3.55-3.60 (m, 1H), 7.11 (d, J=9.0 Hz, 1H), 7.16 (s, 1H), 7.33 (d, J=9.0 Hz, 1H), 7.51 (s, 1H), 7.93 (d, J=8.5 Hz, 1H), 7.97 (d, J=5.5 Hz, 1H), 8.24 (d, J=9.0 Hz, 1H), 8.42-8.43 (m, 2H), 9.23 (s, 1H).

Example 64

(R)—N-[1-{2-(1-methyl-1H-indol-3-yl)ethylamino}propan-2-yl]isoquinoline-6-sulfonamide hydrochloride

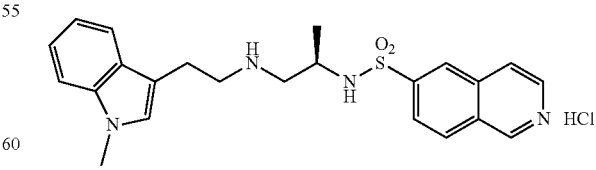

43 mg of the title compound was obtained as a yellow solid (81%) from 51 mg of a free form synthesized according to the method described in Example 1.
$^1$H-NMR spectrum (D$_2$O, δ ppm): 0.72 (d, J=6.1 Hz, 3H), 2.88-3.03 (m, 4H), 3.20 (t, J=7.0 Hz, 2H), 3.56 (br s, 1H), 3.63

(s, 3H), 7.01 (s, 1H), 7.07 (t, J=7.3 Hz, 1H), 7.20 (t, J=7.6 Hz, 1H), 7.35 (d, J=7.9 Hz, 1H), 7.50 (d, J=7.9 Hz, 1H), 7.97 (d, J=9.2 Hz, 1H), 8.08 (d, J=6.1 Hz, 1H), 8.29 (d, J=9.2 Hz, 1H), 8.42 (d, J=6.1 Hz, 1H), 8.46 (s, 1H), 9.28 (s, 1H).

Example 65

(R)—N-[1-{(2-(quinolin-4-yl)ethylamino}propan-2-yl]isoquinoline-6-sulfonamide hydrochloride

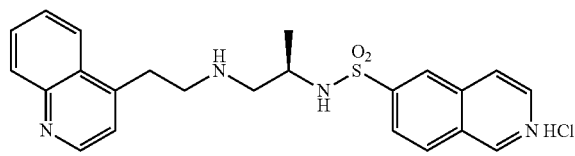

33 mg of the title compound was obtained as a white solid (72%) from 42 mg of a free form synthesized according to the method described in Example 1.

$^1$H-NMR spectrum (D$_2$O, δ ppm): 0.75 (d, J=6.7 Hz, 3H), 2.99 (t, J=11.9 Hz, 1H), 3.08 (d, J=9.8 Hz, 1H), 3.33-3.52 (m, 4H), 3.63 (br s, 1H), 7.45 (d, J=4.9 Hz, 1H), 7.70 (t, J=7.9 Hz, 1H), 7.78 (d, J=6.1 Hz, 1H), 7.82-7.87 (m, 2H), 7.97 (d, J=8.5 Hz, 1H), 8.06 (d, J=8.5 Hz, 1H), 8.12 (d, J=8.5 Hz, 1H), 8.33-8.35 (m, 2H), 8.70 (d, J=4.9 Hz, 1H), 9.07 (s, 1H).

Example 66

(R)—N-[1-{2-(furan-2-yl)ethylamino}propan-2-yl]isoquinoline-6-sulfonamide hydrochloride

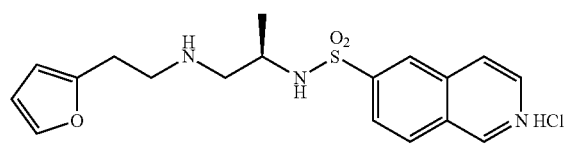

136 mg of the title compound was obtained as a white solid (90%) from 137 mg of a free form synthesized according to the method described in Example 1.

$^1$H-NMR spectrum (D$_2$O, δ ppm): 0.68 (d, J=7.0 Hz, 3H), 2.88-3.05 (m, 4H), 3.18-3.35 (m, 2H), 3.55-3.65 (m, 1H), 6.15 (d, J=2.0 Hz, 1H), 6.30 (s, 1H), 7.36 (s, 1H), 7.90-7.94 (m, 2H), 8.23 (d, J=8.5 Hz, 1H), 8.43-8.47 (m, 2H), 9.26 (s, 1H).

Example 67

(R)—N-[1-{2-(furan-3-yl)ethylamino}propan-2-yl]isoquinoline-6-sulfonamide hydrochloride

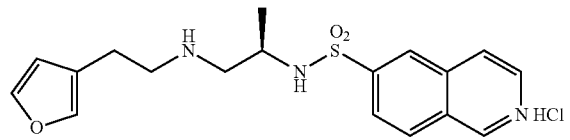

122 mg of the title compound was obtained as a light brown solid (90%) from 123 mg of a free form synthesized according to the method described in Example 1.

$^1$H-NMR spectrum (D$_2$O, δ ppm): 0.69 (d, J=6.7 Hz, 3H), 2.76 (t, J=7.6 Hz, 2H), 2.86-2.95 (m, 1H), 2.97-3.05 (m, 1H), 3.10-3.25 (m, 2H), 3.55-3.65 (m, 1H), 6.33 (s, 1H), 7.33 (s, 1H), 7.39 (s, 1H), 7.91-7.99 (m, 2H), 8.26 (d, J=8.5 Hz, 1H), 8.44-8.47 (m, 2H), 9.29 (s, 1H).

Example 68

(R)—N-[1-{2-(1H-1,2,4-triazol-1-yl)ethylamino}propan-2-yl]isoquinoline-6-sulfonamide hydrochloride

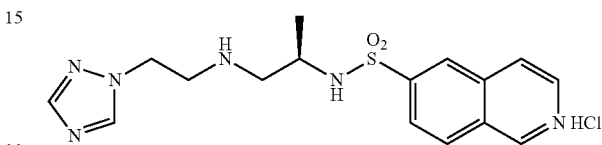

25 mg of the title compound was obtained as a white solid (66%) from 34 mg of a free form synthesized according to the method described in Example 1.

$^1$H-NMR spectrum (D$_2$O, δ ppm): 0.69 (d, J=6.7 Hz, 3H), 2.99 (t, J=11.9 Hz, 1H), 3.08 (dd, J=3.7, 12.8 Hz, 1H), 3.47-3.52 (m, 1H), 3.57-3.68 (m, 2H), 4.59 (t, J=5.5 Hz, 2H), 8.01 (s, 1H), 8.03 (d, J=8.5 Hz, 1H), 8.14 (d, J=6.1 Hz, 1H), 8.37 (d, J=8.5 Hz, 1H), 8.42 (s, 1H), 8.50 (d, J=6.1 Hz, 1H), 8.54 (s, 1H), 9.43 (s, 1H).

Example 69

(R)—N-{1-(4-aminophenethylamino)propan-2-yl}isoquinoline-6-sulfonamide trihydrochloride

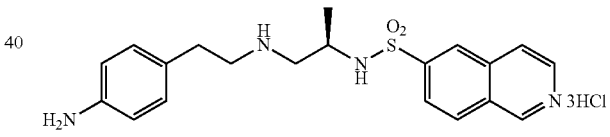

79 mg of the title compound was obtained as a white solid (65%) from 107 mg of a free form synthesized according to the method described in Example 1.

$^1$H-NMR spectrum (D$_2$O, δ ppm): 0.75 (d, J=6.7 Hz, 3H), 2.99-3.13 (m, 4H), 3.25-3.40 (m, 2H), 3.69-3.76 (m, 1H), 7.32 (d, J=8.5 Hz, 2H), 7.39 (d, J=7.9 Hz, 2H), 8.22 (d, J=8.5 Hz, 1H), 8.46 (d, J=6.7 Hz, 1H), 8.57-8.60 (m, 2H), 8.72 (s, 1H), 9.68 (s, 1H).

Example 70

(R)—N-{1-(4-acetamidephenethylamino)propan-2-yl}isoquinoline-6-sulfonamide hydrochloride

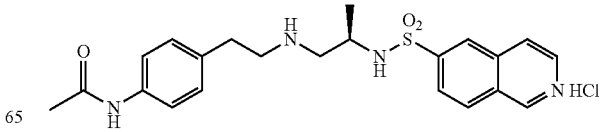

18 mg of the title compound was obtained as a pale yellow solid (61%) from 27 mg of a free form synthesized according to the method described in Example 1.

$^1$H-NMR spectrum (D$_2$O, δ ppm): 0.73 (d, J=6.5 Hz, 3H), 2.05 (s, 3H), 2.86-3.00 (m, 3H), 3.05 (dd, J=4.0, 13.0 Hz, 1H), 3.16-3.30 (m, 2H), 3.59-3.68 (m, 1H), 7.17 (d, J=7.5 Hz, 2H), 7.26 (d, J=8.5 Hz, 2H), 8.07 (d, J=8.5 Hz, 1H), 8.21 (d, J=5.5 Hz, 1H), 8.39 (d, J=8.5 Hz, 1H), 8.51 (d, J=6.0 Hz, 1H), 8.55 (s, 1H), 9.47 (s, 1H).

Example 71

(R)—N-{1-(4-dimethylaminophenethylamino)propan-2-yl}isoquinoline-6-sulfonamide hydrochloride

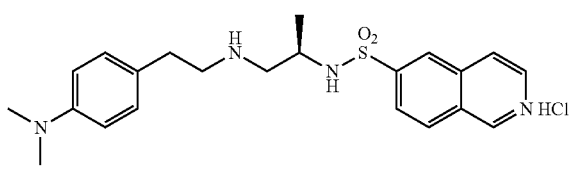

18 mg of the title compound was obtained as a light brown solid (80%) from 27 mg of a free form synthesized according to the method described in Example 1.

$^1$H-NMR spectrum (D$_2$O, δ ppm): 0.72 (d, J=7.0 Hz, 3H), 2.75 (s, 6H), 2.80-2.95 (m, 3H), 3.02 (dd, J=3.5, 12.5 Hz, 1H), 3.12-3.25 (m, 2H), 3.53-3.62 (m, 1H), 6.91 (d, J=8.5 Hz, 2H), 7.12 (d, J=8.5 Hz, 2H), 7.87 (d, J=5.5 Hz, 1H), 7.91 (dd, J=2.0, 8.5 Hz, 1H), 8.21 (d, J=8.5 Hz, 1H), 8.41 (s, 1H), 8.46 (d, J=5.5 Hz, 1H), 9.23 (s, 1H).

Example 72

(R)—N-{1-(4-ureidophenethylamino)propan-2-yl}isoquinoline-6-sulfonamide hydrochloride

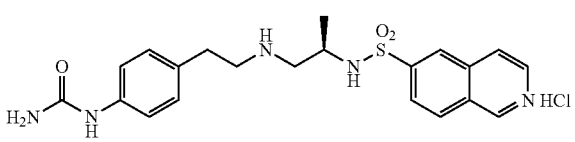

93 mg of the title compound was obtained as a yellow solid (81%) from 106 mg of a free form synthesized according to the method described in Example 1.

$^1$H-NMR spectrum (D$_2$O, δ ppm): 0.74 (d, J=7.0 Hz, 3H), 2.90-3.00 (m, 3H), 3.06 (dd, J=4.0, 13.5 Hz, 1H), 3.18-3.33 (m, 2H), 3.53-3.58 (m, 1H), 3.60-3.74 (m, 4H), 7.15-7.23 (m, 4H), 8.21 (d, J=8.5 Hz, 1H), 8.48 (d, J=7.0 Hz, 1H), 8.52-8.62 (m, 2H), 8.71 (s, 1H), 9.69 (s, 1H).

Example 73

(R)—N-{1-(2-cyanoethylamino)propan-2-yl}isoquinoline-6-sulfonamide hydrochloride

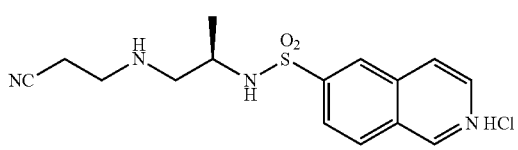

74 mg of the title compound was obtained as a white solid (80%) from 83 mg of a free form synthesized according to the method described in Example 1.

$^1$H-NMR spectrum (D$_2$O, δ ppm): 0.68 (d, J=6.7 Hz, 3H), 2.92-3.00 (m, 3H), 3.09 (dd, J=3.4, 13.1 Hz, 1H), 3.32-3.44 (m, 2H), 3.64 (br s, 1H), 7.98 (d, J=8.5 Hz, 1H), 8.02 (d, J=5.5 Hz, 1H), 8.29 (d, J=8.5 Hz, 1H), 8.47-8.49 (m, 2H), 9.33 (s, 1H).

Example 74

(R)—N-[1-{2-(1H-indol-2-yl)ethylamino}propan-2-yl]isoquinoline-6-sulfonamide hydrochloride

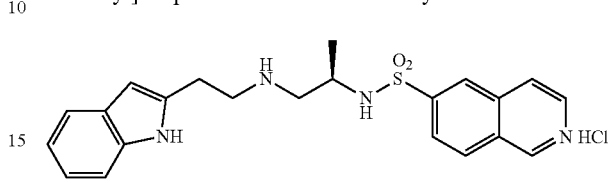

27 mg of the title compound was obtained as a pale yellow solid (70%) from 35 mg of a free form synthesized according to the method described in Example 1.

$^1$H-NMR spectrum (D$_2$O, δ ppm): 0.72 (d, J=6.7 Hz, 3H), 2.96 (d, J=10.4 Hz, 1H), 3.04-3.12 (m, 3H), 3.34 (q, J=6.7 Hz, 2H), 3.53-3.62 (m, 1H), 6.28 (s, 1H), 7.03 (t, J=7.6 Hz, 1H), 7.11 (t, J=7.6 Hz, 1H), 7.36 (d, J=8.5 Hz, 1H), 7.50 (d, J=7.9 Hz, 1H), 7.87-7.92 (m, 2H), 8.20 (d, J=8.5 Hz, 1H), 8.42-8.44 (m, 2H), 9.21 (s, 1H).

Example 75

(R)—N-[1-{(2-(benzofuran-2-yl)ethylamino}propan-2-yl]isoquinoline-6-sulfonamide dihydrochloride

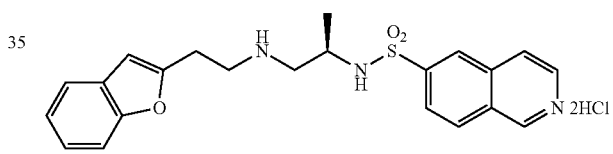

176 mg of the title compound was obtained as a white solid (89%) from 180 mg of a free form synthesized according to the method described in Example 1.

$^1$H-NMR spectrum (D$_2$O, δ ppm): 0.71 (d, J=6.7 Hz, 3H), 2.94-3.14 (m, 4H), 3.30-3.40 (m, 2H), 3.65 (br s, 1H), 6.55 (s, 1H), 7.13 (t, J=7.3 Hz, 1H), 7.18 (t, J=7.6 Hz, 1H), 7.37 (d, J=7.9 Hz, 1H), 7.45 (d, J=7.9 Hz, 1H), 8.12 (d, J=8.5 Hz, 1H), 8.33 (d, J=6.1 Hz, 1H), 8.45-8.47 (m, 2H), 8.61 (s, 1H), 9.53 (s, 1H).

A compound of Example 76 was synthesized according to the method described in Example 1 from 7-bromoisoquinoline-6-sulfonyl chloride obtained by the same approach as in Reference Example 1 and an intermediate used in the synthesis of the compound of Example 53.

Example 76

(R)-7-bromo-N-{1-(4-fluorophenethylamino)propan-2-yl}-isoquinoline-6-sulfonamide hydrochloride

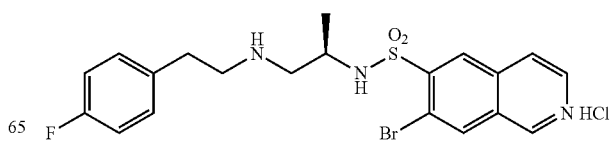

180 mg of the title compound was obtained as a white solid (88%) from 188 mg of a free form synthesized according to the method described in Example 1.

$^1$H-NMR spectrum (D$_2$O, δ ppm): 0.79 (d, J=7.0 Hz, 3H), 2.88-3.00 (m, 4H), 3.13-3.26 (m, 2H), 3.48-3.53 (m, 1H), 6.96-6.99 (m, 2H), 7.15-7.18 (m, 2H), 7.84 (d, J=5.5 Hz, 1H), 8.40 (s, 1H), 8.44 (d, J=5.5 Hz, 1H), 8.57 (s, 1H), 9.12 (s, 1H).

A compound of Example 77 was synthesized according to the method described in Example 1 from 5-bromoisoquinoline-6-sulfonyl chloride obtained by the same approach as in Reference Example 1 and an intermediate used in the synthesis of the compound of Example 53.

Example 77

(R)-5-bromo-N-{1-(4-fluorophenethylamino)propan-2-yl}-isoquinoline-6-sulfonamide hydrochloride

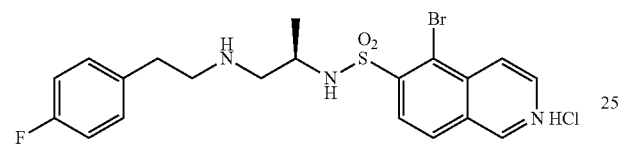

55 mg of the title compound was obtained as a white solid (84%) from 61 mg of a free form synthesized according to the method described in Example 1.

$^1$H-NMR spectrum (D$_2$O, δ ppm): 0.84 (d, J=6.5 Hz, 3H), 2.96-3.09 (m, 4H), 3.22-3.35 (m, 2H), 3.63-3.67 (m, 1H), 7.06 (t, J=8.5 Hz, 2H), 7.24 (dd, J=5.5, 8.5 Hz, 2H), 8.30 (d, J=8.5 Hz, 1H), 8.36 (d, J=9.0 Hz, 1H), 8.50 (d, J=7.0 Hz, 1H), 8.61 (d, J=7.0 Hz, 1H), 9.46 (s, 1H).

Compounds of Examples 78 to 80 were synthesized according to the method described in Example 1 from intermediates synthesized by the method described in Reference Example 4 using the compound of Reference Example 1 and the respective appropriate starting materials.

Example 78

(R)—N-{1-(2-methylallylamino)propan-2-yl}isoquinoline-6-sulfonamide hydrochloride

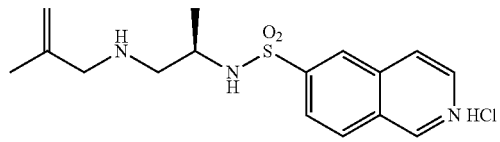

208 mg of the title compound was obtained as a white solid (51%) from 366 mg of a free form synthesized according to the method described in Example 1.

$^1$H-NMR spectrum (D$_2$O, δ ppm): 0.77 (d, J=7.0 Hz, 3H), 1.73 (s, 3H), 2.93 (dd, J=10.0, 13.0 Hz, 1H), 3.05 (dd, J=3.5, 13.0 Hz, 1H), 3.56 (d, J=14.0 Hz, 1H), 3.63 (d, J=14.0 Hz, 1H), 3.66-3.70 (m, 1H), 4.99 (s, 1H), 5.10 (s, 1H), 7.95-7.99 (m, 2H), 8.29 (d, J=9.0 Hz, 1H), 8.49 (s, 1H), 8.51 (d, J=6.0 Hz, 1H), 9.31 (s, 1H).

Example 79

(R)—N-[1-{2-(4-methylthiazol-5-yl)ethylamino}propan-2-yl]isoquinoline-6-sulfonamide dihydrochloride

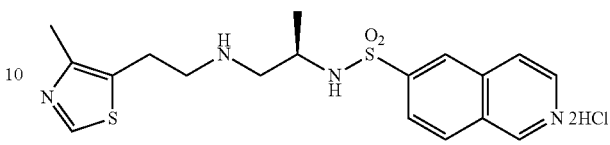

255 mg of the title compound was obtained as a white solid (54%) from 500 mg of a Boc form synthesized according to the method described in Example 1.

$^1$H-NMR spectrum (D$_2$O, δ ppm): 0.70 (d, J=6.7 Hz, 3H), 2.36 (s, 3H), 2.95-3.08 (m, 2H), 3.25-3.34 (m, 4H), 3.66-3.72 (m, 1H), 8.19 (d, J=8.5 Hz, 1H), 8.54-8.57 (m, 3H), 8.69 (s, 1H), 9.22-9.26 (m, 1H), 9.67 (s, 1H).

Example 80

(R)—N-[1-{3-(1H-indol-3-yl)propylamino}propan-2-yl]isoquinoline-6-sulfonamide dihydrochloride

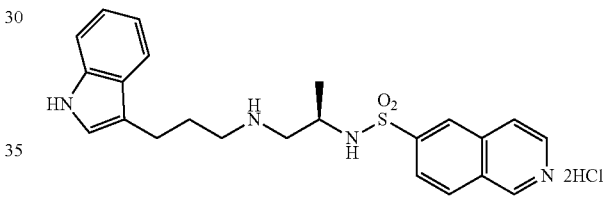

280 mg of the title compound was obtained as an orange solid (83%) from 286 mg of a free form synthesized according to the method described in Example 1.

$^1$H-NMR spectrum (D$_2$O, δ ppm): 0.70 (d, J=7.0 Hz, 3H), 1.93-1.97 (m, 2H), 2.65-2.72 (m, 2H), 2.83-2.87 (m, 1H), 2.95-3.03 (m, 3H), 3.50-3.58 (m, 1H), 7.03 (dd, J=7.0 Hz, 1H), 7.08 (s, 1H), 7.14 (dd, J=7.0 Hz, 1H), 7.38 (d, J=8.0 Hz, 1H), 7.51 (d, J=8.0 Hz, 1H), 8.08 (d, J=8.5 Hz, 1H), 8.32 (d, J=6.5 Hz, 1H), 8.44-8.47 (m, 2H), 8.57 (s, 1H), 9.49 (s, 1H).

Compounds of Examples 81 to 82 were synthesized according to the method described in Example 1 from intermediates synthesized by the method described in Reference Example 5 using the compound of Reference Example 1 and the respective appropriate starting materials.

Example 81

(R)—N-[1-{2-(pyridin-2-yl)ethylamino}propan-2-yl]isoquinoline-6-sulfonamide hydrochloride

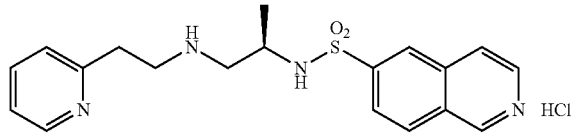 [SMILES: C[C@H](CNCCc1ccccn1)NS(=O)(=O)c1ccc2cnccc2c1 ; Cl]

39 mg of the title compound was obtained as an orange solid (74%) from 48 mg of a free form synthesized according to the method described in Example 1.

$^1$H-NMR spectrum (D$_2$O, δ ppm): 0.73 (d, J=7.5 Hz, 3H), 2.98 (dd, J=10.0, 13.0 Hz, 1H), 3.10 (dd, J=4.0, 13.0 Hz, 1H), 3.12-3.22 (m, 2H), 3.36-3.40 (m, 1H), 3.42-3.46 (m, 1H), 3.67-3.69 (m, 1H), 7.42-7.46 (m, 2H), 7.93-7.96 (m, 1H), 8.03 (d, J=9.0 Hz, 1H), 8.11 (d, J=6.0 Hz, 1H), 8.35 (d, J=9.0 Hz, 1H), 8.45 (d, J=6.0 Hz, 1H), 8.49 (d, J=6.0 Hz, 1H), 8.54 (br s, 1H), 9.40 (br s, 1H).

Example 82

N—(R)-[1-{2-(1H-imidazol-4-yl)ethylamino}propan-2-yl]isoquinoline-6-sulfonamide trihydrochloride

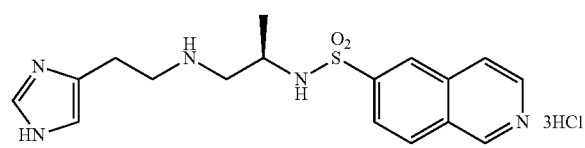 [SMILES: C[C@H](CNCCc1c[nH]cn1)NS(=O)(=O)c1ccc2cnccc2c1 ; "3HCl"]

106 mg of the title compound was obtained as a yellow solid (50%) from 160 mg of a free form synthesized according to the method described in Example 1.

$^1$H-NMR spectrum (D$_2$O, δ ppm): 0.78 (d, J=7.3 Hz, 3H), 3.07 (t, J=11.6 Hz, 1H), 3.15-3.23 (m, 3H), 3.37-3.49 (m, 3H), 3.73-3.79 (m, 1H), 7.36 (s, 1H), 8.23-8.24 (m, 1H), 8.45-8.47 (m, 1H), 8.60-8.64 (m, 3H), 8.74 (s, 1H), 9.69 (s, 1H).

Compounds of Examples 83 to 89 were synthesized according to the method described in Example 1 from intermediates synthesized by the method described in Reference Example 7 using the compound of Reference Example 1 and the respective appropriate starting materials.

Example 83

N—[(R)-1-{(S)-2-hydroxy-2-phenylethylamino}propan-2-yl]isoquinoline-6-sulfonamide hydrochloride

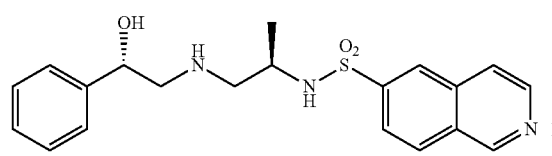

278 mg of the title compound was obtained as a white solid (80%) from 315 mg of a free form synthesized according to the method described in Example 1.

$^1$H-NMR spectrum (D$_2$O, δ ppm): 0.83 (d, J=6.5 Hz, 3H), 3.06-3.11 (m, 1H), 3.17-3.28 (m, 2H), 3.37 (dd, J=4.0, 13 Hz, 1H), 3.74-3.78 (m, 1H), 5.02 (dd, J=3.0, 10 Hz, 1H), 7.37-7.45 (m, 5H), 8.08 (d, J=9.0 Hz, 1H), 8.12 (d, J=6.0 Hz, 1H), 8.38 (d, J=9.0 Hz, 1H), 8.55 (d, J=6.0 Hz, 1H), 8.58 (s, 1H), 9.41 (s, 1H).

Example 84

N—[(R)-1-{(S)-2-(4-fluorophenyl)-2-hydroxyethylamino}propan-2-yl]isoquinoline-6-sulfonamide hydrochloride

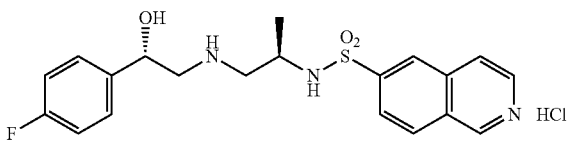 [SMILES: C[C@H](CNC[C@@H](O)c1ccc(F)cc1)NS(=O)(=O)c1ccc2cnccc2c1 ; Cl]

1.24 g of the title compound was obtained as a white solid (88%) from 1.29 g of a free form synthesized according to the method described in Example 1.

$^1$H-NMR spectrum (D$_2$O, δ ppm): 0.73 (d, J=6.5 Hz, 3H), 2.97-3.01 (m, 1H), 3.09-3.16 (m, 2H), 3.23 (d, J=12 Hz, 1H), 3.66 (br s, 1H), 4.92 (d, J=7.5 Hz, 1H), 7.02-7.06 (m, 2H), 7.26-7.30 (m, 2H), 7.88-7.92 (m, 2H), 8.18 (d, J=8.5 Hz, 1H), 8.38 (s, 1H), 8.42 (d, J=5.5 Hz, 1H), 9.21 (s, 1H).

Example 85

N-{(2R)-1-(2-hydroxy-2-phenylpropylamino)propan-2-yl}isoquinoline-6-sulfonamide hydrochloride

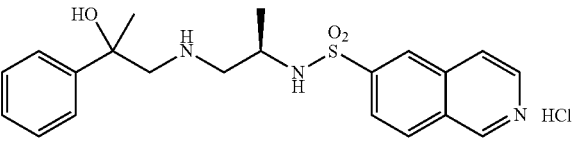 [SMILES: C[C@H](CNCC(C)(O)c1ccccc1)NS(=O)(=O)c1ccc2cnccc2c1 ; Cl]

60 mg of the title compound was obtained as a white solid (91%) from 60 mg of a free form synthesized according to the method described in Example 1.

$^1$H-NMR spectrum (D$_2$O, δ ppm): 0.66-0.70 (m, 3H), 1.57 (s, 3H), 2.78-3.02 (m, 2H), 3.23-3.28 (m, 1H), 3.43-3.51 (m, 1H), 3.55-3.63 (m, 1H), 7.29-7.32 (m, 1H), 7.36-7.44 (m, 4H), 7.97-7.99 (m, 1H), 8.07 (dd, J=6.0, 6.0 Hz, 1H), 8.32 (dd, J=4.0, 8.5 Hz, 1H), 8.47-8.50 (m, 2H), 9.38 (s, 1H).

Example 86

N—[(R)-1-{(S)-2-hydroxy-2-phenylpropylamino}propan-2-yl]isoquinoline-6-sulfonamide hydrochloride

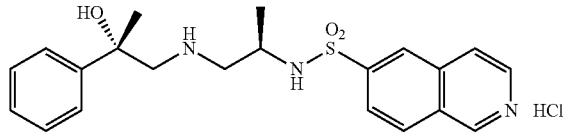 [SMILES: C[C@H](CNC[C@@](C)(O)c1ccccc1)NS(=O)(=O)c1ccc2cnccc2c1 ; Cl]

336 mg of the title compound was obtained as a white solid (87%) from 350 mg of a free form synthesized according to the method described in Example 1.

$^1$H-NMR spectrum (D$_2$O, δ ppm): 0.67 (d, J=5.5 Hz, 3H), 1.58 (s, 3H), 2.82 (dd, J=11, 13 Hz, 1H), 3.03 (dd, J=3.0, 13 Hz, 1H), 3.30 (d, J=13 Hz, 1H), 3.49 (d, J=13 Hz, 1H), 3.55-3.59 (m, 1H), 7.29-7.32 (m, 1H), 7.38-7.46 (m, 4H), 8.18 (d, J=9.5 Hz, 1H), 8.48 (d, J=6.0 Hz, 1H), 8.56-8.58 (m, 2H), 8.69 (s, 1H), 9.69 (s, 1H).

Example 87

N—[(R)-1-{(R)-2-hydroxy-2-phenylethylamino}propan-2-yl]isoquinoline-6-sulfonamide hydrochloride

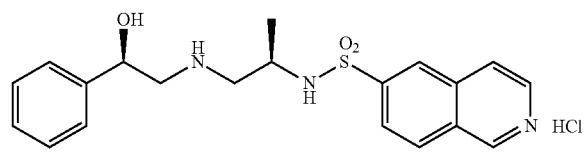 [SMILES: C[C@H](CNC[C@H](O)c1ccccc1)NS(=O)(=O)c1ccc2cnccc2c1 ; Cl]

124 mg of the title compound was obtained as a white solid (78%) from 144 mg of a free form synthesized according to the method described in Example 1.

$^1$H-NMR spectrum (D$_2$O, δ ppm): 0.81 (d, J=7.0 Hz, 3H), 3.04-3.09 (m, 1H), 3.18 (dd, J=4.5, 13.5 Hz, 1H), 3.25-3.35 (m, 2H), 3.73-3.77 (m, 1H), 5.03 (dd, J=3.5, 9.0 Hz, 1H), 7.36-7.43 (m, 5H), 8.03-8.05 (m, 2H), 8.34 (d, J=9.0 Hz, 1H), 8.54-8.55 (m, 2H), 9.37 (s, 1H).

Example 88

N-[(2R)-1-{2-hydroxy-2-(pyridin-3-yl)ethylamino}propan-2-yl]isoquinoline-6-sulfonamide dihydrochloride

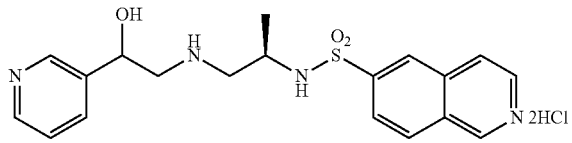 [SMILES: C[C@H](CNCC(O)c1cccnc1)NS(=O)(=O)c1ccc2cnccc2c1 ; "2HCl"]

4 mg of the title compound was obtained as a white solid (3%) from 130 mg of a free form synthesized according to the method described in Example 1.

$^1$H-NMR spectrum (D$_2$O, δ ppm): 0.70 (m, 3H), 2.98-3.31 (m, 4H), 3.68-3.72 (m, 1H), 4.93-4.99 (m, 1H), 7.59-7.61 (m, 1H), 7.97-8.15 (m, 3H), 8.26-8.29 (m, 1H), 8.45-8.51 (m, 4H), 9.32 (br s, 1H).

Example 89

N—[(R)-1-{(S)-2-amino-2-phenylethylamino}propan-2-yl]isoquinoline-6-sulfonamide trihydrochloride

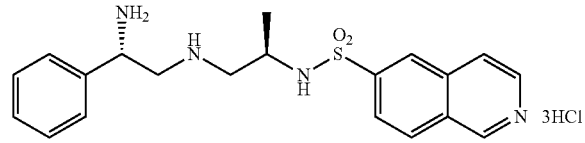 [SMILES: C[C@H](CNC[C@@H](N)c1ccccc1)NS(=O)(=O)c1ccc2cnccc2c1 ; "3HCl"]

103 mg of the title compound was obtained as a white solid (80%) from 126 mg of a Boc form synthesized according to the method described in Example 1.

$^1$H-NMR spectrum (D$_2$O, δ ppm): 0.66 (d, J=6.7 Hz, 3H), 2.90-3.10 (m, 2H), 3.60-3.70 (m, 2H), 3.78 (dd, J=9.8, 12.8 Hz, 1H), 4.76 (dd, J=5.5, 9.2 Hz, 1H), 7.48-7.50 (m, 5H), 8.13 (d, J=9.2 Hz, 1H), 8.36 (d, J=6.1 Hz, 1H), 8.51 (d, J=9.2 Hz, 1H), 8.55 (d, J=6.7 Hz, 1H), 8.63 (s, 1H), 9.61 (s, 1H).

Compounds of Examples 90 to 91 were synthesized according to the method described in Example 38 from intermediates synthesized by the method described in Reference Example 8 using the compound of Reference Example 1 and the respective appropriate starting materials.

Example 90

N—[(R)-1-{(S)-2-hydroxy-2-(thiophen-3-yl)ethylamino}propan-2-yl]isoquinoline-6-sulfonamide hydrochloride

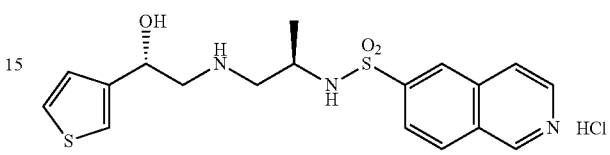

71 mg of the title compound was obtained as a white solid (82%) from 78 mg of a free form synthesized according to the method described in Example 38.

$^1$H-NMR spectrum (D$_2$O, δ ppm): 0.75 (d, J=6.5 Hz, 3H), 3.00 (dd, J=9.0, 13 Hz, 1H), 3.11 (dd, J=4.0, 13 Hz, 1H), 3.23 (dd, J=9.0, 13 Hz, 1H), 3.34 (dd, J=4.0, 13 Hz, 1H), 3.65-3.72 (m, 1H), 5.03 (dd, J=4.0, 9.0 Hz, 1H), 7.04 (d, J=5.0 Hz, 1H), 7.32 (s, 1H), 7.41 (d, J=5.0 Hz, 1H), 8.00 (m, 2H), 8.31 (d, J=9.5 Hz, 1H), 8.49-8.51 (m, 2H), 9.34 (s, 1H).

Example 91

N-[(2R)-1-{2-(3-chlorophenyl)-2-hydroxyethylamino}propan-2-yl]isoquinoline-6-sulfonamide dihydrochloride

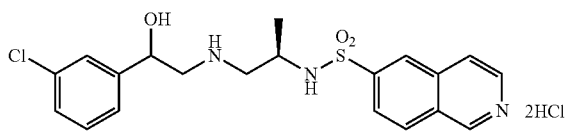 [SMILES: C[C@H](CNCC(O)c1cccc(Cl)c1)NS(=O)(=O)c1ccc2cnccc2c1 ; "2HCl"]

5 mg of the title compound was obtained as a white solid (43%) from 10 mg of a free form synthesized according to the method described in Example 38.

$^1$H-NMR spectrum (D$_2$O, δ ppm): 0.76 (d, J=6.1 Hz, 3H), 3.03 (t, J=11.9 Hz, 1H), 3.12-3.19 (m, 1H), 3.24 (d, J=6.7 Hz, 1H), 3.33 (d, J=12.8 Hz, 1H), 3.75 (s, 1H), 4.97 (t, J=11.0 Hz, 1H), 7.24 (s, 1H), 7.31 (s, 2H), 7.35 (s, 1H), 8.21 (d, J=8.5 Hz, 1H), 8.45 (d, J=5.8 Hz, 1H), 8.56 (d, J=7.3 Hz, 2H), 8.70 (s, 1H), 9.65 (s, 1H).

Example 92

(R)—N-[1-{2-(biphenyl-4-yl)ethylamino}propan-2-yl]isoquinoline-6-sulfonamide dihydrochloride

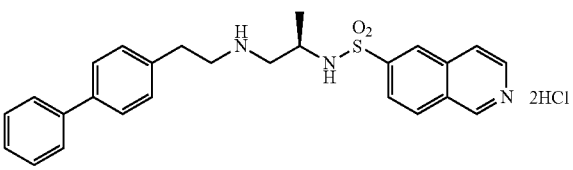 [SMILES: C[C@H](CNCCc1ccc(-c2ccccc2)cc1)NS(=O)(=O)c1ccc2cnccc2c1 ; "2HCl"]

The title compound was synthesized according to the following Scheme 13:

4H), 8.16 (d, J=9.2 Hz, 1H), 8.38 (d, J=6.7 Hz, 1H), 8.49-8.53 (m, 2H), 8.65 (s, 1H), 9.59 (s, 1H).

Example 93

(R)—N-[1-{4-(pyridin-4-yl)phenethylamino}propan-2-yl]isoquinoline-6-sulfonamide trihydrochloride

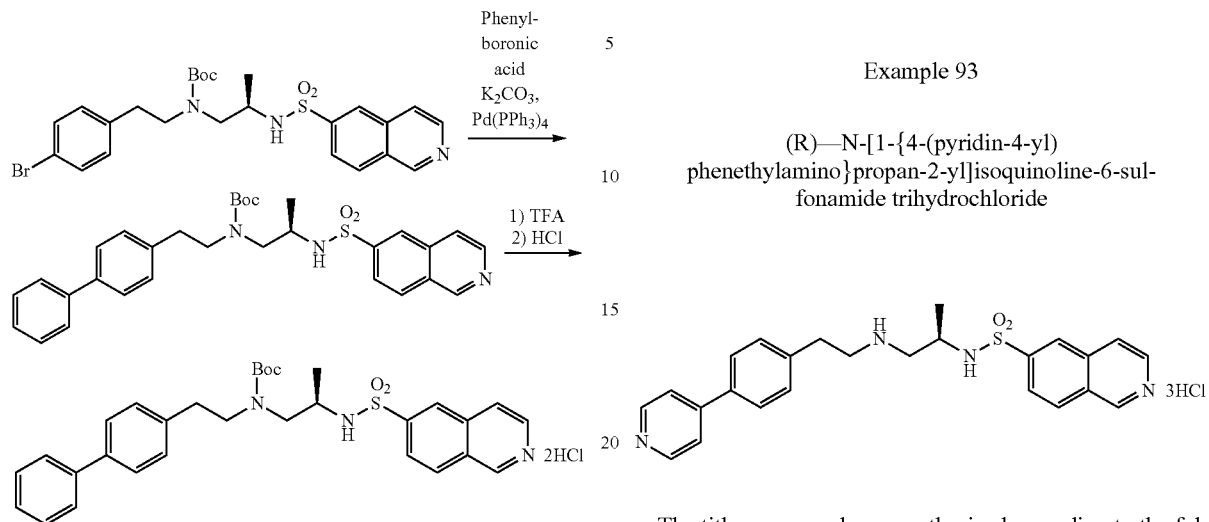

The title compound was synthesized according to the following Scheme 14:

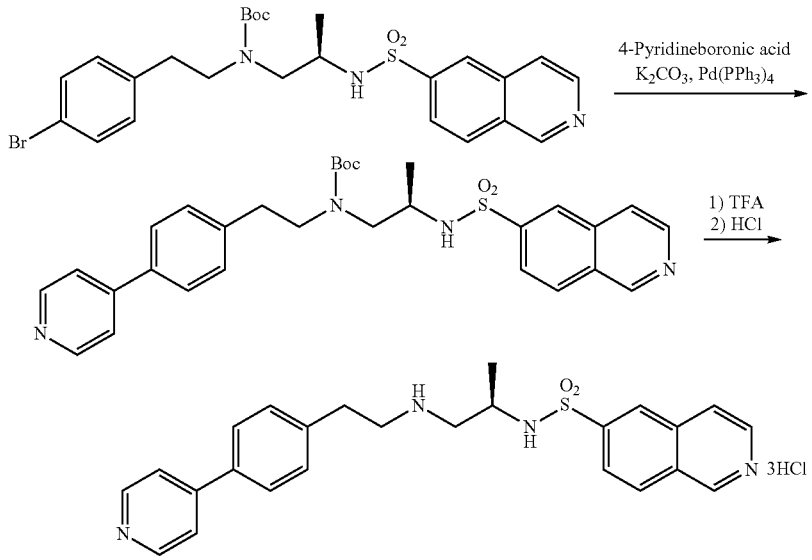

The intermediate (R)-tert-butyl 4-bromophenethyl{2-(isoquinoline-6-sulfonamide)propyl}carbamate (114 mg) synthesized for obtaining the compound of Example 55 was reacted with phenylboric acid (38 mg) in the presence of tetrakis(triphenylphosphine)palladium (24 mg) and potassium carbonate (132 mg) in N,N-dimethylformamide-water according to the method described in Chem. Rev., 95, 2457 (1995) to obtain a coupling product (90 mg, 79%). Subsequently, 50 mg of the title compound was obtained as a white solid (61%) from 70 mg of a free form according to the methods described in Steps 2 and 3 of Example 1.

$^1$H-NMR spectrum (D$_2$O, δ ppm): 0.74 (d, J=6.7 Hz, 3H), 2.98-3.10 (m, 4H), 3.27-3.36 (m, 2H), 3.60-3.64 (m, 1H), 7.30-7.35 (m, 3H), 7.40 (t, J=7.6 Hz, 2H), 7.55 (d, J=7.9 Hz, The intermediate (R)-tert-butyl 4-bromophenethyl{2-(isoquinoline-6-sulfonamide)propyl}carbamate (155 mg) synthesized for obtaining the compound of Example 55 was reacted with 4-pyridineboric acid (87 mg) in the presence of tetrakis(triphenylphosphine)palladium (33 mg) and potassium carbonate (180 mg) in N,N-dimethylformamide-water according to the method described in Chem. Rev., 95, 2457 (1995) to obtain a coupling product (100 mg, 65%). Subsequently, 50 mg of the title compound was obtained as a white solid (62%) from 65 mg of a free form according to the methods described in Steps 2 and 3 of Example 1.

$^1$H-NMR spectrum (D$_2$O, δ ppm): 0.73 (d, J=6.7 Hz, 3H), 2.98-3.13 (m, 4H), 3.29-3.42 (m, 2H), 3.69-3.73 (m, 1H), 7.48 (d, J=7.9 Hz, 2H), 7.85 (d, J=7.9 Hz, 2H), 8.22 (d, J=6.7

Hz, 3H), 8.48 (d, J=6.1 Hz, 1H), 8.57 (t, J=7.3 Hz, 2H), 8.66 (d, J=6.7 Hz, 2H), 8.72 (s, 1H), 9.69 (s, 1H).

Reference Example 9

(R)-tert-butyl 3-butyn-1-yl{2-(isoquinoline-6-sulfonamide)propyl}carbamate

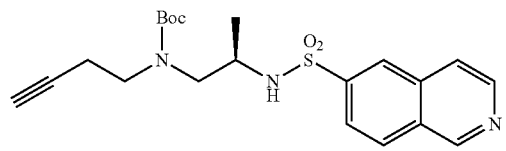 [SMILES: C#CCCN(C[C@@H](C)NS(=O)(=O)c1ccc2cnccc2c1)C(=O)OC(C)(C)C]

The title compound was synthesized according to the following Scheme 15:

Scheme 15

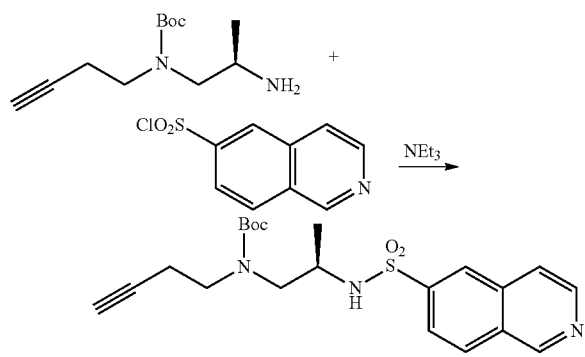

785 mg of (R)-tert-butyl 2-aminopropyl(3-butyn-1-yl)carbamate synthesized by the method described in Reference Example 4 was dissolved in 30 mL of dichloromethane. To the solution, 2.88 mL of triethylamine was added, and the mixture was cooled to 0° C. A dichloromethane solution of isoquinoline-6-sulfonyl chloride prepared in Reference Example 1 was added thereto, and the mixture was stirred overnight at room temperature. Dichloromethane (50 mL) was added thereto, and the organic layer was washed with saturated saline and dried over anhydrous sodium sulfate. After filtration, the filtrate was concentrated under reduced pressure, and the obtained crude product was purified by silica gel column chromatography (hexane:ethyl acetate=1: 1→1:2) to obtain 1.08 g of the title compound as a pale yellow oil (75%).

$^1$H-NMR spectrum (CDCl$_3$, δ ppm): 0.88 (d, J=7.5 Hz, 3H), 1.45 (s, 9H), 2.17 (s, 1H), 2.17-2.30 (m, 2H), 2.90-3.15 (m, 3H), 3.45-3.65 (m, 2H), 6.06 (s, 1H), 7.79 (d, J=6.0 Hz, 1H), 7.97 (d, J=8.5 Hz, 1H), 8.11 (d, J=8.5 Hz, 1H), 8.42 (s, 1H), 8.69 (d, J=5.5 Hz, 1H), 9.37 (s, 1H).

Example 94

(R)—N-[1-{2-(1H-1,2,3-triazol-4-yl)ethylamino}propan-2-yl]isoquinoline-6-sulfonamide hydrochloride

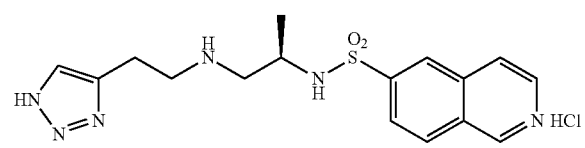 [SMILES: C[C@H](CNCCc1c[nH]nn1)NS(=O)(=O)c1ccc2cnccc2c1 ; Cl]

The title compound was synthesized according to the following Scheme 16:

Scheme 16

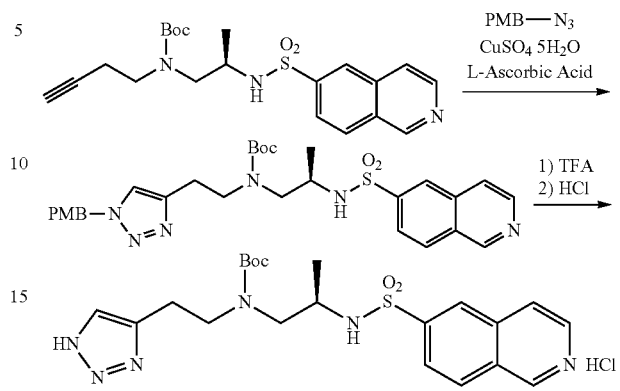

The compound of Reference Example 9 (107 mg) was reacted with p-methoxybenzyl azide (45 mg) in the presence of copper sulfate pentahydrate (18 mg) and sodium L-ascorbate (45 mg) in tert-butanol to form a triazole ring (129 mg, 93%). Trifluoroacetic acid was further added thereto, and the p-methoxybenzyl group and the tert-butoxycarbonyl group were removed by heating to obtain a free form as a crude product. Subsequently, 47 mg of the title compound was obtained as a pale yellow solid (48%) with reference to the method of Step 3 of Example 1.

$^1$H-NMR spectrum (D$_2$O, δ ppm): 0.71 (d, J=6.7 Hz, 3H), 2.96 (m, 1H), 3.03-3.13 (m, 3H), 3.25-3.38 (m, 2H), 3.60-3.68 (m, 1H), 7.71 (s, 1H), 8.04 (d, J=8.5 Hz, 1H), 8.14 (d, J=5.5 Hz, 1H), 8.36 (d, J=8.5 Hz, 1H), 8.48-8.52 (m, 1H), 8.54 (s, 1H), 9.42 (s, 1H).

Example 95

(R)—N-[1-{2-(1H-tetrazol-5-yl)ethylamino}propan-2-yl]isoquinoline-6-sulfonamide dihydrochloride

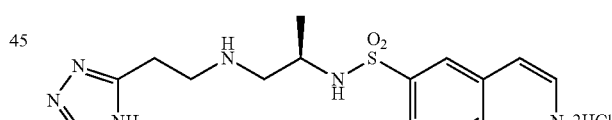

The title compound was synthesized according to the following Scheme 17:

Scheme 17

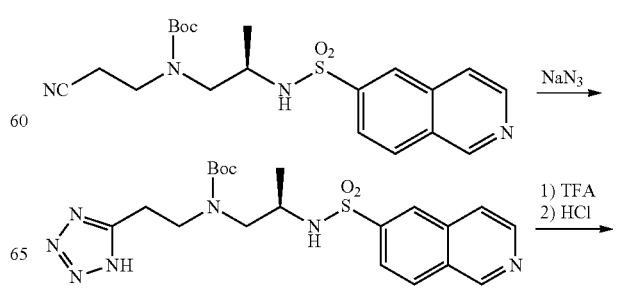

-continued

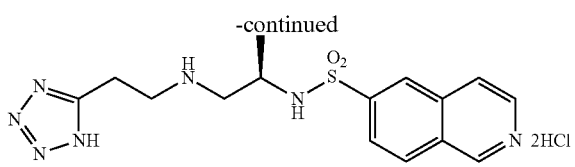

The intermediate (R)-tert-butyl 2-cyanoethyl{2-(isoquinoline-6-sulfonamido)propyl}carbamate (200 mg) synthesized for obtaining the compound of Example 73, and sodium azide (125 mg) were mixed in the presence of ammonium chloride (52 mg) in N,N-dimethylformamide and heated at 100° C. for 48 hours to form a tetrazole ring (90 mg, 40%). Subsequently, 52 mg of the title compound was obtained as a white solid (61%) with reference to the methods of Steps 2 and 3 of Example 1.

$^{1}$H-NMR spectrum (D$_2$O, δ ppm): 0.71 (d, J=6.7 Hz, 3H), 3.02 (t, J=11.6 Hz, 1H), 3.13 (d, J=10.4 Hz, 1H), 3.37 (t, J=7.3 Hz, 2H), 3.44-3.56 (m, 2H), 3.70 (br s, 1H), 8.19 (d, J=8.5 Hz, 1H), 8.46 (d, J=6.1 Hz, 1H), 8.54-8.56 (m, 2H), 8.69 (s, 1H), 9.66 (s, 1H).

Example 96

(R)—N-[1-(butylamino)propan-2-yl]-N-ethylisoquinoline-6-sulfonamide hydrochloride

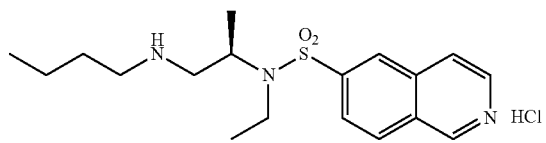 [SMILES: CCCCNC[C@@H](C)N(CC)S(=O)(=O)c1ccc2cnccc2c1 ; Cl]

The title compound was synthesized according to the following Scheme 18:

Scheme 18

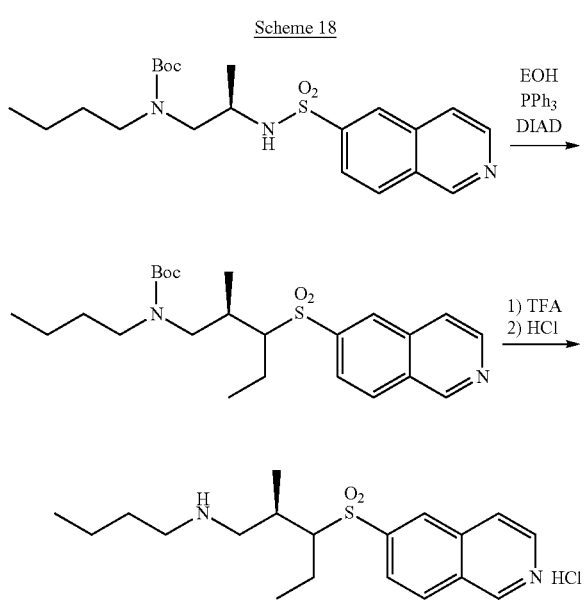

The intermediate (R)-tert-butyl butyl{2-(isoquinoline-6-sulfonamido)propyl}carbamate (352 mg) synthesized for obtaining the compound of Example 5 was N-ethylated (136 mg, 36%) through reaction with ethanol (0.082 mL) using triphenylphosphine (374 mg) and diisopropyl azodicarboxylate (0.277 mL) in tetrahydrofuran. Subsequently, 110 mg of the title compound was obtained as a white solid (88%) with reference to the method of Steps 2 and 3 of Example 1.

$^{1}$H-NMR spectrum (D$_2$O, δ ppm): 0.81-0.84 (m, 6H), 1.14 (t, J=7.0 Hz, 3H), 1.25-1.31 (m, 2H), 1.55-1.61 (m, 2H), 2.97-3.08 (m, 3H), 3.15-3.20 (m, 1H), 3.23-3.29 (m, 1H), 3.31-3.37 (m, 1H), 4.23-4.28 (m, 1H), 8.11 (d, J=9.0 Hz, 1H), 8.33 (br s, 1H), 8.48 (d, J=8.6 Hz, 1H), 8.60-8.70 (m, 2H), 9.64 (br s, 1H).

Example 97

(R)—N-(2-hydroxyethyl)-N-{1-(phenethylamino)propan-2-yl}isoquinoline-6-sulfonamide dihydrochloride

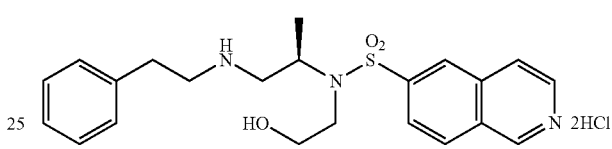

The title compound was synthesized according to the following Scheme 19:

Scheme 19

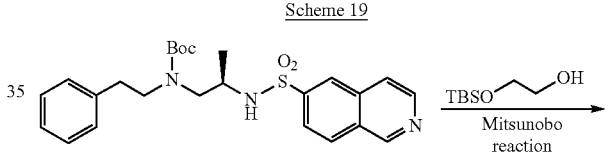

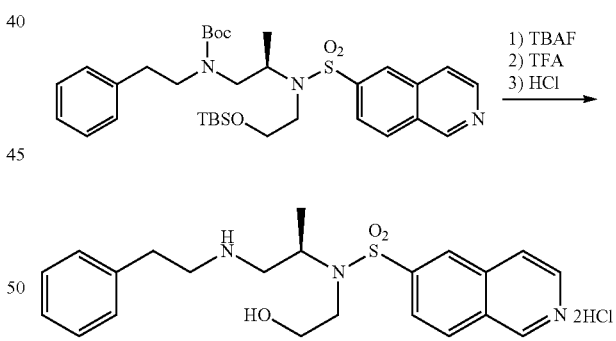

The intermediate (R)-tert-butyl 2-(isoquinoline-6-sulfonamido)propyl(phenethyl)carbamate (200 mg) synthesized for obtaining the compound of Example 23 was reacted with 2-(tert-butyldimethylsilyloxy)ethanol (172 mg) using triphenylphosphine (167 mg) and bis(2-methoxyethyl) azodicarboxylate (149 mg) in tetrahydrofuran. The TBS group in the obtained crude product was removed with tetra-n-butylammonium fluoride, and the Boc group was removed with trifluoroacetic acid (85 mg, 48%). Subsequently, 40 mg of the title compound was obtained as a white solid (39%) with reference to the method of Step 3 of Example 1.

$^{1}$H-NMR spectrum (D$_2$O, δ ppm): 0.62 (d, J=6.7 Hz, 3H), 2.91-2.96 (m, 2H), 3.03-3.08 (m, 3H), 3.15-3.20 (m, 1H), 3.32-3.37 (m, 1H), 3.41 (dt, J=3.4, 15.9 Hz, 1H), 3.62 (dt, J=3.9, 7.5 Hz, 1H), 3.74 (td, J=3.5, 10.5 Hz, 1H), 4.23-4.30 (m, 1H), 7.20-7.26 (m, 3H), 7.31 (t, J=7.3 Hz, 2H), 8.09 (d, J=7.3 Hz, 1H), 8.23 (d, J=6.7 Hz, 1H), 8.42 (d, J=8.5 Hz, 1H), 8.52 (d, J=6.1 Hz, 1H), 8.60 (s, 1H), 9.50 (s, 1H).

Example 98

(R)—N-(2-dimethylaminoethyl)-N-{1-(phenethylamino)propan-2-yl}isoquinoline-6-sulfonamide trihydrochloride

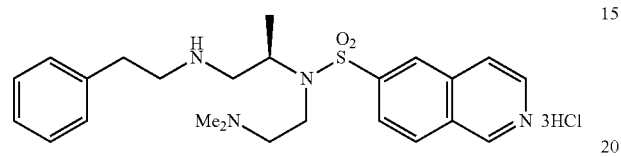

The title compound was synthesized according to the following Scheme 20:

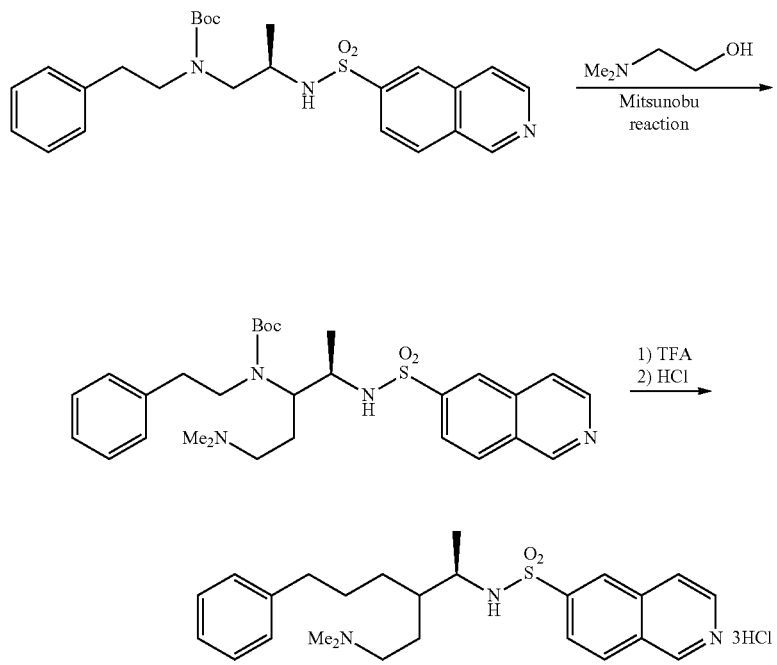

The intermediate (R)-tert-butyl 2-(isoquinoline-6-sulfonamido)propyl(phenethyl)carbamate (60 mg) synthesized for obtaining the compound of Example 23 and 2-(dimethylamino)ethanol (23 mg) were reacted (35 mg, 51%) using triphenylphosphine (67 mg) and bis(2-methoxyethyl) azodicarboxylate (60 mg) in tetrahydrofuran. This reaction was performed again, and 80 mg of the title compound was obtained as a pale yellow solid (56%) with reference to the methods of Steps 2 and 3 of Example 1 using 150 mg of the combined product.

¹H-NMR spectrum (D₂O, δ ppm): 0.82 (d, J=6.7 Hz, 3H), 2.91 (s, 6H), 2.98-3.01 (m, 1H), 3.06-3.10 (m, 1H), 3.14-3.19 (m, 1H), 3.27-3.40 (m, 4H), 3.42-3.47 (m, 1), 3.52-3.57 (m, 1H), 3.62-3.67 (m, 1H), 4.28 (s, 1H), 7.27 (t, J=10.1 Hz, 3H), 7.34 (t, J=7.3 Hz, 2H), 8.22 (d, J=8.5 Hz, 1H), 8.44 (d, J=5.5 Hz, 2H), 8.59 (d, J=5.5 Hz, 1H), 8.76 (s, 1H), 9.68 (s, 1H).

Example 99

(R)—N-[1-{methyl(phenethyl)amino}propan-2-yl]isoquinoline-6-sulfonamide dihydrochloride

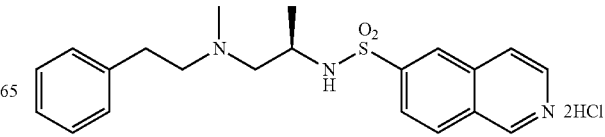

The title compound was synthesized according to the following Scheme 21:

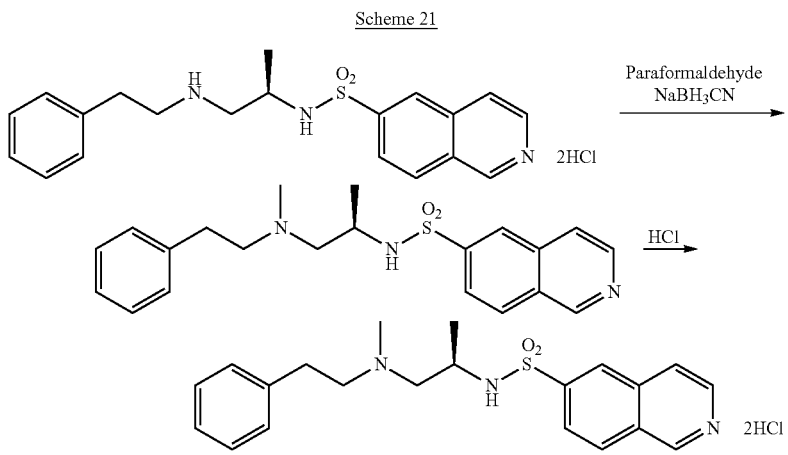

The compound of Example 23 (54 mg) was N-methylated by the action of paraformaldehyde (50 mg) and sodium cyanoborohydride (63 mg) in ethanol to obtain a crude product. Subsequently, 21 mg of the title compound was obtained as a gray solid (35%) with reference to the method of Step 3 of Example 1.

$^1$H-NMR spectrum (D$_2$O, δ ppm): 0.61 (d, J=6.1 Hz, 1.5H), 0.65 (d, J=6.7 Hz, 1.5H), 2.92 (s, 3H), 2.92-3.15 (m, 4H), 3.35-3.60 (m, 2H), 3.82 (s, 1H), 7.17-7.30 (m, 5H), 7.99-8.04 (m, 1H), 8.10 (s, 1H), 8.25-8.38 (m, 1H), 8.48 (s, 2H), 9.36 (br s, 1H).

Example 100

(R)-2-amino-N-[2-(isoquinoline-6-sulfonamido)propyl]-N-phenylethylacetamide hydrochloride

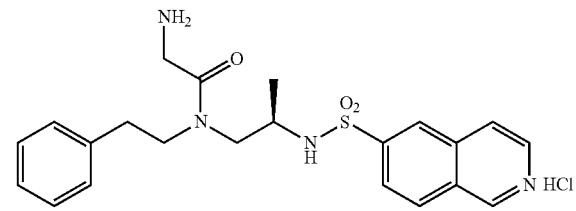 [SMILES: C[C@H](CN(CCc1ccccc1)C(=O)CN)NS(=O)(=O)c1ccc2cnccc2c1 ; Cl]

The title compound was synthesized according to the following Scheme 22:

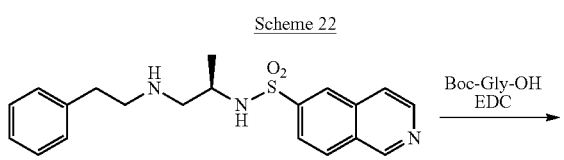

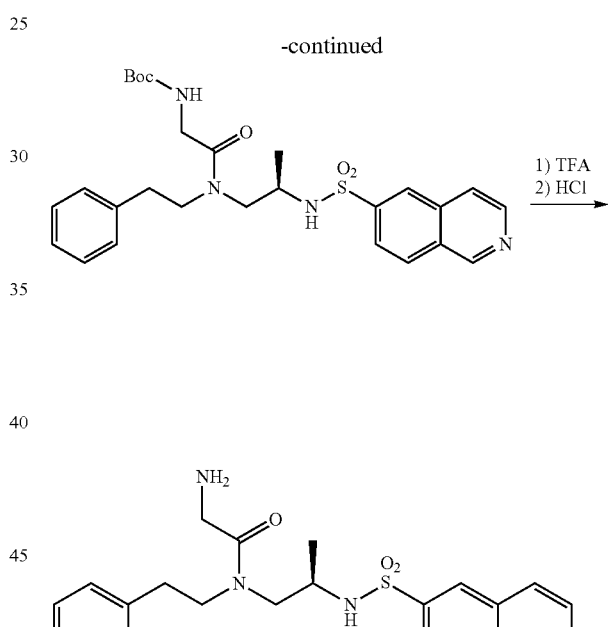

A free form (220 mg) of the compound of Example 23 and N-(tert-butoxycarbonyl)glycine (25 mg) were condensed (230 mg, 73%) using 1-ethyl-3-(3-dimethylaminopropyl)carbodiimide hydrochloride (137 mg) in dichloromethane. Subsequently, 100 mg of the title compound was obtained as a white solid (61%) from 150 mg of a free form according to the methods described in Steps 2 and 3 of Example 1.

$^1$H-NMR spectrum (D$_2$O, δ ppm): 0.75 (d, J=6.7 Hz, 2H), 0.82 (d, J=6.7 Hz, 1H), 2.61 (s, 0.7H), 2.75 (t, J=6.4 Hz, 1.3H), 2.94-3.04 (m, 1H), 3.15-3.21 (m, 1H), 3.27-3.36 (m, 1H), 3.42-3.47 (m, 2H), 3.52-3.67 (m, 1H), 3.92-3.98 (m, 1H), 7.01 (d, J=7.3 Hz, 0.7H), 7.09 (d, J=6.7 Hz, 1.3H), 7.13-7.28 (m, 3H), 8.05 (d, J=9.2 Hz, 0.3H), 8.09 (d, J=9.2 Hz, 0.7H), 8.24 (d, J=6.1 Hz, 0.3H), 8.30 (d, J=6.7 Hz, 0.7H), 8.41 (d, J=8.5 Hz, 0.3H), 8.44 (d, J=8.5 Hz, 0.7H), 8.49 (dd, J=6.1, 13.4 Hz, 1H), 8.53 (d, J=9.8 Hz, 1H), 9.53 (d, J=13.4 Hz, 1H).

Example 101

(R)-2-(isoquinoline-6-sulfonamido)-N-phenethylpropanamide hydrochloride

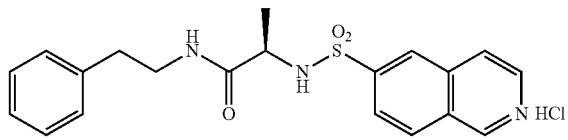 [SMILES: C[C@@H](NS(=O)(=O)c1ccc2cnccc2c1)C(=O)NCCc1ccccc1 ; Cl]

The title compound was synthesized according to the following Scheme 23:

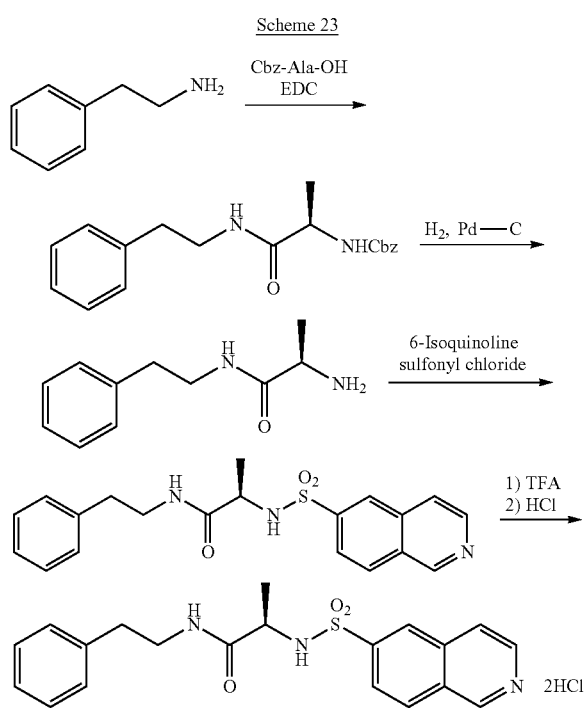

Phenethylamine (285 mg) and N-(benzyloxycarbonyl)-D-alanine (500 mg) were condensed (618 mg, 85%) using 1-ethyl-3-(3-dimethylaminopropyl)carbodiimide hydrochloride (472 mg) in dichloromethane. (R)-2-amino-N-phenethylpropanamide (197 mg) obtained by further hydrogenation reaction in the presence of 10% palladium-carbon, and isoquinoline-6-sulfonyl chloride prepared in Reference Example 1 were condensed (237 mg, 60%) in the presence of triethylamine (0.284 mL) in dichloromethane. Subsequently, 40 mg of the title compound was obtained as a pale yellow solid (13%) with reference to the method of Step 3 of Example 1.

$^1$H-NMR spectrum (D$_2$O, δ ppm): 1.06 (d, J=7.0 Hz, 3H), 2.33-2.44 (m, 2H), 2.90-3.01 (m, 2H), 3.74-3.81 (m, 1H), 6.97-6.99 (m, 2H), 7.11-7.20 (m, 3H), 8.10 (d, J=8.5 Hz, 1H), 8.43 (br s, 1H), 8.48 (d, J=8.5 Hz, 1H), 8.57-8.68 (m, 2H), 9.70 (br s, 1H).

Example 102

(R)—N-(1-aminopropan-2-yl)isoquinoline-6-sulfonamide dihydrochloride

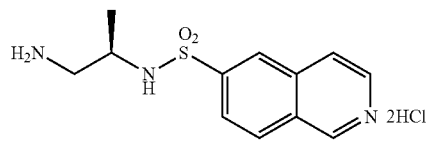 [SMILES: C[C@H](CN)NS(=O)(=O)c1ccc2cnccc2c1 ; "2HCl"]

The title compound was synthesized according to the following Scheme 24:

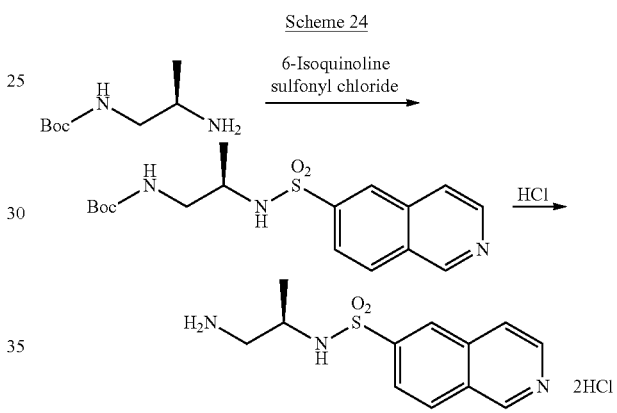

(R)-tert-butyl 2-aminopropylcarbamate (338 mg) synthesized according to the method described in PCT publication No. WO2010/006085 was condensed with isoquinoline-6-sulfonyl chloride prepared in Reference Example 1 in the presence of triethylamine (0.538 mL) in dichloromethane to obtain a crude product. Subsequently, 252 mg of the title compound was obtained as a white solid (38%) with reference to the methods of Steps 2 and 3 of Example 1.

$^1$H-NMR spectrum (D$_2$O, δ ppm): 0.73 (d, J=6.7 Hz, 3H), 2.83 (dd, J=10, 13 Hz, 1H), 3.03 (dd, J=4.0, 13 Hz, 1H), 3.55-3.63 (m, 1H), 8.18 (dd, J=1.8, 8.5 Hz, 1H), 8.40 (d, J=6.1 Hz, 1H), 8.50-8.57 (m, 2H), 8.69 (s, 1H), 9.63 (s, 1H).

Example 103

(R)—N-{2-(isoquinoline-6-sulfonamido)propyl}-2-phenylacetamide hydrochloride

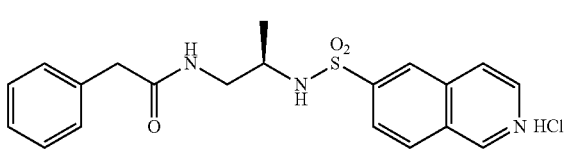 [SMILES: C[C@H](CNC(=O)Cc1ccccc1)NS(=O)(=O)c1ccc2cnccc2c1 ; Cl]

The title compound was synthesized according to the following Scheme 25:

Scheme 25

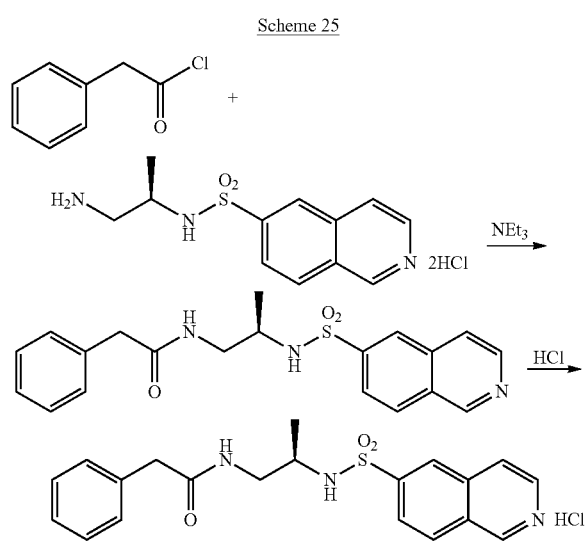

The compound of Example 102 (100 mg) and phenylacetyl chloride (45 mg) were condensed (72 mg, 63%) in the presence of triethylamine (0.123 mL) in dichloromethane. Subsequently, 52 mg of the title compound was obtained as a pale yellow solid (66%) with reference to the method of Step 3 of Example 1.

$^1$H-NMR spectrum (D$_2$O, δ ppm): 0.84 (d, J=7.0 Hz, 3H), 2.33-2.44 (m, 2H), 2.90-3.01 (m, 2H), 3.74-3.81 (m, 1H), 6.97-6.99 (m, 2H), 7.11-7.20 (m, 3H), 8.10 (d, J=8.5 Hz, 1H), 8.43 (br s, 1H), 8.48 (d, J=8.5 Hz, 1H), 8.57-8.68 (m, 2H), 9.70 (br s, 1H).

Example 104

(R)—N-{1-(2-oxo-2-phenylethylamino)propan-2-yl}isoquinoline-6-sulfonamide dihydrochloride

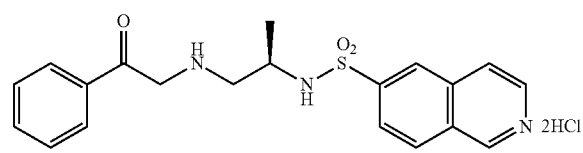 [SMILES: C[C@H](CNCC(=O)c1ccccc1)NS(=O)(=O)c1ccc2cnccc2c1 ; "2HCl"]

The title compound was synthesized according to the following Scheme 26:

Scheme 26

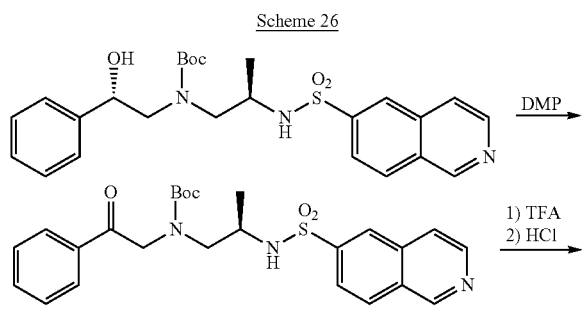

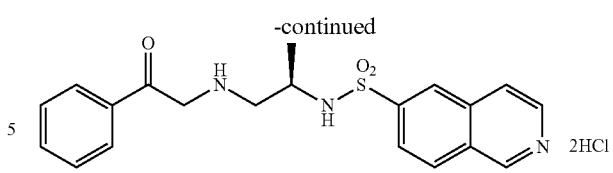

The hydroxyl group in the intermediate tert-butyl (S)-2-hydroxy-2-phenylethyl{(R)-2-(isoquinoline-6-sulfonamido)propyl}carbamate (150 mg) synthesized for obtaining the compound of Example 83 was oxidized into a carbonyl group (90 mg, 60%) using Dess-Martin-periodinane (150 mg) in dichloromethane. Subsequently, 70 mg of the title compound was obtained as a white solid (49%) using a 1 M hydrochloric acid-diethyl ether solution in dichloromethane.

$^1$H-NMR spectrum (D$_2$O, δ ppm): 0.83 (d, J=6.7 Hz, 3H), 3.09 (t, J=11.6 Hz, 1H), 3.17-3.22 (m, 1H), 3.79-3.83 (m, 1H), 4.71 (s, 2H), 7.48 (t, J=7.0 Hz, 2H), 7.65 (t, J=7.0 Hz, 1H), 7.84 (d, J=7.9 Hz, 2H), 8.23 (d, J=9.2 Hz, 1H), 8.47 (d, J=6.1 Hz, 1H), 8.55 (s, 1H), 8.57 (d, J=3.1 Hz, 1H), 8.74 (s, 1H), 9.65 (s, 1H).

Example 105

Methyl (S)-2-{(R)-2-(isoquinoline-6-sulfonamido)propylamino}-3-phenylpropanoate dihydrochloride

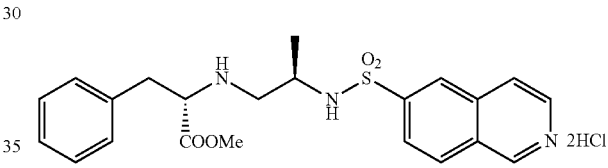

The title compound was synthesized according to the following Scheme 27:

Scheme 27

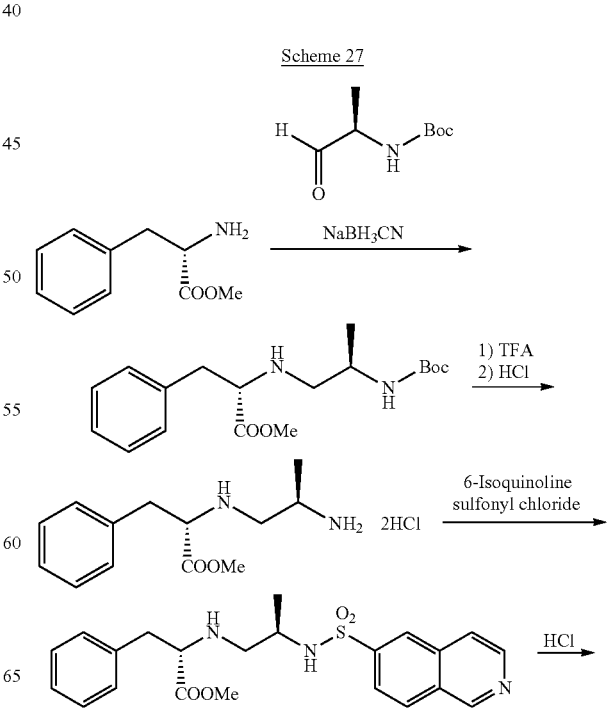

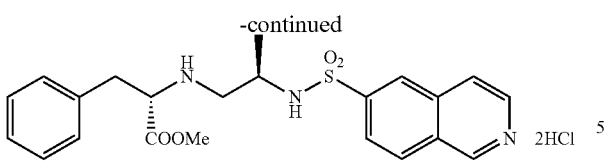

Sodium cyanoborohydride (1.1 g) and acetic acid (0.75 mL) were added to a mixture of methyl (S)-2-amino-3-phenylpropanoate (2.72 g) and (R)-tert-butyl 1-oxopropan-2-ylcarbamate (1.97 g) in methanol to perform reductive amination (2.37 g, 46%). Next, deprotection and conversion to hydrochloride were performed (1.0 g, 45%) using trifluoroacetic acid and a 4 M hydrochloric acid-1,4-dioxane solution, followed by subjecting to condensation with isoquinoline-6-sulfonyl chloride prepared in Reference Example 1 (1.04 g, 75%). 28 mg of the title compound was obtained as a white solid (29%) with reference to the method of Step 3 of Example 1 using 80 mg of the obtained product.

$^1$H-NMR spectrum (D$_2$O, δ ppm): 0.74 (d, J=6.7 Hz, 3H), 2.99-3.04 (m, 1H), 3.14-3.23 (m, 2H), 3.34 (dd, J=5.8, 14.3 Hz, 1H), 3.67-3.72 (m, 4H), 4.40-4.42 (m, 1H), 7.21 (d, J=7.3 Hz, 2H), 7.29-7.35 (m, 3H), 8.19 (d, J=9.2 Hz, 1H), 8.44 (d, J=6.7 Hz, 1H), 8.55-8.58 (m, 2H), 8.70 (s, 1H), 9.66 (s, 1H).

Example 106

(S)-2-{(R)-2-(isoquinoline-6-sulfonamido)propylamino}-3-phenylpropanoic acid dihydrochloride

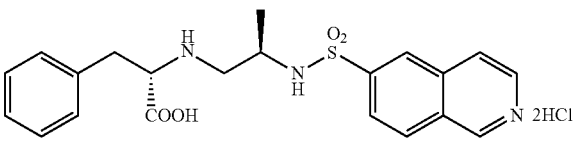

The title compound was synthesized according to the following Scheme 28:

Scheme 28

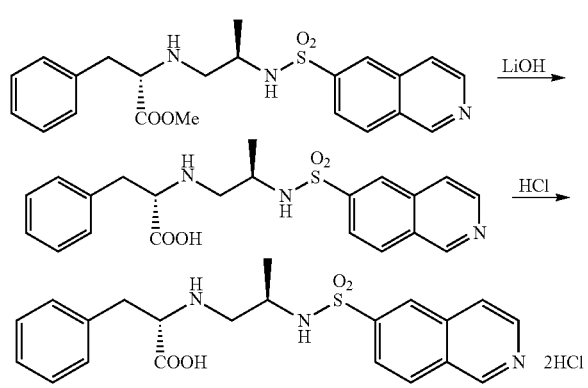

A free form (500 mg) of the compound of Example 105 was hydrolyzed (330 mg, 68%) using lithium hydroxide (56 mg) in tetrahydrofuran-water. Subsequently, 48 mg of the title compound was obtained as a yellow solid (12%) with reference to the method of Step 3 of Example 1.

$^1$H-NMR spectrum (D$_2$O, δ ppm): 0.74 (d, J=6.7 Hz, 3H), 2.95 (dd, J=13.1, 10.7 Hz, 1H), 3.08 (dd, J=3.4, 13.1 Hz, 1H), 3.17 (dd, J=7.0, 14.3 Hz, 1H), 3.21-3.26 (m, 1H), 3.65-3.70 (m, 1H), 4.05-4.08 (m, 1H), 7.23-7.28 (m, 3H), 7.32 (t, J=7.3 Hz, 2H), 8.22 (d, J=8.5 Hz, 1H), 8.52 (d, J=6.1 Hz, 1H), 8.58-8.61 (m, 2H), 8.73 (s, 1H), 9.71 (1H, s).

Example 107

(S)-2-hydroxy-N—{(R)-2-(isoquinoline-6-sulfonamido)propyl}-2-phenylacetamide hydrochloride

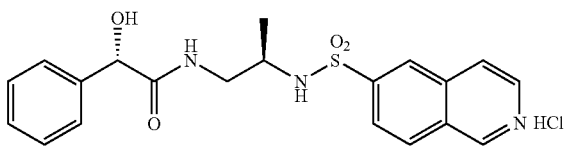 [SMILES: C[C@H](CNC(=O)[C@@H](O)c1ccccc1)NS(=O)(=O)c1ccc2cnccc2c1 ; Cl]

The title compound was synthesized according to the following Scheme 29:

Scheme 29

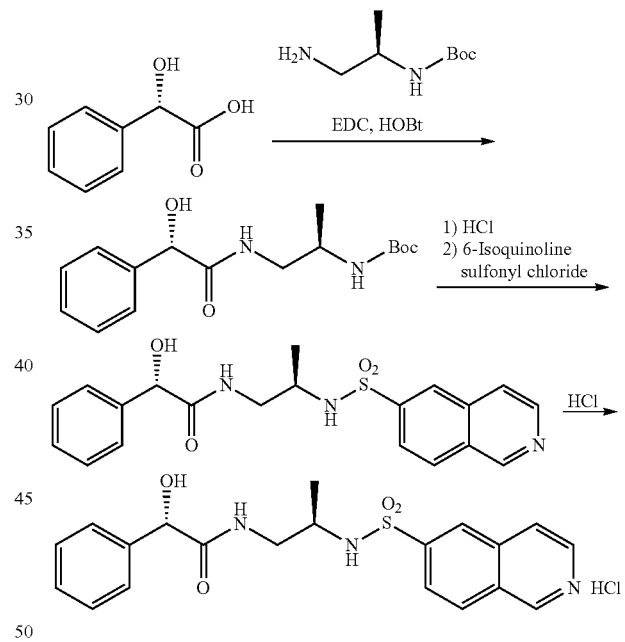

(S)-mandelic acid (261 mg) and (R)-tert-butyl 1-aminopropan-2-ylcarbamate (300 mg) were condensed (423 mg, 80%) using 1-ethyl-3-(3-dimethylaminopropyl)carbodiimide hydrochloride (363 mg) and 1-hydroxybenzotriazole (232 mg) in dichloromethane. Subsequently, the Boc group was removed with a 4 M hydrochloric acid-1,4-dioxane solution (2 mL), and the resulting amine compound and isoquinoline-6-sulfonyl chloride prepared in Reference Example 1 were condensed (370 mg, 67%). Subsequently, 346 mg of the title compound was obtained as a white solid (86%) with reference to Step 3 of Example 1.

$^1$H-NMR spectrum (D$_2$O, δ ppm): 0.82 (d, J=6.7 Hz, 3H), 3.13-3.15 (m, 2H), 3.54 (td, J=13.4, 6.7 Hz, 1H), 4.86 (s, 1H), 7.22-7.27 (m, 5H), 8.16 (d, J=9.2 Hz, 1H), 8.40 (d, J=6.7 Hz, 1H), 8.50 (d, J=9.2 Hz, 1H), 8.52 (d, J=6.1 Hz, 1H), 8.63 (s, 1H), 9.62 (s, 1H).

Example 108

N-{(2R)-1-(2-hydroxy-3-phenoxypropylamino)propan-2-yl}isoquinoline-6-sulfonamide dihydrochloride

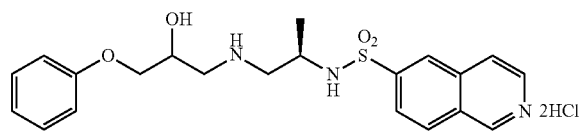 [SMILES: C[C@H](CNCC(O)COc1ccccc1)NS(=O)(=O)c1ccc2cnccc2c1 ; "2HCl"]

The title compound was synthesized according to the following Scheme 30:

Scheme 30

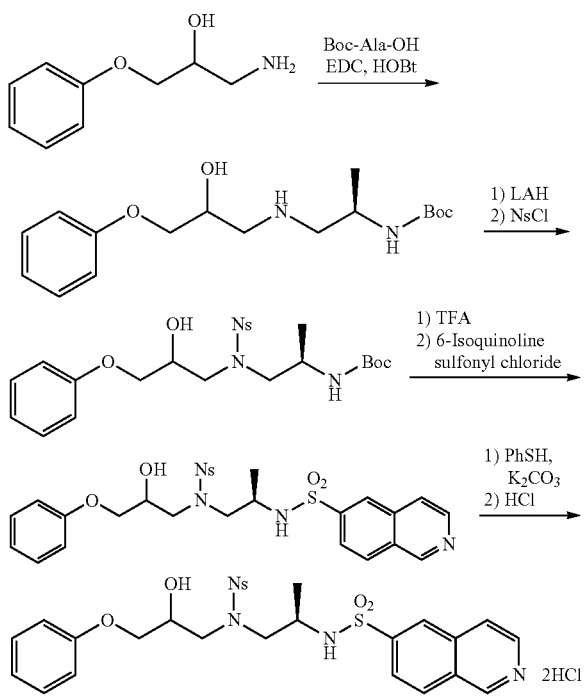

1-amino-3-phenoxypropan-2-ol (500 mg) and N-(tert-butoxycarbonyl)-D-alanine (622 mg) were condensed (500 mg, 49%) using 1-ethyl-3-(3-dimethylaminopropyl)carbodiimide hydrochloride (860 mg) and 1-hydroxybenzotriazole (458 mg) in N,N-dimethylformamide. Subsequently, the condensation product was reduced (120 mg, 25%) using lithium aluminum hydride (500 mg) in tetrahydrofuran. Subsequently, nosylation was performed (100 mg, 76%) using 2-nitrobenzenesulfonyl chloride (98 mg) in dichloromethane. Subsequently, an amine form was obtained by deprotection using trifluoroacetic acid and then condensed (50 mg, 42%) with isoquinoline-6-sulfonyl chloride prepared in Reference Example 1 in dichloromethane. Subsequently, 30 mg of the title compound was obtained as a pale yellow solid (85%) with reference to the methods of Steps 2 and 3 of Example 38.

$^1$H-NMR spectrum (D$_2$O, δ ppm): 0.78 (d, J=6.7 Hz, 3H), 3.04-3.08 (m, 1H), 3.15 (dt, J=5.5, 8.4 Hz, 1H), 3.21-3.40 (m, 2H), 3.76-3.80 (m, 1H), 4.00-4.07 (m, 2H), 4.27-4.32 (m, 1H), 6.92-6.98 (m, 3H), 7.28 (t, J=7.3 Hz, 2H), 8.23 (dd, J=1.5, 8.9 Hz, 1H), 8.48 (d, J=6.7 Hz, 1H), 8.57 (dd, J=7.9, 11.6 Hz, 2H), 8.73 (s, 1H), 9.67 (s, 1H).

Reference Example 10

(R)-tert-butyl 2-(2-oxoisoquinoline-6-sulfonamido)propyl(phenethyl)carbamate

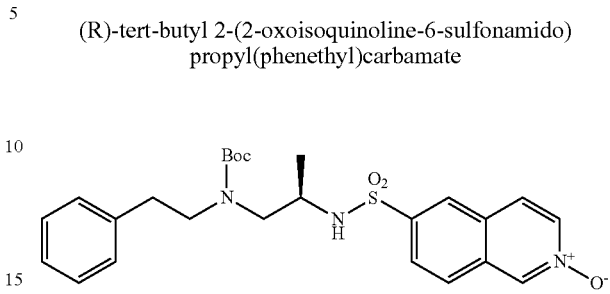

The title compound was synthesized according to the following Scheme 31:

Scheme 31

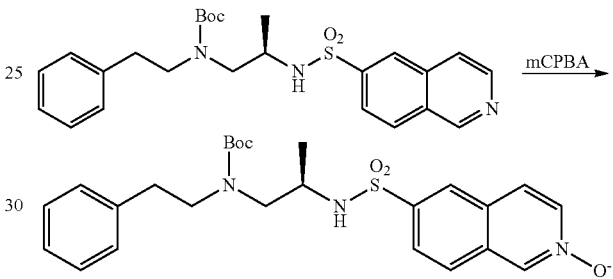

600 mg of the intermediate (R)-tert-butyl 2-(isoquinoline-6-sulfonamido)propyl(phenethyl)carbamate synthesized for obtaining the compound of Example 23 was dissolved in 20 mL of dichloromethane. To the solution, 450 mg of m-chloroperbenzoic acid was added at 0° C., and the mixture was stirred at room temperature for 16 hours. The reaction solution was concentrated under reduced pressure, and the obtained crude product was purified by silica gel column chromatography (dichloromethane:methanol=10:1) to obtain 520 mg of the title compound as a pale yellow oil (66%).

$^1$H-NMR spectrum (CDCl$_3$, δ ppm): 1.07 (d, J=5.5 Hz, 3H), 1.43 (s, 9H), 2.64-2.67 (m, 2H), 2.82 (d, J=14.6 Hz, 1H), 3.03-3.08 (m, 1H), 3.15-3.18 (m, 1H), 3.38 (t, J=12.2 Hz, 1H), 3.56 (s, 1H), 6.40 (s, 1H), 7.03 (d, J=6.7 Hz, 2H), 7.17-7.25 (m, 3H), 7.75 (d, J=6.7 Hz, 1H), 7.81 (d, J=8.5 Hz, 1H), 7.96 (d, J=9.8 Hz, 1H), 8.20 (d, J=6.7 Hz, 1H), 8.34 (s, 1H), 8.81 (s, 1H).

Example 109

(R)-1-amino-N-{1-(phenethylamino)propan-2-yl}isoquinoline-6-sulfonamide hydrochloride

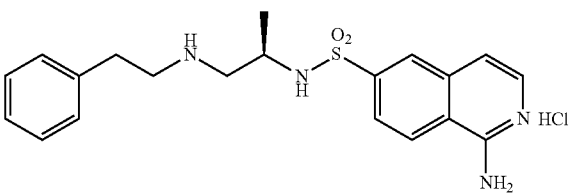 [SMILES: C[C@H](CNCCc1ccccc1)NS(=O)(=O)c1ccc2c(N)nccc2c1 ; Cl]

The title compound was synthesized according to the following Scheme 32:

The title compound was synthesized according to the following Scheme 33:

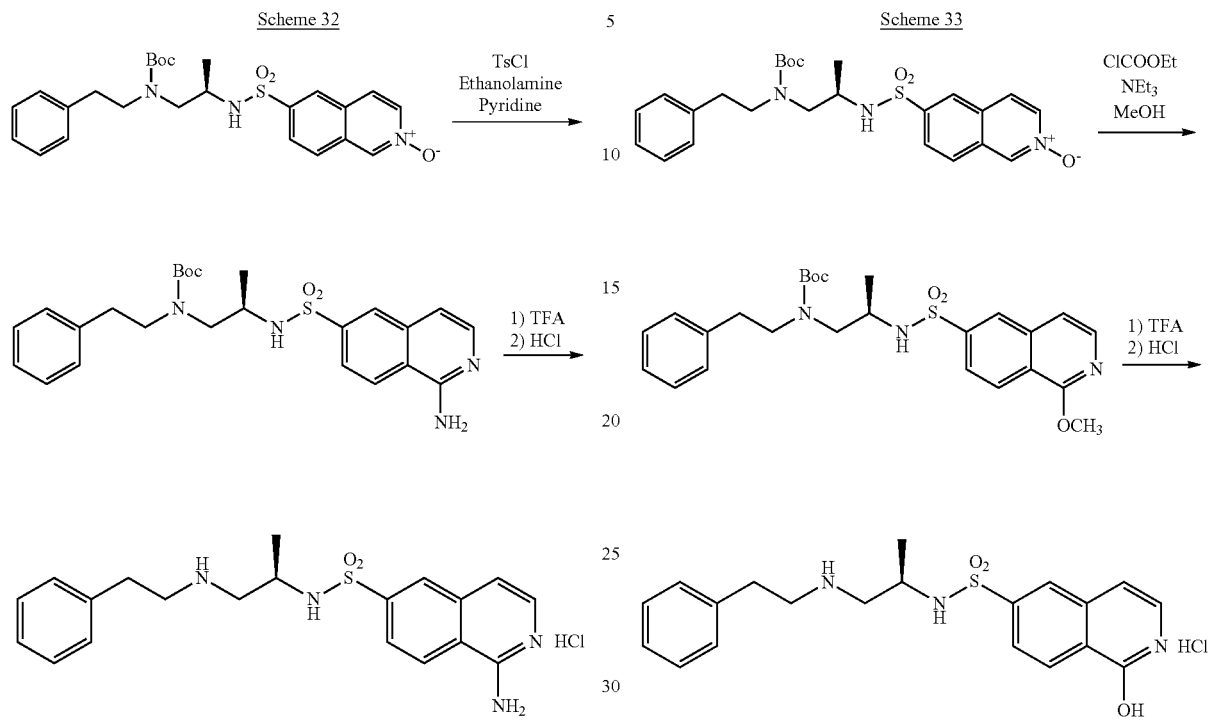

The compound of Reference Example 10 (400 mg) was reacted with p-toluenesulfonyl chloride (202 mg) and ethanolamine (7 mL) at room temperature in pyridine (15 mL) according to the method described in J. Med. Chem., 46, 4405 (2003) to introduce an amino group to the 1st position of the isoquinoline ring (198 mg, 49%).

Subsequently, 116 mg of the title compound was obtained as a white solid (88%) from 120 mg of a free form according to the methods described in Steps 2 and 3 of Example 1.

$^1$H-NMR spectrum (D$_2$O, δ ppm): 0.72 (d, J=6.5 Hz, 3H), 2.87-2.92 (m, 3H), 2.98-3.02 (m, 1H), 3.16-3.21 (m, 2H), 3.50-3.58 (m, 1H), 7.08 (d, J=6.5 Hz, 1H), 7.16-7.23 (m, 3H), 7.27-7.29 (m, 2H), 7.63 (d, J=6.5 Hz, 1H), 7.82 (d, J=9.0 Hz, 1H), 8.15-8.18 (m, 2H).

The compound of Reference Example 10 (320 mg) was reacted with ethyl chlorocarbonate (0.1 mL) in the presence of triethylamine (0.2 mL) in methanol to introduce a methoxy group to the 1st position of the isoquinoline ring (120 mg, 33%). Subsequently, 57 mg of the title compound was obtained as a pale yellow solid (54%) with reference to the methods of Steps 2 and 3 of Example 1.

$^1$H-NMR spectrum (D$_2$O, δ ppm): 0.72 (d, J=6.5 Hz, 3H), 2.85-2.92 (m, 3H), 2.98-3.01 (m, 1H), 3.14-3.21 (m, 2H), 3.50-3.58 (m, 1H), 6.76 (d, J=7.5 Hz, 1H), 7.16-7.28 (m, 6H), 7.79 (d, J=8.5 Hz, 1H), 8.10 (s, 1H), 8.28 (d, J=9.0 Hz, 1H).

This compound may be present as (R)-oxo-N-[1-(phenethylamino)propan-2-yl]-1,2-dihydroisoquinoline-6-sulfonamide hydrochloride), which is a keto-enol isomer.

Example 110

(R)—N-{1-(phenethylamino)propan-2-yl}-1-hydroxyisoquinoline-6-sulfonamide hydrochloride

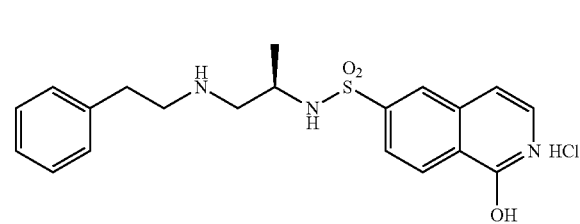 [SMILES: C[C@H](CNCCc1ccccc1)NS(=O)(=O)c1ccc2c(O)nccc2c1 ; Cl]

Example 111

(R)-1-(2-aminoethylthio)-N-{1-(phenethylamino)propan-2-yl}isoquinoline-6-sulfonamide trihydrochloride

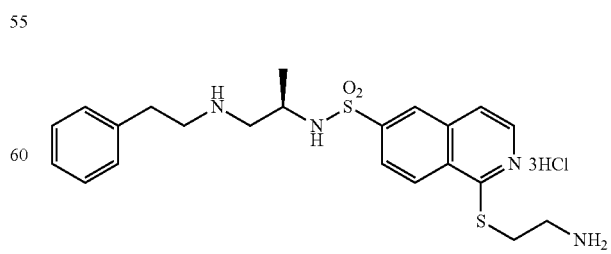

The title compound was synthesized according to the following Scheme 34:

Scheme 34

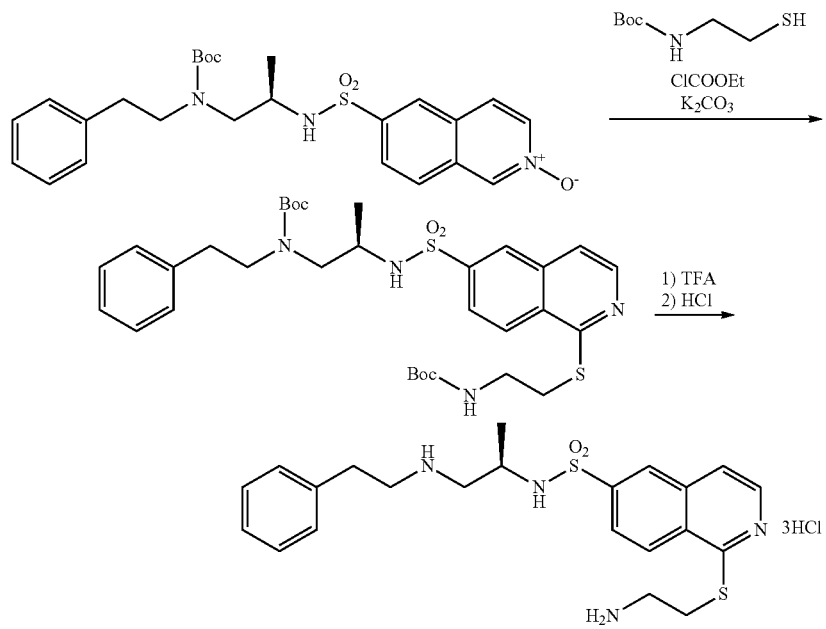

The compound of Reference Example 10 (540 mg) was reacted with ethyl chlorocarbonate (0.159 mL) and 2-(N-tert-butoxycarbonylamino)ethanethiol (0.376 mL) in the presence of potassium carbonate (768 mg) in dichloromethane to introduce a 2-(N-tert-butoxycarbonylamino)ethylthio group to the 1st position of the isoquinoline ring (260 mg, 36%). Subsequently, 110 mg of the title compound was obtained as a pale yellow solid (49%) with reference to the methods of Steps 2 and 3 of Example 1.

$^1$H-NMR spectrum (D$_2$O, δ ppm): 0.72 (d, J=6.7 Hz, 3H), 2.91-2.95 (m, 3H), 3.04 (d, J=12.2 Hz, 1H), 3.21-3.29 (m, 2H), 3.34 (t, J=6.1 Hz, 2H), 3.57 (t, J=5.8 Hz, 2H), 3.60-3.62 (m, 1H), 7.21 (d, J=7.3 Hz, 2H), 7.26 (d, J=7.3 Hz, 1H), 7.31 (t, J=7.0 Hz, 2H), 7.63 (d, J=4.9 Hz, 1H), 7.92 (d, J=8.5 Hz, 1H), 8.34 (d, J=6.1 Hz, 1H), 8.36 (d, J=9.2 Hz, 1H), 8.39 (s, 1H).

Reference Example 11

(R)-6-[N-{tert-butoxycarbonyl(phenethyl)aminopropan-2-yl}sulphamoyl]isoquinolin-4-yl trifluoromethanesulfonate The title compound was synthesized according to the following Scheme 35:

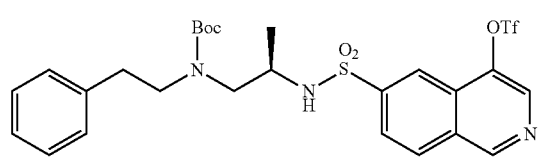 [SMILES: C[C@H](CN(CCc1ccccc1)C(=O)OC(C)(C)C)NS(=O)(=O)c1ccc2cncc(OS(=O)(=O)C(F)(F)F)c2c1]

Scheme 35

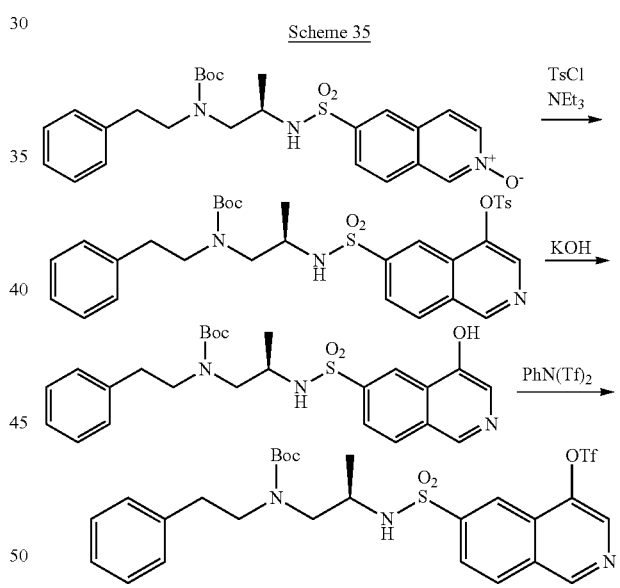

The compound of Reference Example 10 (548 mg) was reacted with p-toluenesulfonyl chloride (215 mg) at 0° C. in the presence of triethylamine (0.156 mL) in dichloromethane according to the method described in Tetrahedron, 25, 5761 (1969) to obtain a compound containing a p-toluenesulfonyloxy group introduced at the 4th position of the isoquinoline ring (485 mg, 67%). A compound (700 mg) obtained by performing this reaction again was dissolved in methanol, and the p-toluenesulfonyloxy group was hydrolyzed into a hydroxyl group (400 mg, 75%) by the addition of a 1 M aqueous potassium hydroxide solution (3 mL). 400 mg of the compound thus obtained was dissolved in 10 mL of dichloromethane. To the solution, 0.172 mL of triethylamine and 450 mg of N-phenyl bis(trifluoromethanesulfonimide) were added at 0° C., and the mixture was stirred at room temperature for 3 hours. The reaction solution was concentrated under reduced pressure, and the obtained crude product was purified by silica gel column chromatography (hexane:ethyl acetate=3:1) to obtain 403 mg of the title compound as a pale yellow oil (79%).

¹H-NMR spectrum (CDCl₃, δ ppm): 0.72 (d, J=5.5 Hz, 3H), 1.44 (s, 9H), 2.62-2.77 (m, 3H), 3.05-3.10 (m, 2H), 3.37-3.40 (m, 1H), 3.58 (br s, 1H), 6.30 (br s, 1H), 6.99-7.00 (m, 2H), 7.19-7.39 (m, 3H), 8.10 (d, J=6.2 Hz, 1H), 8.20 (d, J=6.2 Hz, 1H), 8.59 (s, 1H), 8.68 (br s, 1H), 9.34 (br s, 1H).

Example 112

(R)—N-{1-(phenethylamino)propan-2-yl}-4-methyl-isoquinoline-6-sulfonamide hydrochloride

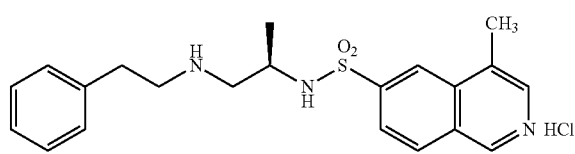 [SMILES: Cc1cncc2ccc(S(=O)(=O)N[C@H](C)CNCCc3ccccc3)cc12 ; Cl]

The title compound was synthesized according to the following Scheme 36:

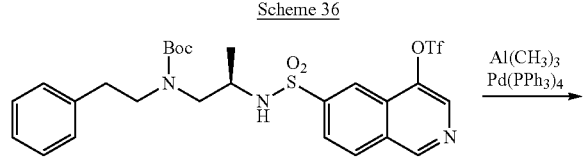

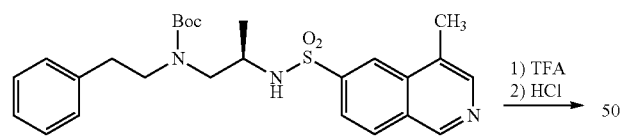

The compound of Reference Example 11 (286 mg) was reacted with a 2 M trimethylaluminum-heptane solution (1.5 mL) in the presence of tetrakis(triphenylphosphine)palladium (53 mg) in tetrahydrofuran according to the method described in J. Chem. Soc., Perkin Trans 1, 12, 2513 (1989) to convert the trifluoromethanesulfonyloxy group to a methyl group (165 mg, 73%). Subsequently, 80 mg of the title compound was obtained as a white solid (63%) from 115 mg of a free form according to the methods described in Steps 2 and 3 of Example 1.

¹H-NMR spectrum (D₂O, δ ppm): 0.72 (d, J=6.5 Hz, 3H), 2.63 (s, 3H), 2.91-2.95 (m, 3H), 3.00-3.04 (m, 1H), 3.18-3.23 (m, 2H), 3.50-3.58 (m, 1H), 7.18-7.23 (m, 3H), 7.26-7.29 (m, 2H), 8.02 (d, J=9.0 Hz, 1H), 8.32-8.34 (m, 2H), 8.53 (s, 1H), 9.24 (s, 1H).

Example 113

(R)—N-{1-(4-fluorophenethylamino)propan-2-yl}-4-methyl-isoquinoline-6-sulfonamide hydrochloride 120 mg of the title compound was obtained as a white solid (68%) with reference to the methods described in Reference Examples 10 and 11 and Example 112 using the intermediate (R)-tert-butyl 2-(isoquinoline-6-sulfonamido)propyl(4-fluorophenethyl)carbamate (232 mg) synthesized for obtaining the compound of Example 53.

¹H-NMR spectrum (D₂O, δ ppm): 0.66 (d, J=7.0 Hz, 3H), 2.40 (s, 3H), 2.83-2.89 (m, 3H), 2.97 (dd, J=3.5, 13.5 Hz, 1H), 3.10-3.14 (m, 2H), 3.58-3.60 (m, 1H), 6.92-6.96 (m, 2H), 7.09-7.12 (m, 2H), 8.06 (d, J=8.5 Hz, 1H), 8.17 (s, 1H), 8.17 (s, 1H), 8.28 (s, 1H), 8.92 (s, 1H).

Example 114

(R)—N-[1-(phenethylamino)propan-2-yl]-4-hydroxy-isoquinoline-6-sulfonamide dihydrochloride

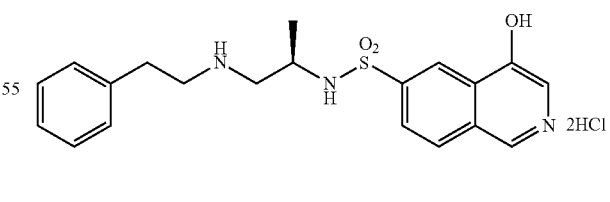

20 mg of the title compound was obtained as a white solid with reference to the methods of Steps 2 and 3 of Example 1 using (R)-tert-butyl 2-(4-hydroxyisoquinoline-6-sulfonamido)propyl(phenethyl)carbamate synthesized in Reference Example 11.

¹H-NMR spectrum (D₂O, δ ppm): 0.70 (d, J=6.5 Hz, 3H), 2.91-2.95 (m, 3H), 3.02 (dd, J=3.5, 13.5 Hz, 1H), 3.17-3.26 (m, 2H), 3.58-3.65 (m, 1H), 7.18-7.22 (m, 3H), 7.26-7.29 (m, 2H), 8.00 (br s, 1H), 8.13 (d, J=8.5 Hz, 1H), 8.42 (d, J=8.5 Hz, 1H), 8.79 (s, 2H), 9.05 (br s, 1H).

Example 115

(R)—N-{1-(phenethylamino)propan-2-yl}-4-(thiophen-3-yl)isoquinoline-6-sulfonamide dihydrochloride

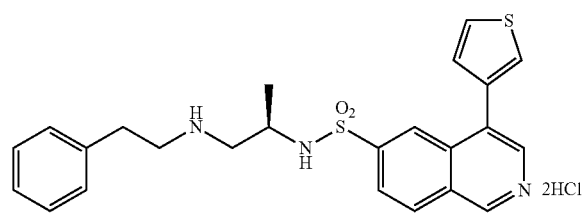 [SMILES: C[C@H](CNCCc1ccccc1)NS(=O)(=O)c1ccc2cncc(-c3ccsc3)c2c1 ; "2HCl"]

The title compound was synthesized according to the following Scheme 37:

Scheme 37

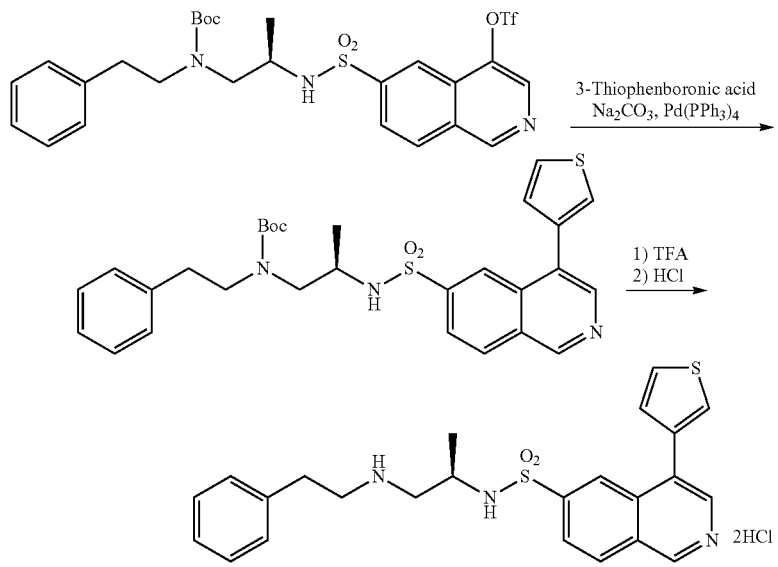

The compound of Reference Example 11 (396 mg) was reacted with 3-thiopheneboronic acid (106 mg) in the presence of sodium carbonate (679 mg) and tetrakis(triphenylphosphine)palladium (74 mg) in 1,4-dioxane-water to obtain a coupling product (266 mg, 75%). Subsequently, 220 mg of the title compound was obtained as a yellow solid (87%) with reference to the methods of Steps 2 and 3 of Example 1.

$^1$H-NMR spectrum (D$_2$O, δ ppm): 0.68 (d, J=6.5 Hz, 3H), 2.86-2.92 (m, 3H), 2.97 (dd, J=4.0, 13.5 Hz, 1H), 3.15-3.20 (m, 2H), 3.48-3.53 (m, 1H), 7.14-7.30 (m, 6H), 7.60-7.62 (m, 1H), 7.69-7.70 (m, 1H), 8.14 (d, J=8.5 Hz, 1H), 8.52-8.54 (m, 3H), 9.53 (br s, 1H).

Example 116

(S)—N-(2-amino-3-phenylpropyl)isoquinoline-6-sulfonamide dihydrochloride

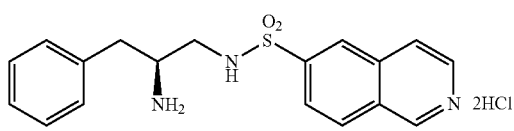 [SMILES: N[C@H](CNS(=O)(=O)c1ccc2cnccc2c1)Cc1ccccc1 ; "2HCl"]

The title compound was synthesized according to the following Scheme 38:

Scheme 38

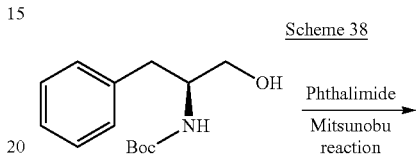

-continued

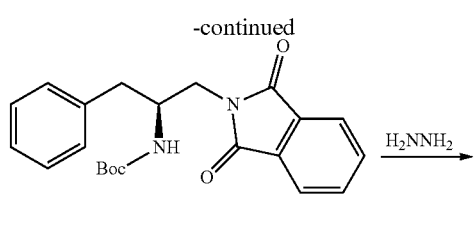

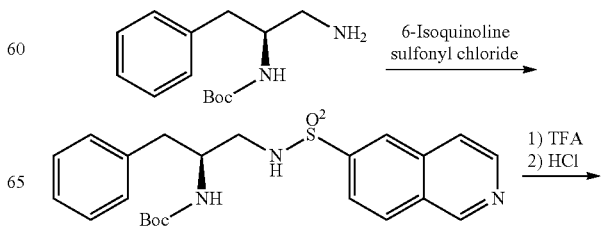

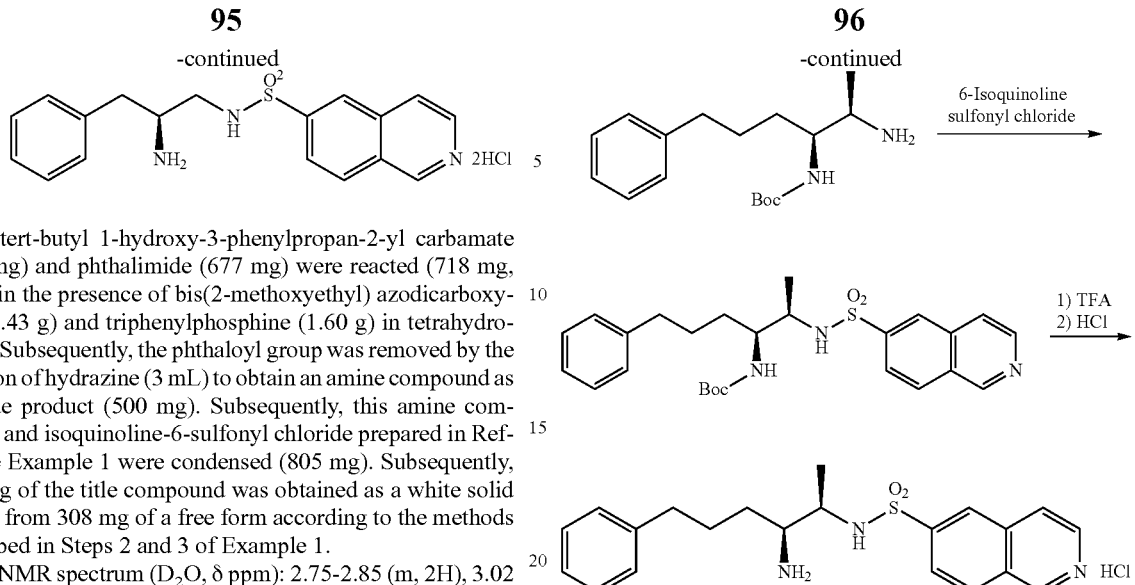

(S)-tert-butyl 1-hydroxy-3-phenylpropan-2-yl carbamate (770 mg) and phthalimide (677 mg) were reacted (718 mg, 61%) in the presence of bis(2-methoxyethyl) azodicarboxylate (1.43 g) and triphenylphosphine (1.60 g) in tetrahydrofuran. Subsequently, the phthaloyl group was removed by the addition of hydrazine (3 mL) to obtain an amine compound as a crude product (500 mg). Subsequently, this amine compound and isoquinoline-6-sulfonyl chloride prepared in Reference Example 1 were condensed (805 mg). Subsequently, 274 mg of the title compound was obtained as a white solid (88%) from 308 mg of a free form according to the methods described in Steps 2 and 3 of Example 1.

$^1$H-NMR spectrum (D$_2$O, δ ppm): 2.75-2.85 (m, 2H), 3.02 (d, J=6.1 Hz, 2H), 3.56-3.61 (m, 1H), 7.09 (d, J=7.3 Hz, 2H), 7.15-7.21 (m, 3H), 8.05 (d, J=8.5 Hz, 1H), 8.37 (d, J=6.1, 1H), 8.46-8.53 (m, 3H), 9.61 (s, 1H).

Example 117

N-{(2R,3S)-3-amino-6-phenylhexan-2-yl)isoquinoline-6-sulfonamide hydrochloride

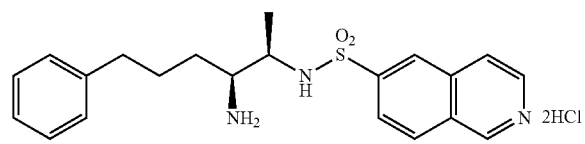 [SMILES: C[C@@H](NS(=O)(=O)c1ccc2cnccc2c1)[C@@H](N)CCCc1ccccc1 ; "2HCl"]

The title compound was synthesized according to the following Scheme 39:

Scheme 39

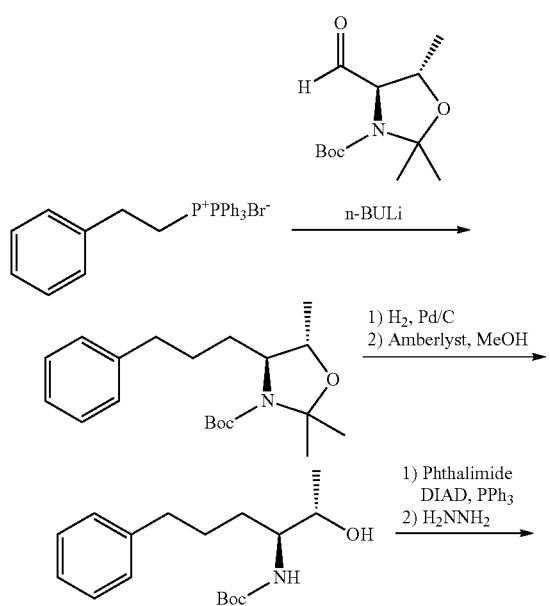

Triphenyl(2-phenylethyl)-phosphonium bromide (480 mg) was dissolved in tetrahydrofuran. To the solution, a 1.6 M normal butyllithium-hexane solution (0.87 mL) was added at −30° C. and reacted with (4R,5S)-tert-butyl 4-formyl-2,2,5-trimethyloxazolidine-3-carboxylate to obtain an olefin compound (214 mg). Subsequently, hydrogenation reaction was performed in the presence of 10% palladium-carbon, and the acetonide group was removed with Amberlyst in methanol (178 mg, 93%). Subsequently, the hydroxyl group was converted to a phthalimide group using triphenylphosphine (318 mg), diisopropyl azodicarboxylate (0.254 mL), and phthalimide (268 mg) in tetrahydrofuran, and the phthaloyl group was removed with hydrazine to obtain an amine compound (148 mg, 83%). Subsequently, this amine compound and isoquinoline-6-sulfonyl chloride prepared in Reference Example 1 were condensed (214 mg, 87%). Subsequently, 115 mg of the title compound was obtained as a white solid (88%) from 119 mg of a free form according to the methods described in Steps 2 and 3 of Example 1.

$^1$H-NMR spectrum (D$_2$O, δ ppm): 0.70 (d, J=7.3 Hz, 3H), 1.35-1.63 (m, 4H), 2.42-2.55 (m, 2H), 3.17-3.20 (m, 1H), 3.43-3.49 (m, 1H), 7.08 (d, J=7.3 Hz, 2H), 7.14 (t, J=7.3 Hz, 1H), 7.22 (t, J=7.3 Hz, 2H), 7.85 (d, J=6.1 Hz, 1H), 7.90 (dd, J=1.8, 8.5 Hz, 1H), 8.21 (d, J=8.5 Hz, 1H), 8.40 (s, 1H), 8.45 (d, J=5.5 Hz, 1H), 9.22 (s, 1H).

Example 118

N-{(2R)-4-amino-6-phenylhexan-2-yl}isoquinoline-6-sulfonamide dihydrochloride (Diastereomer A)

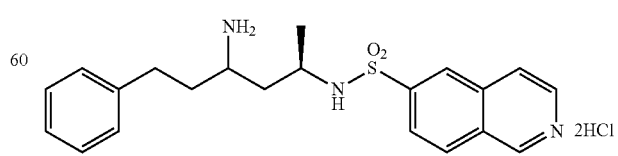

The title compound was synthesized according to the following Scheme 40:

Scheme 40

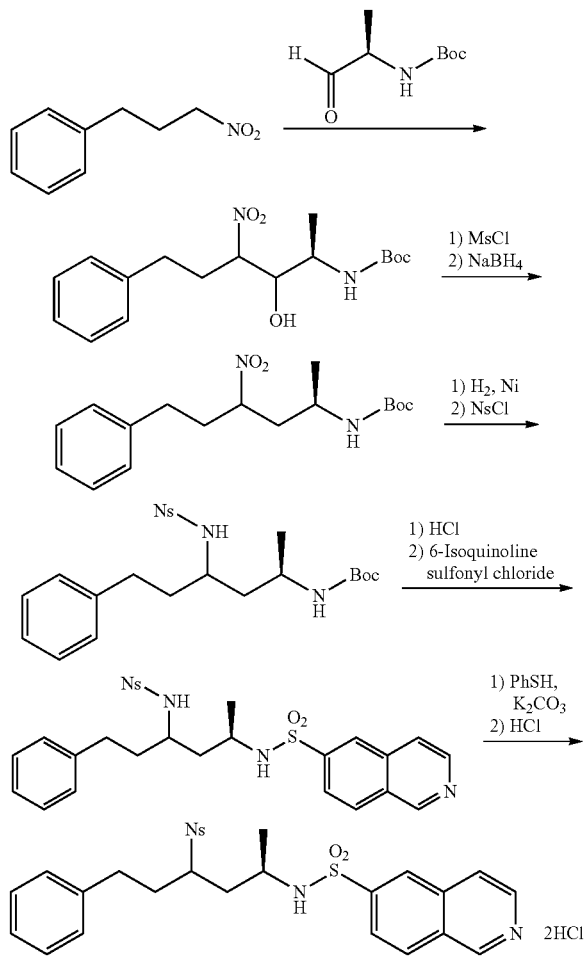

Nitroaldol reaction was performed (1.0 g, 39%) using (3-nitropropyl)benzene (1.47 g) and (R)-tert-butyl 1-oxopropan-2-ylcarbamate (1.3 g) in the presence of triethylamine (1.25 mL) in tetrahydrofuran. Subsequently, mesylation of the hydroxyl group and elimination were performed, and the formed double bond was reduced with sodium borohydride. The diastereomeric mixture of tert-butyl (2R)-4-nitro-6-phenylhexan-2-ylcarbamate thus obtained was resolved by silica gel column chromatography to obtain a more polar diastereomer (234 mg, 24%). A diastereomer (1.96 g) obtained by performing this reaction again was used to perform hydrogenation reaction in the presence of Raney nickel, and an amino group formed by reducing the nitro group was protected with a nosyl group (1.72 g, 59%). Subsequently, the Boc group was removed with a 4 M hydrochloric acid-1,4-dioxane solution, and the resulting amine compound and isoquinoline-6-sulfonyl chloride prepared in Reference Example 1 were condensed (1.5 g, 73%). 45 mg of the title compound was obtained as a pale yellow solid (35%) with reference to Steps 2 and 3 of Example 38 using the obtained compound (160 mg).

$^1$H-NMR spectrum (D$_2$O, δ ppm): 0.89 (d, J=6.7 Hz, 3H), 1.44-1.52 (m, 1H), 1.57-1.73 (m, 3H), 2.18-2.24 (m, 1H), 2.48-2.54 (m, 1H), 3.25 (br s, 1H), 3.42 (br s, 1H), 6.94 (d, J=7.3 Hz, 2H), 7.13 (t, J=7.3 Hz, 1H), 7.18 (t, J=7.3 Hz, 2H), 8.11 (d, J=9.2 Hz, 1H), 8.22 (d, J=6.1 Hz, 1H), 8.41 (d, J=8.5 Hz, 1H), 8.45 (d, J=6.1 Hz, 1H), 8.59 (s, 1H), 9.41 (s, 1H).

Example 119

N-{(2R)-4-amino-6-phenylhexan-2-yl}isoquinoline-6-sulfonamide dihydrochloride (Diastereomer B)

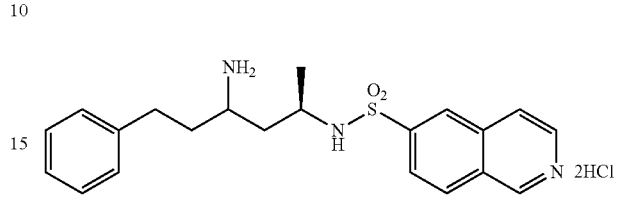

Of the intermediate diastereomeric mixture of tert-butyl (2R)-4-nitro-6-phenylhexan-2-ylcarbamate obtained in the synthesis of the compound of Example 118, a less polar diastereomer was used to obtain 50 mg of the title compound as a pale yellow solid (60%) according to the method described in Example 118.

$^1$H-NMR spectrum (D$_2$O, δ ppm): 0.88 (d, J=6.7 Hz, 3H), 1.66-1.72 (m, 1H), 1.75-1.83 (m, 3H), 2.50 (dq, J=7.3, 30 Hz, 2H), 3.28-3.35 (m, 1H), 3.42-3.48 (m, 1H), 7.12 (d, J=7.9 Hz, 2H), 7.20 (t, J=6.7 Hz, 1H), 7.27 (t, J=7.3 Hz, 2H), 8.20 (dd, J=1.8, 8.5 Hz, 1H), 8.40 (d, J=6.7 Hz, 1H), 8.53-8.55 (m, 2H), 8.69 (s, 1H), 9.62 (s, 1H).

Example 120

N-{(2R)-4-(methylamino)-6-phenylhexan-2-yl}isoquinoline-6-sulfonamide dihydrochloride

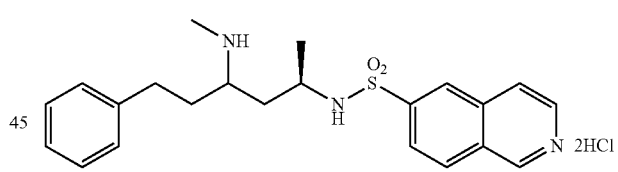

The title compound was synthesized according to the following Scheme 41:

Scheme 41

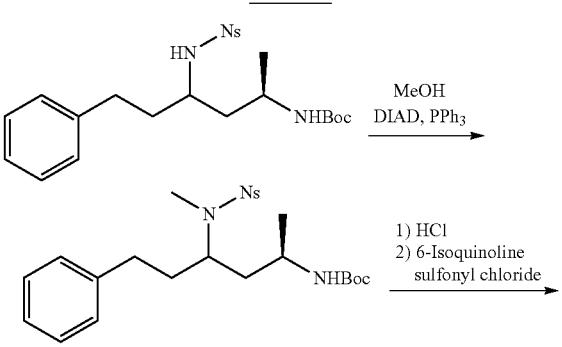

-continued

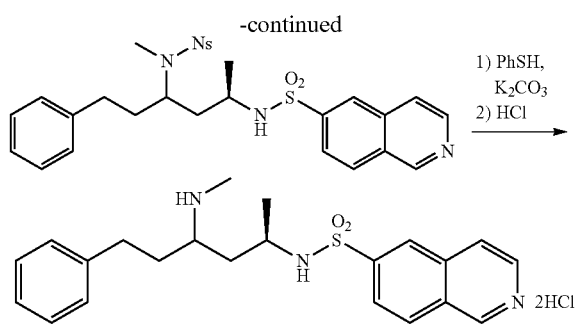

1) PhSH, K₂CO₃
2) HCl

The intermediate tert-butyl (2R)-4-(2-nitrophenylsulfonamido)-6-phenylhexan-2-ylcarbamate (467 mg) synthesized for obtaining the compound of Example 118 was methylated through reaction with methanol (0.038 mL) in the presence of diisopropyl azodicarboxylate (0.4 mL) and triphenylphosphine (513 mg) in tetrahydrofuran. 237 mg of the title compound was obtained as a white solid (74%) from 270 mg of a free form of the obtained crude product according to the methods described in Example 118 and Steps 2 and 3 of Example 38.

$^1$H-NMR spectrum (D$_2$O, δ ppm): 0.88 (d, J=6.7 Hz, 3H), 1.55-1.63 (m, 1H), 1.66-1.75 (m, 3H), 2.29-2.35 (m, 1H), 2.49-2.55 (m, 1H), 2.60 (s, 3H), 3.20 (br s, 1H), 3.41 (br s, 1H), 7.01 (d, J=7.3 Hz, 2H), 7.15 (t, J=7.0 Hz, 1H), 7.21 (t, J=7.3 Hz, 2H), 8.16 (d, J=8.5 Hz, 1H), 8.35 (d, J=6.7 Hz, 1H), 8.49 (d, J=7.3 Hz, 2H), 8.63 (s, 1H), 9.53 (s, 1H).

Compounds of Examples 121 to 252 shown in Tables 1 to 11 below can separately be synthesized according to the method described in Example 1 from intermediates synthesized by the method described in any of Reference Examples 2 to 5, 7, and 8 using the compound of Reference Example 1 and appropriate starting materials, or according to the method described in Example 38 from intermediates synthesized by the method described in Reference Example 6 using the compound of Reference Example 1 and appropriate starting materials, or using a general method well known by those skilled in the art.

TABLE 1

| Example No. | Structural formula | Chemical name |
|---|---|---|
| 121 | | (R)-4-[2-{2-(isoquinoline-6-sulfonamide)propylamino}ethyl]benzoic acid hydrochloride |
| 122 | | (R)-N-{1-(4-cyanophenethylamino)propan-2-yl}isoquinoline-6-sulfonamide hydrochloride |
| 123 | | (R)-N-[1-{2-(1-methyl-6-oxo-1,6-dihydropyridin-2-yl)ethylamino}propan-2-yl]isoquinoline-6-sulfonamide hydrochloride |
| 124 | | (R)-N-{1-(4-formylphenethylamino)propan-2-yl}isoquinoline-6-sulfonamide hydrochloride |
| 125 | | (R)-N-{1-(4-acetylphenethylamino)propan-2-yl}isoquinoline-6-sulfonamide hydrochloride |

TABLE 1-continued

| Example No. | Structural formula | Chemical name |
|---|---|---|
| 126 | 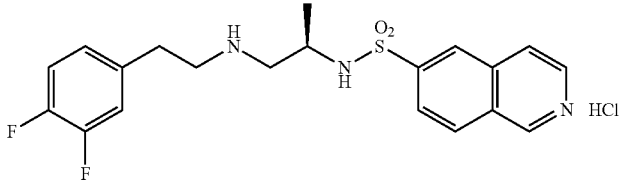 [SMILES: C[C@H](CNCCc1ccc(F)c(F)c1)NS(=O)(=O)c1ccc2cnccc2c1 ; Cl] | (R)-N-{1-(2,3-difluorophenethylamino)propan-2-yl)isoquinoline-6-sulfonamide hydrochloride |
| 127 | 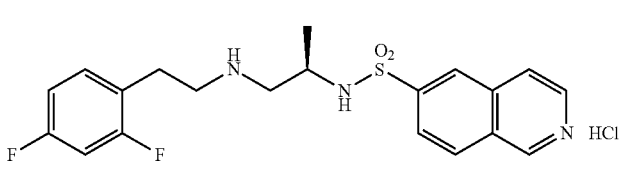 [SMILES: C[C@H](CNCCc1ccc(F)cc1F)NS(=O)(=O)c1ccc2cnccc2c1 ; Cl] | (R)-N-{1-(2,4-difluorophenethylamino)propan-2-yl}isoquinoline-6-sulfonamide hydrochloride |
| 128 | 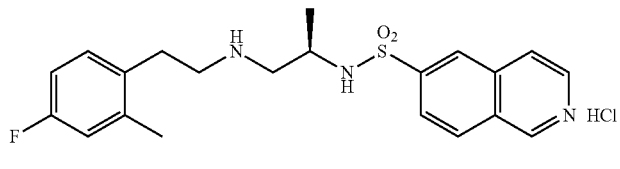 [SMILES: Cc1cc(F)ccc1CCNC[C@@H](C)NS(=O)(=O)c1ccc2cnccc2c1 ; Cl] | (R)-N-{1-(4-difluoro-2-methylphenethylamino)propan-2-yl}isoquinoline-6-sulfonamide hydrochloride |
| 129 | 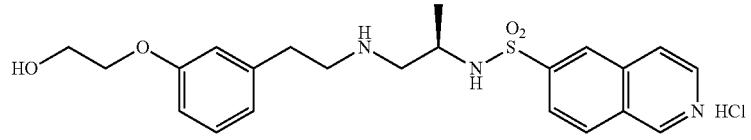 [SMILES: C[C@H](CNCCc1cccc(OCCO)c1)NS(=O)(=O)c1ccc2cnccc2c1 ; Cl] | (R)-N-[1-{3-(2-hydroxyethoxy)phenethylamino}propan-2-yl]isoquinoline-6-sulfonamide hydrochloride |
| 130 | 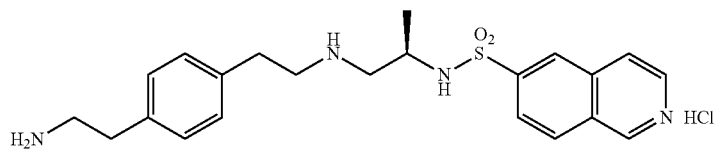 [SMILES: C[C@H](CNCCc1ccc(CCN)cc1)NS(=O)(=O)c1ccc2cnccc2c1 ; Cl] | (R)-N-[1-{4-(2-aminoethyl)phenethylamino}propan-2-yl]isoquinoline-6-sulfonamide hydrochloride |
| 131 | 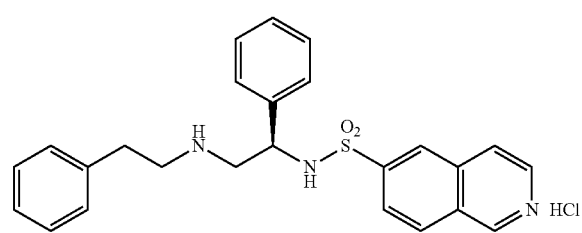 [SMILES: O=S(=O)(N[C@@H](CNCCc1ccccc1)c1ccccc1)c1ccc2cnccc2c1 ; Cl] | (R)-N-{2-(phenethylamino)-1-phenylethyl}isoquinoline-6-sulfonamide hydrochloride |

TABLE 2

| 132 | 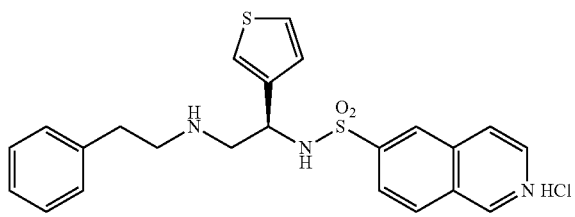 [SMILES: O=S(=O)(N[C@@H](CNCCc1ccccc1)c1ccsc1)c1ccc2cnccc2c1 ; Cl] | (R)-N-{2-(phenethylamino)-1-(thiophen-3-yl)ethyl}isoquinoline-6-sulfonamide hydrochloride |

TABLE 2-continued

| | | |
|---|---|---|
| 133 | | (S)-N-(2-isoquinoline-6-sulfonamide)-3-(phenethylamino)propanoic acid hydrochloride |
| 134 | | (S)-ethyl 2-(isoquinoline-6-sulfonamide)-3-(phenethylamino)propanoate hydrochloride |
| 135 | | N-{2-hydroxy-3-(phenethylamino)propyl}isoquinoline-6-sulfonamide hydrochloride |
| 136 | | (R)-5-cyano-N-{1-(phenethylamino)propan-2-yl}isoquinoline-6-sulfonamide hydrochloride |
| 137 | | (R)-N-{1-(phenethylamino)propan-2-yl}-5-(trifluoromethyl)isoquinoline-6-sulfonamide hydrochloride |
| 138 | | (R)-5-nitro-N-{1-(phenethylamino)propan-2-yl}isoquinoline-6-sulfonamide hydrochloride |
| 139 | | (R)-N-{1-(phenethylamino)propan-2-yl}-5-vinylisoquinoline-6-sulfonamide hydrochloride |
| 140 | | (R)-4-ethynyl-N-{1-(phenethylamino)propan-2-yl}isoquinoline-6-sulfonamide hydrochloride |

TABLE 2-continued

| | | |
|---|---|---|
| 141 | 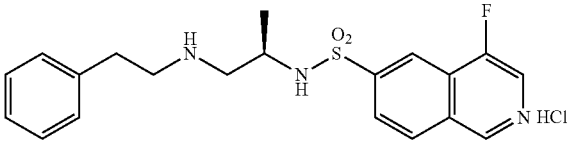 [SMILES: C[C@H](CNCCc1ccccc1)NS(=O)(=O)c1ccc2cncc(F)c2c1 ; Cl] | (R)-4-fluoro-N-{1-(phenethylamino)propan-2-yl}isoquinoline-6-sulfonamide hydrochloride |
| 142 | 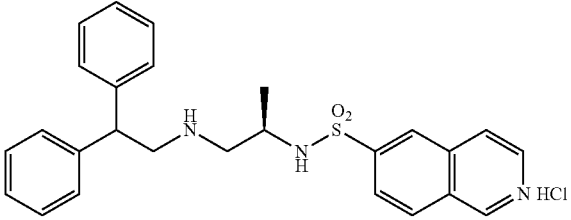 [SMILES: C[C@H](CNCC(c1ccccc1)c1ccccc1)NS(=O)(=O)c1ccc2cnccc2c1 ; Cl] | (R)-N-{1-(2,2-diphenylethylamino)propan-2-yl}isoquinoline-6-sulfonamide hydrochloride |
| 143 | 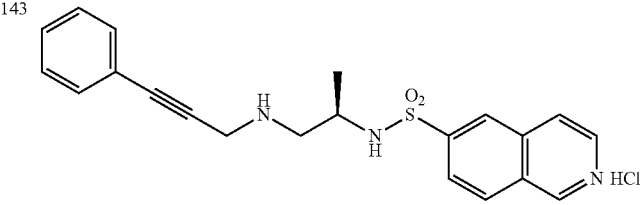 | (R)-N-{1-(3-phenylprop-2-ylamino)propan-2-yl}isoquinoline-6-sulfonamide hydrochloride |

TABLE 3

| | | |
|---|---|---|
| 144 | 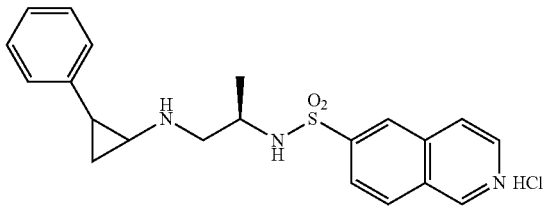 [SMILES: C[C@H](CNC1CC1c1ccccc1)NS(=O)(=O)c1ccc2cnccc2c1 ; Cl] | N-{(2R)-1-(2-phenylcyclopropaneamino)propan-2-yl}isoquinoline-6-sulfonamide hydrochloride |
| 145 | 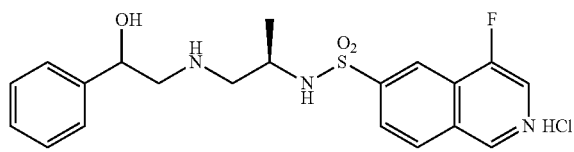 [SMILES: C[C@H](CNCC(O)c1ccccc1)NS(=O)(=O)c1ccc2cncc(F)c2c1 ; Cl] | 4-fluoro-N-{(2R)-1-(2-hydroxy-2-phenylethylamino)propan-2-yl}isoquinoline-6-sulfonamide hydrochloride |
| 146 | 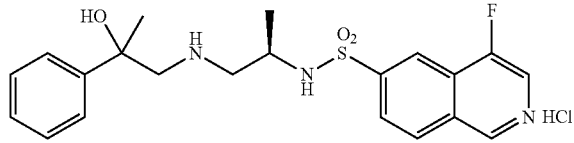 [SMILES: C[C@H](CNCC(C)(O)c1ccccc1)NS(=O)(=O)c1ccc2cncc(F)c2c1 ; Cl] | 4-fluoro-N-{(2R)-1-(2-hydroxy-2-phenylpropylamino)propan-2-yl}isoquinoline-6-sulfonamide hydrochloride |
| 147 | 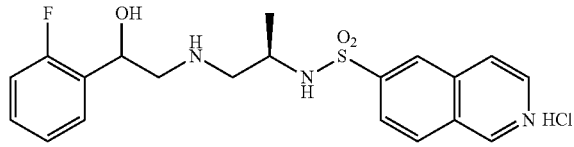 [SMILES: C[C@H](CNCC(O)c1ccccc1F)NS(=O)(=O)c1ccc2cnccc2c1 ; Cl] | N-[(2R)-1-{2-(2-fluorophenyl)-2-hydroxyethylamino)}propan-2-yl]isoquinoline-6-sulfonamide hydrochloride |

TABLE 3-continued

| | Structure | Name |
|---|---|---|
| 148 | 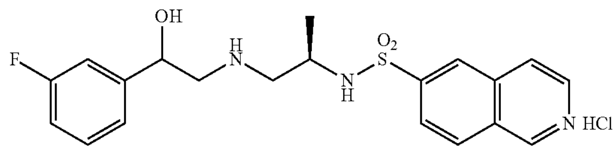 [SMILES: C[C@H](CNCC(O)c1cccc(F)c1)NS(=O)(=O)c1ccc2cnccc2c1 ; Cl] | N-[(2R)-1-{2-(3-fluorophenyl)-2-hydroxyethylamino}propan-2-yl]isoquinoline-6-sulfonamide hydrochloride |
| 149 | 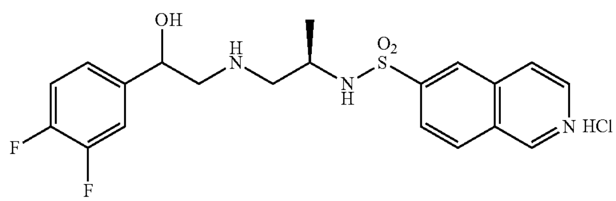 [SMILES: C[C@H](CNCC(O)c1ccc(F)c(F)c1)NS(=O)(=O)c1ccc2cnccc2c1 ; Cl] | N-[(2R)-1-{2-(3,4-difluorophenyl)-2-hydroxyethylamino}propan-2-yl)]isoquinoline-6-sulfonamide hydrochloride |
| 150 | 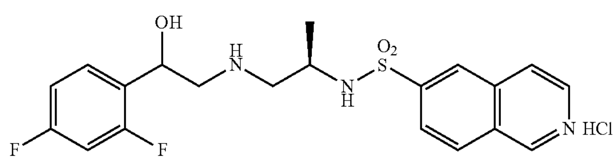 [SMILES: C[C@H](CNCC(O)c1ccc(F)cc1F)NS(=O)(=O)c1ccc2cnccc2c1 ; Cl] | N-[(2R)-1-{2-(2,4-difluorophenyl)-2-hydroxyethylamino}propan-2-yl]isoquinoline-6-sulfonamide hydrochloride |
| 151 | 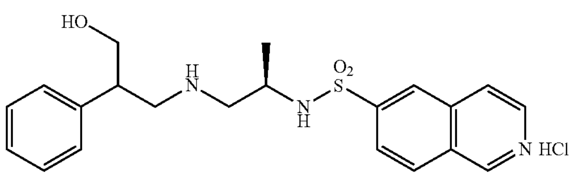 [SMILES: C[C@H](CNCC(CO)c1ccccc1)NS(=O)(=O)c1ccc2cnccc2c1 ; Cl] | N-{(2R)-1-(3-hydroxy-2-phenylpropylamino)propan-2-yl}isoquinoline-6-sulfonamide hydrochloride |
| 152 | 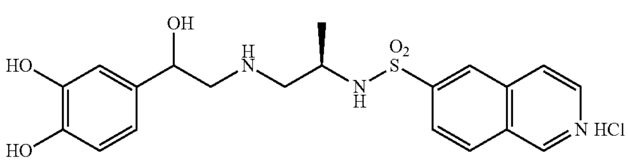 [SMILES: C[C@H](CNCC(O)c1ccc(O)c(O)c1)NS(=O)(=O)c1ccc2cnccc2c1 ; Cl] | N-[(2R)-1-{2-(3,4-dihydroxyphenyl)-2-hydroxyethylamino}propan-2-yl]isoquinoline-6-sulfonamide hydrochloride |
| 153 | 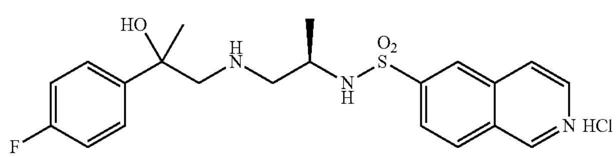 [SMILES: C[C@H](CNCC(C)(O)c1ccc(F)cc1)NS(=O)(=O)c1ccc2cnccc2c1 ; Cl] | N-[(2R)-1-{2-(4-fluorophenyl)-2-hydroxypropylamino)propan-2-yl]isoquinoline-6-sulfonamide hydrochloride |
| 154 | 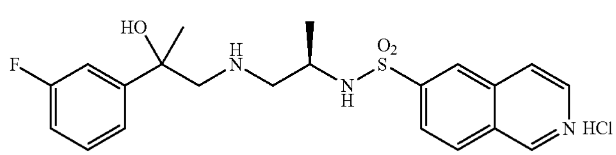 [SMILES: C[C@H](CNCC(C)(O)c1cccc(F)c1)NS(=O)(=O)c1ccc2cnccc2c1 ; Cl] | N-[(2R)-1-{2-(3-fluorophenyl)-2-hydroxypropylamino}propan-2-yl]isoquinoline-6-sulfonamide hydrochloride |
| 155 | 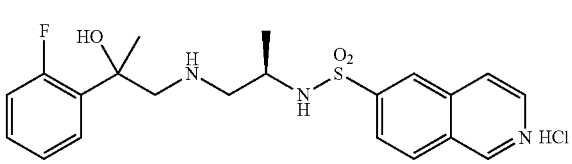 [SMILES: C[C@H](CNCC(C)(O)c1ccccc1F)NS(=O)(=O)c1ccc2cnccc2c1 ; Cl] | N-[(2R)-1-{2-(2-fluorophenyl)-2-hydroxypropylamino}propan-2-yl]isoquinoline-6-sulfonamide hydrochloride |

TABLE 4

| | | |
|---|---|---|
| 156 | (structure) | N-[(2R)-1-{2-hydroxy-2-(thiophen-3-yl)propylamino}propan-2-yl]isoquinoline-6-sulfonamide hydrochloride |
| 157 | (structure) | N-[(2R)-1-{2-hydroxy-2-(thiophen-2-yl)ethylamino}propan-2-yl]isoquinoline-6-sulfonamide hydrochloride |
| 158 | (structure) | N-[(2R)-1-{2-(furan-3-yl)-2-hydroxyethylamino}propan-2-yl]isoquinoline-6-sulfonamide hydrochloride |
| 159 | (structure) | N-[(2R)-1-{2-(furan-3-yl)-2-hydroxypropylamino}propan-2-yl]isoquinoline-6-sulfonamide hydrochloride |
| 160 | (structure) | N-[(2R)-1-{2-(furan-2-yl)-2-hydroxyethylamino}propan-2-yl]isoquinoline-6-sulfonamide hydrochloride |
| 161 | (structure) | (R)-N-[1-{2-(benzofuran-3-yl)ethylamino}propan-2-yl]isoquinoline-6-sulfonamide hydrochloride |
| 162 | (structure) | N-[(2R)-1-{2-(benzofuran-3-yl)-2-hydroxyethylamino}propan-2-yl]isoquinoline-6-sulfonamide hydrochloride |
| 163 | (structure) | N-[(2R)-1-{2-(benzofuran-3-yl)-2-hydroxypropylamino}propan-2-yl]isoquinoline-6-sulfonamide hydrochloride |
| 164 | (structure) | (R)-N-[1-{2-(benzofuran-5-yl)ethylamino}propan-2-yl]isoquinoline-6-sulfonamide hydrochloride |
| 165 | (structure) | N-[(2R)-1-{2-(benzofuran-5-yl)-2-hydroxyethylamino}propan-2-yl]isoquinoline-6-sulfonamide hydrochloride |

TABLE 4-continued

| # | Structure | Name |
|---|---|---|
| 166 | 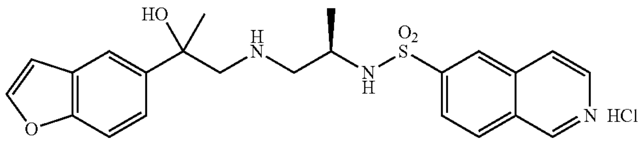 | N-[(2R)-1-{2-(benzofuran-5-yl)-2-hydroxypropylamino}propan-2-yl]isoquinoline-6-sulfonamide hydrochloride |
| 167 | 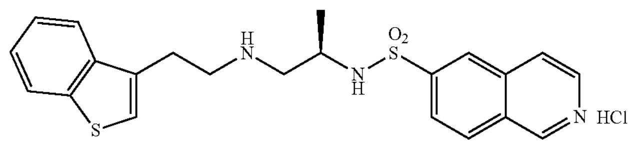 | (R)-N-[1-{2-(benzo[b]thiophen-3-yl)ethylamino}propan-2-yl]isoquinoline-6-sulfonamide hydrochloride |

TABLE 5

| # | Structure | Name |
|---|---|---|
| 168 | 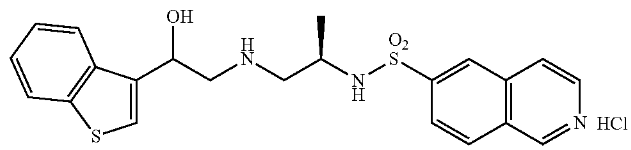 [SMILES: C[C@H](CNCC(O)c1coc2ccccc12)NS(=O)(=O)c1ccc2cnccc2c1 ; Cl] | N-[(2R)-1-{2-(benzo[b]thiophen-3-yl)-2-hydroxyethylamino}propan-2-yl]isoquinoline-6-sulfonamide hydrochloride |
| 169 | 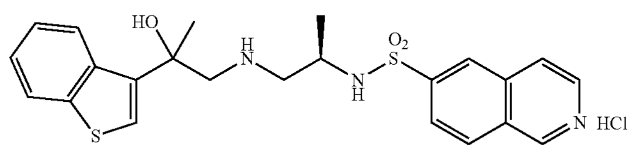 | N-[(2R)-1-{2-(benzo[b]thiophen-3-yl)-2-hydroxypropylamino}propan-2-yl]isoquinoline-6-sulfonamide hydrochloride |
| 170 | 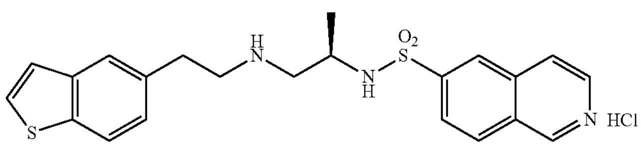 [SMILES: C[C@H](CNCCc1ccc2occc2c1)NS(=O)(=O)c1ccc2cnccc2c1 ; Cl] | (R)-N-[1-{2-(benzo[b]thiophen-5-yl)ethylamino}propan-2-yl]isoquinoline-6-sulfonamide hydrochloride |
| 171 | 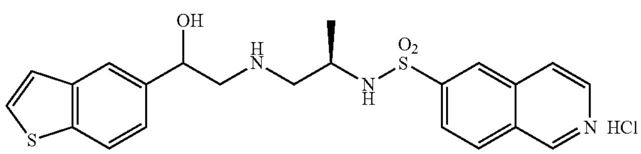 [SMILES: C[C@H](CNCC(O)c1ccc2sccc2c1)NS(=O)(=O)c1ccc2cnccc2c1 ; Cl] | N-[(2R)-1-{2-(benzo[b]thiophen-5-yl)-2-hydroxyethylamino}propan-2-yl]isoquinoline-6-sulfonamide hydrochloride |
| 172 | 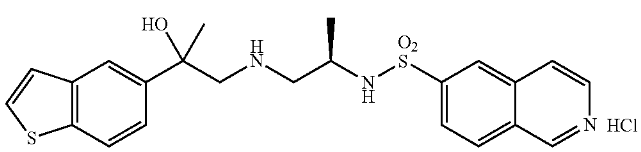 [SMILES: C[C@H](CNCC(C)(O)c1ccc2sccc2c1)NS(=O)(=O)c1ccc2cnccc2c1 ; Cl] | N-[(2R)-1-{2-(benzo[b]thiophen-5-yl)-2-hydroxypropylamino}propan-2-yl]isoquinoline-6-sulfonamide hydrochloride |
| 173 | 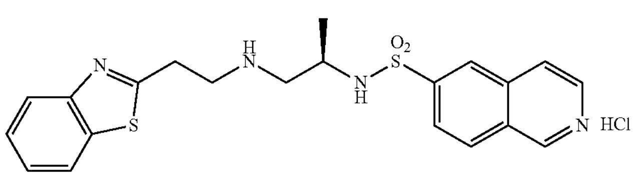 [SMILES: C[C@H](CNCCc1nc2ccccc2s1)NS(=O)(=O)c1ccc2cnccc2c1 ; Cl] | (R)-N-[1-{2-(benzo[d]thiazol-2-yl)ethylamino}propan-2-yl]isoquinoline-6-sulfonamide hydrochloride |
| 174 | 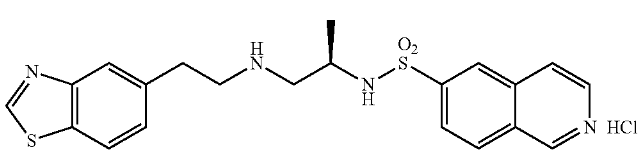 [SMILES: C[C@H](CNCCc1ccc2scnc2c1)NS(=O)(=O)c1ccc2cnccc2c1 ; Cl] | (R)-N-[1-{2-(benzo[d]thiazol-5-yl)ethylamino}propan-2-yl]isoquinoline-6-sulfonamide hydrochloride |

TABLE 5-continued

| | Structure | Name |
|---|---|---|
| 175 | 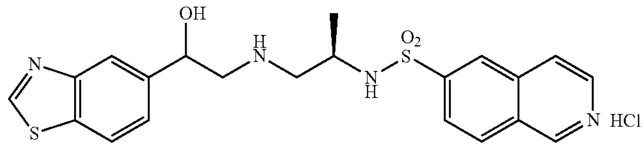 [SMILES: C[C@H](CNCC(O)c1ccc2scnc2c1)NS(=O)(=O)c1ccc2cnccc2c1 ; Cl] | N-[(2R)-1-{2-(benzo[d]thiazol-5-yl)-2-hydroxyethylamino}propan-2-yl]isoquinoline-6-sulfonamide hydrochloride |
| 176 | 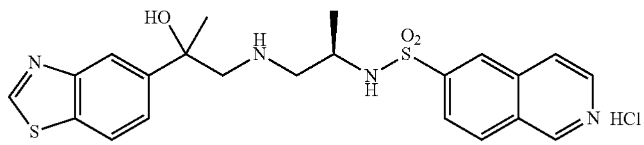 [SMILES: C[C@H](CNCC(C)(O)c1ccc2scnc2c1)NS(=O)(=O)c1ccc2cnccc2c1 ; Cl] | N-[(2R)-1-{2-(benzo[d]thiazol-5-yl)-2-hydroxypropylamino}propan-2-yl]isoquinoline-6-sulfonamide hydrochloride |
| 177 | 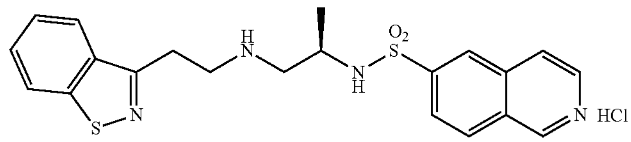 [SMILES: C[C@H](CNCCc1nsc2ccccc12)NS(=O)(=O)c1ccc2cnccc2c1 ; Cl] | (R)-N-[1-{2-(benzo[d]isothiazol-3-yl)ethylamino}propan-2-yl]isoquinoline-6-sulfonamide hydrochloride |
| 178 | 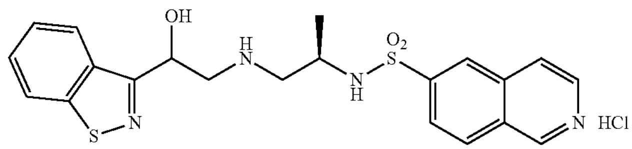 [SMILES: C[C@H](CNCC(O)c1nsc2ccccc12)NS(=O)(=O)c1ccc2cnccc2c1 ; Cl] | N-[(2R)-1-{2-(benzo[d]isothiazol-3-yl)-2-hydroxyethylamino)propan-2-yl]isoquinolin-6-sulfonamide hydrochloride |
| 179 | 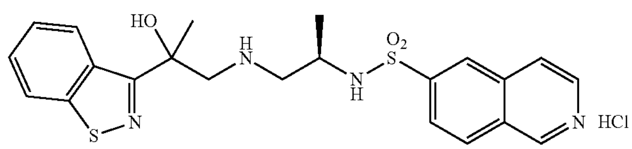 [SMILES: C[C@H](CNCC(C)(O)c1nsc2ccccc12)NS(=O)(=O)c1ccc2cnccc2c1 ; Cl] | N-[(2R)-1-{2-(benzo[d]isothiazol-3-yl)-2-hydroxypropylamino}propan-2-yl]isoquinoline-6-sulfonamide hydrochloride |

TABLE 6

| | Structure | Name |
|---|---|---|
| 180 | 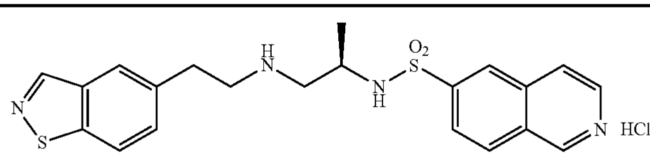 | (R)-N-[1-{2-(benzo[d]isothiazol-5-yl)ethylamino}propan-2-yl]isoquinoline-6-sulfonamide hydrochloride |
| 181 | 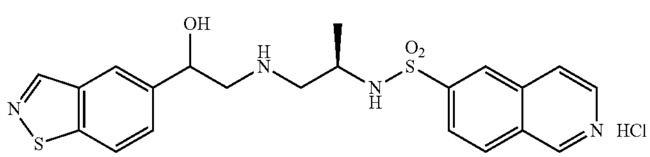 [SMILES: C[C@H](CNCC(O)c1ccc2sncc2c1)NS(=O)(=O)c1ccc2cnccc2c1 ; Cl] | N-[(2R)-1-{2-(benzo[d]isothiazol-5-yl)-2-hydroxyethylamino}propan-2-yl]isoquinoline-6-sulfonamide hydrochloride |
| 182 | 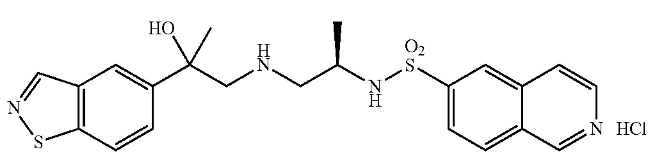 | N-[(2R)-1-{2-(benzo[d]isothiazol-5-yl)-2-hydroxypropylamino)propan-2-yl]isoquinoline-6-sulfonamide hydrochloride |
| 183 | 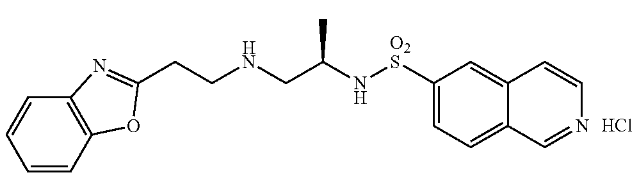 [SMILES: C[C@H](CNCCc1nc2ccccc2o1)NS(=O)(=O)c1ccc2cnccc2c1 ; Cl] | (R)-N-[1-{2-(benzo[d]oxazol-2-yl)ethylamino}propan-2-yl]isoquinoline-6-sulfonamide hydrochloride |

TABLE 6-continued

| # | Structure | Name |
|---|---|---|
| 184 | 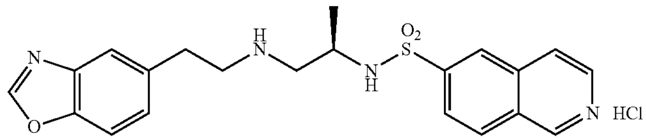 [SMILES: C[C@H](CNCCc1ccc2ocnc2c1)NS(=O)(=O)c1ccc2cnccc2c1 ; Cl] | (R)-N-[1-{2-(benzo[d]oxazol-5-yl)ethylamino}propan-2-yl]isoquinoline-6-sulfonamide hydrochloride |
| 185 | 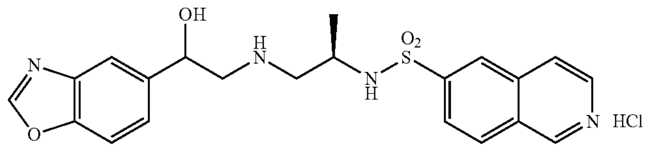 [SMILES: C[C@H](CNCC(O)c1ccc2ocnc2c1)NS(=O)(=O)c1ccc2cnccc2c1 ; Cl] | N-[(2R)-1-{2-(benzo[d]oxazol-5-yl)-2-hydroxyethylamino}propan-2-yl]isoquinoline-6-sulfonamide hydrochloride |
| 186 | 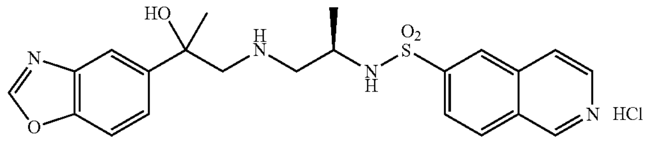 [SMILES: C[C@H](CNCC(C)(O)c1ccc2ocnc2c1)NS(=O)(=O)c1ccc2cnccc2c1 ; Cl] | N-[(R)-1-{2-(benzo[d]oxazol-5-yl)-2-hydroxypropylamino}propan-2-yl]isoquinoline-6-sulfonamide hydrochloride |
| 187 | 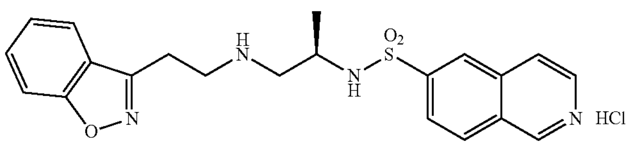 [SMILES: C[C@H](CNCCc1noc2ccccc12)NS(=O)(=O)c1ccc2cnccc2c1 ; Cl] | (R)-N-[1-{2-(benzo[d]isoxazol-3-yl)ethylamino}propan-2-yl]isoquinoline-6-sulfonamide hydrochloride |
| 188 | 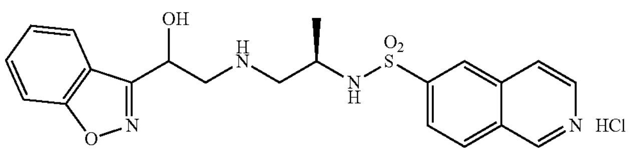 | N-[(2R)-1-{2-(benzo[d]isoxazol-3-yl)-2-hydroxyethylamino}propan-2-yl]isoquinoline-6-sulfonamide hydrochloride |
| 189 | 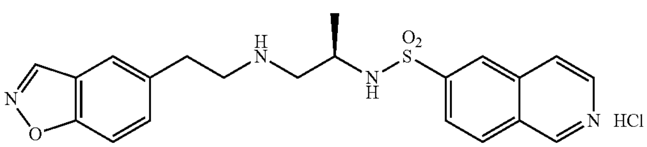 [SMILES: C[C@H](CNCCc1ccc2oncc2c1)NS(=O)(=O)c1ccc2cnccc2c1 ; Cl] | (R)-N-[1-{2-(benzo[d]isoxazol-5-yl)ethylamino}propan-2-yl]isoquinoline-6-sulfonamide hydrochloride |
| 190 | 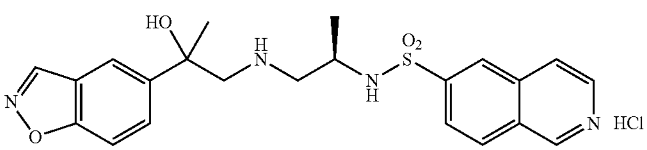 [SMILES: C[C@H](CNCC(C)(O)c1ccc2oncc2c1)NS(=O)(=O)c1ccc2cnccc2c1 ; Cl] | N-[(2R)-1-{2-(benzo[d]isoxazol-5-yl)-2-hydroxypropylamino}propan-2-yl]isoquinoline-6-sulfonamide hydrochloride |
| 191 | 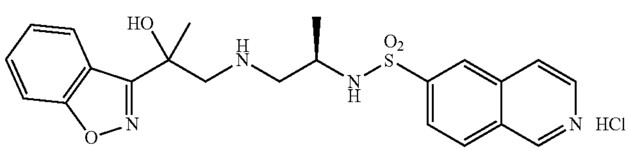 [SMILES: C[C@H](CNCC(C)(O)c1noc2ccccc12)NS(=O)(=O)c1ccc2cnccc2c1 ; Cl] | N-[(2R)-1-{2-(benzo[d]isoxazol-3-yl)-2-hydroxypropylamino}propan-2-yl]isoquinoline-6-sulfonamide hydrochloride |

TABLE 7

| # | Structure | Name |
|---|---|---|
| 192 | 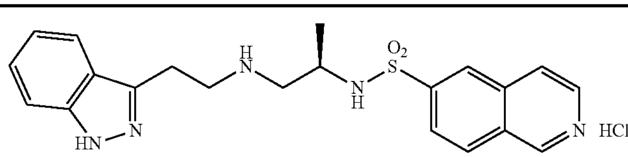 | (R)-N-[1-{2-(1H-indazol-3-yl)ethylamino}propan-2-yl]isoquinoline-6-sulfonamide hydrochloride |

TABLE 7-continued

| 193 | 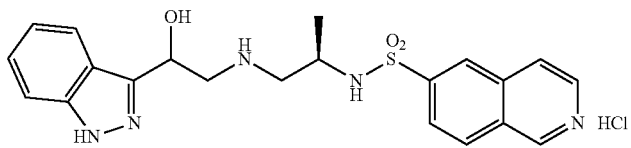 [SMILES: C[C@H](CNCC(O)c1n[nH]c2ccccc12)NS(=O)(=O)c1ccc2cnccc2c1 ; Cl] | N-[(2R)-1-{2-hydroxy-2-(1H-indazol-3-yl)ethylamino}propan-2-yl]isoquinoline-6-sulfonamide hydrochloride |
| 194 | 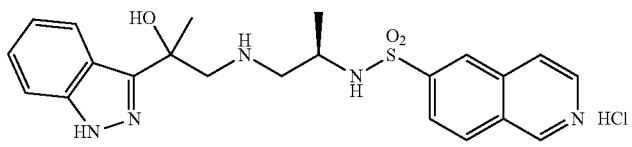 | N-[(2R)-1-{2-hydroxy-2-(1H-indazol-3-yl)propylamino}propan-2-yl]isoquinoline-6-sulfonamide hydrochloride |
| 195 | 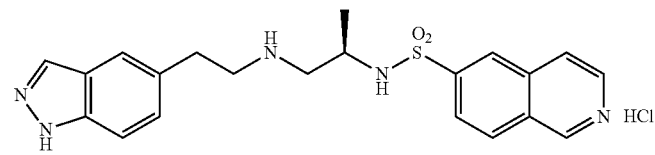 [SMILES: C[C@H](CNCCc1ccc2[nH]ncc2c1)NS(=O)(=O)c1ccc2cnccc2c1 ; Cl] | (R)-N-[1-{2-(1H-indazol-5-yl)ethylamino}propan-2-yl]isoquinoline-6-sulfonamide hydrochloride |
| 196 | 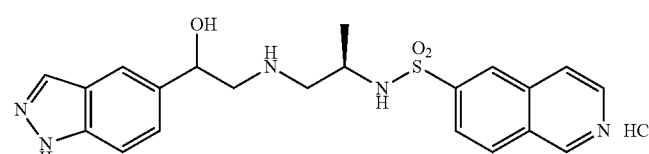 | N-[(2R)-1-{2-hydroxy-2-(1H-indazol-5-yl)ethylamino}propan-2-yl]isoquinoline-6-sulfonamide hydrochloride |
| 197 | 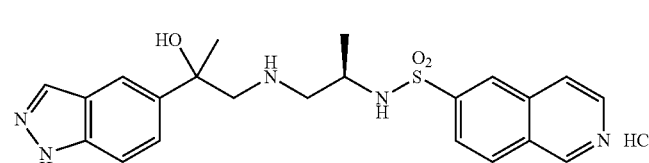 | N-[(2R)-1-{2-hydroxy-2-(1H-indazol-5-yl)propylamino}propan-2-yl]isoquinoline-6-sulfonamide hydrochloride |
| 198 | 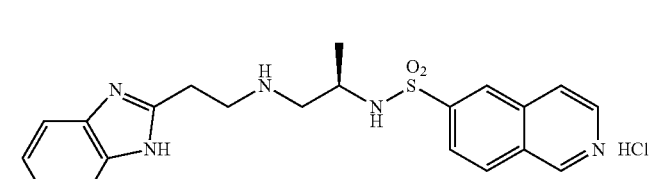 | (R)-N-[1-{2-(1H-benzo[d]imidazol-2-yl)ethylamino}propan-2-yl]isoquinoline-6-sulfonamide hydrochloride |
| 199 | 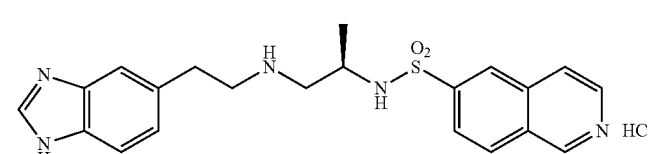 | (R)-N-[1-{2-(1H-benzo[d]imidazol-5-yl)ethylamino}propan-2-yl]isoquinoline-6-sulfonamide hydrochloride |
| 200 | 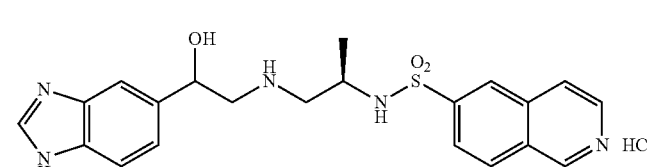 | N-[(2R)-1-{2-(1H-benzo[d]imidazol-5-yl)-2-hydroxyethylamino}propan-2-yl]isoquinoline-6-sulfonamide hydrochloride |
| 201 | 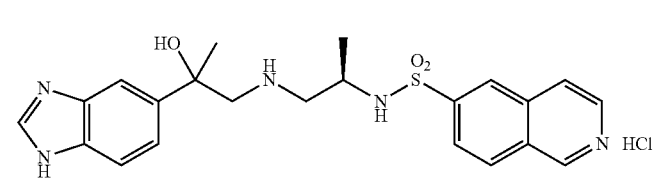 [SMILES: C[C@H](CNCC(C)(O)c1ccc2[nH]cnc2c1)NS(=O)(=O)c1ccc2cnccc2c1 ; Cl] | N-[(2R)-1-{2-(1H-benzo[d]imidazol-5-yl)-2-hydroxypropylamino}propan-2-yl]isoquinoline-6-sulfonamide hydrochloride |

TABLE 7-continued

| | | |
|---|---|---|
| 202 | | (R)-N-[1-{2-(1H-pyrrolo[2,3-c]pyridin-3-yl)ethylamino}propan-2-yl]isoquinoline-6-sulfonamide hydrochloride |
| 203 | | N-[(2R)-1-(2-hydroxy-2-(1H-pyrrolo[2,3-b]pyridin-3-yl)ethylamino}propan-2-yl]isoquinoline-6-sulfonamide hydrochloride |

TABLE 8

| | | |
|---|---|---|
| 204 | | N-[(2R)-1-{2-hydroxy-2-(1H-pyrrolo[2,3-b]pyridin-3-yl)propylamino}propan-2-yl]isoquinoline-6-sulfonamide hydrochloride |
| 205 | | (R)-N-[1-{2-(1H-pyrrolo[2,3-c]pyridin-3-yl)ethylamino}propan-2-yl]isoquinoline-6-sulfonamide hydrochloride |
| 206 | | N-[(2R)-1-(2-hydroxy-2-(1H-pyrrolo[2,3-c]pyridin-3-yl)ethylamino}propan-2-yl]isoquinoline-6-sulfonamide hydrochloride |
| 207 | | N-[(2R)-1-{2-hydroxy-2-(1H-pyrrolo[2,3-c]pyridin-3-yl)propylamino}propan-2-yl]isoquinoline-6-sulfonamide hydrochloride |
| 208 | | N-[(2R)-1-{2-hydroxy-2-(1H-indol-3-yl)ethylamino}propan-2-yl]isoquinoline-6-sulfonamide hydrochloride |
| 209 | | N-[(2R)-1-{2-hydroxy-2-(1H-indol-3-yl)propylamino}propan-2-yl]isoquinoline-6-sulfonamide hydrochloride |
| 210 | | (R)-N-[1-{2-(benzo[d][1,3]dioxo-5-yl)ethylamino}propan-2-yl]isoquinoline-6-sulfonamide hydrochloride |

TABLE 8-continued

| | | |
|---|---|---|
| 211 | 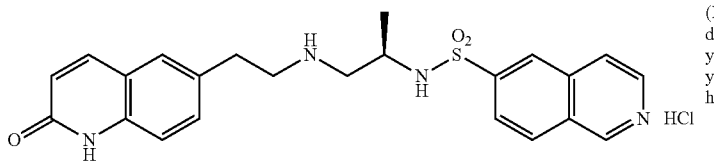 | (R)-N-[1-{2-(2-oxo-1,2-dihydroquinolin-6-yl)ethylamino}propan-2-yl]isoquinoline-6-sulfonamide hydrochloride |
| 212 | 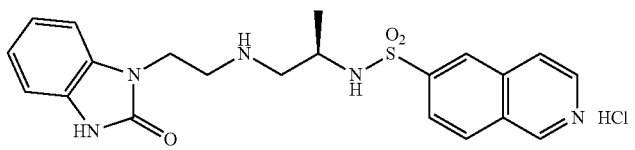 [SMILES: C[C@H](CNCCn1c(=O)[nH]c2ccccc21)NS(=O)(=O)c1ccc2cnccc2c1 ; Cl] | (R)-N-[1-{2-(2-oxo-2,3-dihydro-1H-benzo[d]imidazol-1-yl)ethylamino}propan-2-yl]isoquinoline-6-sulfonamide hydrochloride |
| 213 | 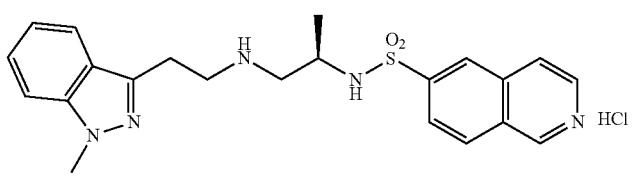 [SMILES: C[C@H](CNCCc1nn(C)c2ccccc12)NS(=O)(=O)c1ccc2cnccc2c1 ; Cl] | (R)-N-[1-{2-(1-methyl-1H-indazol-3-yl)ethylamino}propan-2-yl]isoquinoline-6-sulfonamide hydrochloride |
| 214 | 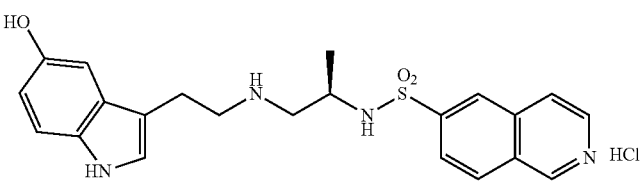 [SMILES: C[C@H](CNCCc1c[nH]c2ccc(O)cc12)NS(=O)(=O)c1ccc2cnccc2c1 ; Cl] | (R)-N-[1-{2-(5-hydroxy-1H-indol-3-yl)ethylamino}propan-2-yl]isoquinooline-6-sulfonamide hydrochloride |

TABLE 9

| | | |
|---|---|---|
| 215 | 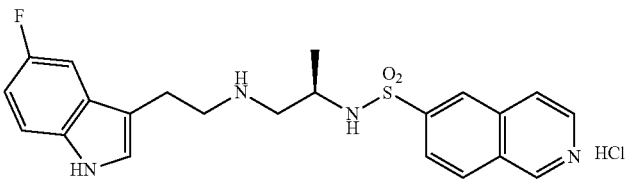 [SMILES: C[C@H](CNCCc1c[nH]c2ccc(F)cc12)NS(=O)(=O)c1ccc2cnccc2c1 ; Cl] | (R)-N-[1-{2-(5-fluoro-1H-indol-3-yl)ethylamino}propan-2-yl]isoquinoline-6-sulfonamide hydrochloride |
| 216 | 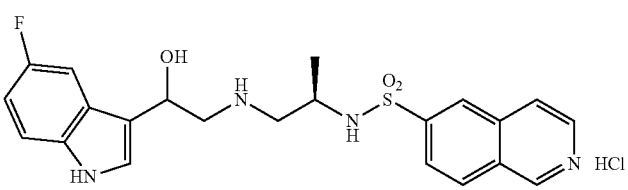 [SMILES: C[C@H](CNCC(O)c1c[nH]c2ccc(F)cc12)NS(=O)(=O)c1ccc2cnccc2c1 ; Cl] | N-[(2R)-1-{2-(5-fluoro-1H-indol-3-yl)-2-hydroxyethylamino}propan-2-yl]isoquinoline-6-sulfonamide hydrochloride |
| 217 | 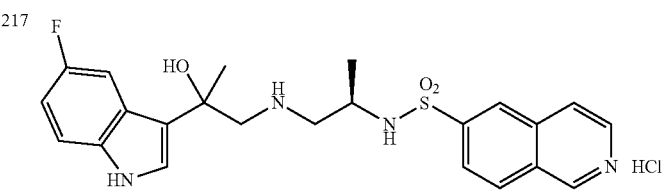 | N-[(2R)-1-{2-(5-fluoro-1H-indol-3-yl)-2-hydroxypropylamino}propan-2-yl]isoquinoline-6-sulfonamide hydrochloride |
| 218 | 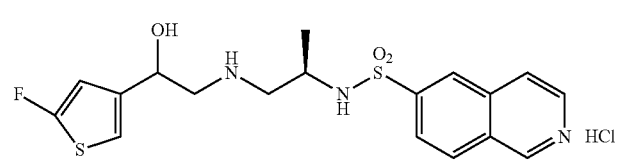 [SMILES: C[C@H](CNCC(O)c1csc(F)c1)NS(=O)(=O)c1ccc2cnccc2c1 ; Cl] | N-[(2R)-1-{(5-fluorothiophen-3-yl)-2-hydroxyethylamino}propan-2-yl]isoquinoline-6-sulfonamide hydrochloride |

TABLE 9-continued

| | Structure | Name |
|---|---|---|
| 219 | 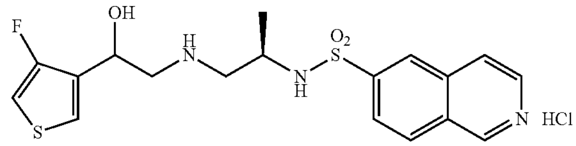 [SMILES: C[C@H](CNCC(O)c1cscc1F)NS(=O)(=O)c1ccc2cnccc2c1 ; Cl] | N-[(2R)-1-{(4-fluorothiophen-3-yl)-2-hydroxyethylamino}propan-2-yl]isoquinoline-6-sulfonamide hydrochloride |
| 220 | 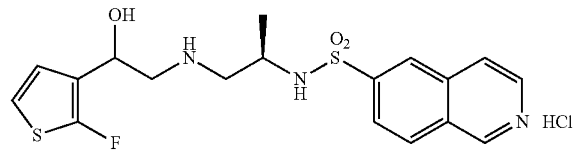 [SMILES: C[C@H](CNCC(O)c1ccsc1F)NS(=O)(=O)c1ccc2cnccc2c1 ; Cl] | N-[(2R)-1-{(2-fluorothiophen-3-yl)-2-hydroxyethylamino}propan-2-yl]isoquinoline-6-sulfonamide hydrochloride |
| 221 | 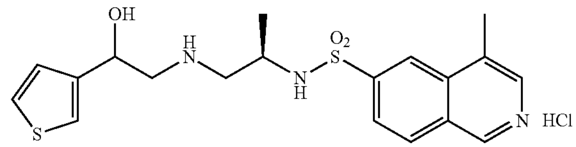 [SMILES: Cc1cncc2ccc(S(=O)(=O)N[C@H](C)CNCC(O)c3ccsc3)cc12 ; Cl] | N-[(2R)-1-{2-hydroxy-2-(thiophen-3-yl)ethylamino}propan-2-yl]-4-methylisoquinoline-6-sulfonamide hydrochloride |
| 222 | 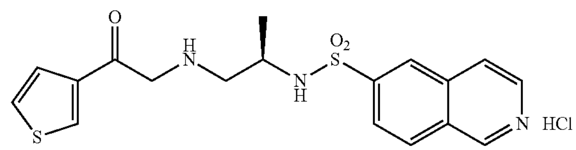 [SMILES: C[C@H](CNCC(=O)c1ccsc1)NS(=O)(=O)c1ccc2cnccc2c1 ; Cl] | (R)-N-[1-{2-oxo-2-(thiophen-3-yl)ethylamino}propan-2-yl]isoquinoline-6-sulfonamide dihydrochloride |
| 223 | 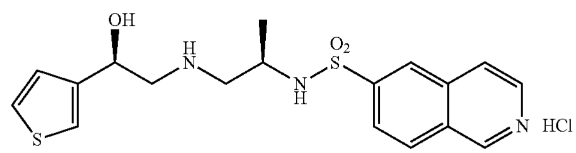 [SMILES: C[C@H](CNC[C@H](O)c1ccsc1)NS(=O)(=O)c1ccc2cnccc2c1 ; Cl] | N-[(R)-1-{(R)-2-hydroxy-2-(thiophen-3-yl)ethylamino}propan-2-yl]isoquinoline-6-sulfonamide hydrochloride |
| 224 | 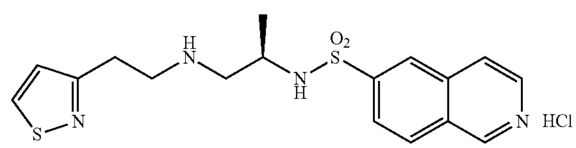 [SMILES: C[C@H](CNCCc1ccsn1)NS(=O)(=O)c1ccc2cnccc2c1 ; Cl] | (R)-N-[1-{2-(isothiazol-3-yl)ethylamino}propan-2-yl]isoquinoline-6-sulfonamide hydrochloride |
| 225 | 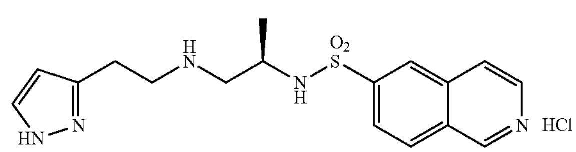 [SMILES: C[C@H](CNCCc1cc[nH]n1)NS(=O)(=O)c1ccc2cnccc2c1 ; Cl] | (R)-N-[1-{2-(1H-pyrazol-3-yl)ethyalamino}propan-2-yl]isoquinoline-6-sulfonamide hydrochloride |
| 226 | 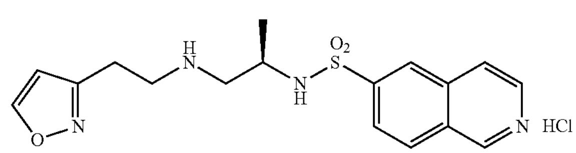 [SMILES: C[C@H](CNCCc1ccon1)NS(=O)(=O)c1ccc2cnccc2c1 ; Cl] | (R)-N-[1-{2-(isoxazol-3-yl)ethylamino)propan-2-yl]isoquinoline-6-sulfonamide hydrochloride |

TABLE 10

| | Structure | Name |
|---|---|---|
| 227 | 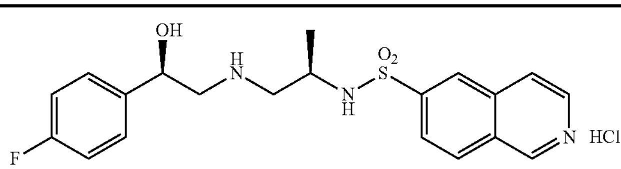 | N-[(R)-1-{(R)-2-(4-fluorophenyl)-2-hydroxyethylamino}propan-2-yl]isoquinoline-6-sulfonamide hydrochloride |

TABLE 10-continued

| # | Structure | Name |
|---|---|---|
| 228 | 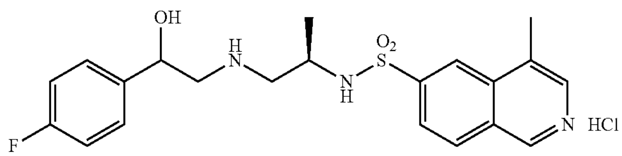 [SMILES: Cc1cncc2ccc(S(=O)(=O)N[C@H](C)CNCC(O)c3ccc(F)cc3)cc12 ; Cl] | N-[(2R)-1-{2-(4-fluorophenyl)-2-hydroxyethylamino}propan-2-yl]-4-methylisoquinoline-6-sulfonamide hydrochloride |
| 229 | 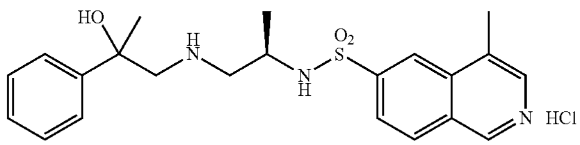 [SMILES: Cc1cncc2ccc(S(=O)(=O)N[C@H](C)CNCC(C)(O)c3ccccc3)cc12 ; Cl] | N-{(2R)-1-(2-hydroxy-2-phenylpropylamino)propan-2-yl}-4-methylisoquinoline-6-sulfonamide hydrochloride |
| 230 | 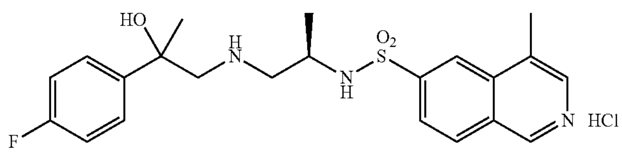 [SMILES: Cc1cncc2ccc(S(=O)(=O)N[C@H](C)CNCC(C)(O)c3ccc(F)cc3)cc12 ; Cl] | N-[(2R)-1-{2-(4-fluorophenyl)-2-hydroxypropylamino}propan-2-yl]-4-methylisoquinoline-6-sulfonamide hydrochloride |
| 231 | 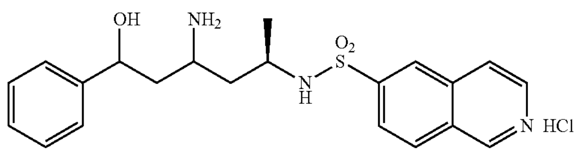 [SMILES: C[C@H](CC(N)CC(O)c1ccccc1)NS(=O)(=O)c1ccc2cnccc2c1 ; Cl] | N-{(2R)-4-amino-6-hydroxy-6-phenylhexan-2-yl}isoquinoline-6-sulfonamide hydrochloride |
| 232 | 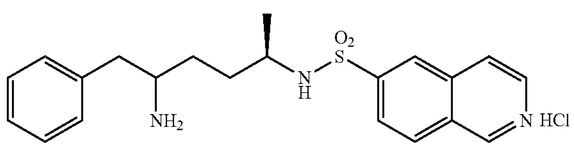 [SMILES: C[C@H](CCC(N)Cc1ccccc1)NS(=O)(=O)c1ccc2cnccc2c1 ; Cl] | N-{(2R)-5-amino-6-phenylhexan-2-yl}isoquinoline-6-sulfonamide hydrochloride |
| 233 | 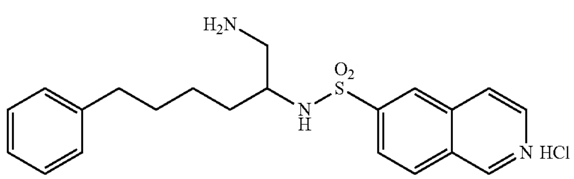 [SMILES: NCC(CCCCc1ccccc1)NS(=O)(=O)c1ccc2cnccc2c1 ; Cl] | N-(1-amino-6-phenylhexan-2-yl)isoquinoline-6-sulfonamide hydrochloride |
| 234 | 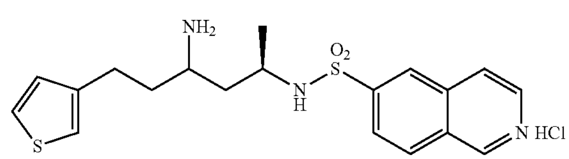 [SMILES: C[C@H](CC(N)CCc1ccsc1)NS(=O)(=O)c1ccc2cnccc2c1 ; Cl] | N-{(2R)-4-amino-6-(thiophen-3-yl)hexan-2-yl}isoquinoline-6-sulfonamide hydrochloride |
| 235 | 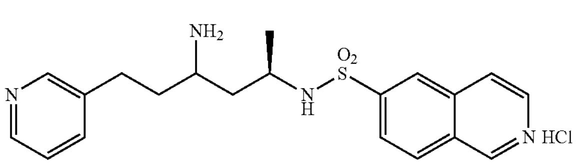 [SMILES: C[C@H](CC(N)CCc1cccnc1)NS(=O)(=O)c1ccc2cnccc2c1 ; Cl] | N-{(2R)-4-amino-6-(pyridin-3-yl)hexan-2-yl}isoquinoline-6-sulfonamide hydrochloride |
| 236 | 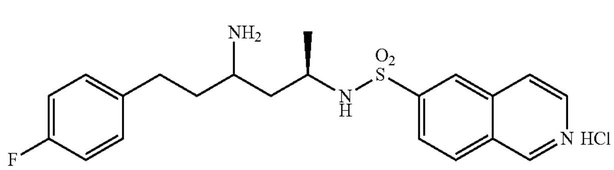 [SMILES: C[C@H](CC(N)CCc1ccc(F)cc1)NS(=O)(=O)c1ccc2cnccc2c1 ; Cl] | N-{(2R)-4-amino-6-(4-fluorophenyl)hexan-2-yl}isoquinoline-6-sulfonamide hydrochloride |

TABLE 10-continued

| | | |
|---|---|---|
| 237 | 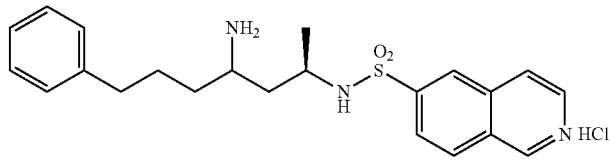 [SMILES: C[C@H](CC(N)CCCc1ccccc1)NS(=O)(=O)c1ccc2cnccc2c1 ; Cl] | N-{(2R)-4-amino-7-phenylheptan-2-yl}isoquinoline-6-sulfonamide hydrochloride |
| 238 | 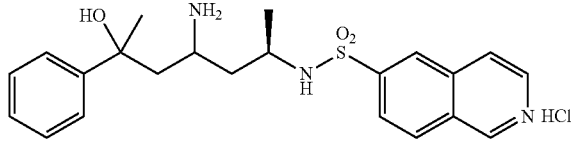 [SMILES: C[C@H](CC(N)CC(C)(O)c1ccccc1)NS(=O)(=O)c1ccc2cnccc2c1 ; Cl] | N-{(2R)-4-amino-6-hydroxy-6-phenylheptan-2-yl}isoquinoline-6-sulfonamide hydrochloride |

TABLE 11

| | | |
|---|---|---|
| 239 | 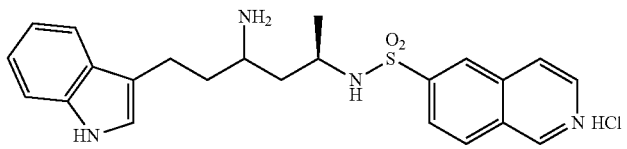 [SMILES: C[C@H](CC(N)CCc1c[nH]c2ccccc12)NS(=O)(=O)c1ccc2cnccc2c1 ; Cl] | N-{(2R)-4-amino-6-(1H-indol-3-yl)hexan-2-yl}isoquinoline-6-sulfonamide hydrochloride |
| 240 | 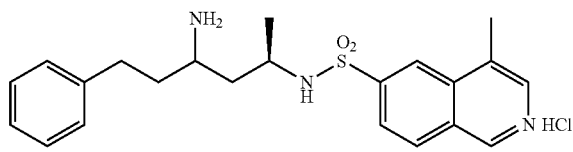 [SMILES: Cc1cncc2ccc(S(=O)(=O)N[C@H](C)CC(N)CCc3ccccc3)cc12 ; Cl] | N-{(2R)-4-amino-6-phenylhexan-2-yl}-4-methylisoquinoline-6-sulfonamide hydrochloride |
| 241 | 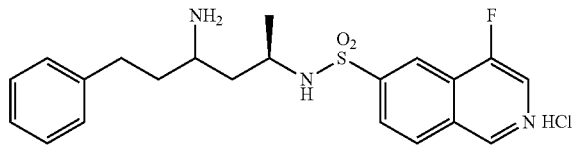 | N-{(2R)-4-amino-6-phenylhexan-2-yl}-4-fluoroisoquinoline-6-sulfonamide hydrochloride |
| 242 | 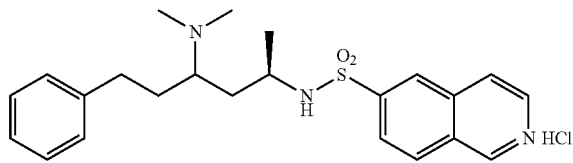 [SMILES: C[C@H](CC(CCc1ccccc1)N(C)C)NS(=O)(=O)c1ccc2cnccc2c1 ; Cl] | N-{(2R)-4-(dimethylamino)-6-phenylhexan-2-yl}isoquinoline-6-sulfonamide hydrochloride |
| 243 | 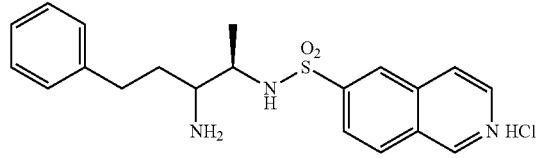 [SMILES: C[C@@H](NS(=O)(=O)c1ccc2cnccc2c1)C(N)CCc1ccccc1 ; Cl] | N-{(2R)-3-amino-5-phenylpentan-2-yl}isoquinoline-6-sulfonamide hydrochloride |
| 244 | 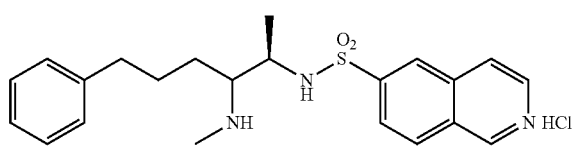 [SMILES: CNC(CCCc1ccccc1)[C@@H](C)NS(=O)(=O)c1ccc2cnccc2c1 ; Cl] | N-{(2R)-3-(methylamino)-6-phenylhexan-2-yl}isoquinoline-6-sulfonamide hydrochloride |

TABLE 11-continued

| 245 | 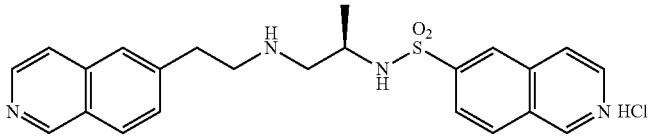 [SMILES: C[C@H](CNCCc1ccc2cnccc2c1)NS(=O)(=O)c1ccc2cnccc2c1 ; Cl] | (R)-N-[1-{2-(isoquinolin-6-yl)ethylamino}propan-2-yl]isoquinoline-6-sulfonamide hydrochloride |
| 246 | 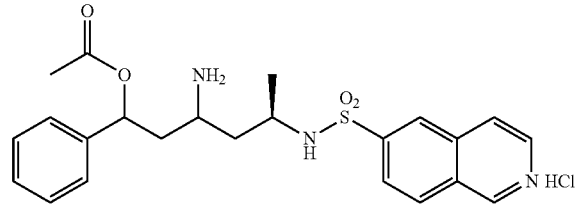 [SMILES: CC(=O)OC(CC(N)C[C@@H](C)NS(=O)(=O)c1ccc2cnccc2c1)c1ccccc1 ; Cl] | 2-{(R)-2-(isoquinoline-6-sulfonamide)propylamino}-1-phenylethylacetate hydrochloride |
| 247 | 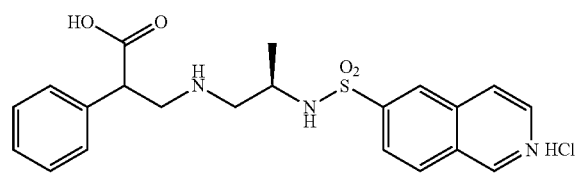 [SMILES: C[C@H](CNCC(C(=O)O)c1ccccc1)NS(=O)(=O)c1ccc2cnccc2c1 ; Cl] | 3-{(R)-2-(isoquinoline-6-sulfonamide)propylamino}-2-phenylpropanoic acid hydrochloride |
| 248 | 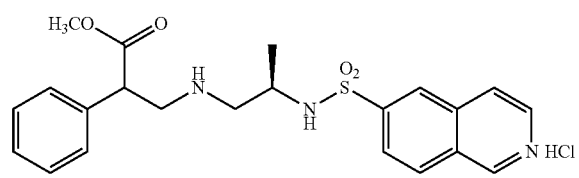 [SMILES: COC(=O)C(CNC[C@@H](C)NS(=O)(=O)c1ccc2cnccc2c1)c1ccccc1 ; Cl] | methyl 3-{(R)-2-(isoquinoline-6-sulfonamide)propylamino}-2-phenylpropanoic acid hydrochloride |
| 249 | 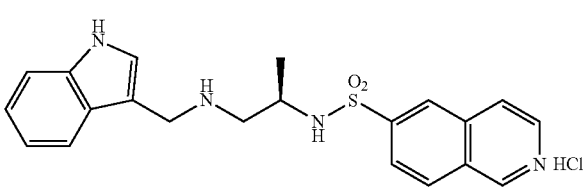 [SMILES: C[C@H](CNCc1c[nH]c2ccccc12)NS(=O)(=O)c1ccc2cnccc2c1 ; Cl] | (R)-N-[1-{(1H-indol-3-yl)methylamino}propan-2-yl]isoquinoline-6-sulfonamide hydrochloride |
| 250 | 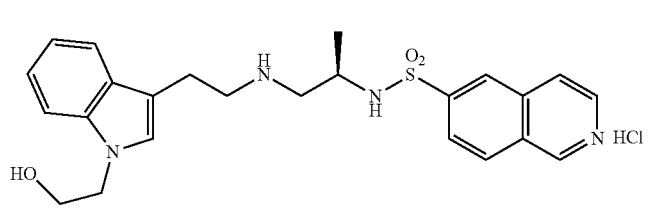 [SMILES: C[C@H](CNCCc1cn(CCO)c2ccccc12)NS(=O)(=O)c1ccc2cnccc2c1 ; Cl] | (R)-N-(1-[2-{(2-hydroxyethyl)-1H-indol-3-yl}ethylamino]propan-2-yl)isoquinoline-6-sulfonamide hydrochloride |
| 251 | 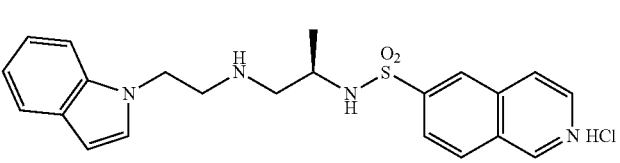 [SMILES: C[C@H](CNCCn1ccc2ccccc21)NS(=O)(=O)c1ccc2cnccc2c1 ; Cl] | (R)-N-[1-{2-(1H-indol-1-yl)ethylamino}propan-2-yl]isoquinoline-6-sulfonamide hydrochloride |
| 252 | 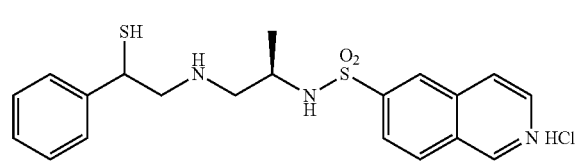 [SMILES: C[C@H](CNCC(S)c1ccccc1)NS(=O)(=O)c1ccc2cnccc2c1 ; Cl] | N-{(2R)-1-(2-mercapto-2-phenylethylamino)propan-2-yl}isoquinoline-6-sulfonamide hydrochloride |

Test Example 1

Blood Pressure Lowering Effect of Compound of the Present Invention in Spontaneously Hypertensive Rats The compound of the present invention was intraperitoneally administered to spontaneously hypertensive rats (SHR/Izm, sex: male, 4 to 6 rats per group) and evaluated for its blood pressure lowering effect. The compounds of Examples 5, 23, 25, 35, 36, 53, 58, 83, 84, 86, 87, and 90 were used as test compounds.

Preparation of Test Compound Solution

Each test compound was dissolved in saline and diluted to prepare a test compound solution with a predetermined concentration.

Test Method

The test compound was intraperitoneally administered at a dose of 10 mg/kg to the animals, and their blood pressures and pulse rates were measured over time using Softron Indirect Blood Pressure Meter BP-98A.

(Results)

All the compounds of Examples 23, 25, 36, 53, 58, 83, and 86 lowered the systolic blood pressures by up to 30% or more compared with the value before administration. All the compounds of Examples 35, 84, 87, and 90 lowered the systolic blood pressures by up to 20%. The compound of Example 5 lowered the systolic blood pressures by up to 16%. It was thus shown that the compound of the present invention has excellent blood pressure lowering effect. Accordingly, the compounds of the present invention are useful as therapeutic agents for cardiovascular diseases including hypertension.

Test Example 2

Ocular hypotensive effect of compound of the present invention in rabbits

The compound of the present invention was administered to rabbits (New Zealand White, sex: male, 3 to 6 per group) and evaluated for its ocular hypotensive effect.

Preparation of Test Compound Solution

Each test compound was dissolved in a vehicle 1 (1.04 g of sodium dihydrogen phosphate dihydrate and 0.5 g of sodium chloride dissolved in purified water and then adjusted to pH 7.0 with sodium hydroxide to make the total amount to 100 mL) or a vehicle 2 (2% (w/v) aqueous boric acid solution) to prepare a test compound solution with a predetermined concentration.

Test Method

The intraocular pressures of the rabbits were measured using Tiolat TonoVet handheld tonometer immediately before administration of test compound. The test compound solution and the vehicle were dropped at a volume of 0.04 mL to one eye and the contralateral eye, respectively, and the intraocular pressures were measured over time in the same way as above. The rate of the intraocular pressure of the eye receiving the test compound solution to that of the eye receiving the vehicle was calculated as an ocular hypotensive rate. The ocular hypotensive activity of the compound was evaluated as ++ when the dropping of the test compound solution with a concentration of 1% (w/v) or lower to the eye resulted in the maximum ocular hypotensive rate of 15% or more. Likewise, the ocular hypotensive activity of the compound was evaluated as + when the dropping thereof resulted in the maximum ocular hypotensive rate of 5% or more and less than 15%.

(Results)

The ocular hypotensive activity of each test compound is shown in Table 12. As shown in Table 12, all the compounds of the present invention exhibited excellent ocular hypotensive effect. This demonstrated that the compounds of the present invention are useful as therapeutic drugs for glaucoma or ocular hypertension.

TABLE 12

Ocular hypotensive activity of compound of the present invention

| Example No. | Ocular hypotensive activity |
|---|---|
| 1 | ++ |
| 2 | ++ |
| 3 | ++ |
| 4 | ++ |
| 5 | ++ |
| 6 | ++ |
| 7 | ++ |
| 8 | ++ |
| 9 | ++ |
| 10 | ++ |
| 11 | + |
| 12 | ++ |
| 13 | + |
| 14 | ++ |
| 15 | ++ |
| 16 | ++ |
| 17 | ++ |
| 18 | ++ |
| 19 | ++ |
| 20 | ++ |
| 21 | + |
| 22 | ++ |
| 23 | ++ |
| 24 | ++ |
| 25 | ++ |
| 26 | ++ |
| 27 | ++ |
| 28 | ++ |
| 29 | ++ |
| 30 | ++ |
| 31 | ++ |
| 32 | ++ |
| 33 | ++ |
| 34 | ++ |
| 35 | ++ |
| 36 | ++ |
| 37 | ++ |
| 38 | ++ |
| 39 | ++ |
| 40 | ++ |
| 41 | ++ |
| 42 | + |
| 43 | ++ |
| 44 | + |
| 45 | ++ |
| 46 | ++ |
| 47 | ++ |
| 48 | ++ |
| 49 | ++ |
| 50 | + |
| 52 | ++ |
| 53 | ++ |
| 54 | ++ |
| 55 | ++ |
| 56 | ++ |

TABLE 12-continued

Ocular hypotensive activity of compound of the present invention

| Example No. | Ocular hypotensive activity |
|---|---|
| 57 | ++ |
| 58 | ++ |
| 59 | ++ |
| 60 | ++ |
| 61 | ++ |
| 62 | ++ |
| 63 | + |
| 64 | ++ |
| 65 | + |
| 66 | ++ |
| 67 | ++ |
| 68 | + |
| 69 | ++ |
| 71 | ++ |
| 72 | + |
| 73 | ++ |
| 74 | ++ |
| 75 | ++ |
| 76 | ++ |
| 77 | + |
| 78 | ++ |
| 79 | ++ |
| 80 | ++ |
| 81 | ++ |
| 83 | ++ |
| 84 | ++ |
| 85 | ++ |
| 86 | ++ |
| 87 | ++ |
| 88 | + |
| 90 | ++ |
| 91 | ++ |
| 92 | ++ |
| 93 | ++ |
| 94 | ++ |
| 95 | + |
| 96 | ++ |
| 97 | ++ |
| 99 | ++ |
| 100 | ++ |
| 103 | ++ |
| 104 | ++ |
| 108 | ++ |
| 109 | + |
| 110 | ++ |
| 111 | + |
| 112 | ++ |
| 113 | ++ |
| 115 | ++ |
| 116 | + |
| 117 | ++ |
| 118 | ++ |
| 119 | ++ |
| 120 | ++ |

[Industrial Applicability]

Compounds represented by Formula (1), salts thereof, or solvates of the compounds or the salt provided by the present invention have ocular hypotensive effect and blood pressure lowering effect. A pharmaceutical agent containing, as an active ingredient, a substance selected from the group consisting of compounds represented by Formula (1), salts thereof, or solvates of the compounds or the salt is useful as a medicine for treatment and/or prevention of glaucoma, ocular hypertension, and cardiovascular disease.

The invention claimed is:

1. An isoquinoline-6-sulfonamide compound represented by Formula (1), a salt thereof, or a solvate of the compound or the salt thereof:

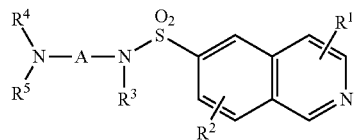

wherein $R^1$ and $R^2$ each independently represent a hydrogen atom, a halogen atom, a cyano group, an alkyl group, a halogenoalkyl group, an alkenyl group, an alkynyl group, an alkoxy group, an alkylthio group, a hydroxyl group, a mercapto group, a nitro group, an amino group, an aminoalkylthio group, or a heteroaryl group;

$R^3$ and $R^4$ each independently represent a hydrogen atom, an alkyl group, a hydroxyalkyl group, a dialkylaminoalkyl group, or an aminoalkanoyl group;

$R^5$ represents a hydrogen atom, an optionally substituted alkyl group, an alkenyl group, an optionally substituted alkynyl group, or an optionally substituted cycloalkyl group, or $R^4$ and $R^5$ optionally form a saturated heterocyclic ring together with an adjacent nitrogen atom, wherein a substituent on the alkyl group, the alkynyl group, or the cycloalkyl group in $R^5$ is at least one substituent selected from (a) the group consisting of a cycloalkyl group, an aryl group, a heteroaryl group, an aryloxy group, a heteroaryloxy group, an arylene group, and a heteroarylene group optionally having, on a ring, at least one substituent selected from the group consisting of a halogen atom, a cyano group, an alkyl group, a halogenoalkyl group, an alkenyl group, an alkynyl group, an alkoxy group, an alkylthio group, a hydroxyl group, an oxo group, a formyl group, an alkanoyl group, a carboxyl group, an alkyloxycarbonyl group, a mercapto group, a nitro group, an amino group, an urea group, a thiourea group, and an aminoalkyl group, (b) a hydroxyl group, (c) an oxo group, (d) an alkanoyloxy group, (e) an amino group, (f) a carboxyl group, (g) an alkoxy group, and (h) an alkyloxycarbonyl group; and A represents a linear or branched alkylene group having 2 to 6 carbon atoms and optionally having at least one substituent selected from the group consisting of a carboxyl group, a halogen atom, a cyano group, an oxo group, an alkenyl group, an alkynyl group, an alkoxy group, a hydroxyl group, an alkyloxycarbonyl group, an aminoalkyl group, an aryl group, a heteroaryl group, an optionally substituted aralkyl group, and an optionally substituted heteroarylalkyl group, wherein the aralkyl group or the heteroarylalkyl group in A optionally has at least one substituent selected from the group consisting of a halogen atom, a cyano group, an alkyl group, a halogenoalkyl group, an alkenyl group, an alkynyl group, an alkoxy group, an alkylthio group, a hydroxyl group, an oxo group, a formyl group, an alkanoyl group, a carboxyl group, an alkyloxycarbonyl group, a mercapto group, a nitro group, an amino group, an urea group, a thiourea group, and an aminoalkyl group.

2. The compound according to claim 1, wherein $R^1$ and $R^2$ are each independently a hydrogen atom, a halogen atom, a $C_{1-8}$ alkyl group, a nitro group, a cyano group, a halogeno $C_{1-8}$ alkyl group, a phenyl group, a $C_{2-8}$ alkenyl group, a $C_{2-8}$ alkynyl group, a hydroxyl group, an amino group, an amino $C_{1-8}$ alkylthio group, or a thienyl group.

3. The compound according to claim 1, wherein a substituent on the alkyl group, the alkynyl group, or the cycloalkyl group, in $R^5$ is at least one substituent selected from the group consisting of (a) an aryl group, a heteroaryl group, or an arylene group optionally having, on the ring, at least one substituent selected from the group consisting of a halogen atom, a cyano group, a $C_{1-8}$ alkyl group, a halogeno $C_{1-8}$ alkyl group, a $C_{2-8}$ alkenyl group, a $C_{2-8}$ alkynyl group, a $C_{1-8}$ alkoxy group, a $C_{1-8}$ alkylthio group, a hydroxyl group, an oxo group, a formyl group, a $C_{1-8}$ alkanoyl group, a carboxyl group, a $C_{1-8}$ alkyloxycarbonyl group, a mercapto group, a nitro group, an amino group, an urea group, a thiourea group, and an amino $C_{1-8}$ alkyl group, (b) a hydroxyl group, (c) an oxo group, (d) an alkanoyloxy group, (e) an amino group, (f) a carboxyl group, (g) an alkoxy group, and (h) an alkyloxycarbonyl group.

4. The compound according to claim 1, wherein $R^5$ represents a hydrogen atom, an optionally substituted $C_{1-8}$ alkyl group, a $C_{2-8}$ alkenyl group, a $C_{2-8}$ alkynyl group, or a $C_{3-8}$ cycloalkyl group, or $R^4$ and $R^5$ optionally form a saturated heterocyclic ring together with the adjacent nitrogen atom, wherein the substituent on the alkyl group is at least one substituent selected from the group consisting of (a) an aryl group, a heteroaryl group, or an arylene group optionally having, on the ring, at least one substituent selected from the group consisting of a halogen atom, a cyano group, a $C_{1-8}$ alkyl group, a halogeno $C_{1-8}$ alkyl group, a $C_{2-8}$ alkenyl group, a $C_{2-8}$ alkynyl group, a $C_{1-8}$ alkoxy group, a $C_{1-8}$ alkylthio group, a hydroxyl group, an oxo group, a formyl group, a $C_{2-8}$ alkanoyl group, a carboxyl group, a $C_{1-8}$ alkyloxycarbonyl group, a nitro group, an amino group, and an amino $C_{1-8}$ alkyl group, (b) a hydroxyl group, (c) an oxo group, and (d) a $C_{2-8}$ alkanoyloxy group.

5. The compound according to claim 1, wherein $R^3$ and $R^4$ are each independently a hydrogen atom, a $C_{1-8}$ alkyl group, a hydroxy $C_{1-8}$ alkyl group, a di($C_{1-8}$ alkyl)amino $C_{1-8}$ alkyl group, or an amino $C_{2-8}$ alkanoyl group.

6. The compound according to claim 1, wherein A is a linear or branched alkylene group having 2 to 6 carbon atoms and optionally having at least one substituent selected from the group consisting of a carboxyl group, a halogen atom, a cyano group, a $C_{2-8}$ alkenyl group, a $C_{2-8}$ alkynyl group, an amino $C_{1-8}$ alkyl group, an optionally substituted phenyl $C_{1-8}$ alkyl group, and an optionally substituted heteroaryl $C_{1-8}$ alkyl group.

7. The compound according to claim 1, wherein A is a linear or branched alkylene group having 2 to 6 carbon atoms.

8. The compound according to claim 1,
wherein when A is a linear or branched alkylene group substituted by a group selected from the group consisting of an optionally substituted aralkyl group and an optionally substituted heteroarylalkyl group, and $R^4$ and $R^5$ are a hydrogen atom or a $C_{1-3}$ alkyl group.

9. A pharmaceutical composition comprising the compound according to claim 1.

10. A method for treating glaucoma or ocular hypertension, comprising:
administering an effective amount of a compound according to claim 1 to a subject in need thereof.

11. A method for treating cardiovascular disease, comprising:
administering an effective amount of a compound according to claim 1 to a subject in need thereof, wherein the cardiovascular disease is hypertension.

* * * * *